US012497659B2

(12) United States Patent
Edwards et al.

(10) Patent No.: US 12,497,659 B2
(45) Date of Patent: Dec. 16, 2025

(54) METHOD OF DETECTING INHERITED EQUINE MYOPATHY

(71) Applicants: UNM RAINFOREST INNOVATIONS, Albuquerque, NM (US); Paul Szauter, Albuquerque, NM (US); Robert B. Sinclair, Asheville, NC (US)

(72) Inventors: Jeremy Scott Edwards, Albuquerque, NM (US); Paul Szauter, Albuquerque, NM (US); Robert B. Sinclair, Ashville, NC (US)

(73) Assignees: UNM RAINFOREST INNOVATIONS, Albuquerque, NM (US); JEREMY SCOTT EDWARDS, Albuquerque, NM (US)

( * ) Notice: Subject to any disclaimer, the term of this patent is extended or adjusted under 35 U.S.C. 154(b) by 0 days.

(21) Appl. No.: 16/088,247

(22) PCT Filed: Mar. 24, 2017

(86) PCT No.: PCT/US2017/023969
§ 371 (c)(1),
(2) Date: Sep. 25, 2018

(87) PCT Pub. No.: WO2017/165733
PCT Pub. Date: Sep. 28, 2017

(65) Prior Publication Data
US 2020/0224270 A1 Jul. 16, 2020

Related U.S. Application Data

(60) Provisional application No. 62/421,625, filed on Nov. 14, 2016, provisional application No. 62/313,272, filed on Mar. 25, 2016.

(51) Int. Cl.
*C12Q 1/68* (2018.01)
*C07H 21/04* (2006.01)
*C12Q 1/6883* (2018.01)

(52) U.S. Cl.
CPC ..... *C12Q 1/6883* (2013.01); *C12Q 2600/124* (2013.01); *C12Q 2600/156* (2013.01)

(58) Field of Classification Search
None
See application file for complete search history.

(56) References Cited

PUBLICATIONS

Williams et al 2020, Candidate gene expression, coding sequence variants and muscle fiber contractile force in Warmblood horses with myofibrillar myopathy, Equine Vet J, (Year: 2020).*
Valberg et al , Equine Vet J. 2020 Commercial genetic testing for type 2 polysaccharide storage myopathy and myofibrillar myopathy does not correspond to a histopathological diagnosis. (Year: 2020).*
GenBank XM_014739030, Nov. 20, 2015. (Year: 2015).*
Williams, BMC Genomics, vol. 22, No. 438, 2021). (Year: 2021).*
Herrick, J. of Equine Veterinary Science, vol. 100, No. 103607, 2021 (Year: 2021).*
Valberg, et al (Equine Vet J. vol. 55, pp. 230-238, 2023).*
Valberg et al Commercial genetic testing for type 2 polysaccharide storage myopathy and myofibrillar myopathy does not correspond to a histopathologic diagnosis. Equine Vet J Jul. 2021; 53(4): 690-700.*
Broad Institute Horse Genome Project (https://www.broadinstitute.org/horse/horse-genome-project, 2007).*
Aurino S, et al. Candidate-gene testing for orphan limb-girdle muscular dystrophies. Acta Myologica, 2008;27:90-97.
Ferlini A, et al. The medical genetics of dystrophinopathies: Molecular genetic diagnosis and its impact on clinical practice. Neuromuscular Disorders, 2013;23:4-14.
Foroud T, et al. A mutation in myotilin causes spheroid bosy myopathy. Neurology, 2005;65(12):abstract.
Kley RA, et al. Impairment of protein degradation in myofibrillar myopathy caused by FLNC/filamin C mutations. Autophagy, 2013;9:422-423.
Mykkanen AK, et al. MCT1, MCT3 and CD147 gene polymorphisms in healthy horses and horses with myopathy. Veterinary Science, 2011;91:473-477.
Nandelstadh, P; et al. A Class III PDZ Binding Motif in the Myotilin and FATZ Families Binds Enigma Family Proteins: a Common Link for Z-Disc Myopathies. Molecular and Cellular Biology, 2009;822-834.
Selcen D, Engel AG. Mutations in myotilin cause myofibrillar myopathy. Neurology, 2004;62(8):abstract.
Thunes C. Feeding Horses with Neuromuscular Disorders. May 2015 (online) https://thehorse.com/112050/feeding-horses-with-neuromuscular-disorders/.
Wackermann K. PSSM2 beim Pferd—die Trainings-Intoleranz. Mar. 2022 (online) https://www.st-georg.de/wissen/ossm2-beim-pferd-die-trainings-intoleranz/.
Wackermann K. PSSM2 in horses (english translation). Mar. 2022 (online) https://www.st-georg.de/wissen/ossm2-beim-pferd-die-trainings-intoleranz/.
Moro LN, et al. Generation of myostatin edited horse embryos using CRISPR/Cas9 technology and somatic cell nuclear transfer. Scientific Reports, 2020;10:15587 https://doi.org/10.1038/s41598-020-72040-4.
Ablondi M, et al. Performance of Swedish Warmblood fragile foal syndrome carriers and breeding prospects. Genetics Selection Evolution, 2022;54:4.
Hames M. EquiSeq Review. EquiSeq Facebook Page, May 1, 2022. https://www.facebook.com/EquiSeq1/ posts/2697622740380203.
Szauter P. Genetic Basis of Exercise Intolerance in Arabian. Al Khamsa Annual Meeting and Convention, Oct. 13, 2019.
Equiseq. Warmblood Fragile Foal Syndrome (WFFS). Aug. 2, 2016 (online) http://equiseq.com/learning_center/health/warmblood-fragile-foal-syndrome-wffs.

* cited by examiner

*Primary Examiner* — Jeanine A Goldberg
(74) *Attorney, Agent, or Firm* — Henry D. Coleman; R. Neil Sudol

(57) ABSTRACT

This disclosure describes detecting genetically distinct kinds of inherited myopathies in horses, variously referred to as Polysaccharide Storage Myopathy type 2 (PSSM2), Myofibrillar Myopathy (MFM), or idiopathic myopathy.

28 Claims, 45 Drawing Sheets

Specification includes a Sequence Listing.

FIG. 1

38,520,183 CTACTGCCAA CACAAGTGAC TTCATGTCTA TTCCTGTTTT ACGAAAGGAC
AATCTGTACT GTGTGCTCCC ATTTCAAACA CACCAGGGGG TCATATCATC
CTTTGTTGTA AAAGAGTAAT CTGAAAAATG AACCACTATC AATTCGAAGT
CTAGCTAATT TTCATAAATC ATGTCTGTTG AACAGTCTTA TTAATTCTGA
GGATTTCTTG CTGGAGTATT AGAAGGTTAG TAGAACTAAC CACAATTGTA
CAAATACAGC CAACATAGAA TTGTTCCTTT CAACTACAAC TACTTAAGTC
TGCTTCATTT CAACCTAACA ATTGCATATT AACATTATCA TTTTGTTTTA
AATTCGAGCA GCACAATTCA GAACACGCAC GACTACAAGT TCCTACATCA
CAAGTGAGGT AAAAATTTTT TAATTTTAAA GACATATATT TTGCTATGTA
AAATGTTTTC CGTTTAAAAG TGTACTATTT CGAAAGCCCT CAAGTTTCCT
ACATAACTTT TATAAAGAAC AACGTGAATT TTCTAATGTC CAACATCATG
ATCAAAATTT TTATCTGTTA ATCATCAGAC CTATCTCGGA GGAAGTTTTT
AAAATGTTTT GGTCAAATAA GCCAGGACCA TGTTTCCATG TTACACAAGT
TTCCTATGAC AATGGAAACC CAATTCTTAT TATACAATCT TTGCACATGA
TAAGAATTGT CCATGGGGTA CTCTGCATTT TAACAGATCA GCTTCTTCAT
TAATTCGTTG CACTGTAAAA AGGAAACAAA GATGTATAAT TTGGGCCAGA
TGTTTCTAAA TTGCTACCAT TTCTACCAGT CATCAAATAT ACCACAGCTA
AATATAGCCT CTCTCCATTG TTATTACACT ATCAGATCAA ACCCACTCTA
GGGTTTTAAA TTTGATGACT AAACTATATC TGTGTGAAAG GAAGAGCAAT
GATAATTTTC CGCATGGTGA TGATTAAACT ATTTTTGCAG AAGCAGATCA
38,519,183 C
CTTCAAGGGG AGATGTGAAT GATCAGGATG CAATCCAGGA GAAGTTTTAC
CCACCTCGTT TCATTCAAGT GCCAGAAAAC ATGTCAATTG ACGAAGGAAG
ATTCTGCAGA ATGGACTTCA AAGTAAGAGA AGAGTTCAAA AGTACTGGAG
GAAAATTAAC AATGTGATAC TAAGTTTTGA AAAATGTGCT CTTCCTCTTC
ATAGCTTGCT CCACAGCTTG AGAAGCAGCA CGTACAGTGG AGAAGAACAC
CAATTCTAGA GCCAAGCTTA CCTGGATTTG GATCCTGGCT CTGCTACTTT
CCAGCTGTGT AACCTCAGAC AAGTCACTTA CCCTGTGCTT TCCTTTTCTT
TTCTATTTTT TTTTAAAGAT TGGCACCTGA ACTAACATCT GTTTGCAATC
TTTTTTTTTC TTCTTCTTCT TCTTCTTCTT CGCCCCAAAG CCCCCTAGCA
CATAGTTGTA TGTTCTAGTT GTGAGTGCCT CTGGTTGTGC TATGTGGGAC
GTCACCTCAG CACAGCCTGA CCAGCGGTGC CACGTCTGCA CTCAGGATCC
GAACCGGCAA AACCCTGGGC CGCCACAGAG CACGTGAACT TAACCGCTTG
GCCACGGGGG CAGCCCCCTA TCCTGTGCTT TTCTCATCTG CAAAACAAGA
ATAACAAATG TACCTAACTC ATAAAGTTGT TTGAGGATTA ACTGAGTAAA
TAGGCATAAG GTACTCACAA TAGTGCCTAC AACCTAATAA ATACTCTATA
TAAGTGAAGC TATCATAATA GGATTTCTAA CGCAGAATGC CTCTTTAATT
CTCCTCCAAT AAGAAATTCA ATCAACCCTC CTTTCTCTTG CCCTAGAAGA
ATTTTTCGGG CTAGAAAGGC CTACATTTTT ATTACCCTCA TTTTGGAGAA
CTTTTTCTTA GAAAATGTTT TCCCGAATTC ATTATGAATG AAAGGCAGTG
CATGGATTTA ATTGTTAAGG CTTACATAAA AACACTTAAA CTGCCATTTG 38,518,183

(SEQ ID NO:1)

FIG. 2

```
83,735,244    ACTATGGAAA ACTTGAAATT TTGTTTTCTT ACTGATAATA ATCTTAAAAA
              CATATTTTAC CAAAAACGTA TTTTTATACT AATAATTTGT AGTTAAAAGA
              TGGTTTGATT GAATAAGACA TTGGATTCCC AGGTCAGTTT CTCAGACTGG
              CGTCCCTTGA TCCCTAGAGG TTAATGAACA TATTCTTGGG TCCAAAAGTA
              TCTAATTCTT TAAAAGCTTC ATCATTCAAT TTGAGGAAGA TTGATTTAGC
              CCAGCCTCTC CCCTGCCAAC ATATTTCAGA GACCTAGGCT GGGAGACCAG
              GCCATGCAGA CGGCCTAGAG CCCTGTCTCC TGGCTCCCAG GGTGCGCCCT
              GGCCACCAGA ATGCAGAGCA CTAGGCTGTG TGGCCTGAGG TCTATGGCGG
              TTGGGGCGCT GGGTGTTGGC GGTGGGTAGG GAGGACAGCC CCAAGCCAGC
              AGAGGGCGTC GGTGCTCTGA GAAGGCCAGA GTGCTCTAAG TACCTTGCTC
              GGATGATGCC CACAGGACGC CGACGGCTGC CCTATCGACA TCAACGTCTT
              CACCACTGGC AACGGCATCT TCCGCTGCTC CTACGTGCCC ACCAAGCCCA
              TTAAACACAC CATCATCATC TCTTGGGGAG GTGTCAACGT GCCCAAGAGC
              CCCTTCCGGG TGCGTCCTCT GAACCCTGCC TGGTGCCCAC TGCCCAGGGG
              TCCCAGAGGG AGGGTGAAGC CCTATGCAGG AGATGTCGGC TGTCGCTGGG
              CCCTGGTCAC TGCTCCCCAC CTCAAGGCCC CCACGAAGGA GCTAAGATTG
              ATCCCATTAA GGCTGAGGCG CCTAGTGCTG GGGAAGAGGA TGGGCTTTGA
              GGGAGGGGCA CCATGCTGAG CATTGACCCC TTCCCACAGG TAAACGTGGG
              AGAGGGCAGT CACCCTGAGA AAGTGAAGGT GTACGGCCCT GGCGTGGAGA
              AGACGGGCCT CAAGGCCAAC GAGCCCACCT ATTTCACCGT GGACTGCAGC
83,736,244    A
              AGGCGGGGCA AGGTGCACCA GCCAGGCGGG GGAGTAGGAG ACGGGGCCTG
              GGGCGGGGTC TGGGTGGGTA GGGCTAGTAC TCCTGGCAGA GCTGTTTCCT
              GGCAGAGCTC TAGTGGGACT GCTCAGGTGG GGCAGGTTGT TGAGCCCCCA
              TCTCATGGCC TCCTGTCTGC CTACCCTCAG GCGATGTGAG CATTGGCATC
              AAGTGCGCCC CCGGCGTGGT GGGCCCCGCA GAGGCTGACA TTGACTTTGA
              CATCATCAAG AATGACAATG ACACCTTCAC AGTCAAGTAC ACACCCCCAG
              GGGCCGGCCG CTACACCATC ATGGTGCTGT TTGCCAACCA GGTACCCTGC
              CCTCAGCTTT TGATACTCAC TAGCGGCCTA CACCTCCCAA TTCTAAACCA
              GCAGCTTGAG ATGCTGTCAT CTGGGGACAA TTCCACAGCC ATTGACTGAG
              CACGTTCCTG TGTGTGGGGA GCATGCCTCA GAAGAAAAAA AAGGGGCTCT
              TTCAGAGACT GCCCTTGTCC ACCATGACGA AGCCTTTTCT CCATGCAGGA
              GATCCCTGCC AGCCCCTTCC ACATCAAGGT GGACCCATCC CATGATGCCA
              GCAAGGTCAA GGCTGAGGGC CCTGGGCTGA ACCGCACAGG TAGGTGTCTG
              GGCAGGGGCT GGGCTGGGCT GGGGTTTGCG CTAGGTGGCT GCCAGGCCCT
              CACCACTGTC TCTGGGTGGG CTCCCCAGGT GTAGAAGTTG GGAAGCCCAC
              TCACTTCACG GTGCTGACCA AGGGAGCTGG CAAGGCTAAG CTGGACGTGC
              ACTTTGCCGG GGCCGGCAAG GGTGAGGCTG TGCGGGACTT TGAGATCATC
              GACAACCACG ACTACTCCTA TACCGTCAAG TACACCGCCG TCCAGCAGGT
              GGGCTCTGCC CCCTCCCATG CCCCTGCCTG TCCTGGCTAA TGGGGGTCCT
              GGGTCTCCTT CCTCACATAG GGCCAGTTCT GGATCTTGGC CCCTTTCCTG   83,737,244

              (SEQ ID NO:2)
```

FIG. 3

```
83,737,769     CCACCCGGTA CCTGGCAGCC CCTTCACTGT GGAGGGTGTC CTGCCCCCCG
               ACCCCTCCAA GGTGAGGAGA TAGAAGCTGA TGGGAGCTGG GAGTTAGGGG
               CTTGTAGGGA AGATGGATGA GTCACAGGGG CAGAGGTCAG AGGGCCTTAT
               GTCCTGGAGT GGGCACAGCC AAGGACCCAG GGCCAGGGCG ATCCCCCACC
               CCAGGACCTC CTTTTGAGAC AGCTTAGTTA GTAAGAACCT GGCCTTGGAT
               CAGACCTGGG CTTGAATCCC AAGTCTACTA ACTGGGACAA ATTATTTAAT
               CTCTCTGCTT CCGTTTCTGC ACCTGGAATT GTTATAGGGC CTCAGTCTGT
               AGTAGCTGCT ACAGTTGAAG ATGCCTGGCT GGGTGGGGGG CCATGAAGGC
               CAAGCACGGG TGAGGCCAAG TGTAGGGAAC TCACATACCT GCTCTTCCCT
               CTAGGTTTGT GCTTATGGCC CTGGTCTCAA GGGTGGGCTG GTAGGCAGCC
               CAGCGCCGTT CTCCATCGAC ACCAAGGGGG CTGGCACCGG TGGCCTGGGG
               CTGACTGTGG AGGGCCCCTG TGAGGCCAAG ATCGAGTGCC AGGACAATGG
               TGATGGCTCA TGTGCGGTCA GCTACCTGCC CACGGAGCCG GGCGAGTACA
               CCATCAACAT CCTGTTCGCC GAAGCCCACA TCCCCGGCTC ACCCTTCAAG
               GCTACCATCC GGCCCGTGTT CGACCCGAGC AAGGTGCGGG CCAGTGGGCC
               AGGCCTGGAG CGTGGCAAGG CTGGTGAGGC AGCCACCTTC ACTGTGGACT
               GCTCGGAGGC GGGCGAGGCT GAGCTGACCA TCGAGATCCT GTCAGACGCT
               GGCGTCAAGG CCGAGGTGCT GATCCACAAC AATGCTGACG GCACCTACCA
               CATCACCTAC AGCCCCGCCT TCCCCGGCAC CTACACTATT ACCATCAAGT
               ACGGTGGGCA CCCCGTACCC AAATTCCCCA CCCGCGTCCA TGTGCAGCCC
83,738,769     A
               CTATCGACAC CAGTGGAGTC AAGGTCTCGG GGCCTGGTGT GGAGCCGCAC
               GGTGAGTGAG AGAGGAGCCA GGAGCCCGTC AGGGAGCCAG GGGAGGCAGC
               AGAAGGGACG GAAGCAAGCC TGAGTGCTTA GCAGAGCACC ATAGTCTGAA
               GGGAGGACTT GGGGACAGCC CTGGCGTCCT TAGGGCTCAG ACACCCCAGA
               GAAGCAGCCA AGGGTGCAGG CGGGGCGTGG AGCTTTGTCT CTGCTCTTGT
               GACACAATTG CATCTGCCCA TGGACATGTT TCTGGGGAGA TTCTTAACTT
               TCATTAGCTT AAGGGGTCCC TGATCTGAGA AAGCTAAGAA CCCTGCTCTA
               GGCAGTGCAG AGGGAAAGCT TTGGGGTAGG GGGTGACGAG AGCCAGGAGA
               CAGCTCAGCT CCATTCAGTA AATGAGAGTG GATCACCTGC TGGGGGCCAG
               ACCCTGGGTT AGGCATGAGG GTGGGCGAGG GACGTAAGAC CCAGACTCAC
               CCATGAGCGG CCCTCAGCCT GGTGGGGCAA CTGACGTGAA CAGAATGTCA
               CCATATGGTG AAGCGAGCAA AGGCAGGGGC TGTGGGAGAC AGGGCCTGGA
               GCTCACAGGG GTGCAGAGGG TGGCCTGGCT CACGCTAGGA AGCAGTCAGT
               GGAAAGGAAG AGCAGCCTTG GAGTCGGGGA GACGAAAAGA GGGGTGAGCA
               ACTGTGTGAA GGTTGATCCC AGCCCATGCT GAGCTCTCTT CTCCTGGGAC
               CCAGGTGTCC TGCGTGAGGT GACCACTGAG TTCACTGTGG ATGCAAGATC
               CCTAACAGCC ACAGGTGGGA ACCATGTGAC GGCTCGTGTG CTCAACCCCT
               CGGGTGCTAA GACGGACACC TACGTGACGG ACAACGGGGA TGGCACCTAC
               CGAGTGCAAT ACACAGCCTA TGAAGAGGGT GAGGGGCCGG CTGGGCGGGG
               ATGGGGGATC TGATCACAGC ATTCTCAGGG CAGGAGGGTG CTGGGGCCGC   83,739,769
```

(SEQ ID NO:3)

FIG. 4

```
27,400,222     TGTTCCAGTT TTTATCTCCA GGTTAGTTTT CTCCCATGAA CACTGGACCC
               ACACATTCAG CTCCCTTCTC ACATTTGAGT GTCTACACAG CTCTTCAAAT
               CTTATATGCC CAATTTTGGA GACCATTAGG AGAGTTGAAC ATGGACTGGG
               CATTATATAA AACAAAATTT ATTCACTTGG AAGGGTAGAG ACCTTTAATT
               GATAAAAGCA AGTTATAAAG CATGATACTA TGATTCCATT TTGGTTAAAA
               ACTCATATAG GAATATATAG TCATTGAAAA AGTATGAAAT GATTTACCTG
               AAAGTGTTAA TAGTGGCAAT CTCTGGGTGG GAGGCAATTC TTTTCTTTTT
               CTCTTCTATC TGTATTTTCT AACTTTCTTC AATGCACATA TGTGCTATTC
               TTATAATAAT AAGAGGCTAT TTTGAATTGA AAAGACCTCG AGTCTAAAAC
               TGAACTCGAT CTTTCCCGCA CCTTCTCCTC CTCCAGCCGT CCCCACCTCA
               GGAGGTGGCT CCATCCTTCC AGTGGCTCAG GCCAGAGCCT CTCCGTAGAC
               TCCCACCCTC TCTCTCTCCT AGCCCATACC CATGGCTGAC CTTTAAGGGA
               TATCTAGAAT CTGATCATTT CTCACTACTT CCACCACTAT GGGCAAAGAG
               CTGCACAGGA AATTCACGGA ATAAATACAA ATGGCCAAAG AACGTCTGAA
               ATGGGGCTCA GTCTCACTGA GTGTCAAACA CATGCAAGTT AAACTCTGAG
               GTGTCATTTC TGCCCATCAG GTGGGCAAAG ATTCGGCTGA ATGATGACTC
               TCAGTGTCGG TAAGTGTGGG GAGAAACCAG GTTTCTCACA CACAATGGAC
               AGTGTGCTGA GGAGGCCTCC TGAGAGGCGG CAGCCTAGGA AGCCTGCGGG
               TTTGGTAGTA AGAGCTGCCT CTGGCCTCTC CTGGCAGTCC CTGTGCTGGA
               CCTGGGCAAG AAGCTGAGCG TGCCCCAGGA CCTGATGATG GAAGAGCTGT
27,399,222     T
               GCTCCGCAAC AACCGGGGAT CCCTCCTCTT CCAGAAGAGG CAGCGCCGCG
               TGCAGAAATT CACCTTTGAG TTTGCAGCCA GCCAGCGGGC GGTGAGTAAG
               CCCCCACTGT GCTCACAGGG AAACTGAGGC CCAGAGAGAG CCAGTGGTTA
               GTCTAAAGCC CAACAGTGAG CCAGGGGAGG ACCTCTGGCC CCTGGGGAGT
               CCCTCAAGCT CCAGCTGGGG AAGACTGTGA TGTTCCCATC GGACTGAGCC
               CCGCCCTGCC GGGTGATCCT AGAAAAGGGT TACCTCTTTA GGCGTCTCCC
               CAGATGTGAA ACATGAAGTG GCATGGGCAG GAGGAGCTGT GGAGTGAAGG
               ACTCTGGCTC CTATAAAAAG GGCTGAAGCA TAGTCATGTG CTCTGGGCTG
               AATTTACAGC AAGCCGGATT TAGGTTAGAC TTGAGCTTGA TCTAAGGTGG
               AAAATGCAGA ATGCCTTTTT CTCTTCTTCC CACTGGAAGA AGGAAAAGGC
               CACGGCACAG TCTGCTGGTA GAGAAAGGAG GCGAGAGCTG TTCATCCTCA
               GGCTGCAAAG AGGCAGGAGG CAGTTTCAGG TACTTCTAAG GAACTCCCGC
               ACATTCCATC CAGATGCTGC TTAGTTTCTG GACTAGACAG GGAGCGGCTG
               AGAGGAGTCA TGTGGCCGAA TGATAAAGAC GACAAACACC TGCCTCCCTT
               TGTGCCCAGG ACGGTGCTAG CTAGCGGCTT TGCATCTATC ATCTCACTTA
               ATGCTCACAG AGTGAGTTAT CGTCATCACC TCCATTTTAC AGAGGAGGAA
               ACTGAGGCTC AGGGAAGTCA AGTATCTGTG CAAAATACAA TATCTGTCAA
               TATTATAATA GCAACTAAGA CGCAGAGCAT TTCTCTGTCC AGGCGCTGGG
               CACCCGGCCC CCCCATCCCC GGGGAGGTGG GCGTTAGGAT TAGGCCACGC
               CCTTTTATTT TCTTGGAGGG AGACCCTGGT CCCTTTCCCC GCTGAGCCCT   27,398,222
```

(SEQ ID NO:4)

FIG. 5

| | |
|---|---|
| 1 | ATGTTTAATT ACGAACGTCC AAAGCACTTC ATCCAATCCC AAAACCCATG |
| 51 | TGGCTCCAGA CTGCAGCCTC CTGGACCGGA AACCTCCAGC TACTCTAGCC |
| 101 | AGACCAAACA GTCTTCCATT ATCATCCAGC CCCGCCAGTG CACAGAGCAA |
| 151 | AGATTTTCTG CCTCCTCAAC AATGAGCTCT CATATCACCA TGTCCTCCTC |
| 201 | TGCTTTCCCT GCTTCTTCCC AGCAGCTTGC TGGCTCCAAT CCAGGCCAAA |
| 251 | GGGTTACAGC CACTTATAAC CAGTCCCCAG CCAGCTTCCT CAGCTCCATA |
| 301 | TTACCATCAC AGCCTGATTA CAGTAGCAGT AAAATCCCTT CCACTGTGGA |
| 351 | CTCCAACTAT CAACAACCTT CATTTGGCCA ACCTGTAAAT GCTAAGCCAT |
| 401 | CCCAAAGTGC GAATGCTAAG CCCATACCAA GGACTCCTGA CCATGAAATC |
| 451 | CAAGGATCAA AGGAAGCTCT GATTCAAGAT TTGGAGAGAA AGCTGAAGTG |
| 501 | CAAGGACAGC CTTCTTCATA ACGGAAATCA ACGGCTAACA TACGAGGAGA |
| 551 | AGATGGCTCG CAGATTGCTA GGACCACAGA ATGCAGCTGC GGTGTTTCAA |
| 601 | GCTCAAAATG ACAGTGAAGC ACAAGATTCA CAGCAGCACA ATTCAGAACA |
| 651 | CGCACGACTA CAAGTTCCTA CATCACAAGT GAG**AAGCAGA TCA<u>T</u>CTTCAA** |
| 701 | **GGGGAGATGT GAATGATCAG GATGCAATCC AGGAGAAGTT TTACCCACCT** |
| 751 | **CGTTTCATTC AAGTGCCAGA AAACATGTCA ATTGACGAAG GAAGATTCTG** |
| 801 | **CAGAATGGAC TTCAAAG**TGA GCGGACTGCC AGCTCCTGAT GTGTCATGGT |
| 851 | ATCTAAATGG AAGACCAGTT CAATCAGACG ATTTTCACAA AATGATAGTG |
| 901 | TCTGAAAAGG GTTTTCATTC ACTCATCTTT GAAGTTGTGA GAGCCTCAGA |
| 951 | TGCAGGGGCT TATGCCTGTG TTGCCAGGAA CAGAGCAGGA GAAGCCACCT |
| 1001 | TTACTGTGCA GCTGGACGTC CTGGCAAAAG AACATAGAAG AGCACCAATG |
| 1051 | TTTATCTACA AACCACAAAG CAAAAAAGTT TTTGAGGGAG AGTCCGTGAA |
| 1101 | GCTAGAATGC CAAATCTCAG CTATACCTCC ACCAAAGCTT TTCTGGAAAA |
| 1151 | GAAACAATGA AATGGTGCAT TTCAATACTG ATCGAATCAG CTTATATCAT |
| 1201 | GATAACTCTG GAAGAGTCAC CTTACTGATA AAAGATGTAA ACAAGAAAGA |
| 1251 | TGCTGGGTGG TATACTGTGT CTGCAGTTAA CGAAGCTGGA GTAACCTCAT |
| 1301 | GTAACACGAG ACTAGATGTT ACAGCCCGTC CAAACCAAAC TCTTCCAGCT |
| 1351 | CCTAAGCAGT TACGTGTTCG ACCAACTTTC AGCAAGTATT TAGCACTTAA |
| 1401 | CGGGAGAGGC TTGAATGTGA AACAAGCTTT TAATCCTGAA GGAGAGTTTC |
| 1451 | AGCGCCTGGC AGCTCAATCT GGACTCTATG AAAGTGAAGA ACTTTAA (SEQ ID NO:5) |

FIG. 6

```
ENS          ------------------------------------------------------------

XM    1      ATGGTTTTTATCCACTTTACTCTGGCCACCAGTTGGCTGAGAATATATGTGGTGGAAAGT     60

ENS          ------------------------------------------------------------

XM   61      ACTGGAAGATCACCTACCACTGAGGATCACTGGTTTGACTTGGATTTAGAAGCCAAGATG    120

ENS          ------------------------------------------------------------

XM  121      GAGGTCACAGTCTGGAAAGACCCTGGCGGAAAGCCGCCCCGTGGGAAGGAAGATTCCAGC    180

ENS          ------

XM  181      AGAATC                                                          186

ENS    1     ACGTTCACGCGCCGGTGCAACGAGCACCTCACGTGCGTGGTCAAGCGCCTGACCGACCTG     60
             ||||||||||||||||||||||||||||||||||||||||||||||||||||||||||||
XM   187     ACGTTCACGCGCCGGTGCAACGAGCACCTCACGTGCGTGGTCAAGCGCCTGACCGACCTG    246

ENS   61     CAGCGAGACCTCAGCGACGGGCTACGCCTCATCGCGCTGCTCGAGGTACTCAGCCAGAAG    120
             ||||||||||||||||||||||||||||||||||||||||||||||||||||||||||||
XM   247     CAGCGAGACCTCAGCGACGGGCTACGCCTCATCGCGCTGCTCGAGGTACTCAGCCAGAAG    306

ENS  121     CGCATGTATCGCAAGTTCCACCCGCGTCCCAACTTCCGTCAGATGAAGCTGGAGAACGTG    180
             ||||||||||||||||||||||||||||||||||||||||||||||||||||||||||||
XM   307     CGCATGTATCGCAAGTTCCACCCGCGTCCCAACTTCCGTCAGATGAAGCTGGAGAACGTG    366

ENS  181     TCCGTGGCCCTCGAGTTCCTCGAGCGCGAGCACATCAAGCTTGTGTCCATCGACAGCAAG    240
             ||||||||||||||||||||||||||||||||||||||||||||||||||||||||||||
XM   367     TCCGTGGCCCTCGAGTTCCTCGAGCGCGAGCACATCAAGCTTGTGTCCATCGACAGCAAG    426

ENS  241     GCCATCGTGGATGGGAACCTGAAGCTGATCCTGGGGCTGATCTGGACGTTGATCCTGCAC    300
             ||||||||||||||||||||||||||||||||||||||||||||||||||||||||||||
XM   427     GCCATCGTGGATGGGAACCTGAAGCTGATCCTGGGGCTGATCTGGACGTTGATCCTGCAC    486

ENS  301     TACTCCATCTCCATGCCCATGTGGGAAGATGAGGATGATGAAGATGCCCGCAAACAGACG    360
             ||||||||||||||||||||||||||||||||||||||||||||||||||||||||||||
XM   487     TACTCCATCTCCATGCCCATGTGGGAAGATGAGGATGATGAAGATGCCCGCAAACAGACG    546

ENS  361     CCCAAGCAGCGTCTGCTTGGCTGGATCCAGAACAAGGTGCCCCAGCTGCCCATCACTAAC    420
             ||||||||||||||||||||||||||||||||||||||||||||||||||||||||||||
XM   547     CCCAAGCAGCGTCTGCTTGGCTGGATCCAGAACAAGGTGCCCCAGCTGCCCATCACTAAC    606

ENS  421     TTCAACCGCGACTGGCAGGATGGCAAAGCTCTGGGTGCCCTGGTGGACAACTGTGCCCCT    480
             ||||||||||||||||||||||||||||||||||||||||||||||||||||||||||||
XM   607     TTCAACCGCGACTGGCAGGATGGCAAAGCTCTGGGTGCCCTGGTGGACAACTGTGCCCCT    666

ENS  481     GGCCTCTGCCCTGACTGGGAGGCCTGGGATCCCAACCAGCCTGTGGAGAACGCCCGGGAG    540
             ||||||||||||||||||||||||||||||||||||||||||||||||||||||||||||
XM   667     GGCCTCTGCCCTGACTGGGAGGCCTGGGATCCCAACCAGCCTGTGGAGAACGCCCGGGAG    726

ENS  541     GCCATGCAGCAGGCGGACGACTGGCTCGGGGTGCCCCAGGTGATTGCCCCCGAGGAGATT    600
             ||||||||||||||||||||||||||||||||||||||||||||||||||||||||||||
XM   727     GCCATGCAGCAGGCGGACGACTGGCTCGGGGTGCCCCAGGTGATTGCCCCCGAGGAGATT    786

ENS  601     GTGGACCCCAATGTAGATGAGCATTCTGTCATGACCTACCTGTCCCAGTTCCCCAAGGCC    660
             ||||||||||||||||||||||||||||||||||||||||||||||||||||||||||||
```

FIG. 6 CONT'D

```
XM  787    GTGGACCCCAATGTAGATGAGCATTCTGTCATGACCTACCTGTCCCAGTTCCCCAAGGCC   846

ENS 661    AAGCTCAAACCTGGTGCCCCTGTTCGCTCCAAGCAGCTGAACCCCAAGAAGGCCATTGCC   720
||||||||||||||||||||||||||||||||||||||||||||||||||||||||||||||||||||
XM  847    AAGCTCAAACCTGGTGCCCCTGTTCGCTCCAAGCAGCTGAACCCCAAGAAGGCCATTGCC   906

ENS 721    TATGGGCCTGGCATTGAGCCCCAGGGCAACACCGTGCTGCAGCCTGCCCACTTCACCGTG   780
           ||||||||||||||||||||||||||||||||||||||||||||||||||||||||||||
XM  907    TATGGGCCTGGCATTGAGCCCCAGGGCAACACCGTGCTGCAGCCTGCCCACTTCACCGTG   966

ENS 781    CAGACCGTGGATGCCGGTGTGGGCGAGGTGCTGGTCTACATTGAGGATCCTGAGGGCCAC   840
           ||||||||||||||||||||||||||||||||||||||||||||||||||||||||||||
XM  967    CAGACCGTGGATGCCGGTGTGGGCGAGGTGCTGGTCTACATTGAGGATCCTGAGGGCCAC   1026

ENS 841    ACCGAGGAGGCCAAGGTGGTTCCCAACAATGACAAGGACCGCACCTATGCTGTCTCCTAC   900
           ||||||||||||||||||||||||||||||||||||||||||||||||||||||||||||
XM  1027   ACCGAGGAGGCCAAGGTGGTTCCCAACAATGACAAGGACCGCACCTATGCTGTCTCCTAC   1086

ENS 901    GTGCCTAAGGTTGCTGGGTTGCACAAGGTGACTGTGCTCTTTGCTGGCCAGAACATCGAA   960
           ||||||||||||||||||||||||||||||||||||||||||||||||||||||||||||
XM  1087   GTGCCTAAGGTTGCTGGGTTGCACAAGGTGACTGTGCTCTTTGCTGGCCAGAACATCGAA   1146

ENS 961    CGCAGCCCCTTTGAGGTGAATGTGGGCATGGCCCTTGGGGATGCCAACAAGGTGTCAGCC   1020
           ||||||||||||||||||||||||||||||||||||||||||||||||||||||||||||
XM  1147   CGCAGCCCCTTTGAGGTGAATGTGGGCATGGCCCTTGGGGATGCCAACAAGGTGTCAGCC   1206

ENS 1021   CGTGGCCCTGGCCTGGAGCCTGTGGGCAATGTGGCCAACAAACCTACCTACTTTGACATC   1080
           ||||||||||||||||||||||||||||||||||||||||||||||||||||||||||||
XM  1207   CGTGGCCCTGGCCTGGAGCCTGTGGGCAATGTGGCCAACAAACCTACCTACTTTGACATC   1266

ENS 1081   TACACTGCAGGGGCCGGCACTGGTGATGTTGCCGTGGTGATCGTGGACCCGCAGGGCCGG   1140
           ||||||||||||||||||||||||||||||||||||||||||||||||||||||||||||
XM  1267   TACACTGCAGGGGCCGGCACTGGTGATGTTGCCGTGGTGATCGTGGACCCGCAGGGCCGG   1326

ENS 1141   CGGGACACAGTGGAGGTGGCCCTGGAGGACAAGGGCGACAGCACGTTCCGCTGCACATAC   1200
           ||||||||||||||||||||||||||||||||||||||||||||||||||||||||||||
XM  1327   CGGGACACAGTGGAGGTGGCCCTGGAGGACAAGGGCGACAGCACGTTCCGCTGCACATAC   1386

ENS 1201   AGGCCTGTGATGGAGGGGCCCCACACAGTGCATGTGGCCTTCGCTGGTGCCCCCATCACC   1260
           ||||||||||||||||||||||||||||||||||||||||||||||||||||||||||||
XM  1387   AGGCCTGTGATGGAGGGGCCCCACACAGTGCATGTGGCCTTCGCTGGTGCCCCCATCACC   1446

ENS 1261   CGCAGTCCTTTCCCCGTCCATGTGGCAGAAG                                1291
           |||||||||||||||||||||||||||||||
XM  1447   CGCAGTCCTTTCCCCGTCCATGTGGCAGAAG                                1477

ENS        ------------------------------------------------------------

XM  1478   AGCCCTTGCCACCGCTCGCCCCTTCCGTGCCCATCGTCCACCAGGCCAAGAGAGTGGTGC   1537

ENS        ---

XM  1538   CAC                                                            1540

ENS 1292   CCTGTAACCCCAATGCCTGCCGCGCCTCTGGGCGGGGCCTGCAGCCCAAGGGTGTGCGGG   1351
           ||||||||||||||||||||||||||||||||||||||||||||||||||||||||||||
XM  1541   CCTGTAACCCCAATGCCTGCCGCGCCTCTGGGCGGGGCCTGCAGCCCAAGGGTGTGCGGG   1600

ENS 1352   TGAAAGAGGTGGCTGACTTCAAGGTGTTCACCAAGGGCGCTGGCAGCGGAGAGCTCAAGG   1411
           ||||||||||||||||||||||||||||||||||||||||||||||||||||||||||||
```

FIG. 6 CONT'D

```
XM  1601  TGAAAGAGGTGGCTGACTTCAAGGTGTTCACCAAGGGCGCTGGCAGCGGAGAGCTCAAGG  1660

ENS 1412  TCACAGTCAAGGGGCCAAAGGGCACAGAGGAGCTGGTGAAGGTGCGAGAGGCTGGGGACG  1471
          ||||||||||||||||||||||||||||||||||||||||||||||||||||||||||||
XM  1661  TCACAGTCAAGGGGCCAAAGGGCACAGAGGAGCTGGTGAAGGTGCGAGAGGCTGGGGACG  1720

ENS 1472  GTGTGTTCGAGTGTGAGTACTACCCTGTGGTGCCTGGGAAGTATGTGGTGACCATCACGT  1531
          ||||||||||||||||||||||||||||||||||||||||||||||||||||||||||||
XM  1721  GTGTGTTCGAGTGTGAGTACTACCCTGTGGTGCCTGGGAAGTATGTGGTGACCATCACGT  1780

ENS 1532  GGGGCGGCTATGCCATCCCCCGCAGTCCCTTTGAGGTACAGGTGAGCCCAGAGGCAGGAG  1591
          ||||||||||||||||||||||||||||||||||||||||||||||||||||||||||||
XM  1781  GGGGCGGCTATGCCATCCCCCGCAGTCCCTTTGAGGTACAGGTGAGCCCAGAGGCAGGAG  1840

ENS 1592  CGCAGAAGGTACGGGCCTGGGGGCCTGGTTTGGAAACTGGCCAGGTGGGCAAGTCAGCTG  1651
          ||||||||||||||||||||||||||||||||||||||||||||||||||||||||||||
XM  1841  CGCAGAAGGTACGGGCCTGGGGGCCTGGTTTGGAAACTGGCCAGGTGGGCAAGTCAGCTG  1900

ENS 1652  ACTTTGTGGTGGAGGCCATTGGCACGGAGGTGGGGACACTGGGCTTCTCCATTGAGGGGC  1711
          ||||||||||||||||||||||||||||||||||||||||||||||||||||||||||||
XM  1901  ACTTTGTGGTGGAGGCCATTGGCACGGAGGTGGGGACACTGGGCTTCTCCATTGAGGGGC  1960

ENS 1712  CTTCACAGGCCAAGATCGAGTGTGATGACAAGGGGGATGGCTCCTGCGATGTACGGTACT  1771
          ||||||||||||||||||||||||||||||||||||||||||||||||||||||||||||
XM  1961  CTTCACAGGCCAAGATCGAGTGTGATGACAAGGGGGATGGCTCCTGCGATGTACGGTACT  2020

ENS 1772  GGCCCACTGAGCCCGGGGAGTACGCCGTGCATGTCATCTGCGATGATGAGGACATCCGAG  1831
          ||||||||||||||||||||||||||||||||||||||||||||||||||||||||||||
XM  2021  GGCCCACTGAGCCCGGGGAGTACGCCGTGCATGTCATCTGCGATGATGAGGACATCCGAG  2080

ENS 1832  ACTCGCCCTTCATTGCCCACATCCAGCCAGCCCCACCTGACTGCTTCCCGGACAAGGTGA  1891
          ||||||||||||||||||||||||||||||||||||||||||||||||||||||||||||
XM  2081  ACTCGCCCTTCATTGCCCACATCCAGCCAGCCCCACCTGACTGCTTCCCGGACAAGGTGA  2140

ENS 1892  AGGCCTTTGGGCCTGGCCTGGAGCCCACTGGCTGCATCGTGGACAAGCCTGCGGAGTTCA  1951
          ||||||||||||||||||||||||||||||||||||||||||||||||||||||||||||
XM  2141  AGGCCTTTGGGCCTGGCCTGGAGCCCACTGGCTGCATCGTGGACAAGCCTGCGGAGTTCA  2200

ENS 1952  CCATTGATGCCTCTGCAGCTGGCAAGGGAGACCTGAAGCTCTATGCCCAGGACGCCGACG  2011
          ||||||||||||||||||||||||||||||||||||||||||||||||||||||||||||
XM  2201  CCATTGATGCCTCTGCAGCTGGCAAGGGAGACCTGAAGCTCTATGCCCAGGACGCCGACG  2260

ENS 2012  GCTGCCCTATCGACATCAACGTCTTCACCACTGGCAACGGCATCTTCCGCTGCTCCTACG  2071
          ||||||||||||||||||||||||||||||||||||||||||||||||||||||||||||
XM  2261  GCTGCCCTATCGACATCAACGTCTTCACCACTGGCAACGGCATCTTCCGCTGCTCCTACG  2320

ENS 2072  TGCCCACCAAGCCCATTAAACACACCATCATCATCTCTTGGGGAGGTGTCAACGTGCCCA  2131
          ||||||||||||||||||||||||||||||||||||||||||||||||||||||||||||
XM  2321  TGCCCACCAAGCCCATTAAACACACCATCATCATCTCTTGGGGAGGTGTCAACGTGCCCA  2380

ENS 2132  AGAGCCCCTTCCGGGTAAACGTGGGAGAGGGCAGTCACCCTGAGAAAGTGAAGGTGTACG  2191
          ||||||||||||||||||||||||||||||||||||||||||||||||||||||||||||
XM  2381  AGAGCCCCTTCCGGGTAAACGTGGGAGAGGGCAGTCACCCTGAGAAAGTGAAGGTGTACG  2440

ENS 2192  GCCCTGGCGTGGAGAAGACGGGCCTCAAGGCCAACGAGCCCACCTATTTCACCGTGGACT  2251
          ||||||||||||||||||||||||||||||||||||||||||||||||||||||||||||
XM  2441  GCCCTGGCGTGGAGAAGACGGGCCTCAAGGCCAACGAGCCCACCTATTTCACCGTGGACT  2500

ENS 2252  GCAGCGAGGCGGGGCAAGGCGATGTGAGCATTGGCATCAAGTGCGCCCCCGGCGTGGTGG  2311
          ||||||||||||||||||||||||||||||||||||||||||||||||||||||||||||
XM  2501  GCAGCGAGGCGGGGCAAGGCGATGTGAGCATTGGCATCAAGTGCGCCCCCGGCGTGGTGG  2560
```

FIG. 6 CONT'D

```
ENS 2312    GCCCCGCAGAGGCTGACATTGACTTTGACATCATCAAGAATGACAATGACACCTTCACAG   2371
            ||||||||||||||||||||||||||||||||||||||||||||||||||||||||||||
XM  2561    GCCCCGCAGAGGCTGACATTGACTTTGACATCATCAAGAATGACAATGACACCTTCACAG   2620

ENS 2372    TCAAGTACACACCCCCAGGGGCCGGCCGCTACACCATCATGGTGCTGTTTGCCAACCAGG   2431
            ||||||||||||||||||||||||||||||||||||||||||||||||||||||||||||
XM  2621    TCAAGTACACACCCCCAGGGGCCGGCCGCTACACCATCATGGTGCTGTTTGCCAACCAGG   2680

ENS 2432    AGATCCCTGCCAGCCCCTTCCACATCAAGGTGGACCCATCCCATGATGCCAGCAAGGTCA   2491
            ||||||||||||||||||||||||||||||||||||||||||||||||||||||||||||
XM  2681    AGATCCCTGCCAGCCCCTTCCACATCAAGGTGGACCCATCCCATGATGCCAGCAAGGTCA   2740

ENS 2492    AGGCTGAGGGCCCTGGGCTGAACCGCACAGGTGTAGAAGTTGGGAAGCCCACTCACTTCA   2551
            ||||||||||||||||||||||||||||||||||||||||||||||||||||||||||||
XM  2741    AGGCTGAGGGCCCTGGGCTGAACCGCACAGGTGTAGAAGTTGGGAAGCCCACTCACTTCA   2800

ENS 2552    CGGTGCTGACCAAGGGAGCTGGCAAGGCTAAGCTGGACGTGCACTTTGCCGGGGCCGGCA   2611
            ||||||||||||||||||||||||||||||||||||||||||||||||||||||||||||
XM  2801    CGGTGCTGACCAAGGGAGCTGGCAAGGCTAAGCTGGACGTGCACTTTGCCGGGGCCGGCA   2860

ENS 2612    AGGGTGAGGCTGTGCGGGACTTTGAGATCATCGACAACCACGACTACTCCTATACCGTCA   2671
            ||||||||||||||||||||||||||||||||||||||||||||||||||||||||||||
XM  2861    AGGGTGAGGCTGTGCGGGACTTTGAGATCATCGACAACCACGACTACTCCTATACCGTCA   2920

ENS 2672    AGTACACCGCCGTCCAGCAGGGCAACATGGCAGTGACAGTGACCTATGGTGGGGACCCCG   2731
            ||||||||||||||||||||||||||||||||||||||||||||||||||||||||||||
XM  2921    AGTACACCGCCGTCCAGCAGGGCAACATGGCAGTGACAGTGACCTATGGTGGGGACCCCG   2980

ENS 2732    TCCCCAAGAGTCCCTTTGTGGTGAATGTGGCACCTCCGCTGGACCTCAGCAAAGTCAAAG   2791
            ||||||||||||||||||||||||||||||||||||||||||||||||||||||||||||
XM  2981    TCCCCAAGAGTCCCTTTGTGGTGAATGTGGCACCTCCGCTGGACCTCAGCAAAGTCAAAG   3040

ENS 2792    TTCAAGGCCTCAACAGTAAGGTGGCTGTGGGGCAAGAACAGGCATTCTCTGTGAACACAC   2851
            ||||||||||||||||||||||||||||||||||||||||||||||||||||||||||||
XM  3041    TTCAAGGCCTCAACAGTAAGGTGGCTGTGGGGCAAGAACAGGCATTCTCTGTGAACACAC   3100

ENS 2852    GAGGGGCTGGTGGTCAGGGCCAGCTGGATGTGCGGATGACCTCACCCTCCCGACGACCGA   2911
            ||||||||||||||||||||||||||||||||||||||||||||||||||||||||||||
XM  3101    GAGGGGCTGGTGGTCAGGGCCAGCTGGATGTGCGGATGACCTCACCCTCCCGACGACCGA   3160

ENS 2912    TCCCCTGCAAGCTGGAGCCTGGGGGCGGAGCTGAAGCCCAGGCTGTGCGCTACATGCCTC   2971
            ||||||||||||||||||||||||||||||||||||||||||||||||||||||||||||
XM  3161    TCCCCTGCAAGCTGGAGCCTGGGGGCGGAGCTGAAGCCCAGGCTGTGCGCTACATGCCTC   3220

ENS 2972    CTGAGGAGGGTCCCTACAAGGTGGACATTACCTACGACGGCCACCCGGTACCTGGCAGCC   3031
            ||||||||||||||||||||||||||||||||||||||||||||||||||||||||||||
XM  3221    CTGAGGAGGGTCCCTACAAGGTGGACATTACCTACGACGGCCACCCGGTACCTGGCAGCC   3280

ENS 3032    CCTTCACTGTGGAGGGTGTCCTGCCCCCCGACCCCTCCAAGGTTTGTGCTTATGGCCCTG   3091
            ||||||||||||||||||||||||||||||||||||||||||||||||||||||||||||
XM  3281    CCTTCACTGTGGAGGGTGTCCTGCCCCCCGACCCCTCCAAGGTTTGTGCTTATGGCCCTG   3340

ENS 3092    GTCTCAAGGGTGGGCTGGTAGGCAGCCCAGCGCCGTTCTCCATCGACACCAAGGGGGCTG   3151
            ||||||||||||||||||||||||||||||||||||||||||||||||||||||||||||
XM  3341    GTCTCAAGGGTGGGCTGGTAGGCAGCCCAGCGCCGTTCTCCATCGACACCAAGGGGGCTG   3400

ENS 3152    GCACCGGTGGCCTGGGGCTGACTGTGGAGGGCCCCTGTGAGGCCAAGATCGAGTGCCAGG   3211
            ||||||||||||||||||||||||||||||||||||||||||||||||||||||||||||
XM  3401    GCACCGGTGGCCTGGGGCTGACTGTGGAGGGCCCCTGTGAGGCCAAGATCGAGTGCCAGG   3460
```

FIG. 6 CONT'D

```
ENS 3212   ACAATGGTGATGGCTCATGTGCGGTCAGCTACCTGCCCACGGAGCCGGGCGAGTACACCA   3271
           ||||||||||||||||||||||||||||||||||||||||||||||||||||||||||||
XM  3461   ACAATGGTGATGGCTCATGTGCGGTCAGCTACCTGCCCACGGAGCCGGGCGAGTACACCA   3520

ENS 3272   TCAACATCCTGTTCGCCGAAGCCCACATCCCCGGCTCACCCTTCAAGGCTACCATCCGGC   3331
           ||||||||||||||||||||||||||||||||||||||||||||||||||||||||||||
XM  3521   TCAACATCCTGTTCGCCGAAGCCCACATCCCCGGCTCACCCTTCAAGGCTACCATCCGGC   3580

ENS 3332   CCGTGTTCGACCCGAGCAAGGTGCGGGCCAGTGGGCCAGGCCTGGAGCGTGGCAAGGCTG   3391
           ||||||||||||||||||||||||||||||||||||||||||||||||||||||||||||
XM  3581   CCGTGTTCGACCCGAGCAAGGTGCGGGCCAGTGGGCCAGGCCTGGAGCGTGGCAAGGCTG   3640

ENS 3392   GTGAGGCAGCCACCTTCACTGTGGACTGCTCGGAGGCGGGCGAGGCTGAGCTGACCATCG   3451
           ||||||||||||||||||||||||||||||||||||||||||||||||||||||||||||
XM  3641   GTGAGGCAGCCACCTTCACTGTGGACTGCTCGGAGGCGGGCGAGGCTGAGCTGACCATCG   3700

ENS 3452   AGATCCTGTCAGACGCTGGCGTCAAGGCCGAGGTGCTGATCCACAACAATGCTGACGGCA   3511
           ||||||||||||||||||||||||||||||||||||||||||||||||||||||||||||
XM  3701   AGATCCTGTCAGACGCTGGCGTCAAGGCCGAGGTGCTGATCCACAACAATGCTGACGGCA   3760

ENS 3512   CCTACCACATCACCTACAGCCCCGCCTTCCCCGGCACCTACACTATTACCATCAAGTACG   3571
           ||||||||||||||||||||||||||||||||||||||||||||||||||||||||||||
XM  3761   CCTACCACATCACCTACAGCCCCGCCTTCCCCGGCACCTACACTATTACCATCAAGTACG   3820

ENS 3572   GTGGGCACCCCGTACCCAAATTCCCCACCCGCGTCCATGTGCAGCCCGCTATCGACACCA   3631
           ||||||||||||||||||||||||||||||||||||||||||||||||||||||||||||
XM  3821   GTGGGCACCCCGTACCCAAATTCCCCACCCGCGTCCATGTGCAGCCCGCTATCGACACCA   3880

ENS 3632   GTGGAGTCAAGGTCTCGGGGCCTGGTGTGGAGCCGCACGGTGTCCTGCGTGAGGTGACCA   3691
           ||||||||||||||||||||||||||||||||||||||||||||||||||||||||||||
XM  3881   GTGGAGTCAAGGTCTCGGGGCCTGGTGTGGAGCCGCACGGTGTCCTGCGTGAGGTGACCA   3940

ENS 3692   CTGAGTTCACTGTGGATGCAAGATCCCTAACAGCCACAGGTGGGAACCATGTGACGGCTC   3751
           ||||||||||||||||||||||||||||||||||||||||||||||||||||||||||||
XM  3941   CTGAGTTCACTGTGGATGCAAGATCCCTAACAGCCACAGGTGGGAACCATGTGACGGCTC   4000

ENS 3752   GTGTGCTCAACCCCTCGGGTGCTAAGACGGACACCTACGTGACGGACAACGGGGATGGCA   3811
           ||||||||||||||||||||||||||||||||||||||||||||||||||||||||||||
XM  4001   GTGTGCTCAACCCCTCGGGTGCTAAGACGGACACCTACGTGACGGACAACGGGGATGGCA   4060

ENS 3812   CCTACCGAGTGCAATACACAGCCTATGAAGAGGGCGTACATTTGGTGGAGGTGCTGTATG   3871
           ||||||||||||||||||||||||||||||||||||||||||||||||||||||||||||
XM  4061   CCTACCGAGTGCAATACACAGCCTATGAAGAGGGCGTACATTTGGTGGAGGTGCTGTATG   4120

ENS 3872   ATGACGTAGCTGTGCCCAAGAGTCCCTTCCGAGTGGGTGTGACCGAGGGCTGTGACCCCA   3931
           ||||||||||||||||||||||||||||||||||||||||||||||||||||||||||||
XM  4121   ATGACGTAGCTGTGCCCAAGAGTCCCTTCCGAGTGGGTGTGACCGAGGGCTGTGACCCCA   4180

ENS 3932   CGCGTGTTCGGGCCTATGGACCAGGCCTGGAGGGTGGCTTGGTCAACAAGGCCAACCGCT   3991
           ||||||||||||||||||||||||||||||||||||||||||||||||||||||||||||
XM  4181   CGCGTGTTCGGGCCTATGGACCAGGCCTGGAGGGTGGCTTGGTCAACAAGGCCAACCGCT   4240

ENS 3992   TCACTGTGGAGACCAGGGGAGCAGGCACTGGGGGCCTAGGCCTAGCCATCGAGGGCCCCT   4051
           ||||||||||||||||||||||||||||||||||||||||||||||||||||||||||||
XM  4241   TCACTGTGGAGACCAGGGGAGCAGGCACTGGGGGCCTAGGCCTAGCCATCGAGGGCCCCT   4300

ENS 4052   CGGAAGCCAAGATGTCCTGCAAAGACAACAAGGATGGCAGCTGCACCGTAGAGTACATCC   4111
           ||||||||||||||||||||||||||||||||||||||||||||||||||||||||||||
XM  4301   CGGAAGCCAAGATGTCCTGCAAAGACAACAAGGATGGCAGCTGCACCGTAGAGTACATCC   4360

ENS 4112   CCTTCACCCCTGGAGACTATGACGTCAATATCACCTTTGGGGGGCGGCCCATCCCAGGGA   4171
```

FIG. 6 CONT'D

```
              ||||||||||||||||||||||||||||||||||||||||||||||||||||||||||||
XM  4361      CCTTCACCCCTGGAGACTATGACGTCAATATCACCTTTGGGGGGCGGCCCATCCCAGGGA  4420

ENS 4172      GCCCGTTCCGGGTGCCAGTGAAGGATGTGGTGGACCCCGGGAAAGTGAAATGCTCAGGAC  4231
              ||||||||||||||||||||||||||||||||||||||||||||||||||||||||||||
XM  4421      GCCCGTTCCGGGTGCCAGTGAAGGATGTGGTGGACCCCGGGAAAGTGAAATGCTCAGGAC  4480

ENS 4232      CAGGGCTGGGGGCCGGTGTCAGGGCCCGGGTACCCCAGACCTTCACGGTGGACTGCAGCC  4291
              ||||||||||||||||||||||||||||||||||||||||||||||||||||||||||||
XM  4481      CAGGGCTGGGGGCCGGTGTCAGGGCCCGGGTACCCCAGACCTTCACGGTGGACTGCAGCC  4540

ENS 4292      AGGCTGGCCGGGCCCCCCTGCAGGTGGCTGTGCTGGGCCCCACAGGTGTGGCTGAGCCTG  4351
              ||||||||||||||||||||||||||||||||||||||||||||||||||||||||||||
XM  4541      AGGCTGGCCGGGCCCCCCTGCAGGTGGCTGTGCTGGGCCCCACAGGTGTGGCTGAGCCTG  4600

ENS 4352      TGGAGATACGTGACAATGGAGATGGCACCCATGCTGTCCACTACACCCCGGCCACTGATG  4411
              ||||||||||||||||||||||||||||||||||||||||||||||||||||||||||||
XM  4601      TGGAGATACGTGACAATGGAGATGGCACCCATGCTGTCCACTACACCCCGGCCACTGATG  4660

ENS 4412      GTCCATACACGGTAGCCGTCAAGTATGCCGACCAGGAAGTGCCACGCAGCCCCTTCAAGA  4471
              ||||||||||||||||||||||||||||||||||||||||||||||||||||||||||||
XM  4661      GTCCATACACGGTAGCCGTCAAGTATGCCGACCAGGAAGTGCCACGCAGCCCCTTCAAGA  4720

ENS 4472      TCAAGGTGCTTCCAGCCCATGATGCCAGCAAGGTGCGGGCCAGTGGCCCTGGCCTCAACG  4531
              ||||||||||||||||||||||||||||||||||||||||||||||||||||||||||||
XM  4721      TCAAGGTGCTTCCAGCCCATGATGCCAGCAAGGTGCGGGCCAGTGGCCCTGGCCTCAACG  4780

ENS 4532      CCGCTGGCATCCCTGCCAGTCTGCCTGTGGAGTTCACCATCGATGCCCGGGATGCTGGTG  4591
              ||||||||||||||||||||||||||||||||||||||||||||||||||||||||||||
XM  4781      CCGCTGGCATCCCTGCCAGTCTGCCTGTGGAGTTCACCATCGATGCCCGGGATGCTGGTG  4840

ENS 4592      AGGGCTTGCTTACCGTCCAGATCCTGGACCCCGAGGGTAAGCCCAAGAAGGCCAACATCC  4651
              ||||||||||||||||||||||||||||||||||||||||||||||||||||||||||||
XM  4841      AGGGCTTGCTTACCGTCCAGATCCTGGACCCCGAGGGTAAGCCCAAGAAGGCCAACATCC  4900

ENS 4652      GAGACAATGGGGATGGCACATACACCGTGTCCTACCTGCCAGACATGAGTGGCCGGTACA  4711
              ||||||||||||||||||||||||||||||||||||||||||||||||||||||||||||
XM  4901      GAGACAATGGGGATGGCACATACACCGTGTCCTACCTGCCAGACATGAGTGGCCGGTACA  4960

ENS 4712      CCATCACCATCAAGTACGGCGGTGACGAGATCCCCTACTCACCCTTCCGCATCCATGCCC  4771
              ||||||||||||||||||||||||||||||||||||||||||||||||||||||||||||
XM  4961      CCATCACCATCAAGTACGGCGGTGACGAGATCCCCTACTCACCCTTCCGCATCCATGCCC  5020

ENS 4772      TGCCCACTGGGGACGCCAGCAAGTGCCTCGTCACAGTGTCCATTGGAGGCCATGGCCTGG  4831
              ||||||||||||||||||||||||||||||||||||||||||||||||||||||||||||
XM  5021      TGCCCACTGGGGACGCCAGCAAGTGCCTCGTCACAGTGTCCATTGGAGGCCATGGCCTGG  5080

ENS 4832      GTGCCTGCCTAGGCCCCCGCATCCAGATCGGGGAGGAGACGGTGATCACAGTGGACGCCA  4891
              ||||||||||||||||||||||||||||||||||||||||||||||||||||||||||||
XM  5081      GTGCCTGCCTAGGCCCCCGCATCCAGATCGGGGAGGAGACGGTGATCACAGTGGACGCCA  5140

ENS 4892      AGGCAGCAGGCAAGGGGAAGGTAACATGCACAGTGTCCACGCCGGATGGGGCAGAGCTCG  4951
              ||||||||||||||||||||||||||||||||||||||||||||||||||||||||||||
XM  5141      AGGCAGCAGGCAAGGGGAAGGTAACATGCACAGTGTCCACGCCGGATGGGGCAGAGCTCG  5200

ENS 4952      ACGTGGACGTGGTTGAGAACCATGACGGTACCTTTGACATCTACTACACAGCGCCCGAGC  5011
              ||||||||||||||||||||||||||||||||||||||||||||||||||||||||||||
XM  5201      ACGTGGACGTGGTTGAGAACCATGACGGTACCTTTGACATCTACTACACAGCGCCCGAGC  5260

ENS 5012      CGGGCAAGTACGTCATCACCATCCGCTTTGGAGGCGAGCACATCCCCAACAGTCCCTTCC  5071
              ||||||||||||||||||||||||||||||||||||||||||||||||||||||||||||
```

FIG. 6 CONT'D

```
XM  5261   CGGGCAAGTACGTCATCACCATCCGCTTTGGAGGCGAGCACATCCCCAACAGTCCCTTCC  5320

ENS 5072   ATGTGCTGGCGTGTGACCCCATGCCCCACGTGGAGGAGCCCTCTGACGTGTTGCAGCTGC  5131
           ||||||||||||||||||||||||||||||||||||||||||||||||||||||||||||
XM  5321   ATGTGCTGGCGTGTGACCCCATGCCCCACGTGGAGGAGCCCTCTGACGTGTTGCAGCTGC  5380

ENS 5132   ACCGGCCCAGCGCCTACCCCACACACTGGGCCACAGAGGAGCCAGTGGTGCCTGTGGAGC  5191
           ||||||||||||||||||||||||||||||||||||||||||||||||||||||||||||
XM  5381   ACCGGCCCAGCGCCTACCCCACACACTGGGCCACAGAGGAGCCAGTGGTGCCTGTGGAGC  5440

ENS 5192   CAATGGAGTCTATGTTGAGGCCCCTTCAACCTGGTCATCCCCTTCACCGTGCAGAAAGGGG  5251
           ||||||||||||||||||||||||||||||||||||||||||||||||||||||||||||
XM  5441   CAATGGAGTCTATGTTGAGGCCCCTTCAACCTGGTCATCCCCTTCACCGTGCAGAAAGGGG  5500

ENS 5252   AGCTCACAGGGGAGGTACGGATGCCCTCTGGGAAAACTGCCCGGCCCAATATCACCGACA  5311
           ||||||||||||||||||||||||||||||||||||||||||||||||||||||||||||
XM  5501   AGCTCACAGGGGAGGTACGGATGCCCTCTGGGAAAACTGCCCGGCCCAATATCACCGACA  5560

ENS 5312   ACAAGGATGGCACCATCACAGTGAGGTACGCGCCCACTGAGAAAGGCCTGCACCAGATGG  5371
           ||||||||||||||||||||||||||||||||||||||||||||||||||||||||||||
XM  5561   ACAAGGATGGCACCATCACAGTGAGGTACGCGCCCACTGAGAAAGGCCTGCACCAGATGG  5620

ENS 5372   GGATCAAGTATGATGGCAACCACATCCCTGGTGA-CCCCCTGCAGTTCTATGTGGATGCC  5430
           ||||||||||||||||||||||||||||||| || |||||||||||||||||||||||||
XM  5621   GGATCAAGTATGATGGCAACCACATCCCTGG-GAGCCCCCTGCAGTTCTATGTGGATGCC  5679

ENS 5431   ATCAACAGCCGCCATGTCAGTGCCTACGGGCCAGGCCTGAGCCATGGCATGGTCAACAAG  5490
           ||||||||||||||||||||||||||||||||||||||||||||||||||||||||||||
XM  5680   ATCAACAGCCGCCATGTCAGTGCCTACGGGCCAGGCCTGAGCCATGGCATGGTCAACAAG  5739

ENS 5491   CCGGCCACCTTCACCATTGTCACCAAGGATGCTGGGGAAGGGGGTCTGTCACTGGCCGTG  5550
           ||||||||||||||||||||||||||||||||||||||||||||||||||||||||||||
XM  5740   CCGGCCACCTTCACCATTGTCACCAAGGATGCTGGGGAAGGGGGTCTGTCACTGGCCGTG  5799

ENS 5551   GAGGGCCCGTCCAAAGCAGAGATCACCTGCAAGGACAACAAGGATGGCACCTGCACGGTG  5610
           ||||||||||||||||||||||||||||||||||||||||||||||||||||||||||||
XM  5800   GAGGGCCCGTCCAAAGCAGAGATCACCTGCAAGGACAACAAGGATGGCACCTGCACGGTG  5859

ENS 5611   TCCTACCTACCCACAGCGCCTGGAGACTACAGCATCATCGTGCGCTTTGATGACAAGCAC  5670
           ||||||||||||||||||||||||||||||||||||||||||||||||||||||||||||
XM  5860   TCCTACCTACCCACAGCGCCTGGAGACTACAGCATCATCGTGCGCTTTGATGACAAGCAC  5919

ENS 5671   ATCCCGGGGAGCCCCTTCACAGCCAAGATCACAGGCGATGACTCGATGAGGACGTCACAG  5730
           ||||||||||||||||||||||||||||||||||||||||||||||||||||||||||||
XM  5920   ATCCCGGGGAGCCCCTTCACAGCCAAGATCACAGGCGATGACTCGATGAGGACGTCACAG  5979

ENS 5731   CTAAACGTGGGCACCTCCACGGATGTGTCACTGAAGATCACCGAGAGTGACCTGAGCCTG  5790
           ||||||||||||||||||||||||||||||||||||||||||||||||||||||||||||
XM  5980   CTAAACGTGGGCACCTCCACGGATGTGTCACTGAAGATCACCGAGAGTGACCTGAGCCTG  6039

ENS 5791   CTGACCGCCAGCATCCGTGCCCCCTCGGGCAACGAGGAGCCCTGCCTGCTGAAGCGCCTG  5850
           ||||||||||||||||||||||||||||||||||||||||||||||||||||||||||||
XM  6040   CTGACCGCCAGCATCCGTGCCCCCTCGGGCAACGAGGAGCCCTGCCTGCTGAAGCGCCTG  6099

ENS 5851   CCCAACCGGCACATTGGCATCTCCTTCACCCCCAAGGAAGTTGGGGAGCATGTGGTGAGC  5910
           ||||||||||||||||||||||||||||||||||||||||||||||||||||||||||||
XM  6100   CCCAACCGGCACATTGGCATCTCCTTCACCCCCAAGGAAGTTGGGGAGCATGTGGTGAGC  6159

ENS 5911   GTGCGCAAGAGTGGGAAGCACGTCACCAATAGCCCCTTCAAGATCCTGGTGGGGCCTTCT  5970
           ||||||||||||||||||||||||||||||||||||||||||||||||||||||||||||
XM  6160   GTGCGCAAGAGTGGGAAGCACGTCACCAATAGCCCCTTCAAGATCCTGGTGGGGCCTTCT  6219
```

FIG. 6 CONT'D

```
ENS 5971   GAGATCGGGGACGCTAGCAAGGTGCGGGTCTGGGGCAAGGGCCTGTCCGAGGGACAAACC   6030
           ||||||||||||||||||||||||||||||||||||||||||||||||||||||||||||
XM  6220   GAGATCGGGGACGCTAGCAAGGTGCGGGTCTGGGGCAAGGGCCTGTCCGAGGGACAAACC   6279

ENS 6031   TTCCAGGTGGCGGAGTTCATCGTGGACACTCGTAATGCAGGTTATGGGGGCCTGGGGCTG   6090
           ||||||||||||||||||||||||||||||||||||||||||||||||||||||||||||
XM  6280   TTCCAGGTGGCGGAGTTCATCGTGGACACTCGTAATGCAGGTTATGGGGGCCTGGGGCTG   6339

ENS 6091   AGTATTGAAGGCCCTAGCAAGGTGGACATCAACTGTGAGGACATGGAGGATGGCACATGC   6150
           ||||||||||||||||||||||||||||||||||||||||||||||||||||||||||||
XM  6340   AGTATTGAAGGCCCTAGCAAGGTGGACATCAACTGTGAGGACATGGAGGATGGCACATGC   6399

ENS 6151   AAAGTCACCTACTGCCCCACTGAACCCGGCACCTACATCATCAACATCAAGTTTGCTGAC   6210
           ||||||||||||||||||||||||||||||||||||||||||||||||||||||||||||
XM  6400   AAAGTCACCTACTGCCCCACTGAACCCGGCACCTACATCATCAACATCAAGTTTGCTGAC   6459

ENS 6211   AAGCATGTGCCAGGAAGCCCCTTCACTGTGAAGGTTACCGGTGAGGGCCGCATGAAGGAA   6270
           ||||||||||||||||||||||||||||||||||||||||||||||||||||||||||||
XM  6460   AAGCATGTGCCAGGAAGCCCCTTCACTGTGAAGGTTACCGGTGAGGGCCGCATGAAGGAA   6519

ENS 6271   AGCATCACCCGGCGCAGGCAGGCACCTTCCATCGCCACCATTGGCAGCACCTGTGACCTC   6330
           ||||||||||||||||||||||||||||||||||||||||||||||||||||||||||||
XM  6520   AGCATCACCCGGCGCAGGCAGGCACCTTCCATCGCCACCATTGGCAGCACCTGTGACCTC   6579

ENS 6331   AACCTCAAGATCCCAGGGAACTGGTTCCAGATGGTGTCTGCCCAGGAGCGCCTGACACGC   6390
           ||||||||||||||||||||||||||||||||||||||||||||||||||||||||||||
XM  6580   AACCTCAAGATCCCAGGGAACTGGTTCCAGATGGTGTCTGCCCAGGAGCGCCTGACACGC   6639

ENS 6391   ACCTTCACGCGCAGCAGCCACACGTACACCCGCACAGAGCGCACGGAGATCAGCAAGACC   6450
           ||||||||||||||||||||||||||||||||||||||||||||||||||||||||||||
XM  6640   ACCTTCACGCGCAGCAGCCACACGTACACCCGCACAGAGCGCACGGAGATCAGCAAGACC   6699

ENS 6451   CGGGGCGGAGAGACCAAGCGTGAGGTGCGGGTGGAGGAGTCCACCCAGGTTGGCGGAGAC   6510
           ||||||||||||||||||||||||||||||||||||||||||||||||||||||||||||
XM  6700   CGGGGCGGAGAGACCAAGCGTGAGGTGCGGGTGGAGGAGTCCACCCAGGTTGGCGGAGAC   6759

ENS 6511   CCCTTCCCCGCGGTCTTCGGGGACTTCCTGGGCCGCGAACGCCTGGGCTCCTTTGGCAGC   6570
           ||||||||||||||||||||||||||||||||||||||||||||||||||||||||||||
XM  6760   CCCTTCCCCGCGGTCTTCGGGGACTTCCTGGGCCGCGAACGCCTGGGCTCCTTTGGCAGC   6819

ENS 6571   ATCACTCGGCAGCAGGAGGGTGAGGCCAGCTCTCAAGACATGACCGCACAGGTGACCAGC   6630
           ||||||||||||||||||||||||||||||||||||||||||||||||||||||||||||
XM  6820   ATCACTCGGCAGCAGGAGGGTGAGGCCAGCTCTCAAGACATGACCGCACAGGTGACCAGC   6879

ENS 6631   CCATCGGGCAAGACAGAAGCCGCAGAGATCGTCGAGGGGGAGGACAGTGCATACAGCGTG   6690
           ||||||||||||||||||||||||||||||||||||||||||||||||||||||||||||
XM  6880   CCATCGGGCAAGACAGAAGCCGCAGAGATCGTCGAGGGGGAGGACAGTGCATACAGCGTG   6939

ENS 6691   CGCTTTGTGCCCCAGGAGATGGGGCCCCATACTGTCACTGTCAAGTACCGTGGCCAGCAC   6750
           ||||||||||||||||||||||||||||||||||||||||||||||||||||||||||||
XM  6940   CGCTTTGTGCCCCAGGAGATGGGGCCCCATACTGTCACTGTCAAGTACCGTGGCCAGCAC   6999

ENS 6751   GTGCCCGGCAGCCCCTTTCAGTTCACTGTGGGGCCACTGGGTGAAGGTGGTGCCCACAAG   6810
           ||||||||||||||||||||||||||||||||||||||||||||||||||||||||||||
XM  7000   GTGCCCGGCAGCCCCTTTCAGTTCACTGTGGGGCCACTGGGTGAAGGTGGTGCCCACAAG   7059

ENS 6811   GTGCGGGCTGGAGGCACAGGGCTGGAGCGAGGTGTGGCTGGCGTGCCAGCTGAGTTCAGC   6870
           ||||||||||||||||||||||||||||||||||||||||||||||||||||||||||||
XM  7060   GTGCGGGCTGGAGGCACAGGGCTGGAGCGAGGTGTGGCTGGCGTGCCAGCTGAGTTCAGC   7119
```

FIG. 6 CONT'D

```
ENS 6871   ATCTGGACCCGAGAAGCAGGTGCCGGGGGCCTGTCGATTGCTGTGGAGGGTCCCAGCAAG   6930
           ||||||||||||||||||||||||||||||||||||||||||||||||||||||||||||
XM  7120   ATCTGGACCCGAGAAGCAGGTGCCGGGGGCCTGTCGATTGCTGTGGAGGGTCCCAGCAAG   7179

ENS 6931   GCAGAGATTGCATTTGAGGACCGCAAAGACGGCTCCTGTGGGGTCTCCTATGTTGTCCAG   6990
           ||||||||||||||||||||||||||||||||||||||||||||||||||||||||||||
XM  7180   GCAGAGATTGCATTTGAGGACCGCAAAGACGGCTCCTGTGGGGTCTCCTATGTTGTCCAG   7239

ENS 6991   GAACCAGGTGACTATGAGGTCTCCATCAAGTTCAATGATGAGCACATCCCAGACAGCCCC   7050
           ||||||||||||||||||||||||||||||||||||||||||||||||||||||||||||
XM  7240   GAACCAGGTGACTATGAGGTCTCCATCAAGTTCAATGATGAGCACATCCCAGACAGCCCC   7299

ENS 7051   TTTGTGGTGCCTGTGGCCTCCCTCTCAGACGATGCTCGCCGCCTCACTGTCACCAGCCTC   7110
           ||||||||||||||||||||||||||||||||||||||||||||||||||||||||||||
XM  7300   TTTGTGGTGCCTGTGGCCTCCCTCTCAGACGATGCTCGCCGCCTCACTGTCACCAGCCTC   7359

ENS 7111   CAGGAGACGGGGCTCAAGGTGAACCAGCCAGCGTCCTTTGCGGTGCAGCTGAATGGTGCG   7170
           ||||||||||||||||||||||||||||||||||||||||||||||||||||||||||||
XM  7360   CAGGAGACGGGGCTCAAGGTGAACCAGCCAGCGTCCTTTGCGGTGCAGCTGAATGGTGCG   7419

ENS 7171   CGGGGCGTGATCGATGCTAGGGTGCACACGCCCTCGGGTGCGGTGGAGGAGTGCTACGTC   7230
           ||||||||||||||||||||||||||||||||||||||||||||||||||||||||||||
XM  7420   CGGGGCGTGATCGATGCTAGGGTGCACACGCCCTCGGGTGCGGTGGAGGAGTGCTACGTC   7479

ENS 7231   TCCGAGCTGGACAGTGACAAGCACACCATCCGCTTCATCCCCCACGAGAATGGCGTCCAC   7290
           ||||||||||||||||||||||||||||||||||||||||||||||||||||||||||||
XM  7480   TCCGAGCTGGACAGTGACAAGCACACCATCCGCTTCATCCCCCACGAGAATGGCGTCCAC   7539

ENS 7291   TCCATCGATGTCAAGTTCAACGGTGCCCACATCCCTGGCAGTCCCTTCAAGATCCGTGTT   7350
           ||||||||||||||||||||||||||||||||||||||||||||||||||||||||||||
XM  7540   TCCATCGATGTCAAGTTCAACGGTGCCCACATCCCTGGCAGTCCCTTCAAGATCCGTGTT   7599

ENS 7351   GGGGAGCAGAGCCAAGCTGGGGACCCAGGCTTGGTGTCAGCCTATGGTCCCGGGCTGGAG   7410
           ||||||||||||||||||||||||||||||||||||||||||||||||||||||||||||
XM  7600   GGGGAGCAGAGCCAAGCTGGGGACCCAGGCTTGGTGTCAGCCTATGGTCCCGGGCTGGAG   7659

ENS 7411   GGAGGCACTACAGGTGTATCATCAGAGTTCATTGTCAACACCCTGAACGCGGGCTCAGGG   7470
           ||||||||||||||||||||||||||||||||||||||||||||||||||||||||||||
XM  7660   GGAGGCACTACAGGTGTATCATCAGAGTTCATTGTCAACACCCTGAACGCGGGCTCAGGG   7719

ENS 7471   GCCTTGTCTGTCACCATCGATGGCCCCTCCAAGGTGCAGCTGGACTGTCGGGAATGTCCT   7530
           ||||||||||||||||||||||||||||||||||||||||||||||||||||||||||||
XM  7720   GCCTTGTCTGTCACCATCGATGGCCCCTCCAAGGTGCAGCTGGACTGTCGGGAATGTCCT   7779

ENS 7531   GAGGGCCACGTGGTCACTTACACTCCCATGGCCCCTGGCAACTACCTCATCGCCATCAAG   7590
           ||||||||||||||||||||||||||||||||||||||||||||||||||||||||||||
XM  7780   GAGGGCCACGTGGTCACTTACACTCCCATGGCCCCTGGCAACTACCTCATCGCCATCAAG   7839

ENS 7591   TATGGTGGCCCGCAGCACATCGTGGGCAGCCCCTTCAAGGCCAAAGTCACAGGTCCCCGG   7650
           ||||||||||||||||||||||||||||||||||||||||||||||||||||||||||||
XM  7840   TATGGTGGCCCGCAGCACATCGTGGGCAGCCCCTTCAAGGCCAAAGTCACAGGTCCCCGG   7899

ENS 7651   CTATCGGGAGGCCACAGCCTTCACGAAACATCCACGGTTCTGGTGGAGACTGTGACCAAG   7710
           ||||||||||||||||||||||||||||||||||||||||||||||||||||||||||||
XM  7900   CTATCGGGAGGCCACAGCCTTCACGAAACATCCACGGTTCTGGTGGAGACTGTGACCAAG   7959

ENS 7711   TCATCCTCAAGCCGGGGCTCCAGCTACAGCTCCATCCCCAAGTTCTCCTCGGATGCCAGC   7770
           ||||||||||||||||||||||||||||||||||||||||||||||||||||||||||||
XM  7960   TCATCCTCAAGCCGGGGCTCCAGCTACAGCTCCATCCCCAAGTTCTCCTCGGATGCCAGC   8019

ENS 7771   AAGGTGGTGACGCGGGGCCCCGGGCTGTCCCAGGCCTTTGTGGGCCAGAAGAACTCCTTC   7830
```

FIG. 6 CONT'D

```
                ||||||||||||||||||||||||||||||||||||||||||||||||||||||||||||
XM   8020      AAGGTGGTGACGCGGGGCCCCGGGCTGTCCCAGGCCTTTGTGGGCCAGAAGAACTCCTTC  8079

ENS  7831      ACCGTGGACTGCAGCAAAGCAGGCA                                     7855
               |||||||||||||||||||||||||
XM   8080      ACCGTGGACTGCAGCAAAGCAGGCA                                     8104

ENS  7856      TGCTGAGGGGGAGAGGGGCAGCCTCCCAG                                 7884

XM             -----------------------------

ENS  7885      GGCACCAACATGATGATGGTGGGTGTGCACGGGCCCAAGACCCCCTGTGAGGAGGTGTAT  7944
               ||||||||||||||||||||||||||||||||||||||||||||||||||||||||||||
XM   8101      GGCACCAACATGATGATGGTGGGTGTGCACGGGCCCAAGACCCCCTGTGAGGAGGTGTAT  8160

ENS  7945      GTGAAGCACATGGGGAACCGGGTGTACAACGTCACCTACACCGTCAAGGAGAAAGGAGAC  8004
               ||||||||||||||||||||||||||||||||||||||||||||||||||||||||||||
XM   8161      GTGAAGCACATGGGGAACCGGGTGTACAACGTCACCTACACCGTCAAGGAGAAAGGAGAC  8220

ENS  8005      TACATCCTCATCGTCAAGTGGGGCGACGAAAGTGTCCCCGGAAGCCCCTTCAAAGTCAAT  8064
               ||||||||||||||||||||||||||||||||||||||||||||||||||||||||||||
XM   8221      TACATCCTCATCGTCAAGTGGGGCGACGAAAGTGTCCCCGGAAGCCCCTTCAAAGTCAAT  8280

ENS  8065      GTGCCCTGA  8073 (SEQ ID NO:6)
               |||||||||
XM   8281      GTGCCCTGA  8289 (SEQ ID NO:7)
```

FIG. 7

| | | | | | |
|---|---|---|---|---|---|
| 1 | ATGATCCCCA | AGGAGCAGAA | GGGGCCCGTG | ATGGCTGCCA | TGGAGGACCT |
| 51 | CGCTGGACCA | G**TCCCTGTGC** | **TGGACCTGGG** | **CAAGAAGCTG** | **AGCGTGCCCC** |
| 101 | **AGGACCTGAT** | **GATGGAAGAG** | **CTGTCGCTCC** | **GCAACAACCG** | **GGGATCCCTC** |
| 151 | **CTCTTCCAGA** | **AGAGGCAGCG** | **CCGCGTGCAG** | **AAATTCACCT** | **TTGAGTTTGC** |
| 201 | **AGCCAGCCAG** | **CGGGCG**ACCG | TGGCCGGAAG | CGCCAAGGGG | AAGGTGCCTG |
| 251 | GAGCAGCAGA | GCCCGGGACG | GTCACCAACG | GCCCCGAGGG | GCAGAACTAC |
| 301 | CGCTCGGAGC | TCCACATCTT | CCCGGCCTCG | CCCGGGGGCC | CCGAGGACGC |
| 351 | GCAGCCCGCA | GCCTCCGGGG | CAAAGAGCGC | CCGCAGCCCC | AGCGCCCTGG |
| 401 | CGCCAGGCTA | CGCGGAGCCC | CTGAAGAGCG | TCCCGCCCGA | GAAGTTCAAC |
| 451 | CACACGGCCA | TCCCCAAGGG | CTACCGCTGC | CCGTGGCAGG | AGTTCATCAG |
| 501 | CTACCGGGAC | TACCAGAGCG | ACGGCCGAAG | TCACACCCCT | AGCCCGGCCG |
| 551 | AGTATCGGAA | TTTCAACAAG | ACCCCGGTGC | CCTTTGGAGG | ACCCCTGGTG |
| 601 | GGGGAGGCCG | TGCCCAGGGC | AGGCACCTCC | TTCATCCCAG | AGCTCACCAG |
| 651 | CGGCTTGGAA | CTCCTCCGCC | TGAGGCCCAG | CTTCAACAGA | GTGGCCCAGG |
| 701 | GCTGGGTCCG | CAACCTCCCG | GAGTCCGAGG | ATCTGTAG | (SEQ ID NO:8) |

FIG. 8

1 MFNYERPKHF IQSQNPCGSR LQPPGPETSS YSSQTKQSSI IIQPRQCTEQ
51 RFSASSTMSS HITMSSSAFP ASSQQLAGSN PGQRVTATYN QSPASFLSSI
101 LPSQPDYSSS KIPSTVDSNY QQPSFGQPVN AKPSQSANAK PIPRTPDHEI
151 QGSKEALIQD LERKLKCKDS LLHNGNQRLT YEEKMARRLL GPQNAAAVFQ
201 AQNDSEAQDS QQHNSEHARL QVPTSQVRSR SSSRGDVNDQ DAIQEKFYPP
251 RFIQVPENMS IDEGRFCRMD FKVSGLPAPD VSWYLNGRPV QSDDFHKMIV
301 SEKGFHSLIF EVVRASDAGA YACVARNRAG EATFTVQLDV LAKEHRRAPM
351 FIYKPQSKKV FEGESVKLEC QISAIPPPKL FWKRNNEMVH FNTDRISLYH
401 DNSGRVTLLI KDVNKKDAGW YTVSAVNEAG VTSCNTRLDV TARPNQTLPA
451 PKQLRVRPTF SKYLALNGRG LNVKQAFNPE GEFQRLAAQS GLYESEEL (SEQ ID NO:9)

1 MFNYERPKHF IQSQNPCGSR LQPPGPETSS YSSQTKQSSI IIQPRQCTEQ
51 RFSASSTMSS HITMSSSAFP ASSQQLAGSN PGQRVTATYN QSPASFLSSI
101 LPSQPDYSSS KIPSTVDSNY QQPSFGQPVN AKPSQSANAK PIPRTPDHEI
151 QGSKEALIQD LERKLKCKDS LLHNGNQRLT YEEKMARRLL GPQNAAAVFQ
201 AQNDSEAQDS QQHNSEHARL QVPTSQVRSR SPSRGDVNDQ DAIQEKFYPP
251 RFIQVPENMS IDEGRFCRMD FKVSGLPAPD VSWYLNGRPV QSDDFHKMIV
301 SEKGFHSLIF EVVRASDAGA YACVARNRAG EATFTVQLDV LAKEHRRAPM
351 FIYKPQSKKV FEGESVKLEC QISAIPPPKL FWKRNNEMVH FNTDRISLYH
401 DNSGRVTLLI KDVNKKDAGW YTVSAVNEAG VTSCNTRLDV TARPNQTLPA
451 PKQLRVRPTF SKYLALNGRG LNVKQAFNPE GEFQRLAAQS GLYESEEL (SEQ ID NO:10)

FIG. 9

| | | | |
|---|---|---|---|
| ENS | 1 | TFTRRCNEHLTCVVKRLTDLQRDLSDGLRLIALLEVLSQKRMYRKFHPRPNFRQMKLENV | 60 |
| XP | 63 | TFTRRCNEHLTCVVKRLTDLQRDLSDGLRLIALLEVLSQKRMYRKFHPRPNFRQMKLENV | 122 |
| ENS | 61 | SVALEFLEREHIKLVSIDSKAIVDGNLKLILGLIWTLILHYSISMPMWEDEDDEDARKQT | 120 |
| XP | 123 | SVALEFLEREHIKLVSIDSKAIVDGNLKLILGLIWTLILHYSISMPMWEDEDDEDARKQT | 182 |
| ENS | 121 | PKQRLLGWIQNKVPQLPITNFNRDWQDGKALGALVDNCAPGLCPDWEAWDPNQPVENARE | 180 |
| XP | 183 | PKQRLLGWIQNKVPQLPITNFNRDWQDGKALGALVDNCAPGLCPDWEAWDPNQPVENARE | 242 |
| ENS | 181 | AMQQADDWLGVPQVIAPEEIVDPNVDEHSVMTYLSQFPKAKLKPGAPVRSKQLNPKKAIA | 240 |
| XP | 243 | AMQQADDWLGVPQVIAPEEIVDPNVDEHSVMTYLSQFPKAKLKPGAPVRSKQLNPKKAIA | 302 |
| ENS | 241 | YGPGIEPQGNTVLQPAHFTVQTVDAGVGEVLVYIEDPEGHTEEAKVVPNNDKDRTYAVSY | 300 |
| XP | 303 | YGPGIEPQGNTVLQPAHFTVQTVDAGVGEVLVYIEDPEGHTEEAKVVPNNDKDRTYAVSY | 362 |
| ENS | 301 | VPKVAGLHKVTVLFAGQNIERSPFEVNVGMALGDANKVSARGPGLEPVGNVANKPTYFDI | 360 |
| XP | 363 | VPKVAGLHKVTVLFAGQNIERSPFEVNVGMALGDANKVSARGPGLEPVGNVANKPTYFDI | 422 |
| ENS | 361 | YTAGAGTGDVAVVIVDPQGRRDTVEVALEDKGDSTFRCTYRPVMEGPHTVHVAFAGAPIT | 420 |
| XP | 423 | YTAGAGTGDVAVVIVDPQGRRDTVEVALEDKGDSTFRCTYRPVMEGPHTVHVAFAGAPIT | 482 |
| ENS | 421 | RSPFPVHVAEA---------------------CNPNACRASGRGLQPKGVRVKEVADFKV | 459 |
| XP | 483 | RSPFPVHVAEEPLPPLAPSVPIVHQAKRVVPPCNPNACRASGRGLQPKGVRVKEVADFKV | 542 |
| ENS | 460 | FTKGAGSGELKVTVKGPKGTEELVKVREAGDGVFECEYYPVVPGKYVVTITWGGYAIPRS | 519 |
| XP | 543 | FTKGAGSGELKVTVKGPKGTEELVKVREAGDGVFECEYYPVVPGKYVVTITWGGYAIPRS | 602 |
| ENS | 520 | PFEVQVSPEAGAQKVRAWGPGLETGQVGKSADFVVEAIGTEVGTLGFSIEGPSQAKIECD | 579 |
| XP | 603 | PFEVQVSPEAGAQKVRAWGPGLETGQVGKSADFVVEAIGTEVGTLGFSIEGPSQAKIECD | 662 |
| ENS | 580 | DKGDGSCDVRYWPTEPGEYAVHVICDDEDIRDSPFIAHIQPAPPDCFPDKVKAFGPGLEP | 639 |
| XP | 663 | DKGDGSCDVRYWPTEPGEYAVHVICDDEDIRDSPFIAHIQPAPPDCFPDKVKAFGPGLEP | 722 |
| ENS | 640 | TGCIVDKPAEFTIDASAAGKGDLKLYAQDADGCPIDINVFTTGNGIFRCSYVPTKPIKHT | 699 |
| XP | 723 | TGCIVDKPAEFTIDASAAGKGDLKLYAQDADGCPIDINVFTTGNGIFRCSYVPTKPIKHT | 782 |
| ENS | 700 | IIISWGGVNVPKSPFR**VNVGEGSHPEKVKVYGPGVEKTGLKANEPTYFTVDCSEAGQ**GDV | 759 |
| XP | 783 | IIISWGGVNVPKSPFR**VNVGEGSHPEKVKVYGPGVEKTGLKANEPTYFTVDCSEAGQ**GDV | 842 |
| ENS | 760 | SIGIKCAPGVVGPAEADIDFDIIKNDNDTFTVKYTPPGAGRYTIMVLFANQEIPASPFHI | 819 |
| XP | 843 | SIGIKCAPGVVGPAEADIDFDIIKNDNDTFTVKYTPPGAGRYTIMVLFANQEIPASPFHI | 902 |
| ENS | 820 | KVDPSHDASKVKAEGPGLNRTGVEVGKPTHFTVLTKGAGKAKLDVHFAGAGKGEAVRDFE | 879 |
| XP | 903 | KVDPSHDASKVKAEGPGLNRTGVEVGKPTHFTVLTKGAGKAKLDVHFAGAGKGEAVRDFE | 962 |
| ENS | 880 | IIDNHDYSYTVKYTAVQQGNMAVTVTYGGDPVPKSPFVVNVAPPLDLSKVKVQGLNSKVA | 939 |
| XP | 963 | IIDNHDYSYTVKYTAVQQGNMAVTVTYGGDPVPKSPFVVNVAPPLDLSKVKVQGLNSKVA | 1022 |
| ENS | 940 | VGQEQAFSVNTRGAGGQGQLDVRMTSPSRRPIPCKLEPGGGAEAQAVRYMPPEEGPYKVD | 999 |
| XP | 1023 | VGQEQAFSVNTRGAGGQGQLDVRMTSPSRRPIPCKLEPGGGAEAQAVRYMPPEEGPYKVD | 1082 |
| ENS | 1000 | ITYDGHPVPGSPFTVEGVLPPDPSK**VCAYGPGLKGGLVGSPAPFSIDTKGAGTGGLGLTV** | 1059 |
| XP | 1083 | ITYDGHPVPGSPFTVEGVLPPDPSK**VCAYGPGLKGGLVGSPAPFSIDTKGAGTGGLGLTV** | 1142 |
| ENS | 1060 | **EGPCEAKIECQDNGDGSCAVSYLPTEPGEYTINILFAEAHIPGSPFKATIRPVFDPSKVR** | 1119 |
| XP | 1143 | **EGPCEAKIECQDNGDGSCAVSYLPTEPGEYTINILFAEAHIPGSPFKATIRPVFDPSKVR** | 1202 |

FIG. 9 CONT'D

ENS 1120 ASGPGLERGKAGEAATFTVDCSEAGEAELTIEILSDAGVKAEVLIHNNADGTYHITYSPA 1179
XP 1203 ASGPGLERGKAGEAATFTVDCSEAGEAELTIEILSDAGVKAEVLIHNNADGTYHITYSPA 1262

ENS 1180 FPGTYTITIKYGGHPVPKFPTRVHVQPAIDTSGVKVSGPGVEPHGVLREVTTEFTVDARS 1239
XP 1263 FPGTYTITIKYGGHPVPKFPTRVHVQPAIDTSGVKVSGPGVEPHGVLREVTTEFTVDARS 1322

ENS 1240 LTATGGNHVTARVLNPSGAKTDTYVTDNGDGTYRVQYTAYEEGVHLVEVLYDDVAVPKSP 1299
XP 1323 LTATGGNHVTARVLNPSGAKTDTYVTDNGDGTYRVQYTAYEEGVHLVEVLYDDVAVPKSP 1382

ENS 1300 FRVGVTEGCDPTRVRAYGPGLEGGLVNKANRFTVETRGAGTGGLGLAIEGPSEAKMSCKD 1359
XP 1383 FRVGVTEGCDPTRVRAYGPGLEGGLVNKANRFTVETRGAGTGGLGLAIEGPSEAKMSCKD 1442

ENS 1360 NKDGSCTVEYIPFTPGDYDVNITFGGRPIPGSPFRVPVKDVVDPGKVKCSGPGLGAGVRA 1419
XP 1443 NKDGSCTVEYIPFTPGDYDVNITFGGRPIPGSPFRVPVKDVVDPGKVKCSGPGLGAGVRA 1502

ENS 1420 RVPQTFTVDCSQAGRAPLQVAVLGPTGVAEPVEIRDNGDGTHAVHYTPATDGPYTVAVKY 1479
XP 1503 RVPQTFTVDCSQAGRAPLQVAVLGPTGVAEPVEIRDNGDGTHAVHYTPATDGPYTVAVKY 1562

ENS 1480 ADQEVPRSPFKIKVLPAHDASKVRASGPGLNAAGIPASLPVEFTIDARDAGEGLLTVQIL 1539
XP 1563 ADQEVPRSPFKIKVLPAHDASKVRASGPGLNAAGIPASLPVEFTIDARDAGEGLLTVQIL 1622

ENS 1540 DPEGKPKKANIRDNGDGTYTVSYLPDMSGRYTITIKYGGDEIPYSPFRIHALPTGDASKC 1599
XP 1623 DPEGKPKKANIRDNGDGTYTVSYLPDMSGRYTITIKYGGDEIPYSPFRIHALPTGDASKC 1682

ENS 1600 LVTVSIGGHGLGACLGPRIQIGEETVITVDAKAAGKGKVTCTVSTPDGAELDVDVVENHD 1659
XP 1683 LVTVSIGGHGLGACLGPRIQIGEETVITVDAKAAGKGKVTCTVSTPDGAELDVDVVENHD 1742

ENS 1660 GTFDIYYTAPEPGKYVITIRFGGEHIPNSPFHVLACDPMPHVEEPSDVLQLHRPSAYPTH 1719
XP 1743 GTFDIYYTAPEPGKYVITIRFGGEHIPNSPFHVLACDPMPHVEEPSDVLQLHRPSAYPTH 1802

ENS 1720 WATEEPVVPVEPMESMLRPFNLVIPFTVQKGELTGEVRMPSGKTARPNITDNKDGTITVR 1779
XP 1803 WATEEPVVPVEPMESMLRPFNLVIPFTVQKGELTGEVRMPSGKTARPNITDNKDGTITVR 1862

ENS 1780 YAPTEKGLHQMGIKYDGNHIPGDPLQFYVDAINSRHVSAYGPGLSHGMVNKPATFTIVTK 1839
XP 1863 YAPTEKGLHQMGIKYDGNHIPGSPLQFYVDAINSRHVSAYGPGLSHGMVNKPATFTIVTK 1922

ENS 1840 DAGEGGLSLAVEGPSKAEITCKDNKDGTCTVSYLPTAPGDYSIIVRFDDKHIPGSPFTAK 1899
XP 1923 DAGEGGLSLAVEGPSKAEITCKDNKDGTCTVSYLPTAPGDYSIIVRFDDKHIPGSPFTAK 1982

ENS 1900 ITGDDSMRTSQLNVGTSTDVSLKITESDLSLLTASIRAPSGNEEPCLLKRLPNRHIGISF 1959
XP 1983 ITGDDSMRTSQLNVGTSTDVSLKITESDLSLLTASIRAPSGNEEPCLLKRLPNRHIGISF 2042

ENS 1960 TPKEVGEHVVSVRKSGKHVTNSPFKILVGPSEIGDASKVRVWGKGLSEGQTFQVAEFIVD 2019
XP 2043 TPKEVGEHVVSVRKSGKHVTNSPFKILVGPSEIGDASKVRVWGKGLSEGQTFQVAEFIVD 2102

ENS 2020 TRNAGYGGLGLSIEGPSKVDINCEDMEDGTCKVTYCPTEPGTYIINIKFADKHVPGSPFT 2079
XP 2103 TRNAGYGGLGLSIEGPSKVDINCEDMEDGTCKVTYCPTEPGTYIINIKFADKHVPGSPFT 2162

ENS 2080 VKVTGEGRMKESITRRRQAPSIATIGSTCDLNLKIPGNWFQMVSAQERLTRTFTRSSHTY 2139
XP 2163 VKVTGEGRMKESITRRRQAPSIATIGSTCDLNLKIPGNWFQMVSAQERLTRTFTRSSHTY 2222

ENS 2140 TRTERTEISKTRGGETKREVRVEESTQVGGDPFPAVFGDFLGRERLGSFGSITRQQEGEA 2199
XP 2223 TRTERTEISKTRGGETKREVRVEESTQVGGDPFPAVFGDFLGRERLGSFGSITRQQEGEA 2282

ENS 2200 SSQDMTAQVTSPSGKTEAAEIVEGEDSAYSVRFVPQEMGPHTVTVKYRGQHVPGSPFQFT 2259
XP 2283 SSQDMTAQVTSPSGKTEAAEIVEGEDSAYSVRFVPQEMGPHTVTVKYRGQHVPGSPFQFT 2342

ENS 2260 VGPLGEGGAHKVRAGGTGLERGVAGVPAEFSIWTREAGAGGLSIAVEGPSKAEIAFEDRK 2319
XP 2343 VGPLGEGGAHKVRAGGTGLERGVAGVPAEFSIWTREAGAGGLSIAVEGPSKAEIAFEDRK 2402

ENS 2320 DGSCGVSYVVQEPGDYEVSIKFNDEHIPDSPFVVPVASLSDDARRLTVTSLQETGLKVNQ 2379

FIG. 9 CONT'D

```
XP    2403   DGSCGVSYVVQEPGDYEVSIKFNDEHIPDSPFVVPVASLSDDARRLTVTSLQETGLKVNQ  2462

ENS   2380   PASFAVQLNGARGVIDARVHTPSGAVEECYVSELDSDKHTIRFIPHENGVHSIDVKFNGA  2439
XP    2463   PASFAVQLNGARGVIDARVHTPSGAVEECYVSELDSDKHTIRFIPHENGVHSIDVKFNGA  2522

ENS   2440   HIPGSPFKIRVGEQSQAGDPGLVSAYGPGLEGGTTGVSSEFIVNTLNAGSGALSVTIDGP  2499
XP    2523   HIPGSPFKIRVGEQSQAGDPGLVSAYGPGLEGGTTGVSSEFIVNTLNAGSGALSVTIDGP  2582

ENS   2500   SKVQLDCRECPEGHVVTYTPMAPGNYLIAIKYGGPQHIVGSPFKAKVTGPRLSGGHSLHE  2559
XP    2583   SKVQLDCRECPEGHVVTYTPMAPGNYLIAIKYGGPQHIVGSPFKAKVTGPRLSGGHSLHE  2642

ENS   2560   TSTVLVETVTKSSSSRGSSYSSIPKFSSDASKVVTRGPGLSQAFVGQKNSFTVDCSKAGM  2619
XP    2643   TSTVLVETVTKSSSSRGSSYSSIPKFSSDASKVVTRGPGLSQAFVGQKNSFTVDCSKA--  2700

ENS   2620   LRGRGAASQGTNMMMVGVHGPKTPCEEVYVKHMGNRVYNVTYTVKEKGDYILIVKWGDES  2679
XP    2701   ----------GTNMMMVGVHGPKTPCEEVYVKHMGNRVYNVTYTVKEKGDYILIVKWGDES  2751

ENS   2680   VPGSPFKVNVP  2690 (SEQ ID NO:11)
XP    2752   VPGSPFKVNVP  2762 (SEQ ID NO:12)


ENS      1   TFTRRCNEHLTCVVKRLTDLQRDLSDGLRLIALLEVLSQKRMYRKFHPRPNFRQMKLENV  60
XP      63   TFTRRCNEHLTCVVKRLTDLQRDLSDGLRLIALLEVLSQKRMYRKFHPRPNFRQMKLENV  122

ENS     61   SVALEFLEREHIKLVSIDSKAIVDGNLKLILGLIWTLILHYSISMPMWEDEDDEDARKQT  120
XP     123   SVALEFLEREHIKLVSIDSKAIVDGNLKLILGLIWTLILHYSISMPMWEDEDDEDARKQT  182

ENS    121   PKQRLLGWIQNKVPQLPITNFNRDWQDGKALGALVDNCAPGLCPDWEAWDPNQPVENARE  180
XP     183   PKQRLLGWIQNKVPQLPITNFNRDWQDGKALGALVDNCAPGLCPDWEAWDPNQPVENARE  242

ENS    181   AMQQADDWLGVPQVIAPEEIVDPNVDEHSVMTYLSQFPKAKLKPGAPVRSKQLNPKKAIA  240
XP     243   AMQQADDWLGVPQVIAPEEIVDPNVDEHSVMTYLSQFPKAKLKPGAPVRSKQLNPKKAIA  302

ENS    241   YGPGIEPQGNTVLQPAHFTVQTVDAGVGEVLVYIEDPEGHTEEAKVVPNNDKDRTYAVSY  300
XP     303   YGPGIEPQGNTVLQPAHFTVQTVDAGVGEVLVYIEDPEGHTEEAKVVPNNDKDRTYAVSY  362

ENS    301   VPKVAGLHKVTVLFAGQNIERSPFEVNVGMALGDANKVSARGPGLEPVGNVANKPTYFDI  360
XP     363   VPKVAGLHKVTVLFAGQNIERSPFEVNVGMALGDANKVSARGPGLEPVGNVANKPTYFDI  422

ENS    361   YTAGAGTGDVAVVIVDPQGRRDTVEVALEDKGDSTFRCTYRPVMEGPHTVHVAFAGAPIT  420
XP     423   YTAGAGTGDVAVVIVDPQGRRDTVEVALEDKGDSTFRCTYRPVMEGPHTVHVAFAGAPIT  482

ENS    421   RSPFPVHVAEA----------------------CNPNACRASGRGLQPKGVRVKEVADFKV  459
XP     483   RSPFPVHVAEEPLPPLAPSVPIVHQAKRVVPPCNPNACRASGRGLQPKGVRVKEVADFKV  542

ENS    460   FTKGAGSGELKVTVKGPKGTEELVKVREAGDGVFECEYYPVVPGKYVVTITWGGYAIPRS  519
XP     543   FTKGAGSGELKVTVKGPKGTEELVKVREAGDGVFECEYYPVVPGKYVVTITWGGYAIPRS  602

ENS    520   PFEVQVSPEAGAQKVRAWGPGLETGQVGKSADFVVEAIGTEVGTLGFSIEGPSQAKIECD  579
XP     603   PFEVQVSPEAGAQKVRAWGPGLETGQVGKSADFVVEAIGTEVGTLGFSIEGPSQAKIECD  662

ENS    580   DKGDGSCDVRYWPTEPGEYAVHVICDDEDIRDSPFIAHIQPAPPDCFPDKVKAFGPGLEP  639
XP     663   DKGDGSCDVRYWPTEPGEYAVHVICDDEDIRDSPFIAHIQPAPPDCFPDKVKAFGPGLEP  722

ENS    640   TGCIVDKPAEFTIDASAAGKGDLKLYAQDADGCPIDINVFTTGNGIFRCSYVPTKPIKHT  699
```

FIG. 9 CONT'D

| | | | |
|---|---|---|---|
| XP | 723 | TGCIVDKPAEFTIDASAAGKGDLKLYAQDADGCPIDINVFTTGNGIFRCSYVPTKPIKHT | 782 |
| ENS | 700 | IIISWGGVNVPKSPFR**VNVGEGSHPEKVKVYGPGVEKTGLKANEPTYFTVDCSKAGQ**GDV | 759 |
| XP | 783 | IIISWGGVNVPKSPFR**VNVGEGSHPEKVKVYGPGVEKTGLKANEPTYFTVDCSKAGQ**GDV | 842 |
| ENS | 760 | SIGIKCAPGVVGPAEADIDFDIIKNDNDTFTVKYTPPGAGRYTIMVLFANQEIPASPFHI | 819 |
| XP | 843 | SIGIKCAPGVVGPAEADIDFDIIKNDNDTFTVKYTPPGAGRYTIMVLFANQEIPASPFHI | 902 |
| ENS | 820 | KVDPSHDASKVKAEGPGLNRTGVEVGKPTHFTVLTKGAGKAKLDVHFAGAGKGEAVRDFE | 879 |
| XP | 903 | KVDPSHDASKVKAEGPGLNRTGVEVGKPTHFTVLTKGAGKAKLDVHFAGAGKGEAVRDFE | 962 |
| ENS | 880 | IIDNHDYSYTVKYTAVQQGNMAVTVTYGGDPVPKSPFVVNVAPPLDLSKVKVQGLNSKVA | 939 |
| XP | 963 | IIDNHDYSYTVKYTAVQQGNMAVTVTYGGDPVPKSPFVVNVAPPLDLSKVKVQGLNSKVA | 1022 |
| ENS | 940 | VGQEQAFSVNTRGAGGQGQLDVRMTSPSRRPIPCKLEPGGGAEAQAVRYMPPEEGPYKVD | 999 |
| XP | 1023 | VGQEQAFSVNTRGAGGQGQLDVRMTSPSRRPIPCKLEPGGGAEAQAVRYMPPEEGPYKVD | 1082 |
| ENS | 1000 | ITYDGHPVPGSPFTVEGVLPPDPSK**VCAYGPGLKGGLVGSPAPFSIDTKGAGTGGLGLTV** | 1059 |
| XP | 1083 | ITYDGHPVPGSPFTVEGVLPPDPSK**VCAYGPGLKGGLVGSPAPFSIDTKGAGTGGLGLTV** | 1142 |
| ENS | 1060 | **EGPCEAKIECQDNGDGSCAVSYLPTEPGEYTINILFAEAHIPGSPFKATIRPVFDPSKVR** | 1119 |
| XP | 1143 | **EGPCEAKIECQDNGDGSCAVSYLPTEPGEYTINILFAEAHIPGSPFKATIRPVFDPSKVR** | 1202 |
| ENS | 1120 | **ASGPGLERGKAGEAATFTVDCSEAGEAELTIEILSDAGVKAEVLIHNNADGTYHITYSPA** | 1179 |
| XP | 1203 | **ASGPGLERGKAGEAATFTVDCSEAGEAELTIEILSDAGVKAEVLIHNNADGTYHITYSPA** | 1262 |
| ENS | 1180 | **FPGTYTITIKYGGHPVPKFPTRVHVQPTIDTSGVKVSGPGVEPH**GVLREVTTEFTVDARS | 1239 |
| XP | 1263 | **FPGTYTITIKYGGHPVPKFPTRVHVQPTIDTSGVKVSGPGVEPH**GVLREVTTEFTVDARS | 1322 |
| ENS | 1240 | LTATGGNHVTARVLNPSGAKTDTYVTDNGDGTYRVQYTAYEEGVHLVEVLYDDVAVPKSP | 1299 |
| XP | 1323 | LTATGGNHVTARVLNPSGAKTDTYVTDNGDGTYRVQYTAYEEGVHLVEVLYDDVAVPKSP | 1382 |
| ENS | 1300 | FRVGVTEGCDPTRVRAYGPGLEGGLVNKANRFTVETRGAGTGGLGLAIEGPSEAKMSCKD | 1359 |
| XP | 1383 | FRVGVTEGCDPTRVRAYGPGLEGGLVNKANRFTVETRGAGTGGLGLAIEGPSEAKMSCKD | 1442 |
| ENS | 1360 | NKDGSCTVEYIPFTPGDYDVNITFGGRPIPGSPFRVPVKDVVDPGKVKCSGPGLGAGVRA | 1419 |
| XP | 1443 | NKDGSCTVEYIPFTPGDYDVNITFGGRPIPGSPFRVPVKDVVDPGKVKCSGPGLGAGVRA | 1502 |
| ENS | 1420 | RVPQTFTVDCSQAGRAPLQVAVLGPTGVAEPVEIRDNGDGTHAVHYTPATDGPYTVAVKY | 1479 |
| XP | 1503 | RVPQTFTVDCSQAGRAPLQVAVLGPTGVAEPVEIRDNGDGTHAVHYTPATDGPYTVAVKY | 1562 |
| ENS | 1480 | ADQEVPRSPFKIKVLPAHDASKVRASGPGLNAAGIPASLPVEFTIDARDAGEGLLTVQIL | 1539 |
| XP | 1563 | ADQEVPRSPFKIKVLPAHDASKVRASGPGLNAAGIPASLPVEFTIDARDAGEGLLTVQIL | 1622 |
| ENS | 1540 | DPEGKPKKANIRDNGDGTYTVSYLPDMSGRYTITIKYGGDEIPYSPFRIHALPTGDASKC | 1599 |
| XP | 1623 | DPEGKPKKANIRDNGDGTYTVSYLPDMSGRYTITIKYGGDEIPYSPFRIHALPTGDASKC | 1682 |
| ENS | 1600 | LVTVSIGGHGLGACLGPRIQIGEETVITVDAKAAGKGKVTCTVSTPDGAELDVDVVENHD | 1659 |
| XP | 1683 | LVTVSIGGHGLGACLGPRIQIGEETVITVDAKAAGKGKVTCTVSTPDGAELDVDVVENHD | 1742 |
| ENS | 1660 | GTFDIYYTAPEPGKYVITIRFGGEHIPNSPFHVLACDPMPHVEEPSDVLQLHRPSAYPTH | 1719 |
| XP | 1743 | GTFDIYYTAPEPGKYVITIRFGGEHIPNSPFHVLACDPMPHVEEPSDVLQLHRPSAYPTH | 1802 |
| ENS | 1720 | WATEEPVVPVEPMESMLRPFNLVIPFTVQKGELTGEVRMPSGKTARPNITDNKDGTITVR | 1779 |
| XP | 1803 | WATEEPVVPVEPMESMLRPFNLVIPFTVQKGELTGEVRMPSGKTARPNITDNKDGTITVR | 1862 |
| ENS | 1780 | YAPTEKGLHQMGIKYDGNHIPGDPLQFYVDAINSRHVSAYGPGLSHGMVNKPATFTIVTK | 1839 |
| XP | 1863 | YAPTEKGLHQMGIKYDGNHIPGSPLQFYVDAINSRHVSAYGPGLSHGMVNKPATFTIVTK | 1922 |
| ENS | 1840 | DAGEGGLSLAVEGPSKAEITCKDNKDGTCTVSYLPTAPGDYSIIVRFDDKHIPGSPFTAK | 1899 |
| XP | 1923 | DAGEGGLSLAVEGPSKAEITCKDNKDGTCTVSYLPTAPGDYSIIVRFDDKHIPGSPFTAK | 1982 |

FIG. 9 CONT'D

```
ENS  1900  ITGDDSMRTSQLNVGTSTDVSLKITESDLSLLTASIRAPSGNEEPCLLKRLPNRHIGISF  1959
XP   1983  ITGDDSMRTSQLNVGTSTDVSLKITESDLSLLTASIRAPSGNEEPCLLKRLPNRHIGISF  2042

ENS  1960  TPKEVGEHVVSVRKSGKHVTNSPFKILVGPSEIGDASKVRVWGKGLSEGQTFQVAEFIVD  2019
XP   2043  TPKEVGEHVVSVRKSGKHVTNSPFKILVGPSEIGDASKVRVWGKGLSEGQTFQVAEFIVD  2102

ENS  2020  TRNAGYGGLGLSIEGPSKVDINCEDMEDGTCKVTYCPTEPGTYIINIKFADKHVPGSPFT  2079
XP   2103  TRNAGYGGLGLSIEGPSKVDINCEDMEDGTCKVTYCPTEPGTYIINIKFADKHVPGSPFT  2162

ENS  2080  VKVTGEGRMKESITRRRQAPSIATIGSTCDLNLKIPGNWFQMVSAQERLTRTFTRSSHTY  2139
XP   2163  VKVTGEGRMKESITRRRQAPSIATIGSTCDLNLKIPGNWFQMVSAQERLTRTFTRSSHTY  2222

ENS  2140  TRTERTEISKTRGGETKREVRVEESTQVGGDPFPAVFGDFLGRERLGSFGSITRQQEGEA  2199
XP   2223  TRTERTEISKTRGGETKREVRVEESTQVGGDPFPAVFGDFLGRERLGSFGSITRQQEGEA  2282

ENS  2200  SSQDMTAQVTSPSGKTEAAEIVEGEDSAYSVRFVPQEMGPHTVTVKYRGQHVPGSPFQFT  2259
XP   2283  SSQDMTAQVTSPSGKTEAAEIVEGEDSAYSVRFVPQEMGPHTVTVKYRGQHVPGSPFQFT  2342

ENS  2260  VGPLGEGGAHKVRAGGTGLERGVAGVPAEFSIWTREAGAGGLSIAVEGPSKAEIAFEDRK  2319
XP   2343  VGPLGEGGAHKVRAGGTGLERGVAGVPAEFSIWTREAGAGGLSIAVEGPSKAEIAFEDRK  2402

ENS  2320  DGSCGVSYVVQEPGDYEVSIKFNDEHIPDSPFVVPVASLSDDARRLTVTSLQETGLKVNQ  2379
XP   2403  DGSCGVSYVVQEPGDYEVSIKFNDEHIPDSPFVVPVASLSDDARRLTVTSLQETGLKVNQ  2462

ENS  2380  PASFAVQLNGARGVIDARVHTPSGAVEECYVSELDSDKHTIRFIPHENGVHSIDVKFNGA  2439
XP   2463  PASFAVQLNGARGVIDARVHTPSGAVEECYVSELDSDKHTIRFIPHENGVHSIDVKFNGA  2522

ENS  2440  HIPGSPFKIRVGEQSQAGDPGLVSAYGPGLEGGTTGVSSEFIVNTLNAGSGALSVTIDGP  2499
XP   2523  HIPGSPFKIRVGEQSQAGDPGLVSAYGPGLEGGTTGVSSEFIVNTLNAGSGALSVTIDGP  2582

ENS  2500  SKVQLDCRECPEGHVVTYTPMAPGNYLIAIKYGGPQHIVGSPFKAKVTGPRLSGGHSLHE  2559
XP   2583  SKVQLDCRECPEGHVVTYTPMAPGNYLIAIKYGGPQHIVGSPFKAKVTGPRLSGGHSLHE  2642

ENS  2560  TSTVLVETVTKSSSSRGSSYSSIPKFSSDASKVVTRGPGLSQAFVGQKNSFTVDCSKAGM  2619
XP   2643  TSTVLVETVTKSSSSRGSSYSSIPKFSSDASKVVTRGPGLSQAFVGQKNSFTVDCSKA--  2700

ENS  2620  LRGRGAASQGTNMMMVGVHGPKTPCEEVYVKHMGNRVYNVTYTVKEKGDYILIVKWGDES  2679
XP   2701  ---------GTNMMMVGVHGPKTPCEEVYVKHMGNRVYNVTYTVKEKGDYILIVKWGDES  2751

ENS  2680  VPGSPFKVNVP  2690 (SEQ ID NO:13)
XP   2752  VPGSPFKVNVP  2762 (SEQ ID NO:14)
```

FIG. 10

1 MIPKEQKGPV MAAMEDLAGP VPVLDLGKKL SVPQDLMMEE LSLRNNRGSL
51 LFQKRQRRVQ KFTFEFAASQ RATVAGSAKG KVPGAAEPGT VTNGPEGQNY
101 RSELHIFPAS PGGPEDAQPA ASGAKSARSP SALAPGYAEP LKSVPPEKFN
151 HTAIPKGYRC PWQEFISYRD YQSDGRSHTP SPAEYRNFNK TPVPFGGPLV
201 GEAVPRAGTS FIPELTSGLE LLRLRPSFNR VAQGWVRNLP ESEDL (SEQ ID NO:15)

1 MIPKEQKGPV MAAMEDLAGP VPVLDLGKKL SVPQDLMMEE LLLRNNRGSL
51 LFQKRQRRVQ KFTFEFAASQ RATVAGSAKG KVPGAAEPGT VTNGPEGQNY
101 RSELHIFPAS PGGPEDAQPA ASGAKSARSP SALAPGYAEP LKSVPPEKFN
151 HTAIPKGYRC PWQEFISYRD YQSDGRSHTP SPAEYRNFNK TPVPFGGPLV
201 GEAVPRAGTS FIPELTSGLE LLRLRPSFNR VAQGWVRNLP ESEDL (SEQ ID NO:16)

FIG. 11

5´-tatgacaat ggaaagggaa ttc-3´ (SEQ ID NO:19)
CTATGACAAT GGAAACCCAA TTCTTATTAT ACAATCTTTG CACATGATAA GAATTGTCCA

TGGGGTACTC TGCATTTTAA CAGATCAGCT TCTTCATTAA TTCGTTGCAC TGTAAAAAGG

AAACAAAGAT GTATAATTTG GGCCAGATGT TTCTAAATTG CTACCATTTC TACCAGTCAT

CAAATATACC ACAGCTAAAT ATAGCCTCTC TCCATTGTTA TTACACTATC AGATCAAACC

CACTCTAGGG TTTTAAATTT GATGACTAAA CTATATCTGT GTGAAAGGAA GAGCAATGAT

AATTTTCCGC ATGGTGATGA TTAAACTATT TTTGCAG 38,519,913 normal A AGC AGA TCA TCT TCA AGG GGA GAT GTG AAT GAT CAG GAT GCA
38,519,913 S232P A AGC AGA TCA CCT TCA AGG GGA GAT GTG AAT GAT CAG GAT GCA normal ATC CAG GAG AAG TTT TAC CCA CCT CGT TTC ATT CAA GTG CCA
S232P ATC CAG GAG AAG TTT TAC CCA CCT CGT TTC ATT CAA GTG CCA normal GAA AAC ATG TCA ATT GAC GAA GGA AGA TTC TGC AGA ATG GAC
S232P GAA AAC ATG TCA ATT GAC GAA GGA AGA TTC TGC AGA ATG GAC normal TTC AAA AAC ATG TCA ATT GAC GAA GGA AGA TTC TGC AGA ATG
S232P TTC AAA AAC ATG TCA ATT GAC GAA GGA AGA TTC TGC AGA ATG normal GAC TTC AAA (SEQ ID NO:17) 38,519,061
S232P GAC TTC AAA (SEQ ID NO:18) 38,519,061

GTAAGAGAAG AGTTCAAAAG TACTGGAGGA AAATTAACAA TGTGATACTA AGTTTTGAAA

AATGTGCTCT TCCTCTTCAT AGCTTGCTCC ACAGCTTGAG AAGCAGCACG TACAGTGGAG
3´-gaacgagg tgtcgaactc tt-5´ (SEQ ID NO:20)

FIG. 12

```
            GGGGAAGAGG ATGGGCTTTG AGGGAGGGGC ACCATGCTGA GCATTGACCC CTTCCCACAG

                                   5´-ggc agt cac cct gag aaa gt-3´ (SEQ ID
NO:23)
83,736,133  normal   GTA AAC GTG GGA GAG GGC AGT CAC CCT GAG AAA GTG
83,736,133  E753K    GTA AAC GTG GGA GAG GGC AGT CAC CCT GAG AAA GTG

            normal   AAG GTG TAC GGC CCT GGC GTG GAG AAG ACG GGC CTC
            E753K    AAG GTG TAC GGC CCT GGC GTG GAG AAG ACG GGC CTC

            normal   AAG GCC AAC GAG CCC ACC TAT TTC ACC GTG GAC TGC
            E753K    AAG GCC AAC GAG CCC ACC TAT TTC ACC GTG GAC TGC

            normal   AGC GAG GCG GGG CAA G  (SEQ ID NO:21)          83,736,256
            E753K    AGC AAG GCG GGG CAA G  (SEQ ID NO:22)          83,736,256

         GTGCACCAGC CAGGCGGGGG AGTAGGAGAC GGGGCCTGGG GCGGGGTCTG GGTGGGTAGG

         GCTAGTACTC CTGGCAGAGC TGTTTCCTGG CAGAGCTCTA GTGGGACTGC TCAGGTGGGG

         CAGGTTGTTG AGCCCCCATC TCATGGCCTC CTGTCTGCCT ACCCTCAGGC GATGTGAGCA
                                              (SEQ ID NO:24) 3´-cactcgt

         TTGGCATCAA GTGCGCCCCC GGCGTGGTGG GCCCCGCAGA GGCTGACATT GACTTTGACA
         aaccgtagtt ca-5´
```

FIG. 13

```
               GAAGGCCAAG CACGGGTGAG GCCAAGTGTA GGGAACTCAC ATACCTGCTC TTCCCTCTAG

83,738,223     normal     GTT TGT GCT TAT GGC CCT GGT CTC AAG GGT GGG CTG
83,738,223     A1207T     GTT TGT GCT TAT GGC CCT GGT CTC AAG GGT GGG CTG

               normal     GTA GGC AGC CCA GCG CCG TTC TCC ATC GAC ACC AAG
               A1207T     GTA GGC AGC CCA GCG CCG TTC TCC ATC GAC ACC AAG

               normal     GGG GCT GGC ACC GGT GGC CTG GGG CTG ACT GTG GAG
               A1207T     GGG GCT GGC ACC GGT GGC CTG GGG CTG ACT GTG GAG

               normal     GGC CCC TGT GAG GCC AAG ATC GAG TGC CAG GAC AAT
               A1207T     GGC CCC TGT GAG GCC AAG ATC GAG TGC CAG GAC AAT

               normal     GGT GAT GGC TCA TGT GCG GTC AGC TAC CTG CCC ACG
               A1207T     GGT GAT GGC TCA TGT GCG GTC AGC TAC CTG CCC ACG

               normal     GAG CCG GGC GAG TAC ACC ATC AAC ATC CTG TTC GCC
               A1207T     GAG CCG GGC GAG TAC ACC ATC AAC ATC CTG TTC GCC

               normal     GAA GCC CAC ATC CCC GGC TCA CCC TTC AAG GCT ACC
               A1207T     GAA GCC CAC ATC CCC GGC TCA CCC TTC AAG GCT ACC

               normal     ATC CGG CCC GTG TTC GAC CCG AGC AAG GTG CGG GCC
               A1207T     ATC CGG CCC GTG TTC GAC CCG AGC AAG GTG CGG GCC

               normal     AGT GGG CCA GGC CTG GAG CGT GGC AAG GCT GGT GAG
               A1207T     AGT GGG CCA GGC CTG GAG CGT GGC AAG GCT GGT GAG

               normal     GCA GCC ACC TTC ACT GTG GAC TGC TCG GAG GCG GGC
               A1207T     GCA GCC ACC TTC ACT GTG GAC TGC TCG GAG GCG GGC

               normal     GAG GCT GAG CTG ACC ATC GAG ATC CTG TCA GAC GCT
               A1207T     GAG GCT GAG CTG ACC ATC GAG ATC CTG TCA GAC GCT

                                      5´-g gtg ctg atc cac aac aat g-3´ (SEQ ID
NO:27)
               normal     GGC GTC AAG GCC GAG GTG CTG ATC CAC AAC AAT GCT
               A1207T     GGC GTC AAG GCC GAG GTG CTG ATC CAC AAC AAT GCT

               normal     GAC GGC ACC TAC CAC ATC ACC TAC AGC CCC GCC TTC
               A1207T     GAC GGC ACC TAC CAC ATC ACC TAC AGC CCC GCC TTC

               normal     CCC GGC ACC TAC ACT ATT ACC ATC AAG TAC GGT GGG
               A1207T     CCC GGC ACC TAC ACT ATT ACC ATC AAG TAC GGT GGG

               normal     CAC CCC GTA CCC AAA TTC CCC ACC CGC GTC CAT GTG
               A1207T     CAC CCC GTA CCC AAA TTC CCC ACC CGC GTC CAT GTG

               normal     CAG CCC GCT ATC GAC ACC AGT GGA GTC AAG GTC TCG
               A1207T     CAG CCC ACT ATC GAC ACC AGT GGA GTC AAG GTC TCG

               normal     GGG CCT GGT GTG GAG CCG CAC G  (SEQ ID NO:25)       83,738,820
               A1207T     GGG CCT GGT GTG GAG CCG CAC G  (SEQ ID NO:26)       83,738,820

               GTGAGTGAGA GAGGAGCCAG GAGCCCGTCA GGGAGCCAGG GGAGGCAGCA GAAGGGACGG

               AAGCAAGCCT GAGTGCTTAG CAGAGCACCA TAGTCTGAAG GGAGGACTTG GGGACAGCCC
```

FIG. 13 CONT'D (SEQ ID NO:28) 3´-catacttc cctcctgaac ccc-5´

FIG. 14

```
        5'-caggtttctc acacacaatg g-3' (SEQ ID NO:31)
        GGGGAGAAAC CAGGTTTCTC ACACACAATG GACAGTGTGC TGAGGAGGCC TCCTGAGAGG
        CGGCAGCCTA GGAAGCCTGC GGGTTTGGTA GTAAGAGCTG CCTCTGGCCT CTCCTGGCAG

27,399,285  normal   TC CCT GTG CTG GAC CTG GGC AAG AAG CTG AGC GTG CCC
27,399,285  S42L     TC CCT GTG CTG GAC CTG GGC AAG AAG CTG AGC GTG CCC

            normal      CAG GAC CTG ATG ATG GAA GAG CTG TCG CTC CGC AAC
            S42L        CAG GAC CTG ATG ATG GAA GAG CTG TTG CTC CGC AAC

            normal      AAC CGG GGA TCC CTC CTC TTC CAG AAG AGG CAG CGC
            S42L        AAC CGG GGA TCC CTC CTC TTC CAG AAG AGG CAG CGC

            normal      CGC GTG CAG AAA TTC ACC TTT GAG TTT GCA GCC AGC
            S42L        CGC GTG CAG AAA TTC ACC TTT GAG TTT GCA GCC AGC

            normal      CAG CGG GCG  (SEQ ID NO:29)     27,399,131
            S42L        CAG CGG GCG  (SEQ ID NO:30)     27,399,131

        GTGAGTAAGC CCCCACTGTG CTCACAGGGA AACTGAGGCC CAGAGAGAGC CAGTGGTTAG

        TCTAAAGCCC AACAGTGAGC CAGGGGAGGA CCTCTGGCCC CTGGGGAGTC CCTCAAGCTC

        CAGCTGGGGA AGACTGTGAT GTTCCCATCG GACTGAGCCC CGCCCTGCCG GGTGATCCTA

        GAAAAGGGTT ACCTCTTTAG GCGTCTCCCC AGATGTGAAA CATGAAGTGG CATGGGCAGG

        AGGAGCTGTG GAGTGAAGGA CTCTGGCTCC TATAAAAAGG GCTGAAGCAT AGTCATGTGC

        TCTGGGCTGA ATTTACAGCA AGCCGGATTT AGGTTAGACT TGAGCTTGAT CTAAGGTGGA
                                                 (SEQ ID NO:32)    3'-cacct

        AAATGCAGAA TGCCTTTTTC TCTTCTTCCC ACTGGAAGAA GGAAAAGGCC ACGGCACAGT
        tttacgtctt acgga-5'
```

FIG. 19

```
                                             5'- g cacatgataa gaattgtcca
            CTATGACAAT GGAAACCCAA TTCTTATTAT ACAATCTTTG CACATGATAA GAATTGTCCA

            tggggtactc tgca-3' (SEQ ID NO:33)
            TGGGGTACTC TGCATTTTAA CAGATCAGCT TCTTCATTAA TTCGTTGCAC TGTAAAAAGG

            AAACAAAGAT GTATAATTTG GGCCAGATGT TTCTAAATTG CTACCATTTC TACCAGTCAT

            CAAATATACC ACAGCTAAAT ATAGCCTCTC TCCATTGTTA TTACACTATC AGATCAAACC

            CACTCTAGGG TTTTAAATTT GATGACTAAA CTATATCTGT GTGAAAGGAA GAGCAATGAT

            AATTTTCCGC ATGGTGATGA TTAAACTATT TTTGCAG

38,519,913  normal   A AGC AGA TCA TCT TCA AGG GGA GAT GTG AAT GAT CAG GAT GCA ATC
                (SEQ ID NO:34)  3'-agc agt tcc cct cta cac tta cta gtc cta cgt t-
5'

38,519,913  S232P    A AGC AGA TCA CCT TCA AGG GGA GAT GTG AAT GAT CAG GAT GCA ATC
                (SEQ ID NO:35)  3'-ggc agt tcc cct cta cac tta cta gtc cta cgt t-
5'

            normal    CAG GAG AAG TTT TAC CCA CCT CGT TTC ATT CAA GTG CCA
            S232P     CAG GAG AAG TTT TAC CCA CCT CGT TTC ATT CAA GTG CCA

            normal    GAA AAC ATG TCA ATT GAC GAA GGA AGA TTC TGC AGA ATG
            S232P     GAA AAC ATG TCA ATT GAC GAA GGA AGA TTC TGC AGA ATG

            normal    GAC TTC AAA AAC ATG TCA ATT GAC GAA GGA AGA TTC TGC
            S232P     GAC TTC AAA AAC ATG TCA ATT GAC GAA GGA AGA TTC TGC

            normal    AGA ATG GAC TTC AAA  (SEQ ID NO:17)     38,519,061
            S232P     AGA ATG GAC TTC AAA  (SEQ ID NO:18)     38,519,061

            GTAAGAGAAG  AGTTCAAAAG  TACTGGAGGA  AAATTAACAA  TGTGATACTA  AGTTTTGAAA

            AATGTGCTCT  TCCTCTTCAT  AGCTTGCTCC  ACAGCTTGAG  AAGCAGCACG  TACAGTGGAG
```

FIG. 20

```
                  (SEQ ID NO:36) 5'- tgtcgctgg gccctggtca ctgctc-3'
            GAGGGTGAAG CCCTATGCAG GAGATGTCGG CTGTCGCTGG GCCCTGGTCA CTGCTCCCCA

            CCTCAAGGCC CCCACGAAGG AGCTAAGATT GATCCCATTA AGGCTGAGGC GCCTAGTGCT

            GGGGAAGAGG ATGGGCTTTG AGGGAGGGGC ACCATGCTGA GCATTGACCC CTTCCCACAG


83,736,133  normal   GTA AAC GTG GGA GAG GGC AGT CAC CCT GAG AAA GTG
83,736,133  E753K    GTA AAC GTG GGA GAG GGC AGT CAC CCT GAG AAA GTG

            normal   AAG GTG TAC GGC CCT GGC GTG GAG AAG ACG GGC CTC
            E753K    AAG GTG TAC GGC CCT GGC GTG GAG AAG ACG GGC CTC

            normal   AAG GCC AAC GAG CCC ACC TAT TTC ACC GTG GAC TGC
            E753K    AAG GCC AAC GAG CCC ACC TAT TTC ACC GTG GAC TGC

            normal   AGC GAG GCG GGG CAA G  (SEQ ID NO:21)             83,736,256
       (SEQ ID NO:37) 3'-ctg cgc ccc gtt c

            E753K    AGC AAG GCG GGG CAA G  (SEQ ID NO:22)             83,736,256
       (SEQ ID NO:38) 3'-ttg cgc ccc gtt c


         GTGCACCAGC CAGGCGGGGG AGTAGGAGAC GGGGCCTGGG GCGGGGTCTG GGTGGGTAGG
         cacgtggtcg g-5' (SEQ ID NO:37)
         cacgtggtcg g-5' (SEQ ID NO:38)

         GCTAGTACTC CTGGCAGAGC TGTTTCCTGG CAGAGCTCTA GTGGGACTGC TCAGGTGGGG
```

FIG. 21

```
            GAAGGCCAAG CACGGGTGAG GCCAAGTGTA GGGAACTCAC ATACCTGCTC TTCCCTCTAG

83,738,223  normal   GTT TGT GCT TAT GGC CCT GGT CTC AAG GGT
83,738,223  A1207T   GTT TGT GCT TAT GGC CCT GGT CTC AAG GGT

            normal   GGG CTG GTA GGC AGC CCA GCG CCG TTC TCC ATC GAC ACC AAG GGG
            A1207T   GGG CTG GTA GGC AGC CCA GCG CCG TTC TCC ATC GAC ACC AAG GGG

            normal   GCT GGC ACC GGT GGC CTG GGG CTG ACT GTG GAG GGC CCC TGT GAG
            A1207T   GCT GGC ACC GGT GGC CTG GGG CTG ACT GTG GAG GGC CCC TGT GAG

            normal   GCC AAG ATC GAG TGC CAG GAC AAT GGT GAT GGC TCA TGT GCG GTC
            A1207T   GCC AAG ATC GAG TGC CAG GAC AAT GGT GAT GGC TCA TGT GCG GTC

            normal   AGC TAC CTG CCC ACG GAG CCG GGC GAG TAC ACC ATC AAC ATC CTG
            A1207T   AGC TAC CTG CCC ACG GAG CCG GGC GAG TAC ACC ATC AAC ATC CTG

            normal   TTC GCC GAA GCC CAC ATC CCC GGC TCA CCC TTC AAG GCT ACC ATC
            A1207T   TTC GCC GAA GCC CAC ATC CCC GGC TCA CCC TTC AAG GCT ACC ATC

            normal   CGG CCC GTG TTC GAC CCG AGC AAG GTG CGG GCC AGT GGG CCA GGC
            A1207T   CGG CCC GTG TTC GAC CCG AGC AAG GTG CGG GCC AGT GGG CCA GGC

            normal   CTG GAG CGT GGC AAG GCT GGT GAG GCA GCC ACC TTC ACT GTG GAC
            A1207T   CTG GAG CGT GGC AAG GCT GGT GAG GCA GCC ACC TTC ACT GTG GAC

            normal   TGC TCG GAG GCG GGC GAG GCT GAG CTG ACC ATC GAG ATC CTG TCA
            A1207T   TGC TCG GAG GCG GGC GAG GCT GAG CTG ACC ATC GAG ATC CTG TCA

            normal   GAC GCT GGC GTC AAG GCC GAG GTG CTG ATC CAC AAC AAT GCT GAC
            A1207T   GAC GCT GGC GTC AAG GCC GAG GTG CTG ATC CAC AAC AAT GCT GAC

            normal   GGC ACC TAC CAC ATC ACC TAC AGC CCC GCC TTC CCC GGC ACC TAC
            A1207T   GGC ACC TAC CAC ATC ACC TAC AGC CCC GCC TTC CCC GGC ACC TAC

            normal   ACT ATT ACC ATC AAG TAC GGT GGG CAC CCC GTA CCC AAA TTC CCC
            A1207T   ACT ATT ACC ATC AAG TAC GGT GGG CAC CCC GTA CCC AAA TTC CCC

                  5'-acc cgc gtc cat gtg cag cgc g-3' (SEQ ID NO:40)
            normal   ACC CGC GTC CAT GTG CAG CCC GCT ATC GAC ACC AGT GGA GTC AAG

                  5'-acc cgc gtc cat gtg cag cgc a-3' (SEQ ID NO:41)
            A1207T   ACC CGC GTC CAT GTG CAG CCC ACT ATC GAC ACC AGT GGA GTC AAG

            normal   GTC TCG GGG CCT GGT GTG GAG CCG CAC G  (SEQ ID NO:25)83,738,820
            A1207T   GTC TCG GGG CCT GGT GTG GAG CCG CAC G  (SEQ ID NO:26)83,738,820

            GTGAGTGAGA GAGGAGCCAG GAGCCCGTCA GGGAGCCAGG GGAGGCAGCA GAAGGGACGG
AAGCAAGCCT

            GAGTGCTTAG CAGAGCACCA TAGTCTGAAG GGAGGACTTG GGGACAGCCC TGGCGTCCTT
AGGGCTCAGA
                        (SEQ ID NO:39)  3'-c cctcctgaac ccctgtcggg acc-5'
```

FIG. 22

```
             GGGGAGAAAC CAGGTTTCTC ACACACAATG GACAGTGTGC TGAGGAGGCC TCCTGAGAGG

             CGGCAGCCTA GGAAGCCTGC GGGTTTGGTA GTAAGAGCTG CCTCTGGCCT CTCCTGGCAG

27,399,285   normal   TC CCT GTG CTG GAC CTG GGC AAG AAG CTG AGC
27,399,285   S42L     TC CCT GTG CTG GAC CTG GGC AAG AAG CTG AGC

                     5'-g ccc cag gac ctg atg atg gaa gag ctc tc-3' (SEQ ID NO:43)
             normal   GTG CCC CAG GAC CTG ATG ATG GAA GAG CTG TCG CTC CGC AAC

                     5'-g ccc cag gac ctg atg atg gaa gag ctc tt-3' (SEQ ID NO:44)
             S42L     GTG CCC CAG GAC CTG ATG ATG GAA GAG CTG TTG CTC CGC AAC

             normal      AAC CGG GGA TCC CTC CTC TTC CAG AAG AGG CAG CGC
             S42L        AAC CGG GGA TCC CTC CTC TTC CAG AAG AGG CAG CGC

             normal      CGC GTG CAG AAA TTC ACC TTT GAG TTT GCA GCC AGC
             S42L        CGC GTG CAG AAA TTC ACC TTT GAG TTT GCA GCC AGC

             normal      CAG CGG GCG  (SEQ ID NO:29)     27,399,131
             S42L        CAG CGG GCG  (SEQ ID NO:30)     27,399,131

             GTGAGTAAGC CCCCACTGTG CTCACAGGGA AACTGAGGCC CAGAGAGAGC CAGTGGTTAG

             TCTAAAGCCC AACAGTGAGC CAGGGGAGGA CCTCTGGCCC CTGGGGAGTC CCTCAAGCTC
             (SEQ ID NO:42) 3'-tcg gtcccctcct ggagaccgg-5'

             CAGCTGGGGA AGACTGTGAT GTTCCCATCG GACTGAGCCC CGCCCTGCCG GGTGATCCTA
```

FIG. 23

```
Human 207    AQDSQQHNSEHARLQVPTSQVRSRSTSRGDVNDQDAIQEKFYPPRFIQVPE  257    (SEQ ID
NO:272)
             AQDSQQHNSEHARLQVPTSQVRSRS+SRGDVNDQDAIQEKFYPPRFIQVPE         (SEQ ID
NO:273)
Horse 207    AQDSQQHNSEHARLQVPTSQVRSRSSSRGDVNDQDAIQEKFYPPRFIQVPE  257    (SEQ ID
NO:274)
MYOT-S232P                            P
```

FIG. 24

```
Human 759    GEGSHPERVKVYGPGVEKTGLKANEPTYFTVDCSEAGQGDVSIGIKCAPGVVGPAEADID  818
             GEGSHPE+VKVYGPGVEKTGLKANEPTYFTVDCSEAGQGDVSIGIKCAPGVVGPAEADID
ENS   719    GEGSHPEKVKVYGPGVEKTGLKANEPTYFTVDCSEAGQGDVSIGIKCAPGVVGPAEADID  778
XP    802    GEGSHPEKVKVYGPGVEKTGLKANEPTYFTVDCSEAGQGDVSIGIKCAPGVVGPAEADID  861
FLNC-E753K                                     K

Human 819    FDIIKNDNDTFTVKYTPPGAGRYTIMVLFANQEIPASPFHIKV  861      (SEQ ID NO:275)
             FDIIKNDNDTFTVKYTPPGAGRYTIMVLFANQEIPASPFHIKV           (SEQ ID NO:276)
ENS   779    FDIIKNDNDTFTVKYTPPGAGRYTIMVLFANQEIPASPFHIKV  821      (SEQ ID NO:277)
XP    862    FDIIKNDNDTFTVKYTPPGAGRYTIMVLFANQEIPASPFHIKV  904      (SEQ ID NO:278)
FLNC-E753K
```

FIG. 25

```
Human  1245   QPAVDTSGVKVSGPGVEPHGVLREVTTEFTVDARSLTATGGNHVTARVLNPSGAKTDTYV  1304
              QPA+DTSGVKVSGPGVEPHGVLREVTTEFTVDARSLTATGGNHVTARVLNPSGAKTDTYV
ENS    1205   QPAIDTSGVKVSGPGVEPHGVLREVTTEFTVDARSLTATGGNHVTARVLNPSGAKTDTYV  1264
XP     1288   QPAIDTSGVKVSGPGVEPHGVLREVTTEFTVDARSLTATGGNHVTARVLNPSGAKTDTYV  1347
FLNC-A1207T     T

Human  1305   TDNGDGTYRVQYTAYEEGVHLVEVLYDEVAVPKSPFRVGV  1344 (SEQ ID NO:279)
              TDNGDGTYRVQYTAYEEGVHLVEVLYD+VAVPKSPFRVGV       (SEQ ID NO:280)
ENS    1265   TDNGDGTYRVQYTAYEEGVHLVEVLYDDVAVPKSPFRVGV  1304 (SEQ ID NO:281)
XP     1348   TDNGDGTYRVQYTAYEEGVHLVEVLYDDVAVPKSPFRVGV  1387 (SEQ ID NO:282)
FLNC-A1207T
```

```
Human     1    MIPKEQKGPVMAAMGDLTEPVPTLDLGKKLSVPQDLMMEELSLRNNRGSLLFQKRQRRVQKFTFELAA
68
               MIPKEQKGPVMAAM DL  PVP LDLGKKLSVPQDLMMEELSLRNNRGSLLFQKRQRRVQKFTFE AA
Horse     1    MIPKEQKGPVMAAMEDLAGPVPVLDLGKKLSVPQDLMMEELSLRNNRGSLLFQKRQRRVQKFTFEFAA
68
MYOZ3-S42L                                         L
```

FIG. 31

| | |
|---|---|
| primate1 | -GAQDSQQHNSEHARLQVPTSQVRSRS**T**SRGDVNDQDAIQEKFYPPRFIQVPEN |
| primate2 | -GAQDSQQHNSEHARLQVPTSQVRSRS**S**SRGDVNDQDAIQEKFYPPRFIQVPEN |
| mammal1 | --AQDSPQHNSEHARLQVPTSQVRSRS**S**SRGDVNDQDAIQEKFYPPRFIQVPEN |
| mammal2 | -AQDSAQQHNIEHARLQVPTSQVRSRS**S**SRGDVNDQDAIQEKFYPPRFIQVPEN |
| mammal3 | -AQDSPQQHHSEHARLQVPTSQVRSRS**S**SRGDVNDQDAIQEKFYPPRFIQVPEN |
| mammal4 | --AQDSPQHNSEHARLQVPTSQVRSRS**S**SRGGVNDEDAIQEKFYPPRFIQVPEN |
| mammal5 | -AQDPAQQHNSEHARLQLPTSQVRSRS**S**SRGDVNDQDAIQEKFYPPRFIQVPEN |
| mammal6 | --AQDSPQHNSEHARLQVPTSQVRSRS**S**SRGTLNEQDAIQEKFYPPRFIQVPEN |
| mammal7 | -AQDSPQQHNSDHVRLQVPTSQIRSRS**S**SRGDVNDQDAIQEKFYPPRFIQVPEN |
| mammal8 | -AQDSPQHHNPEHARLQVPTSQVRSRS**S**SRGDVNDQDAIQEKFYPPRFIQVPEN |
| Cebus_capucinus_imitator | ---QDSQQHNSEYARLQVPTSQVRSRS**S**SRGTVNDQDAIQEKFYPPRFIQVPEN |
| Chlorocebus_sabaeus | -GAQDSQQHNSEYARLQVPTSQVRSRS**S**SRGDANDQDAIQEKFYPPRFIQVPEN |
| Microcebus_murinus | -AQDLPQQHNSEHARLQVPTSQVRSRS**S**SRGDVNDQDAIQEKFYPPRFIQVPEN |
| Otolemur_garnettii | --AQDSPQHNSEHARLQVPTPQVRSRS**S**SRGDVNDQDAIQEKFYPPRFIQVPEN |
| Bubalus_bubalis | -AQDSAQQHNIEHARLQVPTSQVRSRS**S**SRGDMNDQDAIQEKFYPPRFIQVPEN |
| Rattus_norvegicus | --VQDSSQHNPEHARLQVPTSQVRSRS**S**SRADANDQDAIQEKFYPPRFIQVPEN |
| Heterocephalus_glaber | --AQDSPQHNAEHARLQVPTAQVRSRS**S**SRGDVNDQDAIQEKFYPPRFIQVPEN |
| Ovis_aries_musimon | --AQDSAQHNIEHARLQVPTSQVRSRS**S**SRGDMSDQDAIQEKFYPPRFIQVPEN |
| Castor_canadensis | --QDSPQQHNSEHAWLQVPTSQVRSRS**S**SRGDVNDQDAIQEKFYPPRFIQVPEN |
| Canis_lupus_familiaris | -AQDSPQQHNLEHARLQVPTSQVRSRS**S**SRGDVNDQDAIQEKFYPPRFIQVPEN |
| Miniopterus_natalensis | -AQD-SPQHNSAHARLQVPTSQIRSRS**S**SRGDVNDEDAIQEKFYPPRFIQVPEN |
| Pteropus_alecto | AQD-SPQHNSDHVRLQVPTSQIRSRSS**S**RGDVNDQDAIQEKFYPPRFIQVPEN |
| Physeter_catodon | -AQDPAQQHNSEHARLQVPTSQVRSRS**S**SRGDVNDQDAIQEKFYPPRFIQVPE- |
| T_manatus_latirostris | --AQDSPQHTSEHARLQVPTSQVRSRS**S**SRGDVNDQDAIQEKFYPPRFIQVPEN |
| Echinops_telfairi | --AQDSPQHNSEHARLHVPTAQVRSRS**S**SRGDVNDQDAIQEKFYPPRFIQVPEN |
| Erinaceus_europaeus | --VQESSQHNSEHARLQVPTPQIRSRS**S**SRGDVNDQDAIQEKFYPPRFIQVPEN |
| Dasypus_novemcinctus | --AQDSPKYNSEHARLQVPTSQVRSRS**S**SRGDANDQDAIQEKFYPPRFIQVPEN |
| Manis_javanica | --AQDSPQHNSENARLQVPTSQIRSRS**S**SRGDVNDQDAIQEKFYPPRFIQVPEH |
| Orycteropus_afer_afer | --AQDSLQHNSEHARLQVPTSQIRSRS**S**SRGGVNDQDAIQEKFYPPRFIQVPEN |
| Monodelphis_domestica | --SQDSAQHNSENARLQVPVPQIRSRS**S**SRGDTNDQESILEKFYPPRFVQVPEN |
| Sarcophilus_harrisii | --SQNSAQHNSENARLQVPTPQIRSRS**S**SRGDTNDQESILEKFYPPRFVQVPEN |
| Ornithorhynchus_anatinus | --AQDFSQPNSENVRLQVPSPQVRSRS**S**SRGAVNDQDSIQEKFYPPRFVQVPEN |
| bird1 | ---QNAQHQNAENIRLQVPTTHVRSRP**S**SRGDERGHDAIQEKFFQPRFTQVPED |
| bird2 | ---QNAQHQNAENVRLQVPTTHVRSRP**S**SRGDERGHDSIQEKFFQPRFTQVPED |
| bird3 | ---QNAQHQNAENIRLQVPTTHVRSRP**S**SRGDERGHDSIQEKFFQPRFTQVPED |
| bird4 | --VQNAQHQNAENIRLQVPTTHVRSRP**S**SRGDDRGHDSIQEKFFQPRFTQVPED |
| bird5 | ---QNAQHQNAENIRLQVPTTHVRSRP**S**SRGDDRGHDSIQEKFFQPRFTQVPED |
| Gallus_gallus | ---QNTQHQNAENVRLQVPTTHVRSRP**S**SRGDERGHDSIQEKFFQPRFTQVPED |
| Haliaeetus_albicilla | ---QNAQQQNAENIRLQVPTAHVRSRP**S**SRGDERGHDSIQEKFFQPRFTQVPED |
| Tinamus_guttatus | -GLQNAQQQNAENIRLQVPTTHVRSRP**S**SRGDEHGHDSIQEKFFQPRFTQVPED |
| Aptenodytes_forsteri | ---QNAQHQNAENIRLQVPTTHVRSRP**S**SRGDERGHDSIQEKFFQPRFTQVPED |
| Meleagris_gallopavo | --VQNAQHQNAENIRLQVPTTHVRSRP**S**SRGDERGHDSIQEKFFQPRFTQVPED |
| A_chrysaetos_canadensis | ---QNAQQQNAENIRLQVPTTHVRSRP**S**SRGDERGHDSIQEKFFQPRFTQVPED |
| Eurypyga_helias | ---QNAQEHNAENIRLQVPTTHVRSRP**S**SRGDERGHDSIQEKFFQPRFTQVPED |
| Colius_striatus | ---QNAQHHNAENIRLQVPTTHVRSRP**S**SRGDERGHDSIQEKFFQPRFTQVPED |
| Melopsittacus_undulatus | -------QHNAENIRLQVPTTHVRSRP**S**SRGDERGHDSIQEKFFQPRFTQVPED |
| Ficedula_albicollis | ---QSAQHQNSENIRLQVPTTHVRSRP**S**SRGDDRGHDSIQEKFFQPRFTQVPED |
| S_camelus_australis | ---QNAQHQNTENIRLQVPTTHVRSRP**S**SRGDERGHDSIQEKFFQPRFTQVPED |
| A_australis_mantelli | --AQNAQHQNAENIRLQVPTAHVRSRP**S**SRGDEHGHDSIQEKFFQPRFTQVPED |
| Merops_nubicus | ---QNAQHQNAEHVRLQVPTTHVRSRP**S**SRGDERGHDSIQEKFFPPRFTQVPED |
| Pelecanus_crispus | ---QNTQHQNAENVRLQVPTTHVRSRP**S**SRGDERGHDAIQEKFFQPRFTQVPED |
| Egretta_garzetta | ---QNAQHQNAENIRLQVPTTHVRSRP**S**SRGEERGQDSIQEKFFQPRFTQVPED |
| Tyto_alba | ---QNAQHQNAENVRLQVPTTHIRSRP**S**SRGDERGHDSIQEKFFQPRFTQVPED |
| Falco_peregrinus | ---QNTQHQNAENIRLQVPTTHVRSRP**S**SRGDEHGHDSIQEKFFQPRFTQVPED |
| Nestor_notabilis | ---QNTQHQNAENIRLQVPTTHVRSRP**S**SRGDERGHDSIQEKFFQPRFTQVPED |
| Picoides_pubescens | ---QNAQHQNSENIRLQVPTTHVRSRP**S**SRGDERGHDSIQEKFFQPRFTQVPED |
| Opisthocomus_hoazin | ---QNAQHQNAENIRLQVPTTHVRSRP**S**SRGDERGQDSIQEKFFQPRFTQVPED |
| CLUSTAL | . *::* ::*** :**. .::* ***: *** **** |
| MYOT-S232P | --AQDSPQHNSEHARLQVPTSQVRSRS**P**SRGDVNDQDAIQEKFYPPRFIQVPEN |

FIG. 32

```
mammal1                           GEGSHPERVKVYGPGVEKTGLKANEPTYFTVDCSEAGQGDVSIGIKCAPGVVGPAEADIDFDIIKNDNDTFTVKYTPPGAGRYTIMVLFANQEIPASPFHIKV
mammal2                           GEGSHPEKVKVYGPGVEKTGLKANEPTYFTVDCSEAGQGDVSIGIKCAPGVVGPAEADIDFDIIKNDNDTFTVKYTPPGAGRYTIMVLFANQEIPASPFHIKV
mammal3                           GEGSHPERVKVYGPGVEKTGLKANEPTYFTVDCSEAGQGDVSIGIKCAPGVVGPAEADIDFDIIKNDNDTFTVKYTPPGAGHYTIMVLFANQEIPASPFHIKV
mammal4                           GEGSHPERVKVYGPGVEKTGLKANEPTYFTVDCSEAGQGDVSIGIKCAPGVVGPVEADIDFDIIKNDNDTFTVKYTPPGAGHYTIMVLFANQEIPASPFHIKV
mammal5                           GEGSHPERVKVYGPGVEKTGLKANEPTYFTVDCSEAGQGDVSIGIKCAPGVVGPAEADIDFDIIKNDNDTFTVKYTPPGAGQYTIMVLFANQEIPASPFHIKV
Carlito_syrichta                  GEGSHPERVKVYGPGVEKTGLKANEPTYFTVDCSEAGQGDVSIGIKCAPGVVGPAEADIDFDIIKNDNDTFTVKYTPPGAGRYTIMVLFANQEIPASPFNIKV
Cricetulus_griseus                GEGSHPERVKVYGPGVEKTGLKANEPTYFTVDCSEAGQGDVSIGIKCGPGVVGPVEADIDFDIIKNDNDTFTVKYTPPGAGHYTIMVLFANQEIPASPFHIKV
Condylura_cristata                GEGSHPDKVKVYGPGVEKTGLKANEPTYFTVDCSEAGQGDVSIGIKCAPGVVGPAEADIDFDIIKNDNDTFTVKYTPPGAGHYTIMVLFANQEIPASPFHIKV
marsupial1                        GEGSHPEKVRVYGPGVEKTGLKANEPTYFTVDCSEAGQGDVSIGIKCAPGVVGPAEADIDFDIIKNDNDTFTVKYTPPGAGHYTIMVLFANQEIPASPFHIKV
bird1                             GEGSHPSRVKVHGPGVEKTGLKANEPTYFTVDCSEAGQGDVSIGIKCAPGVVGPLEADIDFDIIKNDNDTFTVKYTAPGAGLYTIMVLFANQEIPSSPFRIKV
bird2                             GEGSHPGRVKVYGPGVEKTGLKANEPTYFTVDCSEAGQGDVSIGIKCAPGVVGPLEADIDFDIIKNDNDTFTVKYTPPGAGLYTIMVLFANQEIPSSPFRIKV
bird3                             GEGSHPGRVKVYGPGVEKTGLKANEPTYFTVDCSEAGQGDVSIGIKCAPGVVGPVEADIDFDIIKNDNDTFTVKYTPPGAGLYTIMVLFANQEIPSSPFRIKV
Haliaeetus_leucocephalus          GEGSHPGRVKVYGPGVEKSGLKANEPTYFTVDCSEAGQGDVSIGIKCAPGVVGPLEADIDFDIIKNDNDTFTVKYTPPGAGLYTIMVLFANQEIPSSPFRIKV
Anser_cygnoides_domesticus        GEGSHPGRVRVHGPGVEKTGLKAGEPTYFTVDCSEAGQGDVSIGIKCAPGVVGPLEADIDFDIIKNDNDTFTVKYTPPGAGLYTIMVLFANQEIPSSPFRIKV
Cuculus_canorus                   GEGSHPGRVKVYGPGVEKTGLKANEPTYFTVDCSEAGQGDVSIGIKCAPGVVGPLEADIDFDIIKNDNDTFTVKYTPPGAGLYTIMVLFANQEIPSSPFRISV
Columba_livia                     GEGSHPGRVKVYGPGVEKTGLKANEPTYFTVDCSEAGQGDVSIGIKCAPGVVGPLEADIDFDIIKNDNDTFTVKYTPPGAGLYTIMVLFANQEIPSSPFRVKV
Ficedula_albicollis               GEGSHPSRVKVHGPGVEKTGLKANEPTYFTVDCSEAGQGDVSIGIKCAPGVVGPLEADIDFDIIKNDNDTFTVKYTPPGAGLYTIMVLFANQEIPSSPFRIKV
Lepidothrix_coronata              GEGSHPGRVKVHGPGVEKTGLKANEPTYFTVDCSEAGQGDVSIGIKCAPGVVGPLEADIDFDIIKNDNDTFTVKYTAPGAGLYTIMVLFANQEIPSSPFRIKV
Python_bivittatus                 GEGSHPDKVKVYGPGVEKTGLKANEPTYFTVDCSEAGQGDVSIGIKCAPGVVGPVEADIDFDIIKNDNDTFTVKYTPPGPGRYTIMVLFASQEIPISPFHIKV
Protobothrops_mucrosquamatus      GEGSHPDKVKVYGPGVEKTGLKANEPTYFTVDCSEAGQGDVSIGIKCAPGVVGPAEADIDFDIIKNDNDTFTVKYTPPGPGRYTIMVLFATQEIPTSPFHIKV
Chelonia_mydas                    GEGSHPEKVKVYGPGVEKTGLKANEPTYFTVDCSEAGQGDVSIGIKCAPGVVGPVEADIEFDIIKNDNDTFTVKYTPPGAGRYTIMVLFANQEIPPSPFRIKV
Chrysemys_picta_bellii            GEGSHPDKVKVYGPGVEKTGLKANEPTYFTVDCSEAGQGDVSIGIKCAPGVVGPLEADIEFDIIKNDNDTFTVKYTPPGAGRYTIMVLFANQEIPTSPFRIKV
Gekko_japonicus                   GEGSHPDKVKVYGPGVEKTGLKASEPTYFTVDCSEAGQGDVSIGIKCAPGVVGPLEADIDFDIIKNDNDTFTVKYTPPGPGRYTIMVLFANQEIPISPFHIKV
Anolis_carolinensis               GEGSYPDKVKVYGPGVEKTGLKANEPTYFTVDCSDAGQGDVSIGIKCAPGVVGPVEADIDFDIIKNDNDTFTVKYTPPGPGRYTIMVLFANQEIPISPFHIKV
Alligator_mississippiensis        GEGSHPEKVRVYGPGVEKTGLKASEPTYFTVDCSEAGQGDVSIGIKCAPGVVGPAEADIDFDIIKNDNDTFTVKYTPPGAGLYTIMVLFANQEIPSSPFRIKV
Xenopus_tropicalis                GEGSHPNKVKVYGPGVEKTGLKANEPTYFTVDCSEAGQGDVSIGIKCAPGVVGPAEADIDFDIIKNDNDTFTVKYTPPGAGKYTIMVLFADQEIPTSPFRVKV
Xenopus_laevis                    GEGSHPSKVKVYGPGVEKTGLKASEPTYFTVDCSEAGQGDVSIGIKCAPGVLGPAEADIDFDIIKNDNDTFTVKYTPPGAGRYTIMVLFADQEIPISPFRVKV
Nanorana_parkeri                  GEGSHPNKVKVYGPGVEKTGLKANEPTYFTVDCSEAGQGDVSIGIKCAPGVVAPAEADIDFDIIKNDNDTFTVKYTPPGAGRYTIMVLFADQEIPISPFRVKV
fish1                             GEGSHPENVKVHGPGVEKTGLKANEPTYFTVDCSEAGQGDVSIGIKCAPGVVGPAEADIDFDIIKNDNDTFTVKYTPPGAGRYTIMVLFADQEIPISPFRIKV
fish2                             GEGSHPDRVKVYGPGVEKTGLKANEPTYFTVDCSEAGQGDISIGIKCAPGVVGPAEADIDFDIIKNDNDTFTVKYTPPGPGRYTIMVLFADQEIPVSPFKVKV
fish3                             GEGSHPENVKVYGPGVEKSGLKANEPTYFTVDCSEAGQGDVSIGIKCAPGVVGPAEADIDFDIIKNDNDTFTVKYTPPGPGRYTIMVLFADQEIPISPFRIKV
fish4                             GEGCHPAKVKVYGPGVEKTGLKANEPTYFTVDCAEAGQGDISIGIKCAPGVVGPAEADIDFDIIKNDNDTFTVKYTPPGAGKYTIMVLFAEQEIPISPFRIKV
Lepisosteus_oculatus              GEGSHPENVKVYGPGIEKTGLKANEPTYFTVDCSEAGQGDVSIGIKCAPGVVGPAEADIDFDIIKNDNDTFTVKYTPPGAGRYTIMVLFADQEIPISPFRIKV
Cynoglossus_semilaevis            GEGSHPEKVKVYGPGVEKTGLKANEPTYFTVDCSEAGQGDISIGIKCAPGVVGPAEADIDFDIIKNDNDTFTVKYTPPGAGKYTIMVLFADQEIPVSPFKVKV
Nothobranchius_furzeri            GEGSHPDKVKVYGPGVEKTGLKANEPTYFTVDCSEAGQGDISIGIKCAPGVVGPAEADIDFDIIKNDNDTFTVKYTPPGAGRYTIMVLFADQEIPISPFKVKV
Larimichthys_crocea               GEGSHPENVKVYGPGVEKTGLKANEPTYFTVDCSEAGQGDVSIGIKCAPGVVGPAEADIDFDIIKNDNDTFTVKYTPPGAGQYTIMVLFADQEIPISPFRIKV
Scleropages_formosus              GEGSHPENVKVYGPGVEKTGLKANEPTYFTVDCSEAGQGDVSIGIKCAPGVVGPAEADIDFDIIKNDNDTFTVKYTPPGPGRYTIMVLFADQEIPISPFRIKV
Lates_calcarifer                  GEGSHPDRVKVYGPGVEKTGLKANEPTYFTVDCSEAGQGDISIGIKCAPGVVGPAEADIDFDIIKNDNDTFTVKYTPPGPGRYTIMVLFADQEIPISPFKVKV
Clupea_harengus                   GEGCHPEKVKVYGPGVEKTGLKANEPTYFTVDCSEAGQGDISIGIKCAPGVVGPAEADIDFDIIKNDNDTFTVKYTPPGAGRYTIMVLFAEQEIPTSPYKVKV
Pundamilia_nyererei               GEGSHPDRVKVYGPGVEKTGLKANEPTYFTVDCSEAGQGDISIGIKCAPGVVGPAETDIDFDIIKNDNDTFTVKYTPPGPGRYTIMVLFADQEIPVSPFKVKV
Stegastes_partitus                GEGSHPDRVKVYGPGVEKTGLKANEPTYFTVDCGEAGQGDISIGIKCAPGVVGPAEADIDFDIIKNDNDTFTVKYTPPGPGRYTIMVLFADQEIPVSPFKVKV
Sinocyclocheilus_anshuiensis      GEGSHPENVKVHGPGVEKTGLKASEPTYFTVDCSEAGQGDVSIGIKCAPGVVGPAEADIDFDIIKNDNDTFTVKYTPPGAGRYTIMVLFADQEIPISPFRIKV
Esox_lucius                       GEGCHPDKVKVYGPGVEKTGLKANEPTYFTVDCAEAGQGDISIGIKCAPGVVGPAEADIDFDIIKNDNDTFTVKYTPPGAGKYTIMVLFAEQEIPISPFRVKV
Astyanax_mexicanus                GEGCHPDKVKVYGPGVEKTGLKSSEPTYFTVDCGEAGQGDISIGIKCAAGVVGTAEADIDFDIIKNDNDTFTVKYTPPAPGRYTVMVLFAEKEIPSSPYKVKV
Latimeria_chalumnae               GEGSHPENVKVYGPGVEKTGLKANEPTYFTVDCSEAGQGDVSIGIKCAPGVVGPAEADIDFDIIKNDNDTFTVKYTPPGAGRYTIMVLFADQEIPISPFRIKV
Callorhinchus_milii               GEGSHPNKVRVYGPGVEKAGLKANEPTYFTVDCSDAGQGDISIGIKCAPGVVGPAEADIDFDIIKNDNDTFTVKYTPPGAGRYTIMVLFADQEIPISPFRIKV
CLUSTAL                           ***.:* .*:*:***:**:***:.*********.:*****:******. **:.  *:**:**************** *. * **:***** :*** **:.:.*
FLNC-E753K                        GEGSHPEKVKVYGPGVEKTGLKANEPTYFTVDCSKAGQGDVSIGIKCAPGVVGPAEADIDFDIIKNDNDTFTVKYTPPGAGRYTIMVLFANQEIPASPFHIKV
```

FIG. 33

```
mammal1                        QPAVDTSGVKVSGPGVEPHGVLREVTTEFTVDARSLTATGGNHVTARVLNPSGAKTDTYVTDNGDGTYRVQYTAYEEGVHLVEVLYDEVAVPKSPFRVGV
mammal2                        QPAIDTSGVKVSGPGVEPHGVLREVTTEFTVDARSLTATGGNHVTARVLNPSGAKTDTYVTDNGDGTYRVQYTAYEEGVHLVEVLYDDVAVPKSPFRVGV
mammal3                        QPAVDTSGIKVSGPGVEPHGVLREVTTEFTVDARSLTATGGNHVTARVLNPSGAKTDTYVTDNGDGTYRVQYTAYEEGVHLVEVLYDEVAVPKSPFRVGV
mammal4                        QPAVDTSGVKVSGPGVEPHGVLREVTTEFTVDARSLTATGGNHVTARVLNPSGAKTDTYVTDNGDGTYRVQYTAYEEGVHLVEVLYDDVAVPKSPFRVGV
mammal5                        QPAVDTSGVKVSGPGVEPHGVLREVTTEFTVDARSLTATGGNHVTARVLNPSGAKTDTYVTDNGDGTYRVQYTAYEEGAHLVEVLYDDVAVPKSPFRVGV
mammal6                        QPAVDTSGVKVSGPGVEPHGVLREVTTEFTVDARSLTATGGNHVTARVLNPSGAKTDTYMTDNGDGTYRVQYTAYEEGVHLVEVLYDEVAVPKSPFRVGV
mammal7                        QPAVDTSGIKVSGPGVEPHGVLREVTTEFTVDARSLTATGGNHVTARVLNPSGAKTDTYVTDNGDGTYRVQYTAYEEGVHLVEVLYDDVAVPKSPFRVGV
mammal8                        QPAVDTSGIKVSGPGVEPHGVLREVTTEFTVDARSLTATGGNHITARVLNPSGAKTDTYVTDNGDGTYRVQYTAYEEGVHLVEVLYDDVAVPKSPFRVGV
mammal9                        QPAVDTSGVKVSGPGVEPHGVLREVTTEFTVDARSLTATGGNHVTARVLNPSGAKTDTYVTDNGDGTYRVQYTAYEEGMHLVEVLYDEVAVPKSPFRVGV
B._acutorostrata_scammoni      QPAVDTSGVKVSGPGVEPHGVLREVTTEFTVDARSLTATGGNHVTARVLNPSGAKTDTYMTDNGDGTYRVQYTAYEEGVHLVEVLYDDVAVPKSPFRVGV
Cebus_capucinus_imitator       QPAVDTSGVKVSGPGIEPHGVLREVTTEFTVDARSLTTTGGNHVTARVLNPSGAKTDTYMTDNGDGTYRVQYTAYEEGVHLVEVLYDEVAVPKSPFRVGV
Myotis_lucifugus               QPAVDTSGIKVSGPGVEPHGVLREVTTEFTVDARSLTATGGNHVTARVLNPSGAKTDTY-TDNGDGTYRVQYTAYEEGVHLVEVLYDEVAVPKSPFRVGV
Fukomys_damarensis             QPAVDTSGVKVSGPGVEPHGVLREVTTEFTVDARSLTTMGGNHVTARVLNPSGAKTDTYVTDNGDGTYRVQYTAYEEGVHLVEVLYDDVAVPKSPFRVGV
Orcinus_orca                   QPAVDTSGVKVSGPGVEPHGVLREVTTEFTVDARSLTATGGNHVTARVLNPSGAKTDTYLTDNGDGTYRVQYTAYEEGVHLVEVLYDDVAVPKSPFRVGV
Monodelphis_domestica          QPAVDTSGIKVSGPGVEPHGVLREVTTEFTVDARSLTATGGNHVTARVLNPSGAKTDTYVTDNGDGTYRVQYTAYEEGIHLVEVLYDDVAVPKSPFRVGV
Ornithorhynchus_anatinus       HPAVDTSGVKVSGPGVEPHGVLREVTTEFTVDARSLTATGGNHVTARVLNPSGAKTDTYITDNGDGTYRVQYTAYEEGVHLVEVLYDDVAVPKSPFRVGV
bird1                          -PAVDTSGVKVYGKGVEPRGVLREVGTDFTVDARALTKTGGPHVKAWVVNPSGAKTDTYITDHGDGTYRVDYTPYEDGMHRVEVTYNDVAVPKSPFRVGV
bird2                          -PAIDTSSVKVYGKGVEPRGVLREVGTEFTVDARALAPTGGPHIRARVLNPSGTPIDTFVTDLGDGTYRVEYTPFEEGLHLVEVTYDDVAVPKSPFRVGV
bird3                          -PAVDTSSVKVYGKGVEPRGVLREVGTEFTVDARALAPTGGPHVRARVLNPSGTPIDTFVTDLGDGTYRVEYTPFEEGLHLVEVTYDDVAVPKSPFRVGV
Picoides_pubescens             -PAVDTSGVKVYGKGVEPRGVLREVGTDFTVDARALTKVGGAHVKARVVNPSGATTETYVTDHGDGTYRVDYTPYEDGMHRVEVTYDDVAVPKSPFRVGV
Columba_livia                  -PAVDTSGVKVYGKGVEPRGVLREVATDFTVDARALTKTGGPHVAARVVNPSGATTDTYITDHGDGTYRVEYTPYEDGVHRVEVTYAEVAVPKSPFRVAV
Melopsittacus_undulatus        -PAVDTSGVKVYGKGVEPRGVLREVSTDFTVDARALTKTGGPHVTARVLNPSGAKTDTFITDLGDGTYRVEYTPYEDGVHRVEVLYDDVPVPKSPFRVAV
Sturnus_vulgaris               -PAVDTSSVKVYGKGVEPRGVLREVGTEFTVDARALAPTGGPHVRARVLNPSGTPIDTFVTDLVDGTYRVEYTPFEEGLHLVEVTYDDVAVPKSPFRVG-
Corvus_brachyrhynchos          -PAIDTSSVKVYGKGVEPRGVLREVGTEFMVDARALAPTGGPHIRARVLNPSGTPIDTFVTDLGDGTYRVEYTPFEEGXHLGEVTYDDVPVPKSPFRVGV
Lepidothrix_coronata           -PAVDTSSVKVYGKGVEPRGVLREVGTEFTVDARALAPAGGPHVRARVLNPSGTPIDTFVTDLGDGTYRVEYTPFEEGLHRVEVTYDDVAVPKSPFRVGV
Ficedula_albicollis            -PAVDTSSVKVYGKGVEPRGVLREVGTEFTVDARALAPTGGPHVRARVLNPAGTPIDTFVTDLGDGTYRVEYTPFEEGLHLVEVTYDEVAVPKSPFRVGV
Cuculus_canorus                -PAVDTSGVKVYGQGVEPRGVLREVGTEFMVDTRALSRTGGPHVGVRVLNPSGGTTDTRITDRGDGTYRVQYTPFEEGMHQVEVTYDDVPVPNSPFRVAV
Chrysemys_picta_bellii         QPAVDTSAVKVFGPGVEPRGVLREVTTEFTVDARSLTKTGGSHIKARVINPSGAKTETYLTDNGDGTYRVHYTAYEEGLHRVEVTYDEVPVPKSPFRVAV
Xenopus_tropicalis             EPAVDTSGVKVFGPGVEPRGVLREVTTEFTVDARSLTKTGGSHVTTRILGPSGAVTESFLSDNGDGTYHVQYTAYEDGVHLIEVLYDDVPVPKSPFRVPV
Xenopus_laevis                 EPAVDTSGVKVFGPGVEPRGVLREVTTEFTIDARSLTKTGGSHVTTRVLGPSGVVTESFISDNGDGTYHVQYTAYEDGVHLIEVLYDEVPVPKSPFRVPV
Nanorana_parkeri               EPAVDTSGVKVFGPGVEPRGVLREVATEFTVDARSLTKTGGSHVTTRIISPSGAVTESFISDNGDGTYHVQYTAYEDGIQLVEVLYNDVPVPKSPFRVGV
Protobothrops_mucrosquamatus   -PAVDTSNVKVFGPGVEPRGVLREVTTEFTVDARSLTKTGGNHVKVRVINPSGAKTDTYITDNGDGTYRVQYTPFEDGVHLVEVTYDDVPVPKSPFRVGV
Python_bivittatus              -PAVDTSNVKVFGPGVEPRGVLREVTTEFTVDARSLTKTGGTHIKVRVINPSGAKTDTYITDNGDGTYRVQYTPFEDGMHLVEVTYDDVPVPKSPFRVGV
Anolis_carolinensis            -PAVDTSNVKVFGPGVEPRGVLREVTTEFTVDARSLTKTGGNHIKVRVINPSGAKTDSYITDNGDGTYRVQYTPFEDGVHLVEVTYDDVPVPKSPFRVGV
Alligator_mississippiensis     -PAVDTSPIKVYGPGVEPRGVLREVTTEFTVDARALTKTGGSHIKARVVNPSGAKTDTYITDNADGTYRVQYTAYEDGVHRVEVTYDDVPVPKSPFRVAV
Chelonia_mydas                 QPAVDTSAVKVFGPGVEPRGVLREVTTEFTVDARSLTKTGGSHIKARVINPSGAKTETYLTDNGDGTYRVQYTAYEEGLHRVEVTYDEVPVPKSPFRVAV
fish1                          -PALDTSGIKVYGPGVEPRGVLREVTTHFVVDTRVHSKMGGNHIKVRIVNPSGANTDAYITDKGDGTYRVEYTAYEDGVHLIEVLYDDVPVPKSPFRVAV
Sinocyclocheilus_grahami       -PALDTSGIKVYGPGVEPRGVLREVTTHFVVDTRVHSKMGGNHIKVRIVNPSGANTDAYITDKGDCTYRVEYTAYEDGVHLIEVLYDDVPVPKSPFRVAV
Larimichthys_crocea            -PAIDTSGVKVYGPGVEPRGVLREVTTHFTVDALAHYKSGSSHVKACISNPSGANTDAYITDKGDGTYRVEYTPYEDGLHLIEVLFDEVSVPKSPFRVSV
Pygocentrus_nattereri          EPAVDTSGVKVYGPGVEPKGVLRDVTTHFIVDARAMNKTGGNHVKVRIINPSGSNTDAHITDKGDGTCRVEYTAFEDGVHVIEVFYDDVAVPKSPFRVSV
Astyanax_mexicanus             -PAVDTSGVKVFGPGVEPRGVLREVTTHFIVDTRAHNKTGGNHIKTRIVNPSGSNTDAYITDKGDGTYRVEYTAYEDGVHLIEVLYDEVSVPKSPFRVSV
Cyprinus_carpio                -PALDTSGIKVYGPGVEPRGVLREVTTHFVVDTRVHSKMGGNHIKVRIVNPTGANTDSYITDNGDGTYRVEYTAYEDGVHLIEVLYDDVPVPKSPFRVAV
Ictalurus_punctatus            EPAVNTSGVKVYGPGVEPTGVLREVSTHFIVDARSLTKMGGNHVTVRIVSPSGSITDAYITDKGDGTYRVEYTAFQDGMHLIEVLYDDVMVPNSPFRVSV
Clupea_harengus                EPAVDTTGVTVYGPGVEARGVLRDVTTHFIVDARAQTKSGGNHVKARIMNPSGNNTDAYLTDKGDGTYRVEYTAYEEGIHLIEVLYDDVPIPKSPFRVSV
Oncorhynchus_mykiss            DPAVDTSGVKVYGPGVEPRGVLREVTTHFIVDARAKSKTGGSHVKARIVNPTGANTDAYITDKGEGTYRVEYTAYEDGMHLIEVLYDDVAVPNSPFRVPV
Salmo_salar                    EPAVDTSGVQVYGPGVEPRGVLKEVTTHFIVDARKTTKSGGDHVKARIINPSGANTDAYITDKGDGTYRVEYTAFEDGMHLIEVLYDDVAVPKSPFRVSV
Esox_lucius                    EPAVDTSGVQVYGPGVEPRGVLKEVTTHFIVDARKTTKTGGDHVKACIINPSGTNTETYITDKGDGTYRVEYTAFEDGMHLIEVLYDDVAVPKSPFRVSV
Lepisosteus_oculatus           -PAVDTSGIKVYGPGIEPRGVLREVTTHFIVDVRTLNKTGGNHVKARIVNPSGAKTDAYITDKGDGTYRVEYTAYEDGIHLIEVLYDDVAVPKSPFRVAI
Latimeria_chalumnae            -PAVDTSTVKVFGPGVEPRGVLREVTTEFTVDACTLTKTGGNHVKVRILNPSGAKTDPYVTDKGDGTYRVEYTAYEDGIHLIEVLYDDVAVPKSPFRVAV
Callorhinchus_milii            -PAIDLSGVKVFGPGVEPRGVLREVTTEFTVDCRSVSRSGGAHVKARITNPSGAATDSYVRDNGDGTYRVEYSAYEDGLHVIEVLYDDIPLPKSPFRVGV
                                **:: : : * * *:*  ***::* *.* :*       *. *: . : .*:*   :   *  : * :*.*: :::* :  ** : :: :*:*****

FLNC-A1207T                    QPTIDTSGVKVSGPGVEPHGVLREVTTEFTVDARSLTATGGNHVTARVLNPSGAKTDTYVTDNGDGTYRVQYTAYEEGVHLVEVLYDDVAVPKSPFRVGV
```

FIG. 34 mammal1 MIPKEQKGPVMAAMGD-
LTEPVPTLDLGKKLSVPQDLMMEELSLRNNRGSLLFQKRQRRVQKFTFELAA-----
mammal2 MIPKEQKGPVMAAMGN-
FTEPVPTLDLGKKLSVPQDLMMEELSLRNNRGSLLFQKRQRRVQKFTFELAA-----
mammal3 MIPKEQKGPVMAAMGD-
LTEPVPTLDLGKKLSVPQDLMMEELSLRNNRGSLLFQKRQRRVQKFTFELAE-----
mammal4 MIPKEQKGPVMAAMED-
LAGPVPVLDLGKKLSVPQDLMMEELSLRNNRGSLLFQKRQRRVQKFTFEFAA-----
mammal5 MIPKEQKGPVMTTMGD-
LTEPVPLLDLGKKLSVPQDLMMEELSLRNNRGSLLFQKRQRRVQKFTFEFAA-----
mammal6 MIPKEQKGPVMAAMGD-
LTGPVPLLDLGKKLSVPQDLMMEELSLRNNRGSLLFQKRQRRVQRFTFEFAA-----
mammal7 MIPKEQKGPVMTTTGD-
LTEPVPLLDLGKKLSVPQDLMMEELSLRNNRGSLLFQKRQRRVQKFTFEFAA-----
mammal8 MIPKEQKGPVMAAMGD-
QATPVPLLDLGKKLSVPQDLMMEELSLRNNRGSLLFQKRQRRVQKFTFELAD-----
Propithecus_coquereli MIPKEQKGPVMAAMGD-
LAGPVPSLDLGKKLSVPQDLMIEELSLHNNRGSLLFQKRQRRVQKFTFELAE-----
Pongo_abelii MIPKEQKGPVMAAMGD-
LTEPVPMLDLGKKLSVPQDLMMEELSLRNNRGSLLFQKRQRRVQKFTFELAA-----
Callithrix_jacchus MIPKEQKGPVMAAMGN-
LTESVPTLDLGKKLSVPQDLMMEELSLCNNRGSLLFQKRQRRVQKFTFELAA-----
Macaca_mulatta MIPKEQKGPVMAAMGN-
FTEPVPTLDLGKKLSVPQDLMMEELSLCNNRGSLLFQKRQRRVQKFTFELAA-----
Chlorocebus_sabaeus MIPKEQKGPVMAAMGN-
FTEPVPTLDLGKKLSVPQDLMMEELSLPNNRGSLLFQKRQRRVQKFTFELAA-----
Camelus_bactrianus MIPKEQNGQVMTAMGD-
LTGPVPVLDLGKKLSVPQDLMMEELSLRNNRGSLLFQKRQRRVQKFTFEFTA-----
Vicugna_pacos MIPKEQNGQVMTAMGD-
LTGPVPVLDLGKKLSVPQDLMMEELSLRNNXGSLLFQKRQRRVQKFTFEFTD-----
Ursus_maritimus MIPKEQKGPAMAAVGD-
LSGPEPLLDLGKKLSVPQDLMMEELSLRNNRGSLLFQKRQRRVQRFTFEFAA-----
Ailuropoda melanoleuca MIPKEQKGPAMAAVGD-
LTGPEPLLDLGKKLSVPQDLMMEELSLRNNRGSLLFQKRQRRAQKFTFEFAA-----
Miniopterus natalensis MIPKEQKEPVMAAMGD-
QAGPVPLLDLGKKLSVPQDLMMEELSLRNNRGSLLFQKRQRRVQKFTFELAA-----
C. simum simum MIPKEQKGPVMAATGD-
LAGPVPLLDLGKKLSVPQDLMMEELSLRNNRGSLLFQKRQRRVQKFTFEFAA-----
Mustela putorius furo MIPKEQKGPVMAAMGD-
LAGPAPLLDLGKKLSVPQDLMMEELSLRNNKGSLLFQKRQRRVQRFTFEFAA-----
Felis catus MIPKEQKGSVMAAMGD-
LTEPVPLLDLGKKLSVPQDLMMEELSLRNNRGSLLFQKRQRRVQRFTFEFPA-----
Acinonyx jubatus MIPKEQKGSVMAAMGD-
LTGPVPLLDLGKKLSVPQDLMMEELSLRNNRGSLLFQKRQRRVQRFTFEFPA-----
Canis lupus familiaris MIPKEQKGSVMAAMGD-
LTGPVPLLDLGKKLSVPQDLMMEELSLRNNRGSLLFQKRQRRVQRFTFEFAA-----
Panthera tigris altaica MIPKEQKRPVMAAMGD-
LTGPVPLLDLGKKLSVPQDLMMEELSLRNNRGSLLFQKRQRRVQRFTFEFPA-----
Ochotona princeps MIPKDHKGPAVSAMGD-
FSEPVPLLDLGKKLSVPQDLMIEELSLRNNRGSLLFQKRQRRVQRFTFELPD-----
Oryctolagus cuniculus MIPKEQKGLAMSAPGD-
LSEPVPLLDLGKKLSVPQDLMIEELSLRNNRGSLLFQKRQRRVQRFTFELPD-----
I. tridecemlineatus MIPKEQKEPVMAVMGD-
LAGPVPTLDLGKKLSVPQDLMIEELSLRNNPGSLLFQKRQRRVQRFTFELEE-----
Marmota marmota marmota MIPREQKEPVMAVMGD-
LAGPVPLLDLGKKLSVPQDLMIEELSLRNNPGSLLFQKRQRRVQRFTFELEE-----
Tupaia chinensis MIPKEQKGPVTATMGD-
LCEPVPLLDLGKKLSVPQDLMMEELSLRNNRGSLLFQKRQRRVQRFTFELSA-----
Physeter catodon MIPKEQKGPVMTTMGD-
LTEPVPLLDLGKKLSVPQDLMMEELSLRNNRGSLLFQKRRRRVQKFTFEFAS-----
Panthera pardus MIPKEQKGPVMAAMGD-
LTGPVPLLDLGKKLSVPQDLMMEELSLRNNRGSLLFQKRQRRVQRFTFEFPA-----
Sarcophilus harrisii -VLKKQKALTMAKAQD-
FMETAPSLDLGKKVSVPQDLMVEELSLRSNRGSLLFQKRQRRVQRFTFEYAT-----

FIG. 34 CONT'D

```
Fukomys damarensis        ---MDPKEQQDAVIGD-
FTGPEPSLDLGKKVSVPQDLMIEELSLRNNRGSLLFQKRQRRVQRFTFELAA-----
Python bivittatus         ---
REQHAPIQAIAREIQRGKAPELDLGKKVSTPQDLMMEELSLPINRGSRLYQQRQKRVQRFVLEYPT------
Pelodiscus sinensis       ---RERKRQVAAILRE-
TAGDVLQLDLGKKVSVPQDLMVEELSLQSNRGSQLFQKRQKRVQKFILEHPMGYGAG
Chrysemys picta bellii    ---RERKKQAMAIVTE-
MMGDVPQLDLGKKVSIPQDLMVEELSLQTNRGSQLFQQRQKRVQKFILEHPTGYRA-
Chelonia mydas            ----ERKRQAIAIVRE-
MAEDVPQLDLGKKVSIPQDLMVEELSLQTNRGSQLFQQRQKRVQKFILEHPT------
Anolis carolinensis       ----
EQHAPVSAIMKEIREKYGPKLDLGKKVSIPQDLMMEELSLPVNRGSQLYQKRQKRVQQFVLERPTAY---
A. mississippiensis       --------
KRQAMIVRESPGDAPHLDLGKKVSIPQDLMMEELSLKTNRGSRLYQERQKRMQRFVLEHPS-----
Calidris pugnax           ----------VMTIMRP-
GPEDAPQLDLGKKMSTPQDLMIEELSLGNNRGSQLFHQRQKRMQRFVYEHPS-----
Chlamydotis macqueenii    -----------MTIMKP-
GPEDVPQLDLGKKMSTPQDLMIEELSLRNNRGSQLFQERQKRMQRFVFEYPR------
Monodelphis domestica     -----------MATVQD-
FMGAAPSLDLGKKVSIPQDLMVEELSLRSNRGSLLFQKRQKRVQRFTFEYAA------
Picoides pubescens        -----------MAIMKS-
GPEDVPRLDLGKKISTPQDLMIEELSLRDNRGSQLFQQRQRRMQRFIFEHPS------
Pelecanus crispus         -----------MTIMKP-
GPEDVPRLDLGKKMSTPQDLMIEELSLRNNRGSQLFQQRQRRMQRFIFEHPS------
Charadrius vociferus      -----------MTIMRP-
APEDAPQLDLGKKMSTPQDLMIEELSLRNNRGSQLFQQRQKRMQRFVFEHPS------
Pygoscelis adeliae        -----------MAIMRP-
GPEDAPRLDLGKKMSTPQDLMIEELSLRNNRGSQLFQQRQRRMQRFVFEHPS-----
Nipponia nippon           -----------------
VRDPVPQLDLGKKMSTPQDLMIEELSLRNNRGSQLFQQRQKRMQRFVFEHPS------
Egretta garzetta          ---------------------
EDAPRLDLGKKVSTPQDLMIEELSLRNNRGSQLFQQRQKRMQRFVFEHPG-----
Cathartes aura            ---------------------
PVPRLDLGKKVSVAQDLMIEELSLPNNRGSQLFQQRQRRMHGFLFLPGQ-----
Taeniopygia guttata       --------------------PEPQLDLGKKMSTTHDLMIEELSLPHNRGSRLFQQRQKRVQRFVLE-
-------
Corvus brachyrhynchos     ---------------------
PEPQLDLGKKMSTTQDVMIEELSLRNNRGSRLFQQRQKRMQRFVFEHPS-----
Columba livia             ---------------------
PAPQLDLGKKVSTPQDLMMEELSLRNNRGSRLFQQRQKRMQRFVFEHPRVGG--
Chaetura pelagica         ---------------------
PVPQLILGKKMSTPQDLMIEELSLRNNRGSQLFQQRQRRMQRFVFEHPS-----
Aptenodytes forsteri      ---------------------
PAPRLDLGKKVSTPQDLMIEELSLRNNRGSQLFQQRQRRMQRFVFEHPS-----
Tauraco erythrolophus     --------------------PAPRLDLGKKVSTPQDLMIEELSLRNNRGSQLFQQRQRRMQRFVFE-
-------
Alligator sinensis        ----------------------
APHLDLGKKVSIPQDLMMEELSLKTNRGSRLYQERQKRMQRFVLEHPS-----
S. camelus australis      ----------------------
APRLDLGKKVSTPQDVMIEELSLRTNRGSQLFQQRQRRMQRFIFEYPS-----
Tinamus guttatus          ----------------------
VPRLDLGKKVSTPQDVMIEELSLRTNRGSQLFQQRQRRMQRFIFEYPS-----
bird1                     -----------------------
PRLDLGKKMSTTQDLMIEELSLRNNRGSQLFQQRQRRMQRFIFEHPS-----
Pseudopodoces humilis     -----------------------
PQLDLGKKMSTAQDLMIEELSLQNNRGSRLFQQRQKRVQRFVFEHPR-----
Serinus canaria           -----------------------
PHLDLGKKMSTTHDLMIEELSLPNNRGSRLFQQRQKRVQRFVFEHPS-----
Parus major               -----------------------
PQLDLGKKMSTTQDLMIEELSLQNNRGSRLFQQRQKRVQRFVFEHPS-----
Zonotrichia albicollis    -----------------------
PQLDLGKKMSTTQDLMIEELSLPNNRGSRLFQQRQKRVQRFVFEHPS-----
Cuculus canorus           -----------------------
PRLDLGKKMSTPQDLMIEELSLRNNRGSQLFQQRQRRMQRFVFEHPS-----
A. australis mantelli     ------------------------
LDLGKKVSTPQDVMIEELSLRTNRGSQLFQQRQKRMQRFIFEYPS-----
CLUSTAL                                         * ****:*  :*:*:*****  * ** *:::*::* : *
```

FIG. 34 CONT'D

MYOZ3-S42L MIPKEQKGPVMAAMED-
LAGPVFVLDLGKKLSVPQDLMMEELLLRNNRGSLLFQKRQRRVQKFTFEFAA------

SEQUENCE LISTING

```
<160> NUMBER OF SEQ ID NOS: 307

<210> SEQ ID NO 1
<211> LENGTH: 2001
<212> TYPE: DNA
<213> ORGANISM: Equus

<400> SEQUENCE: 1

ctactgccaa cacaagtgac ttcatgtcta ttcctgtttt acgaaaggac aatctgtact     60

gtgtgctccc atttcaaaca caccaggggg tcatatcatc ctttgttgta aaagagtaat    120

ctgaaaaatg aaccactatc aattcgaagt ctagctaatt ttcataaatc atgtctgttg    180

aacagtctta ttaattctga ggatttcttg ctggagtatt agaaggttag tagaactaac    240

cacaattgta caaatacagc caacatagaa ttgttccttt caactacaac tacttaagtc    300

tgcttcattt caacctaaca attgcatatt aacattatca ttttgtttta aattcgagca    360

gcacaattca gaacacgcac gactacaagt tcctacatca caagtgaggt aaaaattttt    420

taattttaaa gacatatatt ttgctatgta aaatgtttc cgtttaaaag tgtactattt     480

cgaaagccct caagtttcct acataacttt tataaagaac aacgtgaatt ttctaatgtc    540

caacatcatg atcaaaattt ttatctgtta atcatcagac ctatctcgga ggaagttttt    600

aaaatgtttt ggtcaaataa gccaggacca tgtttccatg ttacacaagt ttcctatgac    660

aatggaaacc caattcttat tatacaatct ttgcacatga taagaattgt ccatggggta    720

ctctgcattt taacagatca gcttcttcat taattcgttg cactgtaaaa aggaaacaaa    780

gatgtataat ttgggccaga tgtttctaaa ttgctaccat ttctaccagt catcaaatat    840

accacagcta aatatagcct ctctccattg ttattacact atcagatcaa acccactcta    900

gggttttaaa tttgatgact aaactatatc tgtgtgaaag gaagagcaat gataattttc    960

cgcatggtga tgattaaact atttttgcag aagcagatca ccttcaaggg gagatgtgaa   1020

tgatcaggat gcaatccagg agaagtttta cccacctcgt ttcattcaag tgccagaaaa   1080

catgtcaatt gacgaaggaa gattctgcag aatggacttc aaagtaagag aagagttcaa   1140

aagtactgga ggaaaattaa caatgtgata ctaagttttg aaaaatgtgc tcttcctctt   1200

catagcttgc tccacagctt gagaagcagc acgtacagtg gagaagaaca ccaattctag   1260

agccaagctt acctggattt ggatcctggc tctgctactt tccagctgtg taacctcaga   1320

caagtcactt accctgtgct ttccttttct tttctatttt tttttaaaga ttggcacctg   1380

aactaacatc tgtttgcaat cttttttttt cttcttcttc ttcttcttct tcgccccaaa   1440

gccccctagc acatagttgt atgttctagt tgtgagtgcc tctggttgtg ctatgtggga   1500

cgtcacctca gcacagcctg accagcggtg ccacgtctgc actcaggatc cgaaccggca   1560

aaaccctggg ccgccacaga gcacgtgaac ttaaccgctt ggccacgggg gcagccccct   1620

atcctgtgct tttctcatct gcaaaacaag aataacaaat gtacctaact cataaagttg   1680
```

```
tttgaggatt aactgagtaa ataggcataa ggtactcaca atagtgccta caacctaata   1740

aatactctat ataagtgaag ctatcataat aggatttcta acgcagaatg cctctttaat   1800

tctcctccaa taagaaattc aatcaaccct cctttctctt gccctagaag aatttttcgg   1860

gctagaaagg cctacatttt tattaccctc attttggaga actttttctt agaaaatgtt   1920

ttcccgaatt cattatgaat gaaaggcagt gcatggattt aattgttaag gcttacataa   1980

aaacacttaa actgccattt g                                             2001


<210> SEQ ID NO 2
<211> LENGTH: 2001
<212> TYPE: DNA
<213> ORGANISM: Equus

<400> SEQUENCE: 2

actatggaaa acttgaaatt ttgttttctt actgataata atcttaaaaa catattttac     60

caaaaacgta tttttatact aataatttgt agttaaaaga tggtttgatt gaataagaca    120

ttggattccc aggtcagttt ctcagactgg cgtcccttga tccctagagg ttaatgaaca    180

tattcttggg tccaaaagta tctaattctt taaaagcttc atcattcaat ttgaggaaga    240

ttgatttagc ccagcctctc ccctgccaac atatttcaga gacctaggct gggagaccag    300

gccatgcaga cggcctagag ccctgtctcc tggctcccag ggtgcgccct ggccaccaga    360

atgcagagca ctaggctgtg tggcctgagg tctatggcgg ttggggcgct gggtgttggc    420

ggtgggtagg gaggacagcc ccaagccagc agagggcgtc ggtgctctga gaaggccaga    480

gtgctctaag taccttgctc ggatgatgcc cacaggacgc cgacggctgc cctatcgaca    540

tcaacgtctt caccactggc aacggcatct tccgctgctc ctacgtgccc accaagccca    600

ttaaacacac catcatcatc tcttggggag gtgtcaacgt gcccaagagc cccttccggg    660

tgcgtcctct gaaccctgcc tggtgcccac tgcccagggg tcccagaggg agggtgaagc    720

cctatgcagg agatgtcggc tgtcgctggg ccctggtcac tgctccccac ctcaaggccc    780

ccacgaagga gctaagattg atcccattaa ggctgaggcg cctagtgctg ggaagagga     840

tgggctttga gggaggggca ccatgctgag cattgacccc ttcccacagg taaacgtggg    900

agagggcagt caccctgaga aagtgaaggt gtacggccct ggcgtggaga agacgggcct    960

caaggccaac gagcccacct atttcaccgt ggactgcagc aaggcggggc aaggtgcacc   1020

agccaggcgg gggagtagga gacggggcct ggggcggggt ctgggtgggt agggctagta   1080

ctcctggcag agctgtttcc tggcagagct ctagtgggac tgctcaggtg gggcaggttg   1140

ttgagccccc atctcatggc ctcctgtctg cctaccctca ggcgatgtga gcattggcat   1200

caagtgcgcc cccggcgtgg tgggccccgc agaggctgac attgactttg acatcatcaa   1260

gaatgacaat gacaccttca cagtcaagta cacaccccca ggggccggcc gctacaccat   1320

catggtgctg tttgccaacc aggtaccctg ccctcagctt ttgatactca ctagcggcct   1380

acacctccca attctaaacc agcagcttga gatgctgtca tctggggaca attccacagc   1440

cattgactga gcacgttcct gtgtgtgggg agcatgcctc agaagaaaaa aaaggggctc   1500

tttcagagac tgcccttgtc caccatgacg aagccttttc tccatgcagg agatccctgc   1560

cagcccottc cacatcaagg tggacccatc ccatgatgcc agcaaggtca aggctgaggg   1620

ccctgggctg aaccgcacag gtaggtgtct gggcaggggc tgggctgggc tggggtttgc   1680

gctaggtggc tgccaggccc tcaccactgt ctctgggtgg gctccccagg tgtagaagtt   1740

gggaagccca ctcacttcac ggtgctgacc aagggagctg gcaaggctaa gctggacgtg   1800
```

```
cactttgccg gggccggcaa gggtgaggct gtgcgggact ttgagatcat cgacaaccac   1860

gactactcct ataccgtcaa gtacaccgcc gtccagcagg tgggctctgc cccctcccat   1920

gcccctgcct gtcctggcta atgggggtcc tgggtctcct tcctcacata gggccagttc   1980

tggatcttgg cccctttcct g                                             2001


<210> SEQ ID NO 3
<211> LENGTH: 2001
<212> TYPE: DNA
<213> ORGANISM: Equus

<400> SEQUENCE: 3

ccacccggta cctggcagcc ccttcactgt ggagggtgtc ctgccccccg acccctccaa     60

ggtgaggaga tagaagctga tgggagctgg gagttagggg cttgtaggga agatggatga    120

gtcacagggg cagaggtcag agggccttat gtcctggagt gggcacagcc aaggacccag    180

ggccagggcg atcccccacc ccaggacctc cttttgagac agcttagtta gtaagaacct    240

ggccttggat cagacctggg cttgaatccc aagtctacta actgggacaa attatttaat    300

ctctctgctt ccgtttctgc acctggaatt gttatagggc ctcagtctgt agtagctgct    360

acagttgaag atgcctggct gggtgggggg ccatgaaggc caagcacggg tgaggccaag    420

tgtagggaac tcacatacct gctcttccct ctaggtttgt gcttatggcc ctggtctcaa    480

gggtgggctg gtaggcagcc cagcgccgtt ctccatcgac accaaggggg ctggcaccgg    540

tggcctgggg ctgactgtgg agggcccctg tgaggccaag atcgagtgcc aggacaatgg    600

tgatggctca tgtgcggtca gctacctgcc cacggagccg ggcgagtaca ccatcaacat    660

cctgttcgcc gaagcccaca tccccggctc acccttcaag gctaccatcc ggcccgtgtt    720

cgacccgagc aaggtgcggg ccagtgggcc aggcctggag cgtggcaagg ctggtgaggc    780

agccaccttc actgtggact gctcggaggc gggcgaggct gagctgacca tcgagatcct    840

gtcagacgct ggcgtcaagg ccgaggtgct gatccacaac aatgctgacg gcacctacca    900

catcacctac agccccgcct tccccggcac ctacactatt accatcaagt acggtgggca    960

ccccgtaccc aaattcccca cccgcgtcca tgtgcagccc actatcgaca ccagtggagt   1020

caaggtctcg gggcctggtg tggagccgca cggtgagtga gagaggagcc aggagcccgt   1080

cagggagcca ggggaggcag cagaagggac ggaagcaagc ctgagtgctt agcagagcac   1140

catagtctga agggaggact tggggacagc cctggcgtcc ttagggctca gacaccccag   1200

agaagcagcc aagggtgcag gcggggcgtg gagctttgtc tctgctcttg tgacacaatt   1260

gcatctgccc atggacatgt ttctggggag attcttaact ttcattagct taaggggtcc   1320

ctgatctgag aaagctaaga accctgctct aggcagtgca gagggaaagc tttggggtag   1380

ggggtgacga gagccaggag acagctcagc tccattcagt aaatgagagt ggatcacctg   1440

ctgggggcca gaccctgggt taggcatgag ggtgggcgag ggacgtaaga cccagactca   1500

cccatgagcg gccctcagcc tggtggggca actgacgtga acagaatgtc accatatggt   1560

gaagcgagca aaggcagggg ctgtgggaga cagggcctgg agctcacagg ggtgcagagg   1620

gtggcctggc tcacgctagg aagcagtcag tggaaaggaa gagcagcctt ggagtcgggg   1680

agacgaaaag aggggtgagc aactgtgtga aggttgatcc cagcccatgc tgagctctct   1740

tctcctggga cccaggtgtc ctgcgtgagg tgaccactga gttcactgtg gatgcaagat   1800

ccctaacagc cacaggtggg aaccatgtga cggctcgtgt gctcaacccc tcgggtgcta   1860
```

```
agacggacac ctacgtgacg gacaacgggg atggcaccta ccgagtgcaa tacacagcct   1920

atgaagaggg tgaggggccg gctgggcggg gatgggggat ctgatcacag cattctcagg   1980

gcaggagggt gctggggccg c                                              2001
```

<210> SEQ ID NO 4
<211> LENGTH: 2001
<212> TYPE: DNA
<213> ORGANISM: Equus

<400> SEQUENCE: 4

```
tgttccagtt tttatctcca ggttagtttt ctcccatgaa cactggaccc acacattcag     60

ctcccttctc acatttgagt gtctacacag ctcttcaaat cttatatgcc caattttgga    120

gaccattagg agagttgaac atggactggg cattatataa aacaaaattt attcacttgg    180

aagggtagag acctttaatt gataaaagca agttataaag catgatacta tgattccatt    240

ttggttaaaa actcatatag gaatatatag tcattgaaaa agtatgaaat gatttacctg    300

aaagtgttaa tagtggcaat ctctgggtgg gaggcaattc ttttcttttt ctcttctatc    360

tgtattttct aactttcttc aatgcacata tgtgctattc ttataataat aagaggctat    420

tttgaattga aaagacctcg agtctaaaac tgaactcgat ctttcccgca ccttctcctc    480

ctccagccgt ccccacctca ggaggtggct ccatccttcc agtggctcag gccagagcct    540

ctccgtagac tcccaccctc tctctctcct agcccatacc catggctgac ctttaaggga    600

tatctagaat ctgatcattt ctcactactt ccaccactat gggcaaagag ctgcacagga    660

aattcacgga ataaatacaa atggccaaag aacgtctgaa atggggctca gtctcactga    720

gtgtcaaaca catgcaagtt aaactctgag gtgtcatttc tgcccatcag gtgggcaaag    780

attcggctga atgatgactc tcagtgtcgg taagtgtggg gagaaaccag gtttctcaca    840

cacaatggac agtgtgctga ggaggcctcc tgagaggcgg cagcctagga agcctgcggg    900

tttggtagta agagctgcct ctggcctctc ctggcagtcc ctgtgctgga cctgggcaag    960

aagctgagcg tgccccagga cctgatgatg gaagagctgt tgctccgcaa caaccgggga   1020

tccctcctct tccagaagag gcagcgccgc gtgcagaaat tcacctttga gtttgcagcc   1080

agccagcggg cggtgagtaa gcccccactg tgctcacagg gaaactgagg cccagagaga   1140

gccagtggtt agtctaaagc ccaacagtga gccaggggag gacctctggc ccctggggag   1200

tccctcaagc tccagctggg gaagactgtg atgttcccat cggactgagc cccgccctgc   1260

cgggtgatcc tagaaaaggg ttacctcttt aggcgtctcc ccagatgtga aacatgaagt   1320

ggcatgggca ggaggagctg tggagtgaag gactctggct cctataaaaa gggctgaagc   1380

atagtcatgt gctctgggct gaatttacag caagccggat ttaggttaga cttgagcttg   1440

atctaaggtg gaaaatgcag aatgcctttt tctcttcttc ccactggaag aaggaaaagg   1500

ccacggcaca gtctgctggt agagaaagga ggcgagagct gttcatcctc aggctgcaaa   1560

gaggcaggag gcagtttcag gtacttctaa ggaactcccg cacattccat ccagatgctg   1620

cttagtttct ggactagaca gggagcggct gagaggagtc atgtggccga atgataaaga   1680

cgacaaacac ctgcctccct ttgtgcccag gacggtgcta gctagcggct ttgcatctat   1740

catctcactt aatgctcaca gagtgagtta tcgtcatcac ctccatttta cagaggagga   1800

aactgaggct cagggaagtc aagtatctgt gcaaaataca atatctgtca atattataat   1860

agcaactaag acgcagagca tttctctgtc caggcgctgg gcacccggcc cccccatccc   1920

cggggaggtg ggcgttagga ttaggccacg ccctttttatt ttcttggagg gagaccctgg   1980
```

tccctttccc cgctgagccc t 2001

<210> SEQ ID NO 5
<211> LENGTH: 1497
<212> TYPE: DNA
<213> ORGANISM: Equus

<400> SEQUENCE: 5
atgtttaatt acgaacgtcc aaagcacttc atccaatccc aaaacccatg tggctccaga 60
ctgcagcctc ctggaccgga aacctccagc tactctagcc agaccaaaca gtcttccatt 120
atcatccagc cccgccagtg cacagagcaa agattttctg cctcctcaac aatgagctct 180
catatcacca tgtcctcctc tgctttccct gcttcttccc agcagcttgc tggctccaat 240
ccaggccaaa gggttacagc cacttataac cagtccccag ccagcttcct cagctccata 300
ttaccatcac agcctgatta cagtagcagt aaaatccctt ccactgtgga ctccaactat 360
caacaacctt catttggcca acctgtaaat gctaagccat cccaaagtgc gaatgctaag 420
cccataccaa ggactcctga ccatgaaatc caaggatcaa aggaagctct gattcaagat 480
ttggagagaa agctgaagtg caaggacagc cttcttcata acggaaatca acggctaaca 540
tacgaggaga agatggctcg cagattgcta ggaccacaga atgcagctgc ggtgtttcaa 600
gctcaaaatg acagtgaagc acaagattca cagcagcaca attcagaaca cgcacgacta 660
caagttccta catcacaagt gagaagcaga tcatcttcaa ggggagatgt gaatgatcag 720
gatgcaatcc aggagaagtt ttacccacct cgtttcattc aagtgccaga aaacatgtca 780
attgacgaag gaagattctg cagaatggac ttcaaagtga gcggactgcc agctcctgat 840
gtgtcatggt atctaaatgg aagaccagtt caatcagacg attttcacaa aatgatagtg 900
tctgaaaagg gttttcattc actcatcttt gaagttgtga gagcctcaga tgcaggggct 960
tatgcctgtg ttgccaggaa cagagcagga gaagccacct ttactgtgca gctggacgtc 1020
ctggcaaaag aacatagaag agcaccaatg tttatctaca aaccacaaag caaaaaagtt 1080
tttgagggag agtccgtgaa gctagaatgc caaatctcag ctatacctcc accaaagctt 1140
ttctggaaaa gaaacaatga aatggtgcat ttcaatactg atcgaatcag cttatatcat 1200
gataactctg gaagagtcac cttactgata aaagatgtaa acaagaaaga tgctgggtgg 1260
tatactgtgt ctgcagttaa cgaagctgga gtaacctcat gtaacacgag actagatgtt 1320
acagcccgtc caaaccaaac tcttccagct cctaagcagt tacgtgttcg accaactttc 1380
agcaagtatt tagcacttaa cgggagaggc ttgaatgtga aacaagcttt taatcctgaa 1440
ggagagtttc agcgcctggc agctcaatct ggactctatg aaagtgaaga actttaa 1497

<210> SEQ ID NO 6
<211> LENGTH: 8073
<212> TYPE: DNA
<213> ORGANISM: Equus

<400> SEQUENCE: 6
acgttcacgc gccggtgcaa cgagcacctc acgtgcgtgg tcaagcgcct gaccgacctg 60
cagcgagacc tcagcgacgg gctacgcctc atcgcgctgc tcgaggtact cagccagaag 120
cgcatgtatc gcaagttcca cccgcgtccc aacttccgtc agatgaagct ggagaacgtg 180
tccgtggccc tcgagttcct cgagcgcgag cacatcaagc ttgtgtccat cgacagcaag 240
gccatcgtgg atgggaacct gaagctgatc ctggggctga tctggacgtt gatcctgcac 300

```
tactccatct ccatgcccat gtgggaagat gaggatgatg aagatgcccg caaacagacg    360
cccaagcagc gtctgcttgg ctggatccag aacaaggtgc cccagctgcc catcactaac    420
ttcaaccgcg actggcagga tggcaaagct ctgggtgccc tggtggacaa ctgtgcccct    480
ggcctctgcc ctgactggga ggcctgggat cccaaccagc ctgtggagaa cgcccgggag    540
gccatgcagc aggcggacga ctggctcggg gtgccccagg tgattgcccc cgaggagatt    600
gtggacccca atgtagatga gcattctgtc atgacctacc tgtcccagtt ccccaaggcc    660
aagctcaaac ctggtgcccc tgttcgctcc aagcagctga accccaagaa ggccattgcc    720
tatgggcctg gcattgagcc ccagggcaac accgtgctgc agcctgccca cttcaccgtg    780
cagaccgtgg atgccggtgt gggcgaggtg ctggtctaca ttgaggatcc tgagggccac    840
accgaggagg ccaaggtggt tcccaacaat gacaaggacc gcacctatgc tgtctcctac    900
gtgcctaagg ttgctgggtt gcacaaggtg actgtgctct ttgctggcca gaacatcgaa    960
cgcagcccct ttgaggtgaa tgtgggcatg gcccttgggg atgccaacaa ggtgtcagcc   1020
cgtggccctg gcctggagcc tgtgggcaat gtggccaaca aacctaccta ctttgacatc   1080
tacactgcag gggccggcac tggtgatgtt gccgtggtga tcgtggaccc gcagggccgg   1140
cgggacacag tggaggtggc cctggaggac aagggcgaca gcacgttccg ctgcacatac   1200
aggcctgtga tggagggggcc ccacacagtg catgtggcct tcgctggtgc ccccatcacc   1260
cgcagtcctt tccccgtcca tgtggcagaa gcctgtaacc ccaatgcctg ccgcgcctct   1320
gggcggggcc tgcagcccaa gggtgtgcgg gtgaaagagg tggctgactt caaggtgttc   1380
accaagggcg ctggcagcgg agagctcaag gtcacagtca aggggccaaa gggcacagag   1440
gagctggtga aggtgcgaga ggctggggac ggtgtgttcg agtgtgagta ctaccctgtg   1500
gtgcctggga agtatgtggt gaccatcacg tggggcggct atgccatccc ccgcagtccc   1560
tttgaggtac aggtgagccc agaggcagga gcgcagaagg tacgggcctg ggggcctggt   1620
ttggaaactg gccaggtggg caagtcagct gactttgtgg tggaggccat tggcacggag   1680
gtggggacac tgggcttctc cattgagggg ccttcacagg ccaagatcga gtgtgatgac   1740
aagggggatg gctcctgcga tgtacggtac tggcccactg agcccgggga gtacgccgtg   1800
catgtcatct gcgatgatga ggacatccga gactcgccct tcattgccca catccagcca   1860
gccccacctg actgcttccc ggacaaggtg aaggcctttg ggcctggcct ggagcccact   1920
ggctgcatcg tggacaagcc tgcggagttc accattgatg cctctgcagc tggcaaggga   1980
gacctgaagc tctatgccca ggacgccgac ggctgcccta tcgacatcaa cgtcttcacc   2040
actggcaacg gcatcttccg ctgctcctac gtgcccacca agcccattaa acacaccatc   2100
atcatctctt ggggaggtgt caacgtgccc aagagcccct tccgggtaaa cgtgggagag   2160
ggcagtcacc ctgagaaagt gaaggtgtac ggccctggcg tggagaagac gggcctcaag   2220
gccaacgagc ccacctattt caccgtggac tgcagcgagg cggggcaagg cgatgtgagc   2280
attggcatca agtgcgcccc cggcgtggtg ggcccccgcag aggctgacat tgactttgac   2340
atcatcaaga atgacaatga caccttcaca gtcaagtaca cacccccagg ggccggccgc   2400
tacaccatca tggtgctgtt tgccaaccag gagatccctg ccagcccctt ccacatcaag   2460
gtggacccat cccatgatgc cagcaaggtc aaggctgagg gccctgggct gaaccgcaca   2520
ggtgtagaag ttgggaagcc cactcacttc acggtgctga ccaagggagc tggcaaggct   2580
aagctggacg tgcactttgc cggggccggc aagggtgagg ctgtgcggga ctttgagatc   2640
atcgacaacc acgactactc ctataccgtc aagtacaccg ccgtccagca gggcaacatg   2700
```

```
gcagtgacag tgacctatgg tggggacccc gtccccaaga gtccctttgt ggtgaatgtg   2760
gcacctccgc tggacctcag caaagtcaaa gttcaaggcc tcaacagtaa ggtggctgtg   2820
gggcaagaac aggcattctc tgtgaacaca cgaggggctg gtggtcaggg ccagctggat   2880
gtgcggatga cctcaccctc ccgacgaccg atcccctgca agctggagcc tgggggcgga   2940
gctgaagccc aggctgtgcg ctacatgcct cctgaggagg gtccctacaa ggtggacatt   3000
acctacgacg gccacccggt acctggcagc cccttcactg tggagggtgt cctgcccccc   3060
gacccctcca aggtttgtgc ttatggccct ggtctcaagg gtgggctggt aggcagccca   3120
gcgccgttct ccatcgacac caaggggct ggcaccggtg gcctggggct gactgtggag   3180
ggcccctgtg aggccaagat cgagtgccag gacaatggtg atggctcatg tgcggtcagc   3240
tacctgccca cggagccggg cgagtacacc atcaacatcc tgttcgccga agcccacatc   3300
cccggctcac ccttcaaggc taccatccgg cccgtgttcg acccgagcaa ggtgcgggcc   3360
agtgggccag gcctggagcg tggcaaggct ggtgaggcag ccaccttcac tgtggactgc   3420
tcggaggcgg gcgaggctga gctgaccatc gagatcctgt cagacgctgg cgtcaaggcc   3480
gaggtgctga tccacaacaa tgctgacggc acctaccaca tcacctacag ccccgccttc   3540
cccggcacct acactattac catcaagtac ggtgggcacc ccgtacccaa attccccacc   3600
cgcgtccatg tgcagcccgc tatcgacacc agtggagtca aggtctcggg gcctggtgtg   3660
gagccgcacg gtgtcctgcg tgaggtgacc actgagttca ctgtggatgc aagatcccta   3720
acagccacag gtgggaacca tgtgacggct cgtgtgctca acccctcggg tgctaagacg   3780
gacacctacg tgacggacaa cggggatggc acctaccgag tgcaatacac agcctatgaa   3840
gagggcgtac atttggtgga ggtgctgtat gatgacgtag ctgtgcccaa gagtcccttc   3900
cgagtgggtg tgaccgaggg ctgtgacccc acgcgtgttc gggcctatgg accaggcctg   3960
gagggtggct tggtcaacaa ggccaaccgc ttcactgtgg agaccagggg agcaggcact   4020
gggggcctag gcctagccat cgagggcccc tcggaagcca agatgtcctg caaagacaac   4080
aaggatggca gctgcaccgt agagtacatc cccttcaccc ctggagacta tgacgtcaat   4140
atcacctttg gggggcggcc catcccaggg agcccgttcc gggtgccagt gaaggatgtg   4200
gtggaccccg ggaaagtgaa atgctcagga ccagggctgg gggccggtgt cagggcccgg   4260
gtaccccaga ccttcacggt ggactgcagc caggctggcc gggccccct gcaggtggct   4320
gtgctgggcc ccacaggtgt ggctgagcct gtggagatac gtgacaatgg agatggcacc   4380
catgctgtcc actacacccc ggccactgat ggtccataca cggtagccgt caagtatgcc   4440
gaccaggaag tgccacgcag ccccttcaag atcaaggtgc ttccagccca tgatgccagc   4500
aaggtgcggg ccagtggccc tggcctcaac gccgctggca tccctgccag tctgcctgtg   4560
gagttcacca tcgatgcccg ggatgctggt gagggcttgc ttaccgtcca gatcctggac   4620
cccgagggta agcccaagaa ggccaacatc cgagacaatg ggatggcac atacaccgtg   4680
tcctacctgc cagacatgag tggccggtac accatcacca tcaagtacgg cggtgacgag   4740
atcccctact cacccttccg catccatgcc ctgcccactg ggacgccag caagtgcctc   4800
gtcacagtgt ccattggagg ccatggcctg ggtgcctgcc taggcccccg catccagatc   4860
ggggaggaga cggtgatcac agtggacgcc aaggcagcag gcaaggggaa ggtaacatgc   4920
acagtgtcca cgccggatgg ggcagagctc gacgtggacg tggttgagaa ccatgacggt   4980
acctttgaca tctactacac agcgcccgag ccgggcaagt acgtcatcac catccgcttt   5040
```

ggaggcgagc acatccccaa cagtcccttc catgtgctgg cgtgtgaccc catgccccac 5100
gtggaggagc cctctgacgt gttgcagctg caccggccca gcgcctaccc cacacactgg 5160
gccacagagg agccagtggt gcctgtggag ccaatggagt ctatgttgag gcccttcaac 5220
ctggtcatcc ccttcaccgt gcagaaaggg gagctcacag gggaggtacg gatgccctct 5280
gggaaaactg cccggcccaa tatcaccgac aacaaggatg gcaccatcac agtgaggtac 5340
gcgcccactg agaaaggcct gcaccagatg gggatcaagt atgatggcaa ccacatccct 5400
ggtgaccccc tgcagttcta tgtggatgcc atcaacagcc gccatgtcag tgcctacggg 5460
ccaggcctga gccatggcat ggtcaacaag ccggccacct tcaccattgt caccaaggat 5520
gctggggaag gggtctgtc actggccgtg gagggcccgt ccaaagcaga gatcacctgc 5580
aaggacaaca aggatggcac ctgcacggtg tcctacctac ccacagcgcc tggagactac 5640
agcatcatcg tgcgctttga tgacaagcac atcccgggga gccccttcac agccaagatc 5700
acaggcgatg actcgatgag gacgtcacag ctaaacgtgg gcacctccac ggatgtgtca 5760
ctgaagatca ccgagagtga cctgagcctg ctgaccgcca gcatccgtgc cccctcgggc 5820
aacgaggagc cctgcctgct gaagcgcctg cccaaccggc acattggcat ctccttcacc 5880
cccaaggaag ttggggagca tgtggtgagc gtgcgcaaga gtgggaagca cgtcaccaat 5940
agccccttca agatcctggt ggggccttct gagatcgggg acgctagcaa ggtgcgggtc 6000
tggggcaagg gcctgtccga gggacaaacc ttccaggtgg cggagttcat cgtggacact 6060
cgtaatgcag gttatggggg cctggggctg agtattgaag gccctagcaa ggtggacatc 6120
aactgtgagg acatggagga tggcacatgc aaagtcacct actgccccac tgaacccggc 6180
acctacatca tcaacatcaa gtttgctgac aagcatgtgc caggaagccc cttcactgtg 6240
aaggttaccg gtgagggccg catgaaggaa agcatcaccc ggcgcaggca ggcaccttcc 6300
atcgccacca ttggcagcac ctgtgacctc aacctcaaga tcccagggaa ctggttccag 6360
atggtgtctg cccaggagcg cctgacacgc accttcacgc gcagcagcca cacgtacacc 6420
cgcacagagc gcacggagat cagcaagacc cggggcggag agaccaagcg tgaggtgcgg 6480
gtggaggagt ccacccaggt tggcggagac cccttccccg cggtcttcgg ggacttcctg 6540
ggccgcgaac gcctgggctc ctttggcagc atcactcggc agcaggaggg tgaggccagc 6600
tctcaagaca tgaccgcaca ggtgaccagc ccatcgggca agacagaagc cgcagagatc 6660
gtcgaggggg aggacagtgc atacagcgtg cgctttgtgc cccaggagat ggggccccat 6720
actgtcactg tcaagtaccg tggccagcac gtgcccggca gcccctttca gttcactgtg 6780
gggccactgg gtgaaggtgg tgcccacaag gtgcgggctg gaggcacagg gctggagcga 6840
ggtgtggctg gcgtgccagc tgagttcagc atctggaccc gagaagcagg tgccgggggc 6900
ctgtcgattg ctgtggaggg tcccagcaag gcagagattg catttgagga ccgcaaagac 6960
ggctcctgtg gggtctccta tgttgtccag gaaccaggtg actatgaggt ctccatcaag 7020
ttcaatgatg agcacatccc agacagcccc tttgtggtgc ctgtggcctc cctctcagac 7080
gatgctcgcc gcctcactgt caccagcctc caggagacgg ggctcaaggt gaaccagcca 7140
gcgtcctttg cggtgcagct gaatggtgcg cggggcgtga tcgatgctag ggtgcacacg 7200
ccctcgggtg cggtggagga gtgctacgtc tccgagctgg acagtgacaa gcacaccatc 7260
cgcttcatcc cccacgagaa tggcgtccac tccatcgatg tcaagttcaa cggtgcccac 7320
atccctggca gtcccttcaa gatccgtgtt ggggagcaga gccaagctgg ggacccaggc 7380
ttggtgtcag cctatggtcc cgggctggag ggaggcacta caggtgtatc atcagagttc 7440

```
attgtcaaca ccctgaacgc gggctcaggg gccttgtctg tcaccatcga tggcccctcc   7500

aaggtgcagc tggactgtcg ggaatgtcct gagggccacg tggtcactta cactccccatg  7560

gcccctggca actacctcat cgccatcaag tatggtggcc cgcagcacat cgtgggcagc   7620

cccttcaagg ccaaagtcac aggtccccgg ctatcgggag gccacagcct tcacgaaaca   7680

tccacggttc tggtggagac tgtgaccaag tcatcctcaa gccggggctc cagctacagc   7740

tccatcccca agttctcctc ggatgccagc aaggtggtga cgcggggccc cgggctgtcc   7800

caggcctttg tgggccagaa gaactccttc accgtggact gcagcaaagc aggcatgctg   7860

agggggagag gggcagcctc ccagggcacc aacatgatga tggtgggtgt gcacgggccc   7920

aagacccccct gtgaggaggt gtatgtgaag cacatgggga accgggtgta caacgtcacc  7980

tacaccgtca aggagaaagg agactacatc ctcatcgtca agtggggcga cgaaagtgtc   8040

cccggaagcc ccttcaaagt caatgtgccc tga                                8073
```

<210> SEQ ID NO 7
<211> LENGTH: 8293
<212> TYPE: DNA
<213> ORGANISM: Equus

<400> SEQUENCE: 7

```
atggttttta tccactttac tctggccacc agttggctga gaatatatgt ggtggaaagt     60

actggaagat cacctaccac tgaggatcac tggtttgact tggatttaga agccaagatg    120

gaggtcacag tctggaaaga ccctggcgga aagccgcccc gtgggaagga agattccagc    180

agaatcacgt tcacgcgccg gtgcaacgag cacctcacgt gcgtggtcaa gcgcctgacc    240

gacctgcagc gagacctcag cgacgggcta cgcctcatcg cgctgctcga ggtactcagc    300

cagaagcgca tgtatcgcaa gttccacccg cgtcccaact tccgtcagat gaagctggag    360

aacgtgtccg tggccctcga gttcctcgag cgcgagcaca tcaagcttgt gtccatcgac    420

agcaaggcca tcgtggatgg gaacctgaag ctgatcctgg ggctgatctg gacgttgatc    480

ctgcactact ccatctccat gcccatgtgg gaagatgagg atgatgaaga tgcccgcaaa    540

cagacgccca agcagcgtct gcttggctgg atccagaaca aggtgcccca gctgcccatc    600

actaacttca accgcgactg gcaggatggc aaagctctgg gtgccctggt ggacaactgt    660

gcccctggcc tctgccctga ctgggaggcc tgggatccca accagcctgt ggagaacgcc    720

cgggaggcca tgcagcaggc ggacgactgg ctcggggtgc cccaggtgat tgcccccgag    780

gagattgtgg accccaatgt agatgagcat tctgtcatga cctacctgtc ccagttcccc    840

aaggccaagc tcaaacctgg tgcccctgtt cgctccaagc agctgaaccc caagaaggcc    900

attgcctatg ggcctggcat tgagccccag ggcaacaccg tgctgcagcc tgcccacttc    960

accgtgcaga ccgtggatgc cggtgtgggc gaggtgctgg tctacattga ggatcctgag   1020

ggccacaccg aggaggccaa ggtggttccc aacaatgaca aggaccgcac ctatgctgtc   1080

tcctacgtgc ctaaggttgc tgggttgcac aaggtgactg tgctctttgc tggccagaac   1140

atcgaacgca gcccctttga ggtgaatgtg ggcatggccc ttggggatgc caacaaggtg   1200

tcagcccgtg gccctggcct ggagcctgtg ggcaatgtgg ccaacaaacc tacctacttt   1260

gacatctaca ctgcaggggc cggcactggt gatgttgccg tggtgatcgt ggacccgcag   1320

ggccggcggg acacagtgga ggtggccctg gaggacaagg gcgacagcac gttccgctgc   1380

acatacaggc ctgtgatgga ggggccccac acagtgcatg tggccttcgc tggtgccccc   1440
```

atcacccgca gtcctttccc cgtccatgtg gcagaagagc ccttgccacc gctcgcccct 1500
tccgtgccca tcgtccacca ggccaagaga gtggtgccac cctgtaaccc caatgcctgc 1560
cgcgcctctg ggcggggcct gcagcccaag ggtgtgcggg tgaaagaggt ggctgacttc 1620
aaggtgttca ccaagggcgc tggcagcgga gagctcaagg tcacagtcaa ggggccaaag 1680
ggcacagagg agctggtgaa ggtgcgagag gctggggacg gtgtgttcga gtgtgagtac 1740
taccctgtgg tgcctgggaa gtatgtggtg accatcacgt ggggcggcta tgccatcccc 1800
cgcagtccct ttgaggtaca ggtgagccca gaggcaggag cgcagaaggt acgggcctgg 1860
gggcctggtt tggaaactgg ccaggtgggc aagtcagctg actttgtggt ggaggccatt 1920
ggcacggagg tggggacact gggcttctcc attgaggggc cttcacaggc caagatcgag 1980
tgtgatgaca agggggatgg ctcctgcgat gtacggtact ggcccactga gcccggggag 2040
tacgccgtgc atgtcatctg cgatgatgag gacatccgag actcgccctt cattgcccac 2100
atccagccag ccccacctga ctgcttcccg gacaaggtga aggcctttgg gcctggcctg 2160
gagcccactg gctgcatcgt ggacaagcct gcggagttca ccattgatgc ctctgcagct 2220
ggcaagggag acctgaagct ctatgcccag gacgccgacg gctgccctat cgacatcaac 2280
gtcttcacca ctggcaacgg catcttccgc tgctcctacg tgcccaccaa gcccattaaa 2340
cacaccatca tcatctcttg ggaggtgtc aacgtgccca agagcccctt ccgggtaaac 2400
gtgggagagg gcagtcaccc tgagaaagtg aaggtgtacg gccctggcgt ggagaagacg 2460
ggcctcaagg ccaacgagcc cacctatttc accgtggact gcagcgaggc ggggcaaggc 2520
gatgtgagca ttggcatcaa gtgcgccccc ggcgtggtgg gccccgcaga ggctgacatt 2580
gactttgaca tcatcaagaa tgacaatgac accttcacag tcaagtacac acccccaggg 2640
gccggccgct acaccatcat ggtgctgttt gccaaccagg agatccctgc cagcccccttc 2700 cacatcaagg tggacccatc ccatgatgcc agcaaggtca aggctgaggg ccctgggctg 2760
aaccgcacag gtgtagaagt tgggaagccc actcacttca cggtgctgac caagggagct 2820
ggcaaggcta agctggacgt gcactttgcc ggggccggca agggtgaggc tgtgcgggac 2880
tttgagatca tcgacaacca cgactactcc tataccgtca agtacaccgc cgtccagcag 2940
ggcaacatgg cagtgacagt gacctatggt ggggaccccg tccccaagag tccctttgtg 3000
gtgaatgtgg cacctccgct ggacctcagc aaagtcaaag ttcaaggcct caacagtaag 3060
gtggctgtgg ggcaagaaca ggcattctct gtgaacacac gaggggctgg tggtcagggc 3120
cagctggatg tgcggatgac ctcaccctcc cgacgaccga tcccctgcaa gctggagcct 3180
gggggcggag ctgaagccca ggctgtgcgc tacatgcctc ctgaggaggg tccctacaag 3240
gtggacatta cctacgacgg ccacccggta cctggcagcc ccttcactgt ggagggtgtc 3300
ctgccccccg accccctccaa ggtttgtgct tatggccctg gtctcaaggg tgggctggta 3360
ggcagcccag cgccgttctc catcgacacc aagggggctg gcaccggtgg cctggggctg 3420
actgtggagg gcccctgtga ggccaagatc gagtgccagg acaatggtga tggctcatgt 3480
gcggtcagct acctgcccac ggagccgggc gagtacacca tcaacatcct gttcgccgaa 3540
gcccacatcc ccggctcacc cttcaaggct accatccggc ccgtgttcga cccgagcaag 3600
gtgcgggcca gtgggccagg cctggagcgt ggcaaggctg gtgaggcagc caccttcact 3660
gtggactgct cggaggcggg cgaggctgag ctgaccatcg agatcctgtc agacgctggc 3720
gtcaaggccg aggtgctgat ccacaacaat gctgacggca cctaccacat cacctacagc 3780
cccgccttcc ccggcaccta cactattacc atcaagtacg gtgggcaccc cgtacccaaa 3840

```
ttccccaccc gcgtccatgt gcagcccgct atcgacacca gtggagtcaa ggtctcgggg   3900
cctggtgtgg agccgcacgg tgtcctgcgt gaggtgacca ctgagttcac tgtggatgca   3960
agatccctaa cagccacagg tgggaaccat gtgacggctc gtgtgctcaa cccctcgggt   4020
gctaagacgg acacctacgt gacggacaac ggggatggca cctaccgagt gcaatacaca   4080
gcctatgaag agggcgtaca tttggtggag gtgctgtatg atgacgtagc tgtgcccaag   4140
agtcccttcc gagtgggtgt gaccgagggc tgtgacccca cgcgtgttcg ggcctatgga   4200
ccaggcctgg agggtggctt ggtcaacaag gccaaccgct tcactgtgga gaccagggga   4260
gcaggcactg gggcctagg  cctagccatc gagggcccct cggaagccaa gatgtcctgc   4320
aaagacaaca aggatggcag ctgcaccgta gagtacatcc ccttcacccc tggagactat   4380
gacgtcaata tcacctttgg ggggcggccc atcccaggga gcccgttccg ggtgccagtg   4440
aaggatgtgg tggaccccgg gaaagtgaaa tgctcaggac cagggctggg ggccggtgtc   4500
agggcccggg taccccagac cttcacggtg gactgcagcc aggctggccg ggcccccctg   4560
caggtggctg tgctgggccc cacaggtgtg gctgagcctg tggagatacg tgacaatgga   4620
gatggcaccc atgctgtcca ctacaccccg gccactgatg gtccatacac ggtagccgtc   4680
aagtatgccg accaggaagt gccacgcagc cccttcaaga tcaaggtgct tccagcccat   4740
gatgccagca aggtgcgggc cagtggccct ggcctcaacg ccgctggcat ccctgccagt   4800
ctgcctgtgg agttcaccat cgatgcccgg gatgctggtg agggcttgct taccgtccag   4860
atcctggacc ccgagggtaa gcccaagaag gccaacatcc gagacaatgg ggatggcaca   4920
tacaccgtgt cctacctgcc agacatgagt ggccggtaca ccatcaccat caagtacggc   4980
ggtgacgaga tcccctactc acccttccgc atccatgccc tgcccactgg ggacgccagc   5040
aagtgcctcg tcacagtgtc cattggaggc catggcctgg gtgcctgcct aggcccccgc   5100
atccagatcg gggaggagac ggtgatcaca gtggacgcca aggcagcagg caaggggaag   5160
gtaacatgca cagtgtccac gccggatggg gcagagctcg acgtggacgt ggttgagaac   5220
catgacggta cctttgacat ctactacaca gcgcccgagc cgggcaagta cgtcatcacc   5280
atccgctttg gaggcgagca catccccaac agtcccttcc atgtgctggc gtgtgacccc   5340
atgccccacg tggaggagcc ctctgacgtg ttgcagctgc accggcccag cgcctacccc   5400
acacactggg ccacagagga gccagtggtg cctgtggagc caatggagtc tatgttgagg   5460
cccttcaacc tggtcatccc cttcaccgtg cagaaagggg agctcacagg ggaggtacgg   5520
atgccctctg ggaaaactgc ccggcccaat atcaccgaca acaaggatgg caccatcaca   5580
gtgaggtacg cgcccactga gaaaggcctg caccagatgg ggatcaagta tgatggcaac   5640
cacatccctg ggagccccct gcagttctat gtggatgcca tcaacagccg ccatgtcagt   5700
gcctacgggc caggcctgag ccatggcatg gtcaacaagc cggccacctt caccattgtc   5760
accaaggatg ctggggaagg gggtctgtca ctggccgtgg agggcccgtc caaagcagag   5820
atcacctgca aggacaacaa ggatggcacc tgcacggtgt cctacctacc cacagcgcct   5880
ggagactaca gcatcatcgt gcgctttgat gacaagcaca tcccggggag ccccttcaca   5940
gccaagatca caggcgatga ctcgatgagg acgtcacagc taaacgtggg cacctccacg   6000
gatgtgtcac tgaagatcac cgagagtgac ctgagcctgc tgaccgccag catccgtgcc   6060
ccctcgggca acgaggagcc ctgcctgctg aagcgcctgc ccaaccggca cattggcatc   6120
tccttcaccc ccaaggaagt tggggagcat gtggtgagcg tgcgcaagag tgggaagcac   6180
```

gtcaccaata gccccttcaa gatcctggtg gggccttctg agatcgggga cgctagcaag 6240
gtgcgggtct ggggcaaggg cctgtccgag ggacaaacct tccaggtggc ggagttcatc 6300
gtggacactc gtaatgcagg ttatgggggc ctggggctga gtattgaagg ccctagcaag 6360
gtggacatca actgtgagga catggaggat ggcacatgca aagtcaccta ctgcccccact 6420 gaacccggca cctacatcat caacatcaag tttgctgaca agcatgtgcc aggaagcccc 6480
ttcactgtga aggttaccgg tgagggccgc atgaaggaaa gcatcacccg gcgcaggcag 6540
gcaccttcca tcgccaccat tggcagcacc tgtgacctca acctcaagat cccagggaac 6600
tggttccaga tggtgtctgc ccaggagcgc ctgacacgca ccttcacgcg cagcagccac 6660
acgtacaccc gcacagagcg cacggagatc agcaagaccc ggggcggaga gaccaagcgt 6720
gaggtgcggg tggaggagtc cacccaggtt ggcggagacc ccttccccgc ggtcttcggg 6780
gacttcctgg gccgcgaacg cctgggctcc tttggcagca tcactcggca gcaggagggt 6840
gaggccagct ctcaagacat gaccgcacag gtgaccagcc catcgggcaa gacagaagcc 6900
gcagagatcg tcgagggggga ggacagtgca tacagcgtgc gctttgtgcc ccaggagatg 6960
gggccccata ctgtcactgt caagtaccgt ggccagcacg tgcccggcag ccccttttcag 7020 ttcactgtgg ggccactggg tgaaggtggt gcccacaagg tgcgggctgg aggcacaggg 7080
ctggagcgag gtgtggctgg cgtgccagct gagttcagca tctggacccg agaagcaggt 7140
gccgggggcc tgtcgattgc tgtggagggt cccagcaagg cagagattgc atttgaggac 7200
cgcaaagacg gctcctgtgg ggtctcctat gttgtccagg aaccaggtga ctatgaggtc 7260
tccatcaagt tcaatgatga gcacatccca gacagcccct ttgtggtgcc tgtggcctcc 7320
ctctcagacg atgctcgccg cctcactgtc accagcctcc aggagacggg gctcaaggtg 7380
aaccagccag cgtcctttgc ggtgcagctg aatggtgcgc ggggcgtgat cgatgctagg 7440
gtgcacacgc cctcgggtgc ggtggaggag tgctacgtct ccgagctgga cagtgacaag 7500
cacaccatcc gcttcatccc ccacgagaat ggcgtccact ccatcgatgt caagttcaac 7560
ggtgcccaca tccctggcag tcccttcaag atccgtgttg gggagcagag ccaagctggg 7620
gacccaggct tggtgtcagc ctatggtccc gggctggagg gaggcactac aggtgtatca 7680
tcagagttca ttgtcaacac cctgaacgcg ggctcagggg ccttgtctgt caccatcgat 7740
ggcccctcca aggtgcagct ggactgtcgg gaatgtcctg agggccacgt ggtcacttac 7800
actcccatgg cccctggcaa ctacctcatc gccatcaagt atggtggccc gcagcacatc 7860
gtgggcagcc ccttcaaggc caaagtcaca ggtccccggc tatcgggagg ccacagcctt 7920
cacgaaacat ccacggttct ggtggagact gtgaccaagt catcctcaag ccggggctcc 7980
agctacagct ccatccccaa gttctcctcg gatgccagca aggtggtgac gcggggcccc 8040
gggctgtccc aggcctttgt gggccagaag aactccttca ccgtggactg cagcaaagca 8100
ggcaggcacc aacatgatga tggtgggtgt gcacgggccc aagacccccct gtgaggaggt 8160 gtatgtgaag cacatgggga accgggtgta caacgtcacc tacaccgtca aggagaaagg 8220
agactacatc ctcatcgtca agtggggcga cgaaagtgtc cccggaagcc ccttcaaagt 8280
caatgtgccc tga 8293

<210> SEQ ID NO 8
<211> LENGTH: 738
<212> TYPE: DNA
<213> ORGANISM: Equus

<400> SEQUENCE: 8

```
atgatcccca aggagcagaa ggggcccgtg atggctgcca tggaggacct cgctggacca      60

gtccctgtgc tggacctggg caagaagctg agcgtgcccc aggacctgat gatggaagag     120

ctgtcgctcc gcaacaaccg ggatccctc ctcttccaga agaggcagcg ccgcgtgcag     180

aaattcacct ttgagtttgc agccagccag cgggcgaccg tggccggaag cgccaagggg     240

aaggtgcctg gagcagcaga gcccgggacg gtcaccaacg gccccgaggg gcagaactac     300

cgctcggagc tccacatctt cccggcctcg cccgggggcc ccgaggacgc gcagcccgca     360

gcctccgggg caaagagcgc ccgcagcccc agcgccctgg cgccaggcta cgcggagccc     420

ctgaagagcg tcccgcccga gaagttcaac cacacggcca tccccaaggg ctaccgctgc     480

ccgtggcagg agttcatcag ctaccgggac taccagagcg acggccgaag tcacacccct     540

agcccggccg agtatcggaa tttcaacaag accccggtgc cctttggagg acccctggtg     600

ggggaggccg tgcccagggc aggcacctcc ttcatcccag agctcaccag cggcttggaa     660

ctcctccgcc tgaggcccag cttcaacaga gtggcccagg gctgggtccg caacctcccg     720

gagtccgagg atctgtag                                                   738
```

```
<210> SEQ ID NO 9
<211> LENGTH: 498
<212> TYPE: PRT
<213> ORGANISM: Equus

<400> SEQUENCE: 9

Met Phe Asn Tyr Glu Arg Pro Lys His Phe Ile Gln Ser Gln Asn Pro
1               5                   10                  15

Cys Gly Ser Arg Leu Gln Pro Pro Gly Pro Glu Thr Ser Ser Tyr Ser
            20                  25                  30

Ser Gln Thr Lys Gln Ser Ser Ile Ile Ile Gln Pro Arg Gln Cys Thr
        35                  40                  45

Glu Gln Arg Phe Ser Ala Ser Ser Thr Met Ser Ser His Ile Thr Met
    50                  55                  60

Ser Ser Ser Ala Phe Pro Ala Ser Ser Gln Gln Leu Ala Gly Ser Asn
65                  70                  75                  80

Pro Gly Gln Arg Val Thr Ala Thr Tyr Asn Gln Ser Pro Ala Ser Phe
                85                  90                  95

Leu Ser Ser Ile Leu Pro Ser Gln Pro Asp Tyr Ser Ser Ser Lys Ile
            100                 105                 110

Pro Ser Thr Val Asp Ser Asn Tyr Gln Gln Pro Ser Phe Gly Gln Pro
        115                 120                 125

Val Asn Ala Lys Pro Ser Gln Ser Ala Asn Ala Lys Pro Ile Pro Arg
    130                 135                 140

Thr Pro Asp His Glu Ile Gln Gly Ser Lys Glu Ala Leu Ile Gln Asp
145                 150                 155                 160

Leu Glu Arg Lys Leu Lys Cys Lys Asp Ser Leu Leu His Asn Gly Asn
                165                 170                 175

Gln Arg Leu Thr Tyr Glu Glu Lys Met Ala Arg Arg Leu Leu Gly Pro
            180                 185                 190

Gln Asn Ala Ala Ala Val Phe Gln Ala Gln Asn Asp Ser Glu Ala Gln
        195                 200                 205

Asp Ser Gln Gln His Asn Ser Glu His Ala Arg Leu Gln Val Pro Thr
    210                 215                 220

Ser Gln Val Arg Ser Arg Ser Ser Ser Arg Gly Asp Val Asn Asp Gln
225                 230                 235                 240
```

```
Asp Ala Ile Gln Glu Lys Phe Tyr Pro Pro Arg Phe Ile Gln Val Pro
                245                 250                 255

Glu Asn Met Ser Ile Asp Glu Gly Arg Phe Cys Arg Met Asp Phe Lys
            260                 265                 270

Val Ser Gly Leu Pro Ala Pro Asp Val Ser Trp Tyr Leu Asn Gly Arg
        275                 280                 285

Pro Val Gln Ser Asp Asp Phe His Lys Met Ile Val Ser Glu Lys Gly
    290                 295                 300

Phe His Ser Leu Ile Phe Glu Val Val Arg Ala Ser Asp Ala Gly Ala
305                 310                 315                 320

Tyr Ala Cys Val Ala Arg Asn Arg Ala Gly Glu Ala Thr Phe Thr Val
                325                 330                 335

Gln Leu Asp Val Leu Ala Lys Glu His Arg Arg Ala Pro Met Phe Ile
            340                 345                 350

Tyr Lys Pro Gln Ser Lys Lys Val Phe Glu Gly Glu Ser Val Lys Leu
        355                 360                 365

Glu Cys Gln Ile Ser Ala Ile Pro Pro Pro Lys Leu Phe Trp Lys Arg
    370                 375                 380

Asn Asn Glu Met Val His Phe Asn Thr Asp Arg Ile Ser Leu Tyr His
385                 390                 395                 400

Asp Asn Ser Gly Arg Val Thr Leu Leu Ile Lys Asp Val Asn Lys Lys
                405                 410                 415

Asp Ala Gly Trp Tyr Thr Val Ser Ala Val Asn Glu Ala Gly Val Thr
            420                 425                 430

Ser Cys Asn Thr Arg Leu Asp Val Thr Ala Arg Pro Asn Gln Thr Leu
        435                 440                 445

Pro Ala Pro Lys Gln Leu Arg Val Arg Pro Thr Phe Ser Lys Tyr Leu
    450                 455                 460

Ala Leu Asn Gly Arg Gly Leu Asn Val Lys Gln Ala Phe Asn Pro Glu
465                 470                 475                 480

Gly Glu Phe Gln Arg Leu Ala Ala Gln Ser Gly Leu Tyr Glu Ser Glu
                485                 490                 495

Glu Leu
```

<210> SEQ ID NO 10
<211> LENGTH: 498
<212> TYPE: PRT
<213> ORGANISM: Equus

<400> SEQUENCE: 10

```
Met Phe Asn Tyr Glu Arg Pro Lys His Phe Ile Gln Ser Gln Asn Pro
1               5                   10                  15

Cys Gly Ser Arg Leu Gln Pro Pro Gly Pro Glu Thr Ser Ser Tyr Ser
            20                  25                  30

Ser Gln Thr Lys Gln Ser Ser Ile Ile Ile Gln Pro Arg Gln Cys Thr
        35                  40                  45

Glu Gln Arg Phe Ser Ala Ser Ser Thr Met Ser Ser His Ile Thr Met
    50                  55                  60

Ser Ser Ser Ala Phe Pro Ala Ser Ser Gln Gln Leu Ala Gly Ser Asn
65                  70                  75                  80

Pro Gly Gln Arg Val Thr Ala Thr Tyr Asn Gln Ser Pro Ala Ser Phe
                85                  90                  95

Leu Ser Ser Ile Leu Pro Ser Gln Pro Asp Tyr Ser Ser Ser Lys Ile
            100                 105                 110
```

```
Pro Ser Thr Val Asp Ser Asn Tyr Gln Gln Pro Ser Phe Gly Gln Pro
        115                 120                 125

Val Asn Ala Lys Pro Ser Gln Ser Ala Asn Ala Lys Pro Ile Pro Arg
    130                 135                 140

Thr Pro Asp His Glu Ile Gln Gly Ser Lys Glu Ala Leu Ile Gln Asp
145                 150                 155                 160

Leu Glu Arg Lys Leu Lys Cys Lys Asp Ser Leu Leu His Asn Gly Asn
                165                 170                 175

Gln Arg Leu Thr Tyr Glu Glu Lys Met Ala Arg Arg Leu Leu Gly Pro
            180                 185                 190

Gln Asn Ala Ala Ala Val Phe Gln Ala Gln Asn Asp Ser Glu Ala Gln
        195                 200                 205

Asp Ser Gln Gln His Asn Ser Glu His Ala Arg Leu Gln Val Pro Thr
    210                 215                 220

Ser Gln Val Arg Ser Arg Ser Pro Ser Arg Gly Asp Val Asn Asp Gln
225                 230                 235                 240

Asp Ala Ile Gln Glu Lys Phe Tyr Pro Pro Arg Phe Ile Gln Val Pro
                245                 250                 255

Glu Asn Met Ser Ile Asp Glu Gly Arg Phe Cys Arg Met Asp Phe Lys
            260                 265                 270

Val Ser Gly Leu Pro Ala Pro Asp Val Ser Trp Tyr Leu Asn Gly Arg
        275                 280                 285

Pro Val Gln Ser Asp Asp Phe His Lys Met Ile Val Ser Glu Lys Gly
    290                 295                 300

Phe His Ser Leu Ile Phe Glu Val Val Arg Ala Ser Asp Ala Gly Ala
305                 310                 315                 320

Tyr Ala Cys Val Ala Arg Asn Arg Ala Gly Glu Ala Thr Phe Thr Val
                325                 330                 335

Gln Leu Asp Val Leu Ala Lys Glu His Arg Arg Ala Pro Met Phe Ile
            340                 345                 350

Tyr Lys Pro Gln Ser Lys Lys Val Phe Glu Gly Glu Ser Val Lys Leu
        355                 360                 365

Glu Cys Gln Ile Ser Ala Ile Pro Pro Pro Lys Leu Phe Trp Lys Arg
    370                 375                 380

Asn Asn Glu Met Val His Phe Asn Thr Asp Arg Ile Ser Leu Tyr His
385                 390                 395                 400

Asp Asn Ser Gly Arg Val Thr Leu Leu Ile Lys Asp Val Asn Lys Lys
                405                 410                 415

Asp Ala Gly Trp Tyr Thr Val Ser Ala Val Asn Glu Ala Gly Val Thr
            420                 425                 430

Ser Cys Asn Thr Arg Leu Asp Val Thr Ala Arg Pro Asn Gln Thr Leu
        435                 440                 445

Pro Ala Pro Lys Gln Leu Arg Val Arg Pro Thr Phe Ser Lys Tyr Leu
    450                 455                 460

Ala Leu Asn Gly Arg Gly Leu Asn Val Lys Gln Ala Phe Asn Pro Glu
465                 470                 475                 480

Gly Glu Phe Gln Arg Leu Ala Ala Gln Ser Gly Leu Tyr Glu Ser Glu
                485                 490                 495

Glu Leu
```

<210> SEQ ID NO 11
<211> LENGTH: 2690
<212> TYPE: PRT

<213> ORGANISM: Equus

<400> SEQUENCE: 11

```
Thr Phe Thr Arg Arg Cys Asn Glu His Leu Thr Cys Val Val Lys Arg
1               5                   10                  15

Leu Thr Asp Leu Gln Arg Asp Leu Ser Asp Gly Leu Arg Leu Ile Ala
            20                  25                  30

Leu Leu Glu Val Leu Ser Gln Lys Arg Met Tyr Arg Lys Phe His Pro
        35                  40                  45

Arg Pro Asn Phe Arg Gln Met Lys Leu Glu Asn Val Ser Val Ala Leu
    50                  55                  60

Glu Phe Leu Glu Arg Glu His Ile Lys Leu Val Ser Ile Asp Ser Lys
65                  70                  75                  80

Ala Ile Val Asp Gly Asn Leu Lys Leu Ile Leu Gly Leu Ile Trp Thr
                85                  90                  95

Leu Ile Leu His Tyr Ser Ile Ser Met Pro Met Trp Glu Asp Glu Asp
            100                 105                 110

Asp Glu Asp Ala Arg Lys Gln Thr Pro Lys Gln Arg Leu Leu Gly Trp
        115                 120                 125

Ile Gln Asn Lys Val Pro Gln Leu Pro Ile Thr Asn Phe Asn Arg Asp
    130                 135                 140

Trp Gln Asp Gly Lys Ala Leu Gly Ala Leu Val Asp Asn Cys Ala Pro
145                 150                 155                 160

Gly Leu Cys Pro Asp Trp Glu Ala Trp Asp Pro Asn Gln Pro Val Glu
                165                 170                 175

Asn Ala Arg Glu Ala Met Gln Gln Ala Asp Asp Trp Leu Gly Val Pro
            180                 185                 190

Gln Val Ile Ala Pro Glu Glu Ile Val Asp Pro Asn Val Asp Glu His
        195                 200                 205

Ser Val Met Thr Tyr Leu Ser Gln Phe Pro Lys Ala Lys Leu Lys Pro
    210                 215                 220

Gly Ala Pro Val Arg Ser Lys Gln Leu Asn Pro Lys Lys Ala Ile Ala
225                 230                 235                 240

Tyr Gly Pro Gly Ile Glu Pro Gln Gly Asn Thr Val Leu Gln Pro Ala
                245                 250                 255

His Phe Thr Val Gln Thr Val Asp Ala Gly Val Gly Glu Val Leu Val
            260                 265                 270

Tyr Ile Glu Asp Pro Glu Gly His Thr Glu Glu Ala Lys Val Val Pro
        275                 280                 285

Asn Asn Asp Lys Asp Arg Thr Tyr Ala Val Ser Tyr Val Pro Lys Val
    290                 295                 300

Ala Gly Leu His Lys Val Thr Val Leu Phe Ala Gly Gln Asn Ile Glu
305                 310                 315                 320

Arg Ser Pro Phe Glu Val Asn Val Gly Met Ala Leu Gly Asp Ala Asn
                325                 330                 335

Lys Val Ser Ala Arg Gly Pro Gly Leu Glu Pro Val Gly Asn Val Ala
            340                 345                 350

Asn Lys Pro Thr Tyr Phe Asp Ile Tyr Thr Ala Gly Ala Gly Thr Gly
        355                 360                 365

Asp Val Ala Val Val Ile Val Asp Pro Gln Gly Arg Arg Asp Thr Val
    370                 375                 380

Glu Val Ala Leu Glu Asp Lys Gly Asp Ser Thr Phe Arg Cys Thr Tyr
385                 390                 395                 400
```

-continued

```
Arg Pro Val Met Glu Gly Pro His Thr Val His Val Ala Phe Ala Gly
                405                 410                 415

Ala Pro Ile Thr Arg Ser Pro Phe Pro Val His Val Ala Glu Ala Cys
            420                 425                 430

Asn Pro Asn Ala Cys Arg Ala Ser Gly Arg Gly Leu Gln Pro Lys Gly
        435                 440                 445

Val Arg Val Lys Glu Val Ala Asp Phe Lys Val Phe Thr Lys Gly Ala
    450                 455                 460

Gly Ser Gly Glu Leu Lys Val Thr Val Lys Gly Pro Lys Gly Thr Glu
465                 470                 475                 480

Glu Leu Val Lys Val Arg Glu Ala Gly Asp Gly Val Phe Glu Cys Glu
                485                 490                 495

Tyr Tyr Pro Val Val Pro Gly Lys Tyr Val Val Thr Ile Thr Trp Gly
            500                 505                 510

Gly Tyr Ala Ile Pro Arg Ser Pro Phe Glu Val Gln Val Ser Pro Glu
        515                 520                 525

Ala Gly Ala Gln Lys Val Arg Ala Trp Gly Pro Gly Leu Glu Thr Gly
    530                 535                 540

Gln Val Gly Lys Ser Ala Asp Phe Val Val Glu Ala Ile Gly Thr Glu
545                 550                 555                 560

Val Gly Thr Leu Gly Phe Ser Ile Glu Gly Pro Ser Gln Ala Lys Ile
                565                 570                 575

Glu Cys Asp Asp Lys Gly Asp Gly Ser Cys Asp Val Arg Tyr Trp Pro
            580                 585                 590

Thr Glu Pro Gly Glu Tyr Ala Val His Val Ile Cys Asp Asp Glu Asp
        595                 600                 605

Ile Arg Asp Ser Pro Phe Ile Ala His Ile Gln Pro Ala Pro Pro Asp
    610                 615                 620

Cys Phe Pro Asp Lys Val Lys Ala Phe Gly Pro Gly Leu Glu Pro Thr
625                 630                 635                 640

Gly Cys Ile Val Asp Lys Pro Ala Glu Phe Thr Ile Asp Ala Ser Ala
                645                 650                 655

Ala Gly Lys Gly Asp Leu Lys Leu Tyr Ala Gln Asp Ala Asp Gly Cys
            660                 665                 670

Pro Ile Asp Ile Asn Val Phe Thr Thr Gly Asn Gly Ile Phe Arg Cys
        675                 680                 685

Ser Tyr Val Pro Thr Lys Pro Ile Lys His Thr Ile Ile Ile Ser Trp
    690                 695                 700

Gly Gly Val Asn Val Pro Lys Ser Pro Phe Arg Val Asn Val Gly Glu
705                 710                 715                 720

Gly Ser His Pro Glu Lys Val Lys Val Tyr Gly Pro Gly Val Glu Lys
                725                 730                 735

Thr Gly Leu Lys Ala Asn Glu Pro Thr Tyr Phe Thr Val Asp Cys Ser
            740                 745                 750

Glu Ala Gly Gln Gly Asp Val Ser Ile Gly Ile Lys Cys Ala Pro Gly
        755                 760                 765

Val Val Gly Pro Ala Glu Ala Asp Ile Asp Phe Asp Ile Ile Lys Asn
    770                 775                 780

Asp Asn Asp Thr Phe Thr Val Lys Tyr Thr Pro Pro Gly Ala Gly Arg
785                 790                 795                 800

Tyr Thr Ile Met Val Leu Phe Ala Asn Gln Glu Ile Pro Ala Ser Pro
                805                 810                 815

Phe His Ile Lys Val Asp Pro Ser His Asp Ala Ser Lys Val Lys Ala
```

```
            820                 825                 830

Glu Gly Pro Gly Leu Asn Arg Thr Gly Val Glu Val Gly Lys Pro Thr
        835                 840                 845

His Phe Thr Val Leu Thr Lys Gly Ala Gly Lys Ala Lys Leu Asp Val
    850                 855                 860

His Phe Ala Gly Ala Gly Lys Gly Glu Ala Val Arg Asp Phe Glu Ile
865                 870                 875                 880

Ile Asp Asn His Asp Tyr Ser Tyr Thr Val Lys Tyr Thr Ala Val Gln
                885                 890                 895

Gln Gly Asn Met Ala Val Thr Val Thr Tyr Gly Gly Asp Pro Val Pro
            900                 905                 910

Lys Ser Pro Phe Val Val Asn Val Ala Pro Pro Leu Asp Leu Ser Lys
        915                 920                 925

Val Lys Val Gln Gly Leu Asn Ser Lys Val Ala Val Gly Gln Glu Gln
    930                 935                 940

Ala Phe Ser Val Asn Thr Arg Gly Ala Gly Gly Gln Gly Gln Leu Asp
945                 950                 955                 960

Val Arg Met Thr Ser Pro Ser Arg Arg Pro Ile Pro Cys Lys Leu Glu
                965                 970                 975

Pro Gly Gly Gly Ala Glu Ala Gln Ala Val Arg Tyr Met Pro Pro Glu
            980                 985                 990

Glu Gly Pro Tyr Lys Val Asp Ile Thr Tyr Asp Gly His Pro Val Pro
        995                 1000                1005

Gly Ser Pro Phe Thr Val Glu Gly Val Leu Pro Pro Asp Pro Ser Lys
    1010                1015                1020

Val Cys Ala Tyr Gly Pro Gly Leu Lys Gly Gly Leu Val Gly Ser Pro
1025                1030                1035                1040

Ala Pro Phe Ser Ile Asp Thr Lys Gly Ala Gly Thr Gly Gly Leu Gly
                1045                1050                1055

Leu Thr Val Glu Gly Pro Cys Glu Ala Lys Ile Glu Cys Gln Asp Asn
            1060                1065                1070

Gly Asp Gly Ser Cys Ala Val Ser Tyr Leu Pro Thr Glu Pro Gly Glu
        1075                1080                1085

Tyr Thr Ile Asn Ile Leu Phe Ala Glu Ala His Ile Pro Gly Ser Pro
    1090                1095                1100

Phe Lys Ala Thr Ile Arg Pro Val Phe Asp Pro Ser Lys Val Arg Ala
1105                1110                1115                1120

Ser Gly Pro Gly Leu Glu Arg Gly Lys Ala Gly Glu Ala Ala Thr Phe
                1125                1130                1135

Thr Val Asp Cys Ser Glu Ala Gly Glu Ala Glu Leu Thr Ile Glu Ile
            1140                1145                1150

Leu Ser Asp Ala Gly Val Lys Ala Glu Val Leu Ile His Asn Asn Ala
        1155                1160                1165

Asp Gly Thr Tyr His Ile Thr Tyr Ser Pro Ala Phe Pro Gly Thr Tyr
    1170                1175                1180

Thr Ile Thr Ile Lys Tyr Gly Gly His Pro Val Pro Lys Phe Pro Thr
1185                1190                1195                1200

Arg Val His Val Gln Pro Ala Ile Asp Thr Ser Gly Val Lys Val Ser
                1205                1210                1215

Gly Pro Gly Val Glu Pro His Gly Val Leu Arg Glu Val Thr Thr Glu
            1220                1225                1230

Phe Thr Val Asp Ala Arg Ser Leu Thr Ala Thr Gly Gly Asn His Val
        1235                1240                1245
```

```
Thr Ala Arg Val Leu Asn Pro Ser Gly Ala Lys Thr Asp Thr Tyr Val
    1250                1255                1260

Thr Asp Asn Gly Asp Gly Thr Tyr Arg Val Gln Tyr Thr Ala Tyr Glu
1265                1270                1275                1280

Glu Gly Val His Leu Val Glu Val Leu Tyr Asp Asp Val Ala Val Pro
                1285                1290                1295

Lys Ser Pro Phe Arg Val Gly Val Thr Glu Gly Cys Asp Pro Thr Arg
            1300                1305                1310

Val Arg Ala Tyr Gly Pro Gly Leu Glu Gly Gly Leu Val Asn Lys Ala
        1315                1320                1325

Asn Arg Phe Thr Val Glu Thr Arg Gly Ala Gly Thr Gly Gly Leu Gly
    1330                1335                1340

Leu Ala Ile Glu Gly Pro Ser Glu Ala Lys Met Ser Cys Lys Asp Asn
1345                1350                1355                1360

Lys Asp Gly Ser Cys Thr Val Glu Tyr Ile Pro Phe Thr Pro Gly Asp
                1365                1370                1375

Tyr Asp Val Asn Ile Thr Phe Gly Gly Arg Pro Ile Pro Gly Ser Pro
            1380                1385                1390

Phe Arg Val Pro Val Lys Asp Val Val Asp Pro Gly Lys Val Lys Cys
        1395                1400                1405

Ser Gly Pro Gly Leu Gly Ala Gly Val Arg Ala Arg Val Pro Gln Thr
    1410                1415                1420

Phe Thr Val Asp Cys Ser Gln Ala Gly Arg Ala Pro Leu Gln Val Ala
1425                1430                1435                1440

Val Leu Gly Pro Thr Gly Val Ala Glu Pro Val Glu Ile Arg Asp Asn
                1445                1450                1455

Gly Asp Gly Thr His Ala Val His Tyr Thr Pro Ala Thr Asp Gly Pro
            1460                1465                1470

Tyr Thr Val Ala Val Lys Tyr Ala Asp Gln Glu Val Pro Arg Ser Pro
        1475                1480                1485

Phe Lys Ile Lys Val Leu Pro Ala His Asp Ala Ser Lys Val Arg Ala
    1490                1495                1500

Ser Gly Pro Gly Leu Asn Ala Ala Gly Ile Pro Ala Ser Leu Pro Val
1505                1510                1515                1520

Glu Phe Thr Ile Asp Ala Arg Asp Ala Gly Glu Gly Leu Leu Thr Val
                1525                1530                1535

Gln Ile Leu Asp Pro Glu Gly Lys Pro Lys Lys Ala Asn Ile Arg Asp
            1540                1545                1550

Asn Gly Asp Gly Thr Tyr Thr Val Ser Tyr Leu Pro Asp Met Ser Gly
        1555                1560                1565

Arg Tyr Thr Ile Thr Ile Lys Tyr Gly Gly Asp Glu Ile Pro Tyr Ser
    1570                1575                1580

Pro Phe Arg Ile His Ala Leu Pro Thr Gly Asp Ala Ser Lys Cys Leu
1585                1590                1595                1600

Val Thr Val Ser Ile Gly Gly His Gly Leu Gly Ala Cys Leu Gly Pro
                1605                1610                1615

Arg Ile Gln Ile Gly Glu Glu Thr Val Ile Thr Val Asp Ala Lys Ala
            1620                1625                1630

Ala Gly Lys Gly Lys Val Thr Cys Thr Val Ser Thr Pro Asp Gly Ala
        1635                1640                1645

Glu Leu Asp Val Asp Val Val Glu Asn His Asp Gly Thr Phe Asp Ile
    1650                1655                1660
```

```
Tyr Tyr Thr Ala Pro Glu Pro Gly Lys Tyr Val Ile Thr Ile Arg Phe
1665                1670                1675                1680

Gly Gly Glu His Ile Pro Asn Ser Pro Phe His Val Leu Ala Cys Asp
                1685                1690                1695

Pro Met Pro His Val Glu Glu Pro Ser Asp Val Leu Gln Leu His Arg
            1700                1705                1710

Pro Ser Ala Tyr Pro Thr His Trp Ala Thr Glu Glu Pro Val Val Pro
        1715                1720                1725

Val Glu Pro Met Glu Ser Met Leu Arg Pro Phe Asn Leu Val Ile Pro
    1730                1735                1740

Phe Thr Val Gln Lys Gly Glu Leu Thr Gly Glu Val Arg Met Pro Ser
1745                1750                1755                1760

Gly Lys Thr Ala Arg Pro Asn Ile Thr Asp Asn Lys Asp Gly Thr Ile
                1765                1770                1775

Thr Val Arg Tyr Ala Pro Thr Glu Lys Gly Leu His Gln Met Gly Ile
            1780                1785                1790

Lys Tyr Asp Gly Asn His Ile Pro Gly Asp Pro Leu Gln Phe Tyr Val
        1795                1800                1805

Asp Ala Ile Asn Ser Arg His Val Ser Ala Tyr Gly Pro Gly Leu Ser
    1810                1815                1820

His Gly Met Val Asn Lys Pro Ala Thr Phe Thr Ile Val Thr Lys Asp
1825                1830                1835                1840

Ala Gly Glu Gly Gly Leu Ser Leu Ala Val Glu Gly Pro Ser Lys Ala
                1845                1850                1855

Glu Ile Thr Cys Lys Asp Asn Lys Asp Gly Thr Cys Thr Val Ser Tyr
            1860                1865                1870

Leu Pro Thr Ala Pro Gly Asp Tyr Ser Ile Ile Val Arg Phe Asp Asp
        1875                1880                1885

Lys His Ile Pro Gly Ser Pro Phe Thr Ala Lys Ile Thr Gly Asp Asp
    1890                1895                1900

Ser Met Arg Thr Ser Gln Leu Asn Val Gly Thr Ser Thr Asp Val Ser
1905                1910                1915                1920

Leu Lys Ile Thr Glu Ser Asp Leu Ser Leu Leu Thr Ala Ser Ile Arg
                1925                1930                1935

Ala Pro Ser Gly Asn Glu Glu Pro Cys Leu Leu Lys Arg Leu Pro Asn
            1940                1945                1950

Arg His Ile Gly Ile Ser Phe Thr Pro Lys Glu Val Gly Glu His Val
        1955                1960                1965

Val Ser Val Arg Lys Ser Gly Lys His Val Thr Asn Ser Pro Phe Lys
    1970                1975                1980

Ile Leu Val Gly Pro Ser Glu Ile Gly Asp Ala Ser Lys Val Arg Val
1985                1990                1995                2000

Trp Gly Lys Gly Leu Ser Glu Gly Gln Thr Phe Gln Val Ala Glu Phe
                2005                2010                2015

Ile Val Asp Thr Arg Asn Ala Gly Tyr Gly Gly Leu Gly Leu Ser Ile
            2020                2025                2030

Glu Gly Pro Ser Lys Val Asp Ile Asn Cys Glu Asp Met Glu Asp Gly
        2035                2040                2045

Thr Cys Lys Val Thr Tyr Cys Pro Thr Glu Pro Gly Thr Tyr Ile Ile
    2050                2055                2060

Asn Ile Lys Phe Ala Asp Lys His Val Pro Gly Ser Pro Phe Thr Val
2065                2070                2075                2080

Lys Val Thr Gly Glu Gly Arg Met Lys Glu Ser Ile Thr Arg Arg Arg
```

```
                2085                2090                2095

Gln Ala Pro Ser Ile Ala Thr Ile Gly Ser Thr Cys Asp Leu Asn Leu
            2100                2105                2110

Lys Ile Pro Gly Asn Trp Phe Gln Met Val Ser Ala Gln Glu Arg Leu
        2115                2120                2125

Thr Arg Thr Phe Thr Arg Ser Ser His Thr Tyr Thr Arg Thr Glu Arg
    2130                2135                2140

Thr Glu Ile Ser Lys Thr Arg Gly Gly Glu Thr Lys Arg Glu Val Arg
2145                2150                2155                2160

Val Glu Glu Ser Thr Gln Val Gly Gly Asp Pro Phe Pro Ala Val Phe
                2165                2170                2175

Gly Asp Phe Leu Gly Arg Glu Arg Leu Gly Ser Phe Gly Ser Ile Thr
            2180                2185                2190

Arg Gln Gln Glu Gly Glu Ala Ser Ser Gln Asp Met Thr Ala Gln Val
        2195                2200                2205

Thr Ser Pro Ser Gly Lys Thr Glu Ala Ala Glu Ile Val Glu Gly Glu
    2210                2215                2220

Asp Ser Ala Tyr Ser Val Arg Phe Val Pro Gln Glu Met Gly Pro His
2225                2230                2235                2240

Thr Val Thr Val Lys Tyr Arg Gly Gln His Val Pro Gly Ser Pro Phe
                2245                2250                2255

Gln Phe Thr Val Gly Pro Leu Gly Glu Gly Gly Ala His Lys Val Arg
            2260                2265                2270

Ala Gly Gly Thr Gly Leu Glu Arg Gly Val Ala Gly Val Pro Ala Glu
        2275                2280                2285

Phe Ser Ile Trp Thr Arg Glu Ala Gly Ala Gly Gly Leu Ser Ile Ala
    2290                2295                2300

Val Glu Gly Pro Ser Lys Ala Glu Ile Ala Phe Glu Asp Arg Lys Asp
2305                2310                2315                2320

Gly Ser Cys Gly Val Ser Tyr Val Val Gln Glu Pro Gly Asp Tyr Glu
                2325                2330                2335

Val Ser Ile Lys Phe Asn Asp Glu His Ile Pro Asp Ser Pro Phe Val
            2340                2345                2350

Val Pro Val Ala Ser Leu Ser Asp Asp Ala Arg Arg Leu Thr Val Thr
        2355                2360                2365

Ser Leu Gln Glu Thr Gly Leu Lys Val Asn Gln Pro Ala Ser Phe Ala
    2370                2375                2380

Val Gln Leu Asn Gly Ala Arg Gly Val Ile Asp Ala Arg Val His Thr
2385                2390                2395                2400

Pro Ser Gly Ala Val Glu Glu Cys Tyr Val Ser Glu Leu Asp Ser Asp
                2405                2410                2415

Lys His Thr Ile Arg Phe Ile Pro His Glu Asn Gly Val His Ser Ile
            2420                2425                2430

Asp Val Lys Phe Asn Gly Ala His Ile Pro Gly Ser Pro Phe Lys Ile
        2435                2440                2445

Arg Val Gly Glu Gln Ser Gln Ala Gly Asp Pro Gly Leu Val Ser Ala
    2450                2455                2460

Tyr Gly Pro Gly Leu Glu Gly Gly Thr Thr Gly Val Ser Ser Glu Phe
2465                2470                2475                2480

Ile Val Asn Thr Leu Asn Ala Gly Ser Gly Ala Leu Ser Val Thr Ile
                2485                2490                2495

Asp Gly Pro Ser Lys Val Gln Leu Asp Cys Arg Glu Cys Pro Glu Gly
            2500                2505                2510
```

```
His Val Val Thr Tyr Thr Pro Met Ala Pro Gly Asn Tyr Leu Ile Ala
        2515                2520                2525

Ile Lys Tyr Gly Gly Pro Gln His Ile Val Gly Ser Pro Phe Lys Ala
    2530                2535                2540

Lys Val Thr Gly Pro Arg Leu Ser Gly Gly His Ser Leu His Glu Thr
2545                2550                2555                2560

Ser Thr Val Leu Val Glu Thr Val Thr Lys Ser Ser Ser Ser Arg Gly
                2565                2570                2575

Ser Ser Tyr Ser Ser Ile Pro Lys Phe Ser Ser Asp Ala Ser Lys Val
            2580                2585                2590

Val Thr Arg Gly Pro Gly Leu Ser Gln Ala Phe Val Gly Gln Lys Asn
        2595                2600                2605

Ser Phe Thr Val Asp Cys Ser Lys Ala Gly Met Leu Arg Gly Arg Gly
    2610                2615                2620

Ala Ala Ser Gln Gly Thr Asn Met Met Met Val Gly Val His Gly Pro
2625                2630                2635                2640

Lys Thr Pro Cys Glu Glu Val Tyr Val Lys His Met Gly Asn Arg Val
                2645                2650                2655

Tyr Asn Val Thr Tyr Thr Val Lys Glu Lys Gly Asp Tyr Ile Leu Ile
            2660                2665                2670

Val Lys Trp Gly Asp Glu Ser Val Pro Gly Ser Pro Phe Lys Val Asn
        2675                2680                2685

Val Pro
    2690


<210> SEQ ID NO 12
<211> LENGTH: 2700
<212> TYPE: PRT
<213> ORGANISM: Equus

<400> SEQUENCE: 12

Thr Phe Thr Arg Arg Cys Asn Glu His Leu Thr Cys Val Val Lys Arg
1               5                   10                  15

Leu Thr Asp Leu Gln Arg Asp Leu Ser Asp Gly Leu Arg Leu Ile Ala
            20                  25                  30

Leu Leu Glu Val Leu Ser Gln Lys Arg Met Tyr Arg Lys Phe His Pro
        35                  40                  45

Arg Pro Asn Phe Arg Gln Met Lys Leu Glu Asn Val Ser Val Ala Leu
    50                  55                  60

Glu Phe Leu Glu Arg Glu His Ile Lys Leu Val Ser Ile Asp Ser Lys
65                  70                  75                  80

Ala Ile Val Asp Gly Asn Leu Lys Leu Ile Leu Gly Leu Ile Trp Thr
                85                  90                  95

Leu Ile Leu His Tyr Ser Ile Ser Met Pro Met Trp Glu Asp Glu Asp
            100                 105                 110

Asp Glu Asp Ala Arg Lys Gln Thr Pro Lys Gln Arg Leu Leu Gly Trp
        115                 120                 125

Ile Gln Asn Lys Val Pro Gln Leu Pro Ile Thr Asn Phe Asn Arg Asp
    130                 135                 140

Trp Gln Asp Gly Lys Ala Leu Gly Ala Leu Val Asp Asn Cys Ala Pro
145                 150                 155                 160

Gly Leu Cys Pro Asp Trp Glu Ala Trp Asp Pro Asn Gln Pro Val Glu
                165                 170                 175

Asn Ala Arg Glu Ala Met Gln Gln Ala Asp Asp Trp Leu Gly Val Pro
```

-continued 180 185 190

Gln Val Ile Ala Pro Glu Glu Ile Val Asp Pro Asn Val Asp Glu His
195 200 205

Ser Val Met Thr Tyr Leu Ser Gln Phe Pro Lys Ala Lys Leu Lys Pro
210 215 220

Gly Ala Pro Val Arg Ser Lys Gln Leu Asn Pro Lys Lys Ala Ile Ala
225 230 235 240

Tyr Gly Pro Gly Ile Glu Pro Gln Gly Asn Thr Val Leu Gln Pro Ala
245 250 255

His Phe Thr Val Gln Thr Val Asp Ala Gly Val Gly Glu Val Leu Val
260 265 270

Tyr Ile Glu Asp Pro Glu Gly His Thr Glu Glu Ala Lys Val Val Pro
275 280 285

Asn Asn Asp Lys Asp Arg Thr Tyr Ala Val Ser Tyr Val Pro Lys Val
290 295 300

Ala Gly Leu His Lys Val Thr Val Leu Phe Ala Gly Gln Asn Ile Glu
305 310 315 320

Arg Ser Pro Phe Glu Val Asn Val Gly Met Ala Leu Gly Asp Ala Asn
325 330 335

Lys Val Ser Ala Arg Gly Pro Gly Leu Glu Pro Val Gly Asn Val Ala
340 345 350

Asn Lys Pro Thr Tyr Phe Asp Ile Tyr Thr Ala Gly Ala Gly Thr Gly
355 360 365

Asp Val Ala Val Val Ile Val Asp Pro Gln Gly Arg Arg Asp Thr Val
370 375 380

Glu Val Ala Leu Glu Asp Lys Gly Asp Ser Thr Phe Arg Cys Thr Tyr
385 390 395 400

Arg Pro Val Met Glu Gly Pro His Thr Val His Val Ala Phe Ala Gly
405 410 415

Ala Pro Ile Thr Arg Ser Pro Phe Pro Val His Val Ala Glu Glu Pro
420 425 430

Leu Pro Pro Leu Ala Pro Ser Val Pro Ile Val His Gln Ala Lys Arg
435 440 445

Val Val Pro Pro Cys Asn Pro Asn Ala Cys Arg Ala Ser Gly Arg Gly
450 455 460

Leu Gln Pro Lys Gly Val Arg Val Lys Glu Val Ala Asp Phe Lys Val
465 470 475 480

Phe Thr Lys Gly Ala Gly Ser Gly Glu Leu Lys Val Thr Val Lys Gly
485 490 495

Pro Lys Gly Thr Glu Glu Leu Val Lys Val Arg Glu Ala Gly Asp Gly
500 505 510

Val Phe Glu Cys Glu Tyr Tyr Pro Val Val Pro Gly Lys Tyr Val Val
515 520 525

Thr Ile Thr Trp Gly Gly Tyr Ala Ile Pro Arg Ser Pro Phe Glu Val
530 535 540

Gln Val Ser Pro Glu Ala Gly Ala Gln Lys Val Arg Ala Trp Gly Pro
545 550 555 560

Gly Leu Glu Thr Gly Gln Val Gly Lys Ser Ala Asp Phe Val Val Glu
565 570 575

Ala Ile Gly Thr Glu Val Gly Thr Leu Gly Phe Ser Ile Glu Gly Pro
580 585 590

Ser Gln Ala Lys Ile Glu Cys Asp Asp Lys Gly Asp Gly Ser Cys Asp
595 600 605

```
Val Arg Tyr Trp Pro Thr Glu Pro Gly Glu Tyr Ala Val His Val Ile
    610                 615                 620

Cys Asp Asp Glu Asp Ile Arg Asp Ser Pro Phe Ile Ala His Ile Gln
625                 630                 635                 640

Pro Ala Pro Pro Asp Cys Phe Pro Asp Lys Val Lys Ala Phe Gly Pro
                645                 650                 655

Gly Leu Glu Pro Thr Gly Cys Ile Val Asp Lys Pro Ala Glu Phe Thr
            660                 665                 670

Ile Asp Ala Ser Ala Ala Gly Lys Gly Asp Leu Lys Leu Tyr Ala Gln
        675                 680                 685

Asp Ala Asp Gly Cys Pro Ile Asp Ile Asn Val Phe Thr Thr Gly Asn
    690                 695                 700

Gly Ile Phe Arg Cys Ser Tyr Val Pro Thr Lys Pro Ile Lys His Thr
705                 710                 715                 720

Ile Ile Ile Ser Trp Gly Gly Val Asn Val Pro Lys Ser Pro Phe Arg
                725                 730                 735

Val Asn Val Gly Glu Gly Ser His Pro Glu Lys Val Lys Val Tyr Gly
            740                 745                 750

Pro Gly Val Glu Lys Thr Gly Leu Lys Ala Asn Glu Pro Thr Tyr Phe
        755                 760                 765

Thr Val Asp Cys Ser Glu Ala Gly Gln Gly Asp Val Ser Ile Gly Ile
    770                 775                 780

Lys Cys Ala Pro Gly Val Val Gly Pro Ala Glu Ala Asp Ile Asp Phe
785                 790                 795                 800

Asp Ile Ile Lys Asn Asp Asn Asp Thr Phe Thr Val Lys Tyr Thr Pro
                805                 810                 815

Pro Gly Ala Gly Arg Tyr Thr Ile Met Val Leu Phe Ala Asn Gln Glu
            820                 825                 830

Ile Pro Ala Ser Pro Phe His Ile Lys Val Asp Pro Ser His Asp Ala
        835                 840                 845

Ser Lys Val Lys Ala Glu Gly Pro Gly Leu Asn Arg Thr Gly Val Glu
    850                 855                 860

Val Gly Lys Pro Thr His Phe Thr Val Leu Thr Lys Gly Ala Gly Lys
865                 870                 875                 880

Ala Lys Leu Asp Val His Phe Ala Gly Ala Gly Lys Gly Glu Ala Val
                885                 890                 895

Arg Asp Phe Glu Ile Ile Asp Asn His Asp Tyr Ser Tyr Thr Val Lys
            900                 905                 910

Tyr Thr Ala Val Gln Gln Gly Asn Met Ala Val Thr Val Thr Tyr Gly
        915                 920                 925

Gly Asp Pro Val Pro Lys Ser Pro Phe Val Val Asn Val Ala Pro Pro
    930                 935                 940

Leu Asp Leu Ser Lys Val Lys Val Gln Gly Leu Asn Ser Lys Val Ala
945                 950                 955                 960

Val Gly Gln Glu Gln Ala Phe Ser Val Asn Thr Arg Gly Ala Gly Gly
                965                 970                 975

Gln Gly Gln Leu Asp Val Arg Met Thr Ser Pro Ser Arg Arg Pro Ile
            980                 985                 990

Pro Cys Lys Leu Glu Pro Gly Gly Gly Ala Glu Ala Gln Ala Val Arg
        995                 1000                1005

Tyr Met Pro Pro Glu Glu Gly Pro Tyr Lys Val Asp Ile Thr Tyr Asp
    1010                1015                1020
```

```
Gly His Pro Val Pro Gly Ser Pro Phe Thr Val Glu Gly Val Leu Pro
1025                1030                1035                1040

Pro Asp Pro Ser Lys Val Cys Ala Tyr Gly Pro Gly Leu Lys Gly Gly
                1045                1050                1055

Leu Val Gly Ser Pro Ala Pro Phe Ser Ile Asp Thr Lys Gly Ala Gly
            1060                1065                1070

Thr Gly Gly Leu Gly Leu Thr Val Glu Gly Pro Cys Glu Ala Lys Ile
        1075                1080                1085

Glu Cys Gln Asp Asn Gly Asp Gly Ser Cys Ala Val Ser Tyr Leu Pro
    1090                1095                1100

Thr Glu Pro Gly Glu Tyr Thr Ile Asn Ile Leu Phe Ala Glu Ala His
1105                1110                1115                1120

Ile Pro Gly Ser Pro Phe Lys Ala Thr Ile Arg Pro Val Phe Asp Pro
                1125                1130                1135

Ser Lys Val Arg Ala Ser Gly Pro Gly Leu Glu Arg Gly Lys Ala Gly
            1140                1145                1150

Glu Ala Ala Thr Phe Thr Val Asp Cys Ser Glu Ala Gly Glu Ala Glu
        1155                1160                1165

Leu Thr Ile Glu Ile Leu Ser Asp Ala Gly Val Lys Ala Glu Val Leu
    1170                1175                1180

Ile His Asn Asn Ala Asp Gly Thr Tyr His Ile Thr Tyr Ser Pro Ala
1185                1190                1195                1200

Phe Pro Gly Thr Tyr Thr Ile Thr Ile Lys Tyr Gly Gly His Pro Val
                1205                1210                1215

Pro Lys Phe Pro Thr Arg Val His Val Gln Pro Ala Ile Asp Thr Ser
            1220                1225                1230

Gly Val Lys Val Ser Gly Pro Gly Val Glu Pro His Gly Val Leu Arg
        1235                1240                1245

Glu Val Thr Thr Glu Phe Thr Val Asp Ala Arg Ser Leu Thr Ala Thr
    1250                1255                1260

Gly Gly Asn His Val Thr Ala Arg Val Leu Asn Pro Ser Gly Ala Lys
1265                1270                1275                1280

Thr Asp Thr Tyr Val Thr Asp Asn Gly Asp Gly Thr Tyr Arg Val Gln
                1285                1290                1295

Tyr Thr Ala Tyr Glu Glu Gly Val His Leu Val Glu Val Leu Tyr Asp
            1300                1305                1310

Asp Val Ala Val Pro Lys Ser Pro Phe Arg Val Gly Val Thr Glu Gly
        1315                1320                1325

Cys Asp Pro Thr Arg Val Arg Ala Tyr Gly Pro Gly Leu Glu Gly Gly
    1330                1335                1340

Leu Val Asn Lys Ala Asn Arg Phe Thr Val Glu Thr Arg Gly Ala Gly
1345                1350                1355                1360

Thr Gly Gly Leu Gly Leu Ala Ile Glu Gly Pro Ser Glu Ala Lys Met
                1365                1370                1375

Ser Cys Lys Asp Asn Lys Asp Gly Ser Cys Thr Val Glu Tyr Ile Pro
            1380                1385                1390

Phe Thr Pro Gly Asp Tyr Asp Val Asn Ile Thr Phe Gly Gly Arg Pro
        1395                1400                1405

Ile Pro Gly Ser Pro Phe Arg Val Pro Val Lys Asp Val Val Asp Pro
    1410                1415                1420

Gly Lys Val Lys Cys Ser Gly Pro Gly Leu Gly Ala Gly Val Arg Ala
1425                1430                1435                1440

Arg Val Pro Gln Thr Phe Thr Val Asp Cys Ser Gln Ala Gly Arg Ala
```

```
            1445                1450                1455

Pro Leu Gln Val Ala Val Leu Gly Pro Thr Gly Val Ala Glu Pro Val
        1460                1465                1470

Glu Ile Arg Asp Asn Gly Asp Gly Thr His Ala Val His Tyr Thr Pro
    1475                1480                1485

Ala Thr Asp Gly Pro Tyr Thr Val Ala Val Lys Tyr Ala Asp Gln Glu
    1490                1495                1500

Val Pro Arg Ser Pro Phe Lys Ile Lys Val Leu Pro Ala His Asp Ala
1505                1510                1515                1520

Ser Lys Val Arg Ala Ser Gly Pro Gly Leu Asn Ala Ala Gly Ile Pro
            1525                1530                1535

Ala Ser Leu Pro Val Glu Phe Thr Ile Asp Ala Arg Asp Ala Gly Glu
        1540                1545                1550

Gly Leu Leu Thr Val Gln Ile Leu Asp Pro Glu Gly Lys Pro Lys Lys
    1555                1560                1565

Ala Asn Ile Arg Asp Asn Gly Asp Gly Thr Tyr Thr Val Ser Tyr Leu
    1570                1575                1580

Pro Asp Met Ser Gly Arg Tyr Thr Ile Thr Ile Lys Tyr Gly Gly Asp
1585                1590                1595                1600

Glu Ile Pro Tyr Ser Pro Phe Arg Ile His Ala Leu Pro Thr Gly Asp
            1605                1610                1615

Ala Ser Lys Cys Leu Val Thr Val Ser Ile Gly Gly His Gly Leu Gly
        1620                1625                1630

Ala Cys Leu Gly Pro Arg Ile Gln Ile Gly Glu Glu Thr Val Ile Thr
    1635                1640                1645

Val Asp Ala Lys Ala Ala Gly Lys Gly Lys Val Thr Cys Thr Val Ser
    1650                1655                1660

Thr Pro Asp Gly Ala Glu Leu Asp Val Asp Val Val Glu Asn His Asp
1665                1670                1675                1680

Gly Thr Phe Asp Ile Tyr Tyr Thr Ala Pro Glu Pro Gly Lys Tyr Val
            1685                1690                1695

Ile Thr Ile Arg Phe Gly Gly Glu His Ile Pro Asn Ser Pro Phe His
        1700                1705                1710

Val Leu Ala Cys Asp Pro Met Pro His Val Glu Glu Pro Ser Asp Val
    1715                1720                1725

Leu Gln Leu His Arg Pro Ser Ala Tyr Pro Thr His Trp Ala Thr Glu
    1730                1735                1740

Glu Pro Val Val Pro Val Glu Pro Met Glu Ser Met Leu Arg Pro Phe
1745                1750                1755                1760

Asn Leu Val Ile Pro Phe Thr Val Gln Lys Gly Glu Leu Thr Gly Glu
            1765                1770                1775

Val Arg Met Pro Ser Gly Lys Thr Ala Arg Pro Asn Ile Thr Asp Asn
        1780                1785                1790

Lys Asp Gly Thr Ile Thr Val Arg Tyr Ala Pro Thr Glu Lys Gly Leu
    1795                1800                1805

His Gln Met Gly Ile Lys Tyr Asp Gly Asn His Ile Pro Gly Ser Pro
    1810                1815                1820

Leu Gln Phe Tyr Val Asp Ala Ile Asn Ser Arg His Val Ser Ala Tyr
1825                1830                1835                1840

Gly Pro Gly Leu Ser His Gly Met Val Asn Lys Pro Ala Thr Phe Thr
            1845                1850                1855

Ile Val Thr Lys Asp Ala Gly Glu Gly Gly Leu Ser Leu Ala Val Glu
        1860                1865                1870
```

```
Gly Pro Ser Lys Ala Glu Ile Thr Cys Lys Asp Asn Lys Asp Gly Thr
        1875                1880                1885

Cys Thr Val Ser Tyr Leu Pro Thr Ala Pro Gly Asp Tyr Ser Ile Ile
    1890                1895                1900

Val Arg Phe Asp Asp Lys His Ile Pro Gly Ser Pro Phe Thr Ala Lys
1905                1910                1915                1920

Ile Thr Gly Asp Asp Ser Met Arg Thr Ser Gln Leu Asn Val Gly Thr
                1925                1930                1935

Ser Thr Asp Val Ser Leu Lys Ile Thr Glu Ser Asp Leu Ser Leu Leu
            1940                1945                1950

Thr Ala Ser Ile Arg Ala Pro Ser Gly Asn Glu Glu Pro Cys Leu Leu
        1955                1960                1965

Lys Arg Leu Pro Asn Arg His Ile Gly Ile Ser Phe Thr Pro Lys Glu
    1970                1975                1980

Val Gly Glu His Val Val Ser Val Arg Lys Ser Gly Lys His Val Thr
1985                1990                1995                2000

Asn Ser Pro Phe Lys Ile Leu Val Gly Pro Ser Glu Ile Gly Asp Ala
                2005                2010                2015

Ser Lys Val Arg Val Trp Gly Lys Gly Leu Ser Glu Gly Gln Thr Phe
            2020                2025                2030

Gln Val Ala Glu Phe Ile Val Asp Thr Arg Asn Ala Gly Tyr Gly Gly
        2035                2040                2045

Leu Gly Leu Ser Ile Glu Gly Pro Ser Lys Val Asp Ile Asn Cys Glu
    2050                2055                2060

Asp Met Glu Asp Gly Thr Cys Lys Val Thr Tyr Cys Pro Thr Glu Pro
2065                2070                2075                2080

Gly Thr Tyr Ile Ile Asn Ile Lys Phe Ala Asp Lys His Val Pro Gly
                2085                2090                2095

Ser Pro Phe Thr Val Lys Val Thr Gly Glu Gly Arg Met Lys Glu Ser
            2100                2105                2110

Ile Thr Arg Arg Arg Gln Ala Pro Ser Ile Ala Thr Ile Gly Ser Thr
        2115                2120                2125

Cys Asp Leu Asn Leu Lys Ile Pro Gly Asn Trp Phe Gln Met Val Ser
    2130                2135                2140

Ala Gln Glu Arg Leu Thr Arg Thr Phe Thr Arg Ser Ser His Thr Tyr
2145                2150                2155                2160

Thr Arg Thr Glu Arg Thr Glu Ile Ser Lys Thr Arg Gly Gly Glu Thr
                2165                2170                2175

Lys Arg Glu Val Arg Val Glu Glu Ser Thr Gln Val Gly Gly Asp Pro
            2180                2185                2190

Phe Pro Ala Val Phe Gly Asp Phe Leu Gly Arg Glu Arg Leu Gly Ser
        2195                2200                2205

Phe Gly Ser Ile Thr Arg Gln Gln Glu Gly Glu Ala Ser Ser Gln Asp
    2210                2215                2220

Met Thr Ala Gln Val Thr Ser Pro Ser Gly Lys Thr Glu Ala Ala Glu
2225                2230                2235                2240

Ile Val Glu Gly Glu Asp Ser Ala Tyr Ser Val Arg Phe Val Pro Gln
                2245                2250                2255

Glu Met Gly Pro His Thr Val Thr Val Lys Tyr Arg Gly Gln His Val
            2260                2265                2270

Pro Gly Ser Pro Phe Gln Phe Thr Val Gly Pro Leu Gly Glu Gly Gly
        2275                2280                2285
```

```
Ala His Lys Val Arg Ala Gly Gly Thr Gly Leu Glu Arg Gly Val Ala
    2290                2295                2300

Gly Val Pro Ala Glu Phe Ser Ile Trp Thr Arg Glu Ala Gly Ala Gly
2305                2310                2315                2320

Gly Leu Ser Ile Ala Val Glu Gly Pro Ser Lys Ala Glu Ile Ala Phe
                2325                2330                2335

Glu Asp Arg Lys Asp Gly Ser Cys Gly Val Ser Tyr Val Val Gln Glu
            2340                2345                2350

Pro Gly Asp Tyr Glu Val Ser Ile Lys Phe Asn Asp Glu His Ile Pro
        2355                2360                2365

Asp Ser Pro Phe Val Val Pro Val Ala Ser Leu Ser Asp Asp Ala Arg
    2370                2375                2380

Arg Leu Thr Val Thr Ser Leu Gln Glu Thr Gly Leu Lys Val Asn Gln
2385                2390                2395                2400

Pro Ala Ser Phe Ala Val Gln Leu Asn Gly Ala Arg Gly Val Ile Asp
                2405                2410                2415

Ala Arg Val His Thr Pro Ser Gly Ala Val Glu Glu Cys Tyr Val Ser
            2420                2425                2430

Glu Leu Asp Ser Asp Lys His Thr Ile Arg Phe Ile Pro His Glu Asn
        2435                2440                2445

Gly Val His Ser Ile Asp Val Lys Phe Asn Gly Ala His Ile Pro Gly
    2450                2455                2460

Ser Pro Phe Lys Ile Arg Val Gly Glu Gln Ser Gln Ala Gly Asp Pro
2465                2470                2475                2480

Gly Leu Val Ser Ala Tyr Gly Pro Gly Leu Glu Gly Gly Thr Thr Gly
                2485                2490                2495

Val Ser Ser Glu Phe Ile Val Asn Thr Leu Asn Ala Gly Ser Gly Ala
            2500                2505                2510

Leu Ser Val Thr Ile Asp Gly Pro Ser Lys Val Gln Leu Asp Cys Arg
        2515                2520                2525

Glu Cys Pro Glu Gly His Val Val Thr Tyr Thr Pro Met Ala Pro Gly
    2530                2535                2540

Asn Tyr Leu Ile Ala Ile Lys Tyr Gly Gly Pro Gln His Ile Val Gly
2545                2550                2555                2560

Ser Pro Phe Lys Ala Lys Val Thr Gly Pro Arg Leu Ser Gly Gly His
                2565                2570                2575

Ser Leu His Glu Thr Ser Thr Val Leu Val Glu Thr Val Thr Lys Ser
            2580                2585                2590

Ser Ser Ser Arg Gly Ser Ser Tyr Ser Ser Ile Pro Lys Phe Ser Ser
        2595                2600                2605

Asp Ala Ser Lys Val Val Thr Arg Gly Pro Gly Leu Ser Gln Ala Phe
    2610                2615                2620

Val Gly Gln Lys Asn Ser Phe Thr Val Asp Cys Ser Lys Ala Gly Thr
2625                2630                2635                2640

Asn Met Met Met Val Gly Val His Gly Pro Lys Thr Pro Cys Glu Glu
                2645                2650                2655

Val Tyr Val Lys His Met Gly Asn Arg Val Tyr Asn Val Thr Tyr Thr
            2660                2665                2670

Val Lys Glu Lys Gly Asp Tyr Ile Leu Ile Val Lys Trp Gly Asp Glu
        2675                2680                2685

Ser Val Pro Gly Ser Pro Phe Lys Val Asn Val Pro
    2690                2695                2700
```

```
<210> SEQ ID NO 13
<211> LENGTH: 2690
<212> TYPE: PRT
<213> ORGANISM: Equus

<400> SEQUENCE: 13

Thr Phe Thr Arg Arg Cys Asn Glu His Leu Thr Cys Val Val Lys Arg
1               5                   10                  15

Leu Thr Asp Leu Gln Arg Asp Leu Ser Asp Gly Leu Arg Leu Ile Ala
            20                  25                  30

Leu Leu Glu Val Leu Ser Gln Lys Arg Met Tyr Arg Lys Phe His Pro
        35                  40                  45

Arg Pro Asn Phe Arg Gln Met Lys Leu Glu Asn Val Ser Val Ala Leu
    50                  55                  60

Glu Phe Leu Glu Arg Glu His Ile Lys Leu Val Ser Ile Asp Ser Lys
65                  70                  75                  80

Ala Ile Val Asp Gly Asn Leu Lys Leu Ile Leu Gly Leu Ile Trp Thr
                85                  90                  95

Leu Ile Leu His Tyr Ser Ile Ser Met Pro Met Trp Glu Asp Glu Asp
            100                 105                 110

Asp Glu Asp Ala Arg Lys Gln Thr Pro Lys Gln Arg Leu Leu Gly Trp
        115                 120                 125

Ile Gln Asn Lys Val Pro Gln Leu Pro Ile Thr Asn Phe Asn Arg Asp
    130                 135                 140

Trp Gln Asp Gly Lys Ala Leu Gly Ala Leu Val Asp Asn Cys Ala Pro
145                 150                 155                 160

Gly Leu Cys Pro Asp Trp Glu Ala Trp Asp Pro Asn Gln Pro Val Glu
                165                 170                 175

Asn Ala Arg Glu Ala Met Gln Gln Ala Asp Asp Trp Leu Gly Val Pro
            180                 185                 190

Gln Val Ile Ala Pro Glu Glu Ile Val Asp Pro Asn Val Asp Glu His
        195                 200                 205

Ser Val Met Thr Tyr Leu Ser Gln Phe Pro Lys Ala Lys Leu Lys Pro
    210                 215                 220

Gly Ala Pro Val Arg Ser Lys Gln Leu Asn Pro Lys Lys Ala Ile Ala
225                 230                 235                 240

Tyr Gly Pro Gly Ile Glu Pro Gln Gly Asn Thr Val Leu Gln Pro Ala
                245                 250                 255

His Phe Thr Val Gln Thr Val Asp Ala Gly Val Gly Glu Val Leu Val
            260                 265                 270

Tyr Ile Glu Asp Pro Glu Gly His Thr Glu Glu Ala Lys Val Val Pro
        275                 280                 285

Asn Asn Asp Lys Asp Arg Thr Tyr Ala Val Ser Tyr Val Pro Lys Val
    290                 295                 300

Ala Gly Leu His Lys Val Thr Val Leu Phe Ala Gly Gln Asn Ile Glu
305                 310                 315                 320

Arg Ser Pro Phe Glu Val Asn Val Gly Met Ala Leu Gly Asp Ala Asn
                325                 330                 335

Lys Val Ser Ala Arg Gly Pro Gly Leu Glu Pro Val Gly Asn Val Ala
            340                 345                 350

Asn Lys Pro Thr Tyr Phe Asp Ile Tyr Thr Ala Gly Ala Gly Thr Gly
        355                 360                 365

Asp Val Ala Val Val Ile Val Asp Pro Gln Gly Arg Arg Asp Thr Val
    370                 375                 380
```

-continued

```
Glu Val Ala Leu Glu Asp Lys Gly Asp Ser Thr Phe Arg Cys Thr Tyr
385                 390                 395                 400

Arg Pro Val Met Glu Gly Pro His Thr Val His Val Ala Phe Ala Gly
                405                 410                 415

Ala Pro Ile Thr Arg Ser Pro Phe Pro Val His Val Ala Glu Ala Cys
            420                 425                 430

Asn Pro Asn Ala Cys Arg Ala Ser Gly Arg Gly Leu Gln Pro Lys Gly
        435                 440                 445

Val Arg Val Lys Glu Val Ala Asp Phe Lys Val Phe Thr Lys Gly Ala
    450                 455                 460

Gly Ser Gly Glu Leu Lys Val Thr Val Lys Gly Pro Lys Gly Thr Glu
465                 470                 475                 480

Glu Leu Val Lys Val Arg Glu Ala Gly Asp Gly Val Phe Glu Cys Glu
                485                 490                 495

Tyr Tyr Pro Val Val Pro Gly Lys Tyr Val Val Thr Ile Thr Trp Gly
            500                 505                 510

Gly Tyr Ala Ile Pro Arg Ser Pro Phe Glu Val Gln Val Ser Pro Glu
        515                 520                 525

Ala Gly Ala Gln Lys Val Arg Ala Trp Gly Pro Gly Leu Glu Thr Gly
    530                 535                 540

Gln Val Gly Lys Ser Ala Asp Phe Val Val Glu Ala Ile Gly Thr Glu
545                 550                 555                 560

Val Gly Thr Leu Gly Phe Ser Ile Glu Gly Pro Ser Gln Ala Lys Ile
                565                 570                 575

Glu Cys Asp Asp Lys Gly Asp Gly Ser Cys Asp Val Arg Tyr Trp Pro
            580                 585                 590

Thr Glu Pro Gly Glu Tyr Ala Val His Val Ile Cys Asp Asp Glu Asp
        595                 600                 605

Ile Arg Asp Ser Pro Phe Ile Ala His Ile Gln Pro Ala Pro Pro Asp
    610                 615                 620

Cys Phe Pro Asp Lys Val Lys Ala Phe Gly Pro Gly Leu Glu Pro Thr
625                 630                 635                 640

Gly Cys Ile Val Asp Lys Pro Ala Glu Phe Thr Ile Asp Ala Ser Ala
                645                 650                 655

Ala Gly Lys Gly Asp Leu Lys Leu Tyr Ala Gln Asp Ala Asp Gly Cys
            660                 665                 670

Pro Ile Asp Ile Asn Val Phe Thr Thr Gly Asn Gly Ile Phe Arg Cys
        675                 680                 685

Ser Tyr Val Pro Thr Lys Pro Ile Lys His Thr Ile Ile Ile Ser Trp
    690                 695                 700

Gly Gly Val Asn Val Pro Lys Ser Pro Phe Arg Val Asn Val Gly Glu
705                 710                 715                 720

Gly Ser His Pro Glu Lys Val Lys Val Tyr Gly Pro Gly Val Glu Lys
                725                 730                 735

Thr Gly Leu Lys Ala Asn Glu Pro Thr Tyr Phe Thr Val Asp Cys Ser
            740                 745                 750

Lys Ala Gly Gln Gly Asp Val Ser Ile Gly Ile Lys Cys Ala Pro Gly
        755                 760                 765

Val Val Gly Pro Ala Glu Ala Asp Ile Asp Phe Asp Ile Ile Lys Asn
    770                 775                 780

Asp Asn Asp Thr Phe Thr Val Lys Tyr Thr Pro Pro Gly Ala Gly Arg
785                 790                 795                 800

Tyr Thr Ile Met Val Leu Phe Ala Asn Gln Glu Ile Pro Ala Ser Pro
```

```
                805                 810                 815

Phe His Ile Lys Val Asp Pro Ser His Asp Ala Ser Lys Val Lys Ala
            820                 825                 830

Glu Gly Pro Gly Leu Asn Arg Thr Gly Val Glu Val Gly Lys Pro Thr
        835                 840                 845

His Phe Thr Val Leu Thr Lys Gly Ala Gly Lys Ala Lys Leu Asp Val
    850                 855                 860

His Phe Ala Gly Ala Gly Lys Gly Glu Ala Val Arg Asp Phe Glu Ile
865                 870                 875                 880

Ile Asp Asn His Asp Tyr Ser Tyr Thr Val Lys Tyr Thr Ala Val Gln
                885                 890                 895

Gln Gly Asn Met Ala Val Thr Val Thr Tyr Gly Gly Asp Pro Val Pro
            900                 905                 910

Lys Ser Pro Phe Val Val Asn Val Ala Pro Pro Leu Asp Leu Ser Lys
        915                 920                 925

Val Lys Val Gln Gly Leu Asn Ser Lys Val Ala Val Gly Gln Glu Gln
    930                 935                 940

Ala Phe Ser Val Asn Thr Arg Gly Ala Gly Gly Gln Gly Gln Leu Asp
945                 950                 955                 960

Val Arg Met Thr Ser Pro Ser Arg Arg Pro Ile Pro Cys Lys Leu Glu
                965                 970                 975

Pro Gly Gly Gly Ala Glu Ala Gln Ala Val Arg Tyr Met Pro Pro Glu
            980                 985                 990

Glu Gly Pro Tyr Lys Val Asp Ile Thr Tyr Asp Gly His Pro Val Pro
        995                 1000                1005

Gly Ser Pro Phe Thr Val Glu Gly Val Leu Pro Pro Asp Pro Ser Lys
    1010                1015                1020

Val Cys Ala Tyr Gly Pro Gly Leu Lys Gly Gly Leu Val Gly Ser Pro
1025                1030                1035                1040

Ala Pro Phe Ser Ile Asp Thr Lys Gly Ala Gly Thr Gly Gly Leu Gly
                1045                1050                1055

Leu Thr Val Glu Gly Pro Cys Glu Ala Lys Ile Glu Cys Gln Asp Asn
            1060                1065                1070

Gly Asp Gly Ser Cys Ala Val Ser Tyr Leu Pro Thr Glu Pro Gly Glu
        1075                1080                1085

Tyr Thr Ile Asn Ile Leu Phe Ala Glu Ala His Ile Pro Gly Ser Pro
    1090                1095                1100

Phe Lys Ala Thr Ile Arg Pro Val Phe Asp Pro Ser Lys Val Arg Ala
1105                1110                1115                1120

Ser Gly Pro Gly Leu Glu Arg Gly Lys Ala Gly Glu Ala Ala Thr Phe
                1125                1130                1135

Thr Val Asp Cys Ser Glu Ala Gly Glu Ala Glu Leu Thr Ile Glu Ile
            1140                1145                1150

Leu Ser Asp Ala Gly Val Lys Ala Glu Val Leu Ile His Asn Asn Ala
        1155                1160                1165

Asp Gly Thr Tyr His Ile Thr Tyr Ser Pro Ala Phe Pro Gly Thr Tyr
    1170                1175                1180

Thr Ile Thr Ile Lys Tyr Gly Gly His Pro Val Pro Lys Phe Pro Thr
1185                1190                1195                1200

Arg Val His Val Gln Pro Thr Ile Asp Thr Ser Gly Val Lys Val Ser
                1205                1210                1215

Gly Pro Gly Val Glu Pro His Gly Val Leu Arg Glu Val Thr Thr Glu
            1220                1225                1230
```

Phe Thr Val Asp Ala Arg Ser Leu Thr Ala Thr Gly Gly Asn His Val
1235 1240 1245

Thr Ala Arg Val Leu Asn Pro Ser Gly Ala Lys Thr Asp Thr Tyr Val
1250 1255 1260

Thr Asp Asn Gly Asp Gly Thr Tyr Arg Val Gln Tyr Thr Ala Tyr Glu
1265 1270 1275 1280

Glu Gly Val His Leu Val Glu Val Leu Tyr Asp Asp Val Ala Val Pro
1285 1290 1295

Lys Ser Pro Phe Arg Val Gly Val Thr Glu Gly Cys Asp Pro Thr Arg
1300 1305 1310

Val Arg Ala Tyr Gly Pro Gly Leu Glu Gly Gly Leu Val Asn Lys Ala
1315 1320 1325

Asn Arg Phe Thr Val Glu Thr Arg Gly Ala Gly Thr Gly Gly Leu Gly
1330 1335 1340

Leu Ala Ile Glu Gly Pro Ser Glu Ala Lys Met Ser Cys Lys Asp Asn
1345 1350 1355 1360

Lys Asp Gly Ser Cys Thr Val Glu Tyr Ile Pro Phe Thr Pro Gly Asp
1365 1370 1375

Tyr Asp Val Asn Ile Thr Phe Gly Gly Arg Pro Ile Pro Gly Ser Pro
1380 1385 1390

Phe Arg Val Pro Val Lys Asp Val Val Asp Pro Gly Lys Val Lys Cys
1395 1400 1405

Ser Gly Pro Gly Leu Gly Ala Gly Val Arg Ala Arg Val Pro Gln Thr
1410 1415 1420

Phe Thr Val Asp Cys Ser Gln Ala Gly Arg Ala Pro Leu Gln Val Ala
1425 1430 1435 1440

Val Leu Gly Pro Thr Gly Val Ala Glu Pro Val Glu Ile Arg Asp Asn
1445 1450 1455

Gly Asp Gly Thr His Ala Val His Tyr Thr Pro Ala Thr Asp Gly Pro
1460 1465 1470

Tyr Thr Val Ala Val Lys Tyr Ala Asp Gln Glu Val Pro Arg Ser Pro
1475 1480 1485

Phe Lys Ile Lys Val Leu Pro Ala His Asp Ala Ser Lys Val Arg Ala
1490 1495 1500

Ser Gly Pro Gly Leu Asn Ala Ala Gly Ile Pro Ala Ser Leu Pro Val
1505 1510 1515 1520

Glu Phe Thr Ile Asp Ala Arg Asp Ala Gly Glu Gly Leu Leu Thr Val
1525 1530 1535

Gln Ile Leu Asp Pro Glu Gly Lys Pro Lys Lys Ala Asn Ile Arg Asp
1540 1545 1550

Asn Gly Asp Gly Thr Tyr Thr Val Ser Tyr Leu Pro Asp Met Ser Gly
1555 1560 1565

Arg Tyr Thr Ile Thr Ile Lys Tyr Gly Gly Asp Glu Ile Pro Tyr Ser
1570 1575 1580

Pro Phe Arg Ile His Ala Leu Pro Thr Gly Asp Ala Ser Lys Cys Leu
1585 1590 1595 1600

Val Thr Val Ser Ile Gly Gly His Gly Leu Gly Ala Cys Leu Gly Pro
1605 1610 1615

Arg Ile Gln Ile Gly Glu Glu Thr Val Ile Thr Val Asp Ala Lys Ala
1620 1625 1630

Ala Gly Lys Gly Lys Val Thr Cys Thr Val Ser Thr Pro Asp Gly Ala
1635 1640 1645

```
Glu Leu Asp Val Asp Val Val Glu Asn His Asp Gly Thr Phe Asp Ile
    1650                1655                1660

Tyr Tyr Thr Ala Pro Glu Pro Gly Lys Tyr Val Ile Thr Ile Arg Phe
1665                1670                1675                1680

Gly Gly Glu His Ile Pro Asn Ser Pro Phe His Val Leu Ala Cys Asp
                1685                1690                1695

Pro Met Pro His Val Glu Glu Pro Ser Asp Val Leu Gln Leu His Arg
            1700                1705                1710

Pro Ser Ala Tyr Pro Thr His Trp Ala Thr Glu Glu Pro Val Val Pro
        1715                1720                1725

Val Glu Pro Met Glu Ser Met Leu Arg Pro Phe Asn Leu Val Ile Pro
    1730                1735                1740

Phe Thr Val Gln Lys Gly Glu Leu Thr Gly Glu Val Arg Met Pro Ser
1745                1750                1755                1760

Gly Lys Thr Ala Arg Pro Asn Ile Thr Asp Asn Lys Asp Gly Thr Ile
                1765                1770                1775

Thr Val Arg Tyr Ala Pro Thr Glu Lys Gly Leu His Gln Met Gly Ile
            1780                1785                1790

Lys Tyr Asp Gly Asn His Ile Pro Gly Asp Pro Leu Gln Phe Tyr Val
        1795                1800                1805

Asp Ala Ile Asn Ser Arg His Val Ser Ala Tyr Gly Pro Gly Leu Ser
    1810                1815                1820

His Gly Met Val Asn Lys Pro Ala Thr Phe Thr Ile Val Thr Lys Asp
1825                1830                1835                1840

Ala Gly Glu Gly Gly Leu Ser Leu Ala Val Glu Gly Pro Ser Lys Ala
                1845                1850                1855

Glu Ile Thr Cys Lys Asp Asn Lys Asp Gly Thr Cys Thr Val Ser Tyr
            1860                1865                1870

Leu Pro Thr Ala Pro Gly Asp Tyr Ser Ile Ile Val Arg Phe Asp Asp
        1875                1880                1885

Lys His Ile Pro Gly Ser Pro Phe Thr Ala Lys Ile Thr Gly Asp Asp
    1890                1895                1900

Ser Met Arg Thr Ser Gln Leu Asn Val Gly Thr Ser Thr Asp Val Ser
1905                1910                1915                1920

Leu Lys Ile Thr Glu Ser Asp Leu Ser Leu Leu Thr Ala Ser Ile Arg
                1925                1930                1935

Ala Pro Ser Gly Asn Glu Glu Pro Cys Leu Leu Lys Arg Leu Pro Asn
            1940                1945                1950

Arg His Ile Gly Ile Ser Phe Thr Pro Lys Glu Val Gly Glu His Val
        1955                1960                1965

Val Ser Val Arg Lys Ser Gly Lys His Val Thr Asn Ser Pro Phe Lys
    1970                1975                1980

Ile Leu Val Gly Pro Ser Glu Ile Gly Asp Ala Ser Lys Val Arg Val
1985                1990                1995                2000

Trp Gly Lys Gly Leu Ser Glu Gly Gln Thr Phe Gln Val Ala Glu Phe
                2005                2010                2015

Ile Val Asp Thr Arg Asn Ala Gly Tyr Gly Gly Leu Gly Leu Ser Ile
            2020                2025                2030

Glu Gly Pro Ser Lys Val Asp Ile Asn Cys Glu Asp Met Glu Asp Gly
        2035                2040                2045

Thr Cys Lys Val Thr Tyr Cys Pro Thr Glu Pro Gly Thr Tyr Ile Ile
    2050                2055                2060

Asn Ile Lys Phe Ala Asp Lys His Val Pro Gly Ser Pro Phe Thr Val
```

```
2065                2070                2075                2080

Lys Val Thr Gly Glu Gly Arg Met Lys Glu Ser Ile Thr Arg Arg Arg
                2085                2090                2095

Gln Ala Pro Ser Ile Ala Thr Ile Gly Ser Thr Cys Asp Leu Asn Leu
            2100                2105                2110

Lys Ile Pro Gly Asn Trp Phe Gln Met Val Ser Ala Gln Glu Arg Leu
        2115                2120                2125

Thr Arg Thr Phe Thr Arg Ser Ser His Thr Tyr Thr Arg Thr Glu Arg
    2130                2135                2140

Thr Glu Ile Ser Lys Thr Arg Gly Gly Glu Thr Lys Arg Glu Val Arg
2145                2150                2155                2160

Val Glu Glu Ser Thr Gln Val Gly Gly Asp Pro Phe Pro Ala Val Phe
                2165                2170                2175

Gly Asp Phe Leu Gly Arg Glu Arg Leu Gly Ser Phe Gly Ser Ile Thr
            2180                2185                2190

Arg Gln Gln Glu Gly Glu Ala Ser Ser Gln Asp Met Thr Ala Gln Val
        2195                2200                2205

Thr Ser Pro Ser Gly Lys Thr Glu Ala Ala Glu Ile Val Glu Gly Glu
    2210                2215                2220

Asp Ser Ala Tyr Ser Val Arg Phe Val Pro Gln Glu Met Gly Pro His
2225                2230                2235                2240

Thr Val Thr Val Lys Tyr Arg Gly Gln His Val Pro Gly Ser Pro Phe
                2245                2250                2255

Gln Phe Thr Val Gly Pro Leu Gly Glu Gly Gly Ala His Lys Val Arg
            2260                2265                2270

Ala Gly Gly Thr Gly Leu Glu Arg Gly Val Ala Gly Val Pro Ala Glu
        2275                2280                2285

Phe Ser Ile Trp Thr Arg Glu Ala Gly Ala Gly Gly Leu Ser Ile Ala
    2290                2295                2300

Val Glu Gly Pro Ser Lys Ala Glu Ile Ala Phe Glu Asp Arg Lys Asp
2305                2310                2315                2320

Gly Ser Cys Gly Val Ser Tyr Val Val Gln Glu Pro Gly Asp Tyr Glu
                2325                2330                2335

Val Ser Ile Lys Phe Asn Asp Glu His Ile Pro Asp Ser Pro Phe Val
            2340                2345                2350

Val Pro Val Ala Ser Leu Ser Asp Asp Ala Arg Arg Leu Thr Val Thr
        2355                2360                2365

Ser Leu Gln Glu Thr Gly Leu Lys Val Asn Gln Pro Ala Ser Phe Ala
    2370                2375                2380

Val Gln Leu Asn Gly Ala Arg Gly Val Ile Asp Ala Arg Val His Thr
2385                2390                2395                2400

Pro Ser Gly Ala Val Glu Glu Cys Tyr Val Ser Glu Leu Asp Ser Asp
                2405                2410                2415

Lys His Thr Ile Arg Phe Ile Pro His Glu Asn Gly Val His Ser Ile
            2420                2425                2430

Asp Val Lys Phe Asn Gly Ala His Ile Pro Gly Ser Pro Phe Lys Ile
        2435                2440                2445

Arg Val Gly Glu Gln Ser Gln Ala Gly Asp Pro Gly Leu Val Ser Ala
    2450                2455                2460

Tyr Gly Pro Gly Leu Glu Gly Gly Thr Thr Gly Val Ser Ser Glu Phe
2465                2470                2475                2480

Ile Val Asn Thr Leu Asn Ala Gly Ser Gly Ala Leu Ser Val Thr Ile
                2485                2490                2495
```

```
Asp Gly Pro Ser Lys Val Gln Leu Asp Cys Arg Glu Cys Pro Glu Gly
            2500                2505                2510

His Val Val Thr Tyr Thr Pro Met Ala Pro Gly Asn Tyr Leu Ile Ala
        2515                2520                2525

Ile Lys Tyr Gly Gly Pro Gln His Ile Val Gly Ser Pro Phe Lys Ala
    2530                2535                2540

Lys Val Thr Gly Pro Arg Leu Ser Gly Gly His Ser Leu His Glu Thr
2545                2550                2555                2560

Ser Thr Val Leu Val Glu Thr Val Thr Lys Ser Ser Ser Ser Arg Gly
                2565                2570                2575

Ser Ser Tyr Ser Ser Ile Pro Lys Phe Ser Ser Asp Ala Ser Lys Val
            2580                2585                2590

Val Thr Arg Gly Pro Gly Leu Ser Gln Ala Phe Val Gly Gln Lys Asn
        2595                2600                2605

Ser Phe Thr Val Asp Cys Ser Lys Ala Gly Met Leu Arg Gly Arg Gly
    2610                2615                2620

Ala Ala Ser Gln Gly Thr Asn Met Met Met Val Gly Val His Gly Pro
2625                2630                2635                2640

Lys Thr Pro Cys Glu Glu Val Tyr Val Lys His Met Gly Asn Arg Val
                2645                2650                2655

Tyr Asn Val Thr Tyr Thr Val Lys Glu Lys Gly Asp Tyr Ile Leu Ile
            2660                2665                2670

Val Lys Trp Gly Asp Glu Ser Val Pro Gly Ser Pro Phe Lys Val Asn
        2675                2680                2685

Val Pro
    2690


<210> SEQ ID NO 14
<211> LENGTH: 2700
<212> TYPE: PRT
<213> ORGANISM: Equus

<400> SEQUENCE: 14

Thr Phe Thr Arg Arg Cys Asn Glu His Leu Thr Cys Val Val Lys Arg
1               5                   10                  15

Leu Thr Asp Leu Gln Arg Asp Leu Ser Asp Gly Leu Arg Leu Ile Ala
            20                  25                  30

Leu Leu Glu Val Leu Ser Gln Lys Arg Met Tyr Arg Lys Phe His Pro
        35                  40                  45

Arg Pro Asn Phe Arg Gln Met Lys Leu Glu Asn Val Ser Val Ala Leu
    50                  55                  60

Glu Phe Leu Glu Arg Glu His Ile Lys Leu Val Ser Ile Asp Ser Lys
65                  70                  75                  80

Ala Ile Val Asp Gly Asn Leu Lys Leu Ile Leu Gly Leu Ile Trp Thr
                85                  90                  95

Leu Ile Leu His Tyr Ser Ile Ser Met Pro Met Trp Glu Asp Glu Asp
            100                 105                 110

Asp Glu Asp Ala Arg Lys Gln Thr Pro Lys Gln Arg Leu Leu Gly Trp
        115                 120                 125

Ile Gln Asn Lys Val Pro Gln Leu Pro Ile Thr Asn Phe Asn Arg Asp
    130                 135                 140

Trp Gln Asp Gly Lys Ala Leu Gly Ala Leu Val Asp Asn Cys Ala Pro
145                 150                 155                 160

Gly Leu Cys Pro Asp Trp Glu Ala Trp Asp Pro Asn Gln Pro Val Glu
```

```
                165                 170                 175

Asn Ala Arg Glu Ala Met Gln Gln Ala Asp Asp Trp Leu Gly Val Pro
            180                 185                 190

Gln Val Ile Ala Pro Glu Glu Ile Val Asp Pro Asn Val Asp Glu His
        195                 200                 205

Ser Val Met Thr Tyr Leu Ser Gln Phe Pro Lys Ala Lys Leu Lys Pro
    210                 215                 220

Gly Ala Pro Val Arg Ser Lys Gln Leu Asn Pro Lys Lys Ala Ile Ala
225                 230                 235                 240

Tyr Gly Pro Gly Ile Glu Pro Gln Gly Asn Thr Val Leu Gln Pro Ala
                245                 250                 255

His Phe Thr Val Gln Thr Val Asp Ala Gly Val Gly Glu Val Leu Val
            260                 265                 270

Tyr Ile Glu Asp Pro Glu Gly His Thr Glu Glu Ala Lys Val Val Pro
        275                 280                 285

Asn Asn Asp Lys Asp Arg Thr Tyr Ala Val Ser Tyr Val Pro Lys Val
    290                 295                 300

Ala Gly Leu His Lys Val Thr Val Leu Phe Ala Gly Gln Asn Ile Glu
305                 310                 315                 320

Arg Ser Pro Phe Glu Val Asn Val Gly Met Ala Leu Gly Asp Ala Asn
                325                 330                 335

Lys Val Ser Ala Arg Gly Pro Gly Leu Glu Pro Val Gly Asn Val Ala
            340                 345                 350

Asn Lys Pro Thr Tyr Phe Asp Ile Tyr Thr Ala Gly Ala Gly Thr Gly
        355                 360                 365

Asp Val Ala Val Val Ile Val Asp Pro Gln Gly Arg Arg Asp Thr Val
    370                 375                 380

Glu Val Ala Leu Glu Asp Lys Gly Asp Ser Thr Phe Arg Cys Thr Tyr
385                 390                 395                 400

Arg Pro Val Met Glu Gly Pro His Thr Val His Val Ala Phe Ala Gly
                405                 410                 415

Ala Pro Ile Thr Arg Ser Pro Phe Pro Val His Val Ala Glu Glu Pro
            420                 425                 430

Leu Pro Pro Leu Ala Pro Ser Val Pro Ile Val His Gln Ala Lys Arg
        435                 440                 445

Val Val Pro Pro Cys Asn Pro Asn Ala Cys Arg Ala Ser Gly Arg Gly
    450                 455                 460

Leu Gln Pro Lys Gly Val Arg Val Lys Glu Val Ala Asp Phe Lys Val
465                 470                 475                 480

Phe Thr Lys Gly Ala Gly Ser Gly Glu Leu Lys Val Thr Val Lys Gly
                485                 490                 495

Pro Lys Gly Thr Glu Glu Leu Val Lys Val Arg Glu Ala Gly Asp Gly
            500                 505                 510

Val Phe Glu Cys Glu Tyr Tyr Pro Val Val Pro Gly Lys Tyr Val Val
        515                 520                 525

Thr Ile Thr Trp Gly Gly Tyr Ala Ile Pro Arg Ser Pro Phe Glu Val
    530                 535                 540

Gln Val Ser Pro Glu Ala Gly Ala Gln Lys Val Arg Ala Trp Gly Pro
545                 550                 555                 560

Gly Leu Glu Thr Gly Gln Val Gly Lys Ser Ala Asp Phe Val Val Glu
                565                 570                 575

Ala Ile Gly Thr Glu Val Gly Thr Leu Gly Phe Ser Ile Glu Gly Pro
            580                 585                 590
```

```
Ser Gln Ala Lys Ile Glu Cys Asp Asp Lys Gly Asp Gly Ser Cys Asp
        595                 600                 605

Val Arg Tyr Trp Pro Thr Glu Pro Gly Glu Tyr Ala Val His Val Ile
    610                 615                 620

Cys Asp Asp Glu Asp Ile Arg Asp Ser Pro Phe Ile Ala His Ile Gln
625                 630                 635                 640

Pro Ala Pro Pro Asp Cys Phe Pro Asp Lys Val Lys Ala Phe Gly Pro
                645                 650                 655

Gly Leu Glu Pro Thr Gly Cys Ile Val Asp Lys Pro Ala Glu Phe Thr
            660                 665                 670

Ile Asp Ala Ser Ala Ala Gly Lys Gly Asp Leu Lys Leu Tyr Ala Gln
        675                 680                 685

Asp Ala Asp Gly Cys Pro Ile Asp Ile Asn Val Phe Thr Thr Gly Asn
    690                 695                 700

Gly Ile Phe Arg Cys Ser Tyr Val Pro Thr Lys Pro Ile Lys His Thr
705                 710                 715                 720

Ile Ile Ile Ser Trp Gly Gly Val Asn Val Pro Lys Ser Pro Phe Arg
                725                 730                 735

Val Asn Val Gly Glu Gly Ser His Pro Glu Lys Val Lys Val Tyr Gly
            740                 745                 750

Pro Gly Val Glu Lys Thr Gly Leu Lys Ala Asn Glu Pro Thr Tyr Phe
        755                 760                 765

Thr Val Asp Cys Ser Lys Ala Gly Gln Gly Asp Val Ser Ile Gly Ile
    770                 775                 780

Lys Cys Ala Pro Gly Val Val Gly Pro Ala Glu Ala Asp Ile Asp Phe
785                 790                 795                 800

Asp Ile Ile Lys Asn Asp Asn Asp Thr Phe Thr Val Lys Tyr Thr Pro
                805                 810                 815

Pro Gly Ala Gly Arg Tyr Thr Ile Met Val Leu Phe Ala Asn Gln Glu
            820                 825                 830

Ile Pro Ala Ser Pro Phe His Ile Lys Val Asp Pro Ser His Asp Ala
        835                 840                 845

Ser Lys Val Lys Ala Glu Gly Pro Gly Leu Asn Arg Thr Gly Val Glu
    850                 855                 860

Val Gly Lys Pro Thr His Phe Thr Val Leu Thr Lys Gly Ala Gly Lys
865                 870                 875                 880

Ala Lys Leu Asp Val His Phe Ala Gly Ala Gly Lys Gly Glu Ala Val
                885                 890                 895

Arg Asp Phe Glu Ile Ile Asp Asn His Asp Tyr Ser Tyr Thr Val Lys
            900                 905                 910

Tyr Thr Ala Val Gln Gln Gly Asn Met Ala Val Thr Val Thr Tyr Gly
        915                 920                 925

Gly Asp Pro Val Pro Lys Ser Pro Phe Val Val Asn Val Ala Pro Pro
    930                 935                 940

Leu Asp Leu Ser Lys Val Lys Val Gln Gly Leu Asn Ser Lys Val Ala
945                 950                 955                 960

Val Gly Gln Glu Gln Ala Phe Ser Val Asn Thr Arg Gly Ala Gly Gly
                965                 970                 975

Gln Gly Gln Leu Asp Val Arg Met Thr Ser Pro Ser Arg Arg Pro Ile
            980                 985                 990

Pro Cys Lys Leu Glu Pro Gly Gly Gly Ala Glu Ala Gln Ala Val Arg
        995                 1000                1005
```

```
Tyr Met Pro Pro Glu Glu Gly Pro Tyr Lys Val Asp Ile Thr Tyr Asp
    1010                1015                1020

Gly His Pro Val Pro Gly Ser Pro Phe Thr Val Glu Gly Val Leu Pro
1025                1030                1035                1040

Pro Asp Pro Ser Lys Val Cys Ala Tyr Gly Pro Gly Leu Lys Gly Gly
                1045                1050                1055

Leu Val Gly Ser Pro Ala Pro Phe Ser Ile Asp Thr Lys Gly Ala Gly
            1060                1065                1070

Thr Gly Gly Leu Gly Leu Thr Val Glu Gly Pro Cys Glu Ala Lys Ile
        1075                1080                1085

Glu Cys Gln Asp Asn Gly Asp Gly Ser Cys Ala Val Ser Tyr Leu Pro
    1090                1095                1100

Thr Glu Pro Gly Glu Tyr Thr Ile Asn Ile Leu Phe Ala Glu Ala His
1105                1110                1115                1120

Ile Pro Gly Ser Pro Phe Lys Ala Thr Ile Arg Pro Val Phe Asp Pro
                1125                1130                1135

Ser Lys Val Arg Ala Ser Gly Pro Gly Leu Glu Arg Gly Lys Ala Gly
            1140                1145                1150

Glu Ala Ala Thr Phe Thr Val Asp Cys Ser Glu Ala Gly Glu Ala Glu
        1155                1160                1165

Leu Thr Ile Glu Ile Leu Ser Asp Ala Gly Val Lys Ala Glu Val Leu
    1170                1175                1180

Ile His Asn Asn Ala Asp Gly Thr Tyr His Ile Thr Tyr Ser Pro Ala
1185                1190                1195                1200

Phe Pro Gly Thr Tyr Thr Ile Thr Ile Lys Tyr Gly Gly His Pro Val
                1205                1210                1215

Pro Lys Phe Pro Thr Arg Val His Val Gln Pro Thr Ile Asp Thr Ser
            1220                1225                1230

Gly Val Lys Val Ser Gly Pro Gly Val Glu Pro His Gly Val Leu Arg
        1235                1240                1245

Glu Val Thr Thr Glu Phe Thr Val Asp Ala Arg Ser Leu Thr Ala Thr
    1250                1255                1260

Gly Gly Asn His Val Thr Ala Arg Val Leu Asn Pro Ser Gly Ala Lys
1265                1270                1275                1280

Thr Asp Thr Tyr Val Thr Asp Asn Gly Asp Gly Thr Tyr Arg Val Gln
                1285                1290                1295

Tyr Thr Ala Tyr Glu Glu Gly Val His Leu Val Glu Val Leu Tyr Asp
            1300                1305                1310

Asp Val Ala Val Pro Lys Ser Pro Phe Arg Val Gly Val Thr Glu Gly
        1315                1320                1325

Cys Asp Pro Thr Arg Val Arg Ala Tyr Gly Pro Gly Leu Glu Gly Gly
    1330                1335                1340

Leu Val Asn Lys Ala Asn Arg Phe Thr Val Glu Thr Arg Gly Ala Gly
1345                1350                1355                1360

Thr Gly Gly Leu Gly Leu Ala Ile Glu Gly Pro Ser Glu Ala Lys Met
                1365                1370                1375

Ser Cys Lys Asp Asn Lys Asp Gly Ser Cys Thr Val Glu Tyr Ile Pro
            1380                1385                1390

Phe Thr Pro Gly Asp Tyr Asp Val Asn Ile Thr Phe Gly Gly Arg Pro
        1395                1400                1405

Ile Pro Gly Ser Pro Phe Arg Val Pro Val Lys Asp Val Val Asp Pro
    1410                1415                1420

Gly Lys Val Lys Cys Ser Gly Pro Gly Leu Gly Ala Gly Val Arg Ala
```

```
1425                1430                1435                1440

Arg Val Pro Gln Thr Phe Thr Val Asp Cys Ser Gln Ala Gly Arg Ala
                1445                1450                1455

Pro Leu Gln Val Ala Val Leu Gly Pro Thr Gly Val Ala Glu Pro Val
            1460                1465                1470

Glu Ile Arg Asp Asn Gly Asp Gly Thr His Ala Val His Tyr Thr Pro
        1475                1480                1485

Ala Thr Asp Gly Pro Tyr Thr Val Ala Val Lys Tyr Ala Asp Gln Glu
    1490                1495                1500

Val Pro Arg Ser Pro Phe Lys Ile Lys Val Leu Pro Ala His Asp Ala
1505                1510                1515                1520

Ser Lys Val Arg Ala Ser Gly Pro Gly Leu Asn Ala Ala Gly Ile Pro
                1525                1530                1535

Ala Ser Leu Pro Val Glu Phe Thr Ile Asp Ala Arg Asp Ala Gly Glu
            1540                1545                1550

Gly Leu Leu Thr Val Gln Ile Leu Asp Pro Glu Gly Lys Pro Lys Lys
        1555                1560                1565

Ala Asn Ile Arg Asp Asn Gly Asp Gly Thr Tyr Thr Val Ser Tyr Leu
    1570                1575                1580

Pro Asp Met Ser Gly Arg Tyr Thr Ile Thr Ile Lys Tyr Gly Gly Asp
1585                1590                1595                1600

Glu Ile Pro Tyr Ser Pro Phe Arg Ile His Ala Leu Pro Thr Gly Asp
                1605                1610                1615

Ala Ser Lys Cys Leu Val Thr Val Ser Ile Gly Gly His Gly Leu Gly
            1620                1625                1630

Ala Cys Leu Gly Pro Arg Ile Gln Ile Gly Glu Glu Thr Val Ile Thr
        1635                1640                1645

Val Asp Ala Lys Ala Ala Gly Lys Gly Lys Val Thr Cys Thr Val Ser
    1650                1655                1660

Thr Pro Asp Gly Ala Glu Leu Asp Val Asp Val Val Glu Asn His Asp
1665                1670                1675                1680

Gly Thr Phe Asp Ile Tyr Tyr Thr Ala Pro Glu Pro Gly Lys Tyr Val
                1685                1690                1695

Ile Thr Ile Arg Phe Gly Gly Glu His Ile Pro Asn Ser Pro Phe His
            1700                1705                1710

Val Leu Ala Cys Asp Pro Met Pro His Val Glu Glu Pro Ser Asp Val
        1715                1720                1725

Leu Gln Leu His Arg Pro Ser Ala Tyr Pro Thr His Trp Ala Thr Glu
    1730                1735                1740

Glu Pro Val Val Pro Val Glu Pro Met Glu Ser Met Leu Arg Pro Phe
1745                1750                1755                1760

Asn Leu Val Ile Pro Phe Thr Val Gln Lys Gly Glu Leu Thr Gly Glu
                1765                1770                1775

Val Arg Met Pro Ser Gly Lys Thr Ala Arg Pro Asn Ile Thr Asp Asn
            1780                1785                1790

Lys Asp Gly Thr Ile Thr Val Arg Tyr Ala Pro Thr Glu Lys Gly Leu
        1795                1800                1805

His Gln Met Gly Ile Lys Tyr Asp Gly Asn His Ile Pro Gly Ser Pro
    1810                1815                1820

Leu Gln Phe Tyr Val Asp Ala Ile Asn Ser Arg His Val Ser Ala Tyr
1825                1830                1835                1840

Gly Pro Gly Leu Ser His Gly Met Val Asn Lys Pro Ala Thr Phe Thr
                1845                1850                1855
```

Ile Val Thr Lys Asp Ala Gly Glu Gly Gly Leu Ser Leu Ala Val Glu
1860 1865 1870

Gly Pro Ser Lys Ala Glu Ile Thr Cys Lys Asp Asn Lys Asp Gly Thr
1875 1880 1885

Cys Thr Val Ser Tyr Leu Pro Thr Ala Pro Gly Asp Tyr Ser Ile Ile
1890 1895 1900

Val Arg Phe Asp Asp Lys His Ile Pro Gly Ser Pro Phe Thr Ala Lys
1905 1910 1915 1920

Ile Thr Gly Asp Asp Ser Met Arg Thr Ser Gln Leu Asn Val Gly Thr
1925 1930 1935

Ser Thr Asp Val Ser Leu Lys Ile Thr Glu Ser Asp Leu Ser Leu Leu
1940 1945 1950

Thr Ala Ser Ile Arg Ala Pro Ser Gly Asn Glu Glu Pro Cys Leu Leu
1955 1960 1965

Lys Arg Leu Pro Asn Arg His Ile Gly Ile Ser Phe Thr Pro Lys Glu
1970 1975 1980

Val Gly Glu His Val Val Ser Val Arg Lys Ser Gly Lys His Val Thr
1985 1990 1995 2000

Asn Ser Pro Phe Lys Ile Leu Val Gly Pro Ser Glu Ile Gly Asp Ala
2005 2010 2015

Ser Lys Val Arg Val Trp Gly Lys Gly Leu Ser Glu Gly Gln Thr Phe
2020 2025 2030

Gln Val Ala Glu Phe Ile Val Asp Thr Arg Asn Ala Gly Tyr Gly Gly
2035 2040 2045

Leu Gly Leu Ser Ile Glu Gly Pro Ser Lys Val Asp Ile Asn Cys Glu
2050 2055 2060

Asp Met Glu Asp Gly Thr Cys Lys Val Thr Tyr Cys Pro Thr Glu Pro
2065 2070 2075 2080

Gly Thr Tyr Ile Ile Asn Ile Lys Phe Ala Asp Lys His Val Pro Gly
2085 2090 2095

Ser Pro Phe Thr Val Lys Val Thr Gly Glu Gly Arg Met Lys Glu Ser
2100 2105 2110

Ile Thr Arg Arg Arg Gln Ala Pro Ser Ile Ala Thr Ile Gly Ser Thr
2115 2120 2125

Cys Asp Leu Asn Leu Lys Ile Pro Gly Asn Trp Phe Gln Met Val Ser
2130 2135 2140

Ala Gln Glu Arg Leu Thr Arg Thr Phe Thr Arg Ser Ser His Thr Tyr
2145 2150 2155 2160

Thr Arg Thr Glu Arg Thr Glu Ile Ser Lys Thr Arg Gly Gly Glu Thr
2165 2170 2175

Lys Arg Glu Val Arg Val Glu Glu Ser Thr Gln Val Gly Gly Asp Pro
2180 2185 2190

Phe Pro Ala Val Phe Gly Asp Phe Leu Gly Arg Glu Arg Leu Gly Ser
2195 2200 2205

Phe Gly Ser Ile Thr Arg Gln Gln Glu Gly Glu Ala Ser Ser Gln Asp
2210 2215 2220

Met Thr Ala Gln Val Thr Ser Pro Ser Gly Lys Thr Glu Ala Ala Glu
2225 2230 2235 2240

Ile Val Glu Gly Glu Asp Ser Ala Tyr Ser Val Arg Phe Val Pro Gln
2245 2250 2255

Glu Met Gly Pro His Thr Val Thr Val Lys Tyr Arg Gly Gln His Val
2260 2265 2270

```
Pro Gly Ser Pro Phe Gln Phe Thr Val Gly Pro Leu Gly Glu Gly Gly
        2275                2280                2285

Ala His Lys Val Arg Ala Gly Gly Thr Gly Leu Glu Arg Gly Val Ala
    2290                2295                2300

Gly Val Pro Ala Glu Phe Ser Ile Trp Thr Arg Glu Ala Gly Ala Gly
2305                2310                2315                2320

Gly Leu Ser Ile Ala Val Glu Gly Pro Ser Lys Ala Glu Ile Ala Phe
                2325                2330                2335

Glu Asp Arg Lys Asp Gly Ser Cys Gly Val Ser Tyr Val Val Gln Glu
            2340                2345                2350

Pro Gly Asp Tyr Glu Val Ser Ile Lys Phe Asn Asp Glu His Ile Pro
        2355                2360                2365

Asp Ser Pro Phe Val Val Pro Val Ala Ser Leu Ser Asp Asp Ala Arg
    2370                2375                2380

Arg Leu Thr Val Thr Ser Leu Gln Glu Thr Gly Leu Lys Val Asn Gln
2385                2390                2395                2400

Pro Ala Ser Phe Ala Val Gln Leu Asn Gly Ala Arg Gly Val Ile Asp
                2405                2410                2415

Ala Arg Val His Thr Pro Ser Gly Ala Val Glu Glu Cys Tyr Val Ser
            2420                2425                2430

Glu Leu Asp Ser Asp Lys His Thr Ile Arg Phe Ile Pro His Glu Asn
        2435                2440                2445

Gly Val His Ser Ile Asp Val Lys Phe Asn Gly Ala His Ile Pro Gly
    2450                2455                2460

Ser Pro Phe Lys Ile Arg Val Gly Glu Gln Ser Gln Ala Gly Asp Pro
2465                2470                2475                2480

Gly Leu Val Ser Ala Tyr Gly Pro Gly Leu Glu Gly Gly Thr Thr Gly
                2485                2490                2495

Val Ser Ser Glu Phe Ile Val Asn Thr Leu Asn Ala Gly Ser Gly Ala
            2500                2505                2510

Leu Ser Val Thr Ile Asp Gly Pro Ser Lys Val Gln Leu Asp Cys Arg
        2515                2520                2525

Glu Cys Pro Glu Gly His Val Val Thr Tyr Thr Pro Met Ala Pro Gly
    2530                2535                2540

Asn Tyr Leu Ile Ala Ile Lys Tyr Gly Gly Pro Gln His Ile Val Gly
2545                2550                2555                2560

Ser Pro Phe Lys Ala Lys Val Thr Gly Pro Arg Leu Ser Gly Gly His
                2565                2570                2575

Ser Leu His Glu Thr Ser Thr Val Leu Val Glu Thr Val Thr Lys Ser
            2580                2585                2590

Ser Ser Ser Arg Gly Ser Ser Tyr Ser Ser Ile Pro Lys Phe Ser Ser
        2595                2600                2605

Asp Ala Ser Lys Val Val Thr Arg Gly Pro Gly Leu Ser Gln Ala Phe
    2610                2615                2620

Val Gly Gln Lys Asn Ser Phe Thr Val Asp Cys Ser Lys Ala Gly Thr
2625                2630                2635                2640

Asn Met Met Met Val Gly Val His Gly Pro Lys Thr Pro Cys Glu Glu
                2645                2650                2655

Val Tyr Val Lys His Met Gly Asn Arg Val Tyr Asn Val Thr Tyr Thr
            2660                2665                2670

Val Lys Glu Lys Gly Asp Tyr Ile Leu Ile Val Lys Trp Gly Asp Glu
        2675                2680                2685

Ser Val Pro Gly Ser Pro Phe Lys Val Asn Val Pro
```

2690 2695 2700

<210> SEQ ID NO 15
<211> LENGTH: 245
<212> TYPE: PRT
<213> ORGANISM: Equus

<400> SEQUENCE: 15

Met Ile Pro Lys Glu Gln Lys Gly Pro Val Met Ala Ala Met Glu Asp
1 5 10 15

Leu Ala Gly Pro Val Pro Val Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Lys Phe Thr Phe
50 55 60

Glu Phe Ala Ala Ser Gln Arg Ala Thr Val Ala Gly Ser Ala Lys Gly
65 70 75 80

Lys Val Pro Gly Ala Ala Glu Pro Gly Thr Val Thr Asn Gly Pro Glu
85 90 95

Gly Gln Asn Tyr Arg Ser Glu Leu His Ile Phe Pro Ala Ser Pro Gly
100 105 110

Gly Pro Glu Asp Ala Gln Pro Ala Ala Ser Gly Ala Lys Ser Ala Arg
115 120 125

Ser Pro Ser Ala Leu Ala Pro Gly Tyr Ala Glu Pro Leu Lys Ser Val
130 135 140

Pro Pro Glu Lys Phe Asn His Thr Ala Ile Pro Lys Gly Tyr Arg Cys
145 150 155 160

Pro Trp Gln Glu Phe Ile Ser Tyr Arg Asp Tyr Gln Ser Asp Gly Arg
165 170 175

Ser His Thr Pro Ser Pro Ala Glu Tyr Arg Asn Phe Asn Lys Thr Pro
180 185 190

Val Pro Phe Gly Gly Pro Leu Val Gly Glu Ala Val Pro Arg Ala Gly
195 200 205

Thr Ser Phe Ile Pro Glu Leu Thr Ser Gly Leu Glu Leu Leu Arg Leu
210 215 220

Arg Pro Ser Phe Asn Arg Val Ala Gln Gly Trp Val Arg Asn Leu Pro
225 230 235 240

Glu Ser Glu Asp Leu
245

<210> SEQ ID NO 16
<211> LENGTH: 245
<212> TYPE: PRT
<213> ORGANISM: Equus

<400> SEQUENCE: 16

Met Ile Pro Lys Glu Gln Lys Gly Pro Val Met Ala Ala Met Glu Asp
1 5 10 15

Leu Ala Gly Pro Val Pro Val Leu Asp Leu Gly Lys Lys Leu Ser Val
20 25 30

Pro Gln Asp Leu Met Met Glu Glu Leu Leu Leu Arg Asn Asn Arg Gly
35 40 45

Ser Leu Leu Phe Gln Lys Arg Gln Arg Arg Val Gln Lys Phe Thr Phe
50 55 60

Glu Phe Ala Ala Ser Gln Arg Ala Thr Val Ala Gly Ser Ala Lys Gly

```
65                  70                  75                  80

Lys Val Pro Gly Ala Ala Glu Pro Gly Thr Val Thr Asn Gly Pro Glu
                85                  90                  95

Gly Gln Asn Tyr Arg Ser Glu Leu His Ile Phe Pro Ala Ser Pro Gly
            100                 105                 110

Gly Pro Glu Asp Ala Gln Pro Ala Ala Ser Gly Ala Lys Ser Ala Arg
        115                 120                 125

Ser Pro Ser Ala Leu Ala Pro Gly Tyr Ala Glu Pro Leu Lys Ser Val
    130                 135                 140

Pro Pro Glu Lys Phe Asn His Thr Ala Ile Pro Lys Gly Tyr Arg Cys
145                 150                 155                 160

Pro Trp Gln Glu Phe Ile Ser Tyr Arg Asp Tyr Gln Ser Asp Gly Arg
                165                 170                 175

Ser His Thr Pro Ser Pro Ala Glu Tyr Arg Asn Phe Asn Lys Thr Pro
            180                 185                 190

Val Pro Phe Gly Gly Pro Leu Val Gly Glu Ala Val Pro Arg Ala Gly
        195                 200                 205

Thr Ser Phe Ile Pro Glu Leu Thr Ser Gly Leu Glu Leu Leu Arg Leu
    210                 215                 220

Arg Pro Ser Phe Asn Arg Val Ala Gln Gly Trp Val Arg Asn Leu Pro
225                 230                 235                 240

Glu Ser Glu Asp Leu
                245


<210> SEQ ID NO 17
<211> LENGTH: 178
<212> TYPE: DNA
<213> ORGANISM: Equus
<220> FEATURE:
<223> OTHER INFORMATION: MYOT-normal Exon 6

<400> SEQUENCE: 17

aagcagatca tcttcaaggg gagatgtgaa tgatcaggat gcaatccagg agaagtttta     60

cccacctcgt ttcattcaag tgccagaaaa catgtcaatt gacgaaggaa gattctgcag    120

aatggacttc aaaaacatgt caattgacga aggaagattc tgcagaatgg acttcaaa      178


<210> SEQ ID NO 18
<211> LENGTH: 178
<212> TYPE: DNA
<213> ORGANISM: Equus
<220> FEATURE:
<223> OTHER INFORMATION: MYOT-S323P Exon 6

<400> SEQUENCE: 18

aagcagatca ccttcaaggg gagatgtgaa tgatcaggat gcaatccagg agaagtttta     60

cccacctcgt ttcattcaag tgccagaaaa catgtcaatt gacgaaggaa gattctgcag    120

aatggacttc aaaaacatgt caattgacga aggaagattc tgcagaatgg acttcaaa      178


<210> SEQ ID NO 19
<211> LENGTH: 22
<212> TYPE: DNA
<213> ORGANISM: Artificial Sequence
<220> FEATURE:
<223> OTHER INFORMATION: MYOT Exon 6 Forward Primer

<400> SEQUENCE: 19

tatgacaatg gaaagggaat tc                                              22
```

<210> SEQ ID NO 20
<211> LENGTH: 20
<212> TYPE: DNA
<213> ORGANISM: Artificial Sequence
<220> FEATURE:
<223> OTHER INFORMATION: MYOT Exon 6 Reverse Primer

<400> SEQUENCE: 20
ttctcaagct gtggagcaag 20

<210> SEQ ID NO 21
<211> LENGTH: 124
<212> TYPE: DNA
<213> ORGANISM: Equus
<220> FEATURE:
<223> OTHER INFORMATION: FLNC-Normal Exon 15

<400> SEQUENCE: 21
gtaaacgtgg gagagggcag tcaccctgag aaagtgaagg tgtacggccc tggcgtggag 60
aagacgggcc tcaaggccaa cgagcccacc tatttcaccg tggactgcag cgaggcgggg 120
caag 124

<210> SEQ ID NO 22
<211> LENGTH: 124
<212> TYPE: DNA
<213> ORGANISM: Equus
<220> FEATURE:
<223> OTHER INFORMATION: FLNC-E735K Exon 15

<400> SEQUENCE: 22
gtaaacgtgg gagagggcag tcaccctgag aaagtgaagg tgtacggccc tggcgtggag 60
aagacgggcc tcaaggccaa cgagcccacc tatttcaccg tggactgcag caaggcgggg 120
caag 124

<210> SEQ ID NO 23
<211> LENGTH: 20
<212> TYPE: DNA
<213> ORGANISM: Equus
<220> FEATURE:
<223> OTHER INFORMATION: FLNC Exon 15 Forward Primer

<400> SEQUENCE: 23
ggcagtcacc ctgagaaagt 20

<210> SEQ ID NO 24
<211> LENGTH: 19
<212> TYPE: DNA
<213> ORGANISM: Equus
<220> FEATURE:
<223> OTHER INFORMATION: FLNC Exon 15 Reverse Primer

<400> SEQUENCE: 24
acttgatgcc aatgctcac 19

<210> SEQ ID NO 25
<211> LENGTH: 598
<212> TYPE: DNA
<213> ORGANISM: Equus
<220> FEATURE:
<223> OTHER INFORMATION: FLNC-Normal Exon 21

<400> SEQUENCE: 25
gtttgtgctt atggccctgg tctcaagggt gggctggtag gcagcccagc gccgttctcc 60

```
atcgacacca agggggctgg caccggtggc ctggggctga ctgtggaggg cccctgtgag    120

gccaagatcg agtgccagga caatggtgat ggctcatgtg cggtcagcta cctgcccacg    180

gagccgggcg agtacaccat caacatcctg ttcgccgaag cccacatccc cggctcaccc    240

ttcaaggcta ccatccggcc cgtgttcgac ccgagcaagg tgcgggccag tgggccaggc    300

ctggagcgtg gcaaggctgg tgaggcagcc accttcactg tggactgctc ggaggcgggc    360

gaggctgagc tgaccatcga gatcctgtca gacgctggcg tcaaggccga ggtgctgatc    420

cacaacaatg ctgacggcac ctaccacatc acctacagcc ccgccttccc cggcacctac    480

actattacca tcaagtacgg tggcaccccc gtacccaaat tccccacccg cgtccatgtg    540

cagcccgcta tcgacaccag tggagtcaag gtctcggggc ctggtgtgga gccgcacg      598
```

<210> SEQ ID NO 26
<211> LENGTH: 598
<212> TYPE: DNA
<213> ORGANISM: Equus
<220> FEATURE:
<223> OTHER INFORMATION: FLNC-A1207T Exon 21

<400> SEQUENCE: 26

```
gtttgtgctt atggccctgg tctcaagggt gggctggtag gcagcccagc gccgttctcc     60

atcgacacca agggggctgg caccggtggc ctggggctga ctgtggaggg cccctgtgag    120

gccaagatcg agtgccagga caatggtgat ggctcatgtg cggtcagcta cctgcccacg    180

gagccgggcg agtacaccat caacatcctg ttcgccgaag cccacatccc cggctcaccc    240

ttcaaggcta ccatccggcc cgtgttcgac ccgagcaagg tgcgggccag tgggccaggc    300

ctggagcgtg gcaaggctgg tgaggcagcc accttcactg tggactgctc ggaggcgggc    360

gaggctgagc tgaccatcga gatcctgtca gacgctggcg tcaaggccga ggtgctgatc    420

cacaacaatg ctgacggcac ctaccacatc acctacagcc ccgccttccc cggcacctac    480

actattacca tcaagtacgg tgggcacccc gtacccaaat tccccacccg cgtccatgtg    540

cagcccacta tcgacaccag tggagtcaag gtctcggggc ctggtgtgga gccgcacg      598
```

<210> SEQ ID NO 27
<211> LENGTH: 20
<212> TYPE: DNA
<213> ORGANISM: Equus
<220> FEATURE:
<223> OTHER INFORMATION: FLNC Exon 21 Forward Primer

<400> SEQUENCE: 27

```
ggtgctgatc cacaacaatg                                                  20
```

<210> SEQ ID NO 28
<211> LENGTH: 21
<212> TYPE: DNA
<213> ORGANISM: Equus
<220> FEATURE:
<223> OTHER INFORMATION: FLNC Exon 21 Reverse Primer

<400> SEQUENCE: 28

```
ccccaagtcc tcccttcata c                                                21
```

<210> SEQ ID NO 29
<211> LENGTH: 155
<212> TYPE: DNA
<213> ORGANISM: Equus
<220> FEATURE:

<223> OTHER INFORMATION: MYOZ3-Normal Exon 3

<400> SEQUENCE: 29
tccctgtgct ggacctgggc aagaagctga gcgtgcccca ggacctgatg atggaagagc 60
tgtcgctccg caacaaccgg ggatccctcc tcttccagaa gaggcagcgc cgcgtgcaga 120
aattcacctt tgagtttgca gccagccagc gggcg 155

<210> SEQ ID NO 30
<211> LENGTH: 155
<212> TYPE: DNA
<213> ORGANISM: Equus
<220> FEATURE:
<223> OTHER INFORMATION: MYOZ3-S42L Exon 3

<400> SEQUENCE: 30
tccctgtgct ggacctgggc aagaagctga gcgtgcccca ggacctgatg atggaagagc 60
tgttgctccg caacaaccgg ggatccctcc tcttccagaa gaggcagcgc cgcgtgcaga 120
aattcacctt tgagtttgca gccagccagc gggcg 155

<210> SEQ ID NO 31
<211> LENGTH: 21
<212> TYPE: DNA
<213> ORGANISM: Equus
<220> FEATURE:
<223> OTHER INFORMATION: MYOZ3 Exon 3 Forward Primer

<400> SEQUENCE: 31
caggtttctc acacacaatg g 21

<210> SEQ ID NO 32
<211> LENGTH: 20
<212> TYPE: DNA
<213> ORGANISM: Equus
<220> FEATURE:
<223> OTHER INFORMATION: MYOZ3 Exon 3 Reverse Primer

<400> SEQUENCE: 32
aggcattctg cattttccac 20

<210> SEQ ID NO 33
<211> LENGTH: 35
<212> TYPE: DNA
<213> ORGANISM: Equus
<220> FEATURE:
<223> OTHER INFORMATION: MYOT Exon 6 Forward Primer

<400> SEQUENCE: 33
gcacatgata agaattgtcc atggggtact ctgca 35

<210> SEQ ID NO 34
<211> LENGTH: 34
<212> TYPE: DNA
<213> ORGANISM: Equus
<220> FEATURE:
<223> OTHER INFORMATION: MYOT Exon 6-Normal Reverse Primer

<400> SEQUENCE: 34
ttgcatcctg atcattcaca tctccccttg acga 34

<210> SEQ ID NO 35
<211> LENGTH: 34
<212> TYPE: DNA
<213> ORGANISM: Equus

<220> FEATURE:
<223> OTHER INFORMATION: MYOT Exon 6-S232P Reverse Primer

<400> SEQUENCE: 35
ttgcatcctg atcattcaca tctccccttg acgg 34

<210> SEQ ID NO 36
<211> LENGTH: 25
<212> TYPE: DNA
<213> ORGANISM: Equus
<220> FEATURE:
<223> OTHER INFORMATION: FLNC Exon 15 Forward Primer

<400> SEQUENCE: 36
tgtcgctggg ccctggtcac tgctc 25

<210> SEQ ID NO 37
<211> LENGTH: 24
<212> TYPE: DNA
<213> ORGANISM: Equus
<220> FEATURE:
<223> OTHER INFORMATION: FLNC Exon 15-Normal Reverse Primer

<400> SEQUENCE: 37
ggctggtgca ccttgccccg cgtc 24

<210> SEQ ID NO 38
<211> LENGTH: 24
<212> TYPE: DNA
<213> ORGANISM: Equus
<220> FEATURE:
<223> OTHER INFORMATION: FLNC Exon 15-E753K Reverse Primer

<400> SEQUENCE: 38
ggctggtgca ccttgccccg cgtt 24

<210> SEQ ID NO 39
<211> LENGTH: 24
<212> TYPE: DNA
<213> ORGANISM: Equus
<220> FEATURE:
<223> OTHER INFORMATION: FLNC Exon 21 Reverse Primer

<400> SEQUENCE: 39
ccagggctgt ccccaagtcc tccc 24

<210> SEQ ID NO 40
<211> LENGTH: 22
<212> TYPE: DNA
<213> ORGANISM: Equus
<220> FEATURE:
<223> OTHER INFORMATION: FLNC Exon 21-Normal Forward Primer

<400> SEQUENCE: 40
acccgcgtcc atgtgcagcg cg 22

<210> SEQ ID NO 41
<211> LENGTH: 22
<212> TYPE: DNA
<213> ORGANISM: Equus
<220> FEATURE:
<223> OTHER INFORMATION: FLNC Exon 21-Normal Forward Primer

<400> SEQUENCE: 41
acccgcgtcc atgtgcagcg ca 22

<210> SEQ ID NO 42
<211> LENGTH: 22
<212> TYPE: DNA
<213> ORGANISM: Equus
<220> FEATURE:
<223> OTHER INFORMATION: MYOZ3 Exon 3 Reverse Primer

<400> SEQUENCE: 42
ggccagaggt cctcccctgg ct 22

<210> SEQ ID NO 43
<211> LENGTH: 30
<212> TYPE: DNA
<213> ORGANISM: Equus
<220> FEATURE:
<223> OTHER INFORMATION: MYOZ3 Exon 3-Normal Forward Primer

<400> SEQUENCE: 43
gccccaggac ctgatgatgg aagagctctc 30

<210> SEQ ID NO 44
<211> LENGTH: 30
<212> TYPE: DNA
<213> ORGANISM: Equus
<220> FEATURE:
<223> OTHER INFORMATION: MYOZ3 Exon 3-S42L Forward Primer

<400> SEQUENCE: 44
gccccaggac ctgatgatgg aagagctctt 30

<210> SEQ ID NO 45
<211> LENGTH: 51
<212> TYPE: PRT
<213> ORGANISM: Homo sapiens

<400> SEQUENCE: 45

Ala Gln Asp Ser Gln Gln His Asn Ser Glu His Ala Arg Leu Gln Val
1 5 10 15

Pro Thr Ser Gln Val Arg Ser Arg Ser Thr Ser Arg Gly Asp Val Asn
20 25 30

Asp Gln Asp Ala Ile Gln Glu Lys Phe Tyr Pro Pro Arg Phe Ile Gln
35 40 45

Val Pro Glu
50

<210> SEQ ID NO 46
<211> LENGTH: 51
<212> TYPE: PRT
<213> ORGANISM: Homo sapiens
<220> FEATURE:
<221> NAME/KEY: VARIANT
<222> LOCATION: 26
<223> OTHER INFORMATION: T or S

<400> SEQUENCE: 46

Ala Gln Asp Ser Gln Gln His Asn Ser Glu His Ala Arg Leu Gln Val
1 5 10 15

Pro Thr Ser Gln Val Arg Ser Arg Ser Xaa Ser Arg Gly Asp Val Asn
20 25 30

Asp Gln Asp Ala Ile Gln Glu Lys Phe Tyr Pro Pro Arg Phe Ile Gln
35 40 45

Val Pro Glu
50

<210> SEQ ID NO 47
<211> LENGTH: 11
<212> TYPE: DNA
<213> ORGANISM: Equus
<220> FEATURE:
<223> OTHER INFORMATION: Homozygous Wild-Type

<400> SEQUENCE: 47
tgaagatgat c 11

<210> SEQ ID NO 48
<211> LENGTH: 11
<212> TYPE: DNA
<213> ORGANISM: Equus
<220> FEATURE:
<223> OTHER INFORMATION: Homozygous Wild-Type

<400> SEQUENCE: 48
gcagcgaggc g 11

<210> SEQ ID NO 49
<211> LENGTH: 11
<212> TYPE: DNA
<213> ORGANISM: Equus
<220> FEATURE:
<223> OTHER INFORMATION: Homozygous Wild-Type

<400> SEQUENCE: 49
agcccgctat c 11

<210> SEQ ID NO 50
<211> LENGTH: 10
<212> TYPE: DNA
<213> ORGANISM: Equus
<220> FEATURE:
<223> OTHER INFORMATION: Homozygous Wild-Type

<400> SEQUENCE: 50
aagagctgtc 10

<210> SEQ ID NO 51
<211> LENGTH: 53
<212> TYPE: PRT
<213> ORGANISM: Primates
<220> FEATURE:
<223> OTHER INFORMATION: primate1

<400> SEQUENCE: 51

```
Gly Ala Gln Asp Ser Gln Gln His Asn Ser Glu His Ala Arg Leu Gln
1               5                   10                  15

Val Pro Thr Ser Gln Val Arg Ser Arg Ser Thr Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50
```

<210> SEQ ID NO 52
<211> LENGTH: 53
<212> TYPE: PRT
<213> ORGANISM: Primates
<220> FEATURE:
<223> OTHER INFORMATION: primate2

<400> SEQUENCE: 52

```
Gly Ala Gln Asp Ser Gln Gln His Asn Ser Glu His Ala Arg Leu Gln
1               5                   10                  15

Val Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50
```

<210> SEQ ID NO 53
<211> LENGTH: 52
<212> TYPE: PRT
<213> ORGANISM: Mammalia
<220> FEATURE:
<223> OTHER INFORMATION: mammal1

<400> SEQUENCE: 53

```
Ala Gln Asp Ser Pro Gln His Asn Ser Glu His Ala Arg Leu Gln Val
1               5                   10                  15

Pro Thr Ser Gln Val Arg Ser Arg Ser Ser Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu Asn
    50
```

<210> SEQ ID NO 54
<211> LENGTH: 53
<212> TYPE: PRT
<213> ORGANISM: Mammalia
<220> FEATURE:
<223> OTHER INFORMATION: mammal2

<400> SEQUENCE: 54

```
Ala Gln Asp Ser Ala Gln Gln His Asn Ile Glu His Ala Arg Leu Gln
1               5                   10                  15

Val Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50
```

<210> SEQ ID NO 55
<211> LENGTH: 53
<212> TYPE: PRT
<213> ORGANISM: Mammalia
<220> FEATURE:
<223> OTHER INFORMATION: mammal3

<400> SEQUENCE: 55

```
Ala Gln Asp Ser Pro Gln Gln His His Ser Glu His Ala Arg Leu Gln
1               5                   10                  15

Val Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50
```

```
<210> SEQ ID NO 56
<211> LENGTH: 52
<212> TYPE: PRT
<213> ORGANISM: Mammalia
<220> FEATURE:
<223> OTHER INFORMATION: mammal4

<400> SEQUENCE: 56

Ala Gln Asp Ser Pro Gln His Asn Ser Glu His Ala Arg Leu Gln Val
1               5                   10                  15

Pro Thr Ser Gln Val Arg Ser Arg Ser Ser Ser Arg Gly Gly Val Asn
            20                  25                  30

Asp Glu Asp Ala Ile Gln Glu Lys Phe Tyr Pro Pro Arg Phe Ile Gln
        35                  40                  45

Val Pro Glu Asn
    50


<210> SEQ ID NO 57
<211> LENGTH: 53
<212> TYPE: PRT
<213> ORGANISM: Mammalia
<220> FEATURE:
<223> OTHER INFORMATION: mammal5

<400> SEQUENCE: 57

Ala Gln Asp Pro Ala Gln Gln His Asn Ser Glu His Ala Arg Leu Gln
1               5                   10                  15

Leu Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50


<210> SEQ ID NO 58
<211> LENGTH: 52
<212> TYPE: PRT
<213> ORGANISM: Mammalia
<220> FEATURE:
<223> OTHER INFORMATION: mammal6

<400> SEQUENCE: 58

Ala Gln Asp Ser Pro Gln His Asn Ser Glu His Ala Arg Leu Gln Val
1               5                   10                  15

Pro Thr Ser Gln Val Arg Ser Arg Ser Ser Ser Arg Gly Thr Leu Asn
            20                  25                  30

Glu Gln Asp Ala Ile Gln Glu Lys Phe Tyr Pro Pro Arg Phe Ile Gln
        35                  40                  45

Val Pro Glu Asn
    50


<210> SEQ ID NO 59
<211> LENGTH: 53
<212> TYPE: PRT
<213> ORGANISM: Mammalia
<220> FEATURE:
<223> OTHER INFORMATION: mammal7

<400> SEQUENCE: 59

Ala Gln Asp Ser Pro Gln Gln His Asn Ser Asp His Val Arg Leu Gln
1               5                   10                  15
```

```
Val Pro Thr Ser Gln Ile Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50


<210> SEQ ID NO 60
<211> LENGTH: 53
<212> TYPE: PRT
<213> ORGANISM: Mammalia
<220> FEATURE:
<223> OTHER INFORMATION: mammal8

<400> SEQUENCE: 60

Ala Gln Asp Ser Pro Gln His His Asn Pro Glu His Ala Arg Leu Gln
1               5                   10                  15

Val Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50


<210> SEQ ID NO 61
<211> LENGTH: 51
<212> TYPE: PRT
<213> ORGANISM: Cebus capucinus
<220> FEATURE:
<223> OTHER INFORMATION: Cebus_capucinus_imitator

<400> SEQUENCE: 61

Gln Asp Ser Gln Gln His Asn Ser Glu Tyr Ala Arg Leu Gln Val Pro
1               5                   10                  15

Thr Ser Gln Val Arg Ser Arg Ser Ser Ser Arg Gly Thr Val Asn Asp
            20                  25                  30

Gln Asp Ala Ile Gln Glu Lys Phe Tyr Pro Pro Arg Phe Ile Gln Val
        35                  40                  45

Pro Glu Asn
    50


<210> SEQ ID NO 62
<211> LENGTH: 53
<212> TYPE: PRT
<213> ORGANISM: Chlorocebus sabaeus
<220> FEATURE:
<223> OTHER INFORMATION: Chlorocebus_sabaeus

<400> SEQUENCE: 62

Gly Ala Gln Asp Ser Gln Gln His Asn Ser Glu Tyr Ala Arg Leu Gln
1               5                   10                  15

Val Pro Thr Ser Gln Val Arg Ser Arg Ser Ser Ser Arg Gly Asp Ala
            20                  25                  30

Asn Asp Gln Asp Ala Ile Gln Glu Lys Phe Tyr Pro Pro Arg Phe Ile
        35                  40                  45

Gln Val Pro Glu Asn
    50


<210> SEQ ID NO 63
<211> LENGTH: 53
```

<212> TYPE: PRT
<213> ORGANISM: Microcebus murinus
<220> FEATURE:
<223> OTHER INFORMATION: Microcebus_murinus

<400> SEQUENCE: 63

Ala Gln Asp Leu Pro Gln Gln His Asn Ser Glu His Ala Arg Leu Gln
1 5 10 15

Val Pro Thr Ser Gln Val Arg Ser Arg Ser Ser Ser Arg Gly Asp Val
20 25 30

Asn Asp Gln Asp Ala Ile Gln Glu Lys Phe Tyr Pro Pro Arg Phe Ile
35 40 45

Gln Val Pro Glu Asn
50

<210> SEQ ID NO 64
<211> LENGTH: 52
<212> TYPE: PRT
<213> ORGANISM: Otolemur garnettii
<220> FEATURE:
<223> OTHER INFORMATION: Otolemur_garnettii

<400> SEQUENCE: 64

Ala Gln Asp Ser Pro Gln His Asn Ser Glu His Ala Arg Leu Gln Val
1 5 10 15

Pro Thr Pro Gln Val Arg Ser Arg Ser Ser Ser Arg Gly Asp Val Asn
20 25 30

Asp Gln Asp Ala Ile Gln Glu Lys Phe Tyr Pro Pro Arg Phe Ile Gln
35 40 45

Val Pro Glu Asn
50

<210> SEQ ID NO 65
<211> LENGTH: 53
<212> TYPE: PRT
<213> ORGANISM: Bubalus bubalis
<220> FEATURE:
<223> OTHER INFORMATION: Bubalus_bubalis

<400> SEQUENCE: 65

Ala Gln Asp Ser Ala Gln Gln His Asn Ile Glu His Ala Arg Leu Gln
1 5 10 15

Val Pro Thr Ser Gln Val Arg Ser Arg Ser Ser Ser Arg Gly Asp Met
20 25 30

Asn Asp Gln Asp Ala Ile Gln Glu Lys Phe Tyr Pro Pro Arg Phe Ile
35 40 45

Gln Val Pro Glu Asn
50

<210> SEQ ID NO 66
<211> LENGTH: 52
<212> TYPE: PRT
<213> ORGANISM: Rattus norvegicus
<220> FEATURE:
<223> OTHER INFORMATION: Rattus_norvegicus

<400> SEQUENCE: 66

Val Gln Asp Ser Ser Gln His Asn Pro Glu His Ala Arg Leu Gln Val
1 5 10 15

Pro Thr Ser Gln Val Arg Ser Arg Ser Ser Ser Arg Ala Asp Ala Asn
20 25 30

```
Asp Gln Asp Ala Ile Gln Glu Lys Phe Tyr Pro Pro Arg Phe Ile Gln
        35                  40                  45

Val Pro Glu Asn
    50


<210> SEQ ID NO 67
<211> LENGTH: 52
<212> TYPE: PRT
<213> ORGANISM: Heterocephalus glaber
<220> FEATURE:
<223> OTHER INFORMATION: Heterocephalus_glaber

<400> SEQUENCE: 67

Ala Gln Asp Ser Pro Gln His Asn Ala Glu His Ala Arg Leu Gln Val
1               5                   10                  15

Pro Thr Ala Gln Val Arg Ser Arg Ser Ser Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu Asn
    50


<210> SEQ ID NO 68
<211> LENGTH: 52
<212> TYPE: PRT
<213> ORGANISM: Ovis aries musimon
<220> FEATURE:
<223> OTHER INFORMATION: Ovis_aries_musimon

<400> SEQUENCE: 68

Ala Gln Asp Ser Ala Gln His Asn Ile Glu His Ala Arg Leu Gln Val
1               5                   10                  15

Pro Thr Ser Gln Val Arg Ser Arg Ser Ser Ser Arg Gly Asp Met Ser
            20                  25                  30

Asp Gln Asp Ala Ile Gln Glu Lys Phe Tyr Pro Pro Arg Phe Ile Gln
        35                  40                  45

Val Pro Glu Asn
    50


<210> SEQ ID NO 69
<211> LENGTH: 52
<212> TYPE: PRT
<213> ORGANISM: Castor canadensis
<220> FEATURE:
<223> OTHER INFORMATION: Castor_canadensis

<400> SEQUENCE: 69

Gln Asp Ser Pro Gln Gln His Asn Ser Glu His Ala Trp Leu Gln Val
1               5                   10                  15

Pro Thr Ser Gln Val Arg Ser Arg Ser Ser Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu Asn
    50


<210> SEQ ID NO 70
<211> LENGTH: 53
<212> TYPE: PRT
<213> ORGANISM: Canis lupus familiaris
<220> FEATURE:
<223> OTHER INFORMATION: Canis_lupus_familiaris
```

<400> SEQUENCE: 70

```
Ala Gln Asp Ser Pro Gln Gln His Asn Leu Glu His Ala Arg Leu Gln
1               5                   10                  15

Val Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu Asn
    50
```

<210> SEQ ID NO 71
<211> LENGTH: 52
<212> TYPE: PRT
<213> ORGANISM: Miniopterus natalensis
<220> FEATURE:
<223> OTHER INFORMATION: Miniopterus_natalensis

<400> SEQUENCE: 71

```
Ala Gln Asp Ser Pro Gln His Asn Ser Ala His Ala Arg Leu Gln Val
1               5                   10                  15

Pro Thr Ser Gln Ile Arg Ser Arg Ser Ser Ser Arg Gly Asp Val Asn
            20                  25                  30

Asp Glu Asp Ala Ile Gln Glu Lys Phe Tyr Pro Pro Arg Phe Ile Gln
        35                  40                  45

Val Pro Glu Asn
    50
```

<210> SEQ ID NO 72
<211> LENGTH: 52
<212> TYPE: PRT
<213> ORGANISM: Pteropus alecto
<220> FEATURE:
<223> OTHER INFORMATION: Pteropus_alecto

<400> SEQUENCE: 72

```
Ala Gln Asp Ser Pro Gln His Asn Ser Asp His Val Arg Leu Gln Val
1               5                   10                  15

Pro Thr Ser Gln Ile Arg Ser Arg Ser Ser Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu Asn
    50
```

<210> SEQ ID NO 73
<211> LENGTH: 52
<212> TYPE: PRT
<213> ORGANISM: Physeter catodon
<220> FEATURE:
<223> OTHER INFORMATION: Physeter_catodon

<400> SEQUENCE: 73

```
Ala Gln Asp Pro Ala Gln Gln His Asn Ser Glu His Ala Arg Leu Gln
1               5                   10                  15

Val Pro Thr Ser Gln Val Arg Ser Arg Ser Ser Ser Arg Gly Asp Val
            20                  25                  30

Asn Asp Gln Asp Ala Ile Gln Glu Lys Phe Tyr Pro Pro Arg Phe Ile
        35                  40                  45

Gln Val Pro Glu
```

50

<210> SEQ ID NO 74
<211> LENGTH: 52
<212> TYPE: PRT
<213> ORGANISM: Trichechus manatus latirostris
<220> FEATURE:
<223> OTHER INFORMATION: T_manatus_latirostris

<400> SEQUENCE: 74

Ala Gln Asp Ser Pro Gln His Thr Ser Glu His Ala Arg Leu Gln Val
1 5 10 15

Pro Thr Ser Gln Val Arg Ser Arg Ser Ser Ser Arg Gly Asp Val Asn
20 25 30

Asp Gln Asp Ala Ile Gln Glu Lys Phe Tyr Pro Pro Arg Phe Ile Gln
35 40 45

Val Pro Glu Asn
50

<210> SEQ ID NO 75
<211> LENGTH: 52
<212> TYPE: PRT
<213> ORGANISM: Echinops telfairi
<220> FEATURE:
<223> OTHER INFORMATION: Echinops_telfairi

<400> SEQUENCE: 75

Ala Gln Asp Ser Pro Gln His Asn Ser Glu His Ala Arg Leu His Val
1 5 10 15

Pro Thr Ala Gln Val Arg Ser Arg Ser Ser Ser Arg Gly Asp Val Asn
20 25 30

Asp Gln Asp Ala Ile Gln Glu Lys Phe Tyr Pro Pro Arg Phe Ile Gln
35 40 45

Val Pro Glu Asn
50

<210> SEQ ID NO 76
<211> LENGTH: 52
<212> TYPE: PRT
<213> ORGANISM: Erinaceus europaeus
<220> FEATURE:
<223> OTHER INFORMATION: Erinaceus_europaeus

<400> SEQUENCE: 76

Val Gln Glu Ser Ser Gln His Asn Ser Glu His Ala Arg Leu Gln Val
1 5 10 15

Pro Thr Pro Gln Ile Arg Ser Arg Ser Ser Ser Arg Gly Asp Val Asn
20 25 30

Asp Gln Asp Ala Ile Gln Glu Lys Phe Tyr Pro Pro Arg Phe Ile Gln
35 40 45

Val Pro Glu Asn
50

<210> SEQ ID NO 77
<211> LENGTH: 52
<212> TYPE: PRT
<213> ORGANISM: Dasypus novemcinctus
<220> FEATURE:
<223> OTHER INFORMATION: Dasypus_novemcinctus

<400> SEQUENCE: 77

Ala Gln Asp Ser Pro Lys Tyr Asn Ser Glu His Ala Arg Leu Gln Val

```
1               5                   10                  15

Pro Thr Ser Gln Val Arg Ser Arg Ser Ser Ser Arg Gly Asp Ala Asn
            20                  25                  30

Asp Gln Asp Ala Ile Gln Glu Lys Phe Tyr Pro Pro Arg Phe Ile Gln
        35                  40                  45

Val Pro Glu Asn
    50


<210> SEQ ID NO 78
<211> LENGTH: 52
<212> TYPE: PRT
<213> ORGANISM: Manis javanica
<220> FEATURE:
<223> OTHER INFORMATION: Manis_javanica

<400> SEQUENCE: 78

Ala Gln Asp Ser Pro Gln His Asn Ser Glu Asn Ala Arg Leu Gln Val
1               5                   10                  15

Pro Thr Ser Gln Ile Arg Ser Arg Ser Ser Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu His
    50


<210> SEQ ID NO 79
<211> LENGTH: 52
<212> TYPE: PRT
<213> ORGANISM: Orycteropus afer
<220> FEATURE:
<223> OTHER INFORMATION: Orycteropus_afer_afer

<400> SEQUENCE: 79

Ala Gln Asp Ser Leu Gln His Asn Ser Glu His Ala Arg Leu Gln Val
1               5                   10                  15

Pro Thr Ser Gln Ile Arg Ser Arg Ser Ser Ser Arg Gly Gly Val Asn
            20                  25                  30

Asp Gln Asp Ala Ile Gln Glu Lys Phe Tyr Pro Pro Arg Phe Ile Gln
        35                  40                  45

Val Pro Glu Asn
    50


<210> SEQ ID NO 80
<211> LENGTH: 52
<212> TYPE: PRT
<213> ORGANISM: Monodelphis domestica
<220> FEATURE:
<223> OTHER INFORMATION: Monodelphis_domestica

<400> SEQUENCE: 80

Ser Gln Asp Ser Ala Gln His Asn Ser Glu Asn Ala Arg Leu Gln Val
1               5                   10                  15

Pro Val Pro Gln Ile Arg Ser Arg Ser Ser Ser Arg Gly Asp Thr Asn
            20                  25                  30

Asp Gln Glu Ser Ile Leu Glu Lys Phe Tyr Pro Pro Arg Phe Val Gln
        35                  40                  45

Val Pro Glu Asn
    50


<210> SEQ ID NO 81
```

<211> LENGTH: 52
<212> TYPE: PRT
<213> ORGANISM: Sarcophilus harrisii
<220> FEATURE:
<223> OTHER INFORMATION: Sarcophilus_harrisii

<400> SEQUENCE: 81

Ser Gln Asn Ser Ala Gln His Asn Ser Glu Asn Ala Arg Leu Gln Val
1               5                   10                  15

Pro Thr Pro Gln Ile Arg Ser Arg Ser Ser Ser Arg Gly Asp Thr Asn
            20                  25                  30

Asp Gln Glu Ser Ile Leu Glu Lys Phe Tyr Pro Pro Arg Phe Val Gln
        35                  40                  45

Val Pro Glu Asn
    50

<210> SEQ ID NO 82
<211> LENGTH: 52
<212> TYPE: PRT
<213> ORGANISM: Ornithorhynchus anatinus
<220> FEATURE:
<223> OTHER INFORMATION: Ornithorhynchus_anatinus

<400> SEQUENCE: 82

Ala Gln Asp Phe Ser Gln Pro Asn Ser Glu Asn Val Arg Leu Gln Val
1               5                   10                  15

Pro Ser Pro Gln Val Arg Ser Arg Ser Ser Ser Arg Gly Ala Val Asn
            20                  25                  30

Asp Gln Asp Ser Ile Gln Glu Lys Phe Tyr Pro Pro Arg Phe Val Gln
        35                  40                  45

Val Pro Glu Asn
    50

<210> SEQ ID NO 83
<211> LENGTH: 51
<212> TYPE: PRT
<213> ORGANISM: Aves
<220> FEATURE:
<223> OTHER INFORMATION: bird1

<400> SEQUENCE: 83

Gln Asn Ala Gln His Gln Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ala Ile Gln Glu Lys Phe Phe Gln Pro Arg Phe Thr Gln Val
        35                  40                  45

Pro Glu Asp
    50

<210> SEQ ID NO 84
<211> LENGTH: 51
<212> TYPE: PRT
<213> ORGANISM: Aves
<220> FEATURE:
<223> OTHER INFORMATION: bird2

<400> SEQUENCE: 84

Gln Asn Ala Gln His Gln Asn Ala Glu Asn Val Arg Leu Gln Val Pro
1               5                   10                  15

Thr Thr His Val Arg Ser Arg Pro Ser Ser Arg Gly Asp Glu Arg Gly
            20                  25                  30

```
His Asp Ser Ile Gln Glu Lys Phe Phe Gln Pro Arg Phe Thr Gln Val
        35                  40                  45

Pro Glu Asp
    50


<210> SEQ ID NO 85
<211> LENGTH: 51
<212> TYPE: PRT
<213> ORGANISM: Aves
<220> FEATURE:
<223> OTHER INFORMATION: bird3

<400> SEQUENCE: 85

Gln Asn Ala Gln His Gln Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 86
<211> LENGTH: 52
<212> TYPE: PRT
<213> ORGANISM: Aves
<220> FEATURE:
<223> OTHER INFORMATION: bird4

<400> SEQUENCE: 86

Val Gln Asn Ala Gln His Gln Asn Ala Glu Asn Ile Arg Leu Gln Val
1               5                   10                  15

Pro Thr Thr His Val Arg Ser Arg Pro Ser Ser Arg Gly Asp Asp Arg
            20                  25                  30

Gly His Asp Ser Ile Gln Glu Lys Phe Phe Gln Pro Arg Phe Thr Gln
        35                  40                  45

Val Pro Glu Asp
    50


<210> SEQ ID NO 87
<211> LENGTH: 51
<212> TYPE: PRT
<213> ORGANISM: Aves
<220> FEATURE:
<223> OTHER INFORMATION: bird5

<400> SEQUENCE: 87

Gln Asn Ala Gln His Gln Asn Ala Glu Asn Ile Arg Leu Gln Val Pro
1               5                   10                  15

Thr Thr His Val Arg Ser Arg Pro Ser Ser Arg Gly Asp Asp Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 88
<211> LENGTH: 51
<212> TYPE: PRT
<213> ORGANISM: Gallus gallus
<220> FEATURE:
```

<223> OTHER INFORMATION: Gallus_gallus

<400> SEQUENCE: 88

Gln Asn Thr Gln His Gln Asn Ala Glu Asn Val Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50

<210> SEQ ID NO 89
<211> LENGTH: 51
<212> TYPE: PRT
<213> ORGANISM: Haliaeetus albicilla
<220> FEATURE:
<223> OTHER INFORMATION: Haliaeetus_albicilla

<400> SEQUENCE: 89

Gln Asn Ala Gln Gln Gln Asn Ala Glu Asn Ile Arg Leu Gln Val Pro
1               5                   10                  15

Thr Ala His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50

<210> SEQ ID NO 90
<211> LENGTH: 53
<212> TYPE: PRT
<213> ORGANISM: Tinamus guttatus
<220> FEATURE:
<223> OTHER INFORMATION: Tinamus_guttatus

<400> SEQUENCE: 90

Gly Leu Gln Asn Ala Gln Gln Gln Asn Ala Glu Asn Ile Arg Leu Gln
1               5                   10                  15

Val Pro Thr Thr His Val Arg Ser Arg Pro Ser Ser Arg Gly Asp Glu
            20                  25                  30

His Gly His Asp Ser Ile Gln Glu Lys Phe Phe Gln Pro Arg Phe Thr
        35                  40                  45

Gln Val Pro Glu Asp
    50

<210> SEQ ID NO 91
<211> LENGTH: 51
<212> TYPE: PRT
<213> ORGANISM: Aptenodytes forsteri
<220> FEATURE:
<223> OTHER INFORMATION: Aptenodytes_forsteri

<400> SEQUENCE: 91

Gln Asn Ala Gln His Gln Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50

<210> SEQ ID NO 92
<211> LENGTH: 52
<212> TYPE: PRT
<213> ORGANISM: Meleagris gallopavo
<220> FEATURE:
<223> OTHER INFORMATION: Meleagris_gallopavo

<400> SEQUENCE: 92

Val Gln Asn Ala Gln His Gln Asn Ala Glu Asn Ile Arg Leu Gln Val
1               5                   10                  15

Pro Thr Thr His Val Arg Ser Arg Pro Ser Ser Arg Gly Asp Glu Arg
            20                  25                  30

Gly His Asp Ser Ile Gln Glu Lys Phe Phe Gln Pro Arg Phe Thr Gln
        35                  40                  45

Val Pro Glu Asp
    50

<210> SEQ ID NO 93
<211> LENGTH: 51
<212> TYPE: PRT
<213> ORGANISM: Aquila chrysaetos canadensis
<220> FEATURE:
<223> OTHER INFORMATION: A_chrysaetos_canadensis

<400> SEQUENCE: 93

Gln Asn Ala Gln Gln Gln Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50

<210> SEQ ID NO 94
<211> LENGTH: 51
<212> TYPE: PRT
<213> ORGANISM: Eurypyga helias
<220> FEATURE:
<223> OTHER INFORMATION: Eurypyga_helias

<400> SEQUENCE: 94

Gln Asn Ala Gln Glu His Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50

<210> SEQ ID NO 95
<211> LENGTH: 51
<212> TYPE: PRT
<213> ORGANISM: Colius striatus
<220> FEATURE:
<223> OTHER INFORMATION: Colius_striatus

<400> SEQUENCE: 95

```
Gln Asn Ala Gln His His Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 96
<211> LENGTH: 47
<212> TYPE: PRT
<213> ORGANISM: Melopsittacus undulatus
<220> FEATURE:
<223> OTHER INFORMATION: Melopsittacus_undulatus

<400> SEQUENCE: 96

Gln His Asn Ala Glu Asn Ile Arg Leu Gln Val Pro Thr Thr His Val
1               5                   10                  15

Arg Ser Arg Pro Ser Ser Arg Gly Asp Glu Arg Gly His Asp Ser Ile
            20                  25                  30

Gln Glu Lys Phe Phe Gln Pro Arg Phe Thr Gln Val Pro Glu Asp
        35                  40                  45


<210> SEQ ID NO 97
<211> LENGTH: 51
<212> TYPE: PRT
<213> ORGANISM: Ficedula albicollis
<220> FEATURE:
<223> OTHER INFORMATION: Ficedula_albicollis

<400> SEQUENCE: 97

Gln Ser Ala Gln His Gln Asn Ser Glu Asn Ile Arg Leu Gln Val Pro
1               5                   10                  15

Thr Thr His Val Arg Ser Arg Pro Ser Ser Arg Gly Asp Asp Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 98
<211> LENGTH: 51
<212> TYPE: PRT
<213> ORGANISM: Struthio camelus australis
<220> FEATURE:
<223> OTHER INFORMATION: S_camelus_australis

<400> SEQUENCE: 98

Gln Asn Ala Gln His Gln Asn Thr Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 99
<211> LENGTH: 52
<212> TYPE: PRT
```

<213> ORGANISM: Apteryx australis mantelli
<220> FEATURE:
<223> OTHER INFORMATION: A_australis_mantelli

<400> SEQUENCE: 99

```
Ala Gln Asn Ala Gln His Gln Asn Ala Glu Asn Ile Arg Leu Gln Val
1               5                   10                  15

Pro Thr Ala His Val Arg Ser Arg Pro Ser Ser Arg Gly Asp Glu His
            20                  25                  30

Gly His Asp Ser Ile Gln Glu Lys Phe Phe Gln Pro Arg Phe Thr Gln
        35                  40                  45

Val Pro Glu Asp
    50
```

<210> SEQ ID NO 100
<211> LENGTH: 51
<212> TYPE: PRT
<213> ORGANISM: Merops nubicus
<220> FEATURE:
<223> OTHER INFORMATION: Merops_nubicus

<400> SEQUENCE: 100

```
Gln Asn Ala Gln His Gln Asn Ala Glu His Val Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Pro Pro Arg Phe Thr Gln Val
        35                  40                  45

Pro Glu Asp
    50
```

<210> SEQ ID NO 101
<211> LENGTH: 51
<212> TYPE: PRT
<213> ORGANISM: Pelecanus crispus
<220> FEATURE:
<223> OTHER INFORMATION: Pelecanus_crispus

<400> SEQUENCE: 101

```
Gln Asn Thr Gln His Gln Asn Ala Glu Asn Val Arg Leu Gln Val Pro
1               5                   10                  15

Thr Thr His Val Arg Ser Arg Pro Ser Ser Arg Gly Asp Glu Arg Gly
            20                  25                  30

His Asp Ala Ile Gln Glu Lys Phe Phe Gln Pro Arg Phe Thr Gln Val
        35                  40                  45

Pro Glu Asp
    50
```

<210> SEQ ID NO 102
<211> LENGTH: 51
<212> TYPE: PRT
<213> ORGANISM: Egretta garzetta
<220> FEATURE:
<223> OTHER INFORMATION: Egretta_garzetta

<400> SEQUENCE: 102

```
Gln Asn Ala Gln His Gln Asn Ala Glu Asn Ile Arg Leu Gln Val Pro
1               5                   10                  15

Thr Thr His Val Arg Ser Arg Pro Ser Ser Arg Gly Glu Glu Arg Gly
            20                  25                  30

Gln Asp Ser Ile Gln Glu Lys Phe Phe Gln Pro Arg Phe Thr Gln Val
```

```
        35                  40                  45

Pro Glu Asp
    50


<210> SEQ ID NO 103
<211> LENGTH: 51
<212> TYPE: PRT
<213> ORGANISM: Tyto alba
<220> FEATURE:
<223> OTHER INFORMATION: Tyto_alba

<400> SEQUENCE: 103

Gln Asn Ala Gln His Gln Asn Ala Glu Asn Val Arg Leu Gln Val Pro
1               5                   10                  15

Thr Thr His Ile Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 104
<211> LENGTH: 51
<212> TYPE: PRT
<213> ORGANISM: Falco peregrinus
<220> FEATURE:
<223> OTHER INFORMATION: Falco_peregrinus

<400> SEQUENCE: 104

Gln Asn Thr Gln His Gln Asn Ala Glu Asn Ile Arg Leu Gln Val Pro
1               5                   10                  15

Thr Thr His Val Arg Ser Arg Pro Ser Ser Arg Gly Asp Glu His Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 105
<211> LENGTH: 51
<212> TYPE: PRT
<213> ORGANISM: Nestor notabilis
<220> FEATURE:
<223> OTHER INFORMATION: Nestor_notabilis

<400> SEQUENCE: 105

Gln Asn Thr Gln His Gln Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50


<210> SEQ ID NO 106
<211> LENGTH: 51
<212> TYPE: PRT
<213> ORGANISM: Picoides pubescens
<220> FEATURE:
<223> OTHER INFORMATION: Picoides_pubescens
```

<400> SEQUENCE: 106

Gln Asn Ala Gln His Gln Asn Ser Glu Asn Ile Arg Leu Gln Val Pro
1               5                   10                  15

Thr Thr His Val Arg Ser Arg Pro Ser Ser Arg Gly Asp Glu Arg Gly
            20                  25                  30

His Asp Ser Ile Gln Glu Lys Phe Phe Gln Pro Arg Phe Thr Gln Val
        35                  40                  45

Pro Glu Asp
    50

<210> SEQ ID NO 107
<211> LENGTH: 51
<212> TYPE: PRT
<213> ORGANISM: Opisthocomus hoazin
<220> FEATURE:
<223> OTHER INFORMATION: Opisthocomus_hoazin

<400> SEQUENCE: 107

Gln Asn Ala Gln His Gln Asn Ala Glu Asn Ile Arg Leu Gln Val Pro
1               5                   10                  15

Thr Thr His Val Arg Ser Arg Pro Ser Ser Arg Gly Asp Glu Arg Gly
            20                  25                  30

Gln Asp Ser Ile Gln Glu Lys Phe Phe Gln Pro Arg Phe Thr Gln Val
        35                  40                  45

Pro Glu Asp
    50

<210> SEQ ID NO 108
<211> LENGTH: 52
<212> TYPE: PRT
<213> ORGANISM: Equus
<220> FEATURE:
<223> OTHER INFORMATION: MYOT-S232P

<400> SEQUENCE: 108

Ala Gln Asp Ser Pro Gln His Asn Ser Glu His Ala Arg Leu Gln Val
1               5                   10                  15

Pro Thr Ser Gln Val Arg Ser Arg Ser Pro Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu Asn
    50

<210> SEQ ID NO 109
<211> LENGTH: 103
<212> TYPE: PRT
<213> ORGANISM: Mammalia
<220> FEATURE:
<223> OTHER INFORMATION: mammal1

<400> SEQUENCE: 109

Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

```
Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Ala
                85                  90                  95

Ser Pro Phe His Ile Lys Val
            100


<210> SEQ ID NO 110
<211> LENGTH: 103
<212> TYPE: PRT
<213> ORGANISM: Mammalia
<220> FEATURE:
<223> OTHER INFORMATION: mammal2

<400> SEQUENCE: 110

Gly Glu Gly Ser His Pro Glu Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Ala
                85                  90                  95

Ser Pro Phe His Ile Lys Val
            100


<210> SEQ ID NO 111
<211> LENGTH: 103
<212> TYPE: PRT
<213> ORGANISM: Mammalia
<220> FEATURE:
<223> OTHER INFORMATION: mammal3

<400> SEQUENCE: 111

Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly His Tyr Thr Ile Met Val Leu Phe Ala Asn Gln Glu Ile Pro Ala
                85                  90                  95

Ser Pro Phe His Ile Lys Val
            100


<210> SEQ ID NO 112
<211> LENGTH: 103
<212> TYPE: PRT
<213> ORGANISM: Mammalia
<220> FEATURE:
<223> OTHER INFORMATION: mammal4
```

<400> SEQUENCE: 112

Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Val Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly His Tyr Thr Ile Met Val Leu Phe Ala Asn Gln Glu Ile Pro Ala
                85                  90                  95

Ser Pro Phe His Ile Lys Val
            100

<210> SEQ ID NO 113
<211> LENGTH: 103
<212> TYPE: PRT
<213> ORGANISM: Mammalia
<220> FEATURE:
<223> OTHER INFORMATION: mammal5

<400> SEQUENCE: 113

Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Gln Tyr Thr Ile Met Val Leu Phe Ala Asn Gln Glu Ile Pro Ala
                85                  90                  95

Ser Pro Phe His Ile Lys Val
            100

<210> SEQ ID NO 114
<211> LENGTH: 103
<212> TYPE: PRT
<213> ORGANISM: Carlito syrichta
<220> FEATURE:
<223> OTHER INFORMATION: Carlito_syrichta

<400> SEQUENCE: 114

Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

```
Gly Arg Tyr Thr Ile Met Val Leu Phe Ala Asn Gln Glu Ile Pro Ala
                85                  90                  95

Ser Pro Phe Asn Ile Lys Val
            100
```

<210> SEQ ID NO 115
<211> LENGTH: 103
<212> TYPE: PRT
<213> ORGANISM: Cricetulus griseus
<220> FEATURE:
<223> OTHER INFORMATION: Cricetulus_griseus

<400> SEQUENCE: 115

```
Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Gly
        35                  40                  45

Pro Gly Val Val Gly Pro Val Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly His Tyr Thr Ile Met Val Leu Phe Ala Asn Gln Glu Ile Pro Ala
                85                  90                  95

Ser Pro Phe His Ile Lys Val
            100
```

<210> SEQ ID NO 116
<211> LENGTH: 103
<212> TYPE: PRT
<213> ORGANISM: Condylura cristata
<220> FEATURE:
<223> OTHER INFORMATION: Condylura_cristata

<400> SEQUENCE: 116

```
Gly Glu Gly Ser His Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly His Tyr Thr Ile Met Val Leu Phe Ala Asn Gln Glu Ile Pro Ala
                85                  90                  95

Ser Pro Phe His Ile Lys Val
            100
```

<210> SEQ ID NO 117
<211> LENGTH: 103
<212> TYPE: PRT
<213> ORGANISM: Mammalia
<220> FEATURE:
<223> OTHER INFORMATION: marsupial1

<400> SEQUENCE: 117

```
Gly Glu Gly Ser His Pro Glu Lys Val Arg Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly His Tyr Thr Ile Met Val Leu Phe Ala Asn Gln Glu Ile Pro Ala
                85                  90                  95

Ser Pro Phe His Ile Lys Val
            100


<210> SEQ ID NO 118
<211> LENGTH: 103
<212> TYPE: PRT
<213> ORGANISM: Aves
<220> FEATURE:
<223> OTHER INFORMATION: bird1

<400> SEQUENCE: 118

Gly Glu Gly Ser His Pro Ser Arg Val Lys Val His Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Ala Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100


<210> SEQ ID NO 119
<211> LENGTH: 103
<212> TYPE: PRT
<213> ORGANISM: Aves
<220> FEATURE:
<223> OTHER INFORMATION: bird2

<400> SEQUENCE: 119

Gly Glu Gly Ser His Pro Gly Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95
```

```
Ser Pro Phe Arg Ile Lys Val
            100


<210> SEQ ID NO 120
<211> LENGTH: 103
<212> TYPE: PRT
<213> ORGANISM: Aves
<220> FEATURE:
<223> OTHER INFORMATION: bird3

<400> SEQUENCE: 120

Gly Glu Gly Ser His Pro Gly Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Val Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100


<210> SEQ ID NO 121
<211> LENGTH: 103
<212> TYPE: PRT
<213> ORGANISM: Haliaeetus leucocephalus
<220> FEATURE:
<223> OTHER INFORMATION: Haliaeetus_leucocephalus

<400> SEQUENCE: 121

Gly Glu Gly Ser His Pro Gly Arg Val Lys Val Tyr Gly Pro Gly Val
1               5                   10                  15

Glu Lys Ser Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100


<210> SEQ ID NO 122
<211> LENGTH: 103
<212> TYPE: PRT
<213> ORGANISM: Anser cygnoides domesticus
<220> FEATURE:
<223> OTHER INFORMATION: Anser_cygnoides_domesticus

<400> SEQUENCE: 122

Gly Glu Gly Ser His Pro Gly Arg Val Arg Val His Gly Pro Gly Val
1               5                   10                  15
```

```
Glu Lys Thr Gly Leu Lys Ala Gly Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100


<210> SEQ ID NO 123
<211> LENGTH: 103
<212> TYPE: PRT
<213> ORGANISM: Cuculus canorus
<220> FEATURE:
<223> OTHER INFORMATION: Cuculus_canorus

<400> SEQUENCE: 123

Gly Glu Gly Ser His Pro Gly Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Ser Val
            100


<210> SEQ ID NO 124
<211> LENGTH: 103
<212> TYPE: PRT
<213> ORGANISM: Columba livia
<220> FEATURE:
<223> OTHER INFORMATION: Columba_livia

<400> SEQUENCE: 124

Gly Glu Gly Ser His Pro Gly Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Val Lys Val
            100
```

<210> SEQ ID NO 125
<211> LENGTH: 103
<212> TYPE: PRT
<213> ORGANISM: Ficedula albicollis
<220> FEATURE:
<223> OTHER INFORMATION: Ficedula_albicollis

<400> SEQUENCE: 125

```
Gly Glu Gly Ser His Pro Ser Arg Val Lys Val His Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100
```

<210> SEQ ID NO 126
<211> LENGTH: 103
<212> TYPE: PRT
<213> ORGANISM: Lepidothrix coronata
<220> FEATURE:
<223> OTHER INFORMATION: Lepidothrix_coronata

<400> SEQUENCE: 126

```
Gly Glu Gly Ser His Pro Gly Arg Val Lys Val His Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Ala Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100
```

<210> SEQ ID NO 127
<211> LENGTH: 103
<212> TYPE: PRT
<213> ORGANISM: Python bivittatus
<220> FEATURE:
<223> OTHER INFORMATION: Python_bivittatus

<400> SEQUENCE: 127

```
Gly Glu Gly Ser His Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30
```

```
Cys Ser Glu Ala Gly Gln Gly Asp Val Ser Ile Gly Ile Lys Cys Ala
        35                  40                  45

Pro Gly Val Val Gly Pro Val Glu Ala Asp Ile Asp Phe Asp Ile Ile
    50                  55                  60

Lys Asn Asp Asn Asp Thr Phe Thr Val Lys Tyr Thr Pro Pro Gly Pro
65                  70                  75                  80

Gly Arg Tyr Thr Ile Met Val Leu Phe Ala Ser Gln Glu Ile Pro Ile
                85                  90                  95

Ser Pro Phe His Ile Lys Val
            100


<210> SEQ ID NO 128
<211> LENGTH: 103
<212> TYPE: PRT
<213> ORGANISM: Protobothrops mucrosquamatus
<220> FEATURE:
<223> OTHER INFORMATION: Protobothrops_mucrosquamatus

<400> SEQUENCE: 128

Gly Glu Gly Ser His Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Pro
65                  70                  75                  80

Gly Arg Tyr Thr Ile Met Val Leu Phe Ala Thr Gln Glu Ile Pro Thr
                85                  90                  95

Ser Pro Phe His Ile Lys Val
            100


<210> SEQ ID NO 129
<211> LENGTH: 103
<212> TYPE: PRT
<213> ORGANISM: Chelonia mydas
<220> FEATURE:
<223> OTHER INFORMATION: Chelonia_mydas

<400> SEQUENCE: 129

Gly Glu Gly Ser His Pro Glu Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Val Glu Ala Asp Ile Glu Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Pro
                85                  90                  95

Ser Pro Phe Arg Ile Lys Val
            100


<210> SEQ ID NO 130
```

<211> LENGTH: 103
<212> TYPE: PRT
<213> ORGANISM: Chrysemys picta bellii
<220> FEATURE:
<223> OTHER INFORMATION: Chrysemys_picta_bellii

<400> SEQUENCE: 130

Gly Glu Gly Ser His Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Glu Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Thr
                85                  90                  95

Ser Pro Phe Arg Ile Lys Val
            100

<210> SEQ ID NO 131
<211> LENGTH: 103
<212> TYPE: PRT
<213> ORGANISM: Gekko japonicus
<220> FEATURE:
<223> OTHER INFORMATION: Gekko_japonicus

<400> SEQUENCE: 131

Gly Glu Gly Ser His Pro Asp Lys Val Lys Val Tyr Gly Pro Gly Val
1               5                   10                  15

Glu Lys Thr Gly Leu Lys Ala Ser Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Leu Glu Ala Asp Ile Asp Phe Asp Ile Ile
    50                  55                  60

Lys Asn Asp Asn Asp Thr Phe Thr Val Lys Tyr Thr Pro Pro Gly Pro
65                  70                  75                  80

Gly Arg Tyr Thr Ile Met Val Leu Phe Ala Asn Gln Glu Ile Pro Ile
                85                  90                  95

Ser Pro Phe His Ile Lys Val
            100

<210> SEQ ID NO 132
<211> LENGTH: 103
<212> TYPE: PRT
<213> ORGANISM: Anolis carolinensis
<220> FEATURE:
<223> OTHER INFORMATION: Anolis_carolinensis

<400> SEQUENCE: 132

Gly Glu Gly Ser Tyr Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Asp Ala Gly Gln Gly Asp Val Ser Ile Gly Ile Lys Cys Ala
        35                  40                  45

```
Pro Gly Val Val Gly Pro Val Glu Ala Asp Ile Asp Phe Asp Ile Ile
    50                  55                  60

Lys Asn Asp Asn Asp Thr Phe Thr Val Lys Tyr Thr Pro Pro Gly Pro
65                  70                  75                  80

Gly Arg Tyr Thr Ile Met Val Leu Phe Ala Asn Gln Glu Ile Pro Ile
                85                  90                  95

Ser Pro Phe His Ile Lys Val
            100


<210> SEQ ID NO 133
<211> LENGTH: 103
<212> TYPE: PRT
<213> ORGANISM: Alligator mississippiensis
<220> FEATURE:
<223> OTHER INFORMATION: Alligator_mississippiensis

<400> SEQUENCE: 133

Gly Glu Gly Ser His Pro Glu Lys Val Arg Val Tyr Gly Pro Gly Val
1               5                   10                  15

Glu Lys Thr Gly Leu Lys Ala Ser Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Leu Tyr Thr Ile Met Val Leu Phe Ala Asn Gln Glu Ile Pro Ser
                85                  90                  95

Ser Pro Phe Arg Ile Lys Val
            100


<210> SEQ ID NO 134
<211> LENGTH: 103
<212> TYPE: PRT
<213> ORGANISM: Xenopus (Silurana) tropicalis
<220> FEATURE:
<223> OTHER INFORMATION: Xenopus_tropicalis

<400> SEQUENCE: 134

Gly Glu Gly Ser His Pro Asn Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Lys Tyr Thr Ile Met Val Leu Phe Ala Asp Gln Glu Ile Pro Thr
                85                  90                  95

Ser Pro Phe Arg Val Lys Val
            100


<210> SEQ ID NO 135
<211> LENGTH: 103
<212> TYPE: PRT
<213> ORGANISM: Xenopus laevis
```

<220> FEATURE:
<223> OTHER INFORMATION: Xenopus_laevis

<400> SEQUENCE: 135

```
Gly Glu Gly Ser His Pro Ser Lys Val Lys Val Tyr Gly Pro Gly Val
1               5                   10                  15

Glu Lys Thr Gly Leu Lys Ala Ser Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Leu Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Val Lys Val
            100
```

<210> SEQ ID NO 136
<211> LENGTH: 103
<212> TYPE: PRT
<213> ORGANISM: Nanorana parkeri
<220> FEATURE:
<223> OTHER INFORMATION: Nanorana_parkeri

<400> SEQUENCE: 136

```
Gly Glu Gly Ser His Pro Asn Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Ala Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Val Lys Val
            100
```

<210> SEQ ID NO 137
<211> LENGTH: 103
<212> TYPE: PRT
<213> ORGANISM: Chordata
<220> FEATURE:
<223> OTHER INFORMATION: fish1

<400> SEQUENCE: 137

```
Gly Glu Gly Ser His Pro Glu Asn Val Lys Val His Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60
```

```
Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Ile Lys Val
            100


<210> SEQ ID NO 138
<211> LENGTH: 103
<212> TYPE: PRT
<213> ORGANISM: Chordata
<220> FEATURE:
<223> OTHER INFORMATION: fish2

<400> SEQUENCE: 138

Gly Glu Gly Ser His Pro Asp Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Ile Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Pro
65                  70                  75                  80

Gly Arg Tyr Thr Ile Met Val Leu Phe Ala Asp Gln Glu Ile Pro Val
                85                  90                  95

Ser Pro Phe Lys Val Lys Val
            100


<210> SEQ ID NO 139
<211> LENGTH: 103
<212> TYPE: PRT
<213> ORGANISM: Chordata
<220> FEATURE:
<223> OTHER INFORMATION: fish3

<400> SEQUENCE: 139

Gly Glu Gly Ser His Pro Glu Asn Val Lys Val Tyr Gly Pro Gly Val
1               5                   10                  15

Glu Lys Ser Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Pro
65                  70                  75                  80

Gly Arg Tyr Thr Ile Met Val Leu Phe Ala Asp Gln Glu Ile Pro Ile
                85                  90                  95

Ser Pro Phe Arg Ile Lys Val
            100


<210> SEQ ID NO 140
<211> LENGTH: 103
<212> TYPE: PRT
<213> ORGANISM: Chordata
<220> FEATURE:
<223> OTHER INFORMATION: fish4
```

<400> SEQUENCE: 140

```
Gly Glu Gly Cys His Pro Ala Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ala Glu Ala Gly Gln Gly Asp Ile Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Lys Tyr Thr Ile Met Val Leu Phe Ala Glu Gln Glu Ile Pro Ile
                85                  90                  95

Ser Pro Phe Arg Ile Lys Val
            100
```

<210> SEQ ID NO 141
<211> LENGTH: 103
<212> TYPE: PRT
<213> ORGANISM: Lepisosteus oculatus
<220> FEATURE:
<223> OTHER INFORMATION: Lepisosteus_oculatus

<400> SEQUENCE: 141

```
Gly Glu Gly Ser His Pro Glu Asn Val Lys Val Tyr Gly Pro Gly Ile
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Ile Lys Val
            100
```

<210> SEQ ID NO 142
<211> LENGTH: 103
<212> TYPE: PRT
<213> ORGANISM: Cynoglossus semilaevis
<220> FEATURE:
<223> OTHER INFORMATION: Cynoglossus_semilaevis

<400> SEQUENCE: 142

```
Gly Glu Gly Ser His Pro Glu Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Ile Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80
```

```
Gly Lys Tyr Thr Ile Met Val Leu Phe Ala Asp Gln Glu Ile Pro Val
                85                  90                  95

Ser Pro Phe Lys Val Lys Val
            100


<210> SEQ ID NO 143
<211> LENGTH: 103
<212> TYPE: PRT
<213> ORGANISM: Nothobranchius furzeri
<220> FEATURE:
<223> OTHER INFORMATION: Nothobranchius_furzeri

<400> SEQUENCE: 143

Gly Glu Gly Ser His Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Ile Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Lys Val Lys Val
            100


<210> SEQ ID NO 144
<211> LENGTH: 103
<212> TYPE: PRT
<213> ORGANISM: Larimichthys crocea
<220> FEATURE:
<223> OTHER INFORMATION: Larimichthys_crocea

<400> SEQUENCE: 144

Gly Glu Gly Ser His Pro Glu Asn Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Gln Tyr Thr Ile Met Val Leu Phe Ala Asp Gln Glu Ile Pro Ile
                85                  90                  95

Ser Pro Phe Arg Ile Lys Val
            100


<210> SEQ ID NO 145
<211> LENGTH: 103
<212> TYPE: PRT
<213> ORGANISM: Scleropages formosus
<220> FEATURE:
<223> OTHER INFORMATION: Scleropages_formosus

<400> SEQUENCE: 145

Gly Glu Gly Ser His Pro Glu Asn Val Lys Val Tyr Gly Pro Gly Val
```

1 5 10 15

Glu Lys Thr Gly Leu Lys Ala Asn Glu Pro Thr Tyr Phe Thr Val Asp
20 25 30

Cys Ser Glu Ala Gly Gln Gly Asp Val Ser Ile Gly Ile Lys Cys Ala
35 40 45

Pro Gly Val Val Gly Pro Ala Glu Ala Asp Ile Asp Phe Asp Ile Ile
50 55 60

Lys Asn Asp Asn Asp Thr Phe Thr Val Lys Tyr Thr Pro Pro Gly Pro
65 70 75 80

Gly Arg Tyr Thr Ile Met Val Leu Phe Ala Asp Gln Glu Ile Pro Ile
85 90 95

Ser Pro Phe Arg Ile Lys Val
100

<210> SEQ ID NO 146
<211> LENGTH: 103
<212> TYPE: PRT
<213> ORGANISM: Lates calcarifer
<220> FEATURE:
<223> OTHER INFORMATION: Lates_calcarifer

<400> SEQUENCE: 146

Gly Glu Gly Ser His Pro Asp Arg Val Lys Val Tyr Gly Pro Gly Val
1 5 10 15

Glu Lys Thr Gly Leu Lys Ala Asn Glu Pro Thr Tyr Phe Thr Val Asp
20 25 30

Cys Ser Glu Ala Gly Gln Gly Asp Ile Ser Ile Gly Ile Lys Cys Ala
35 40 45

Pro Gly Val Val Gly Pro Ala Glu Ala Asp Ile Asp Phe Asp Ile Ile
50 55 60

Lys Asn Asp Asn Asp Thr Phe Thr Val Lys Tyr Thr Pro Pro Gly Pro
65 70 75 80

Gly Arg Tyr Thr Ile Met Val Leu Phe Ala Asp Gln Glu Ile Pro Ile
85 90 95

Ser Pro Phe Lys Val Lys Val
100

<210> SEQ ID NO 147
<211> LENGTH: 103
<212> TYPE: PRT
<213> ORGANISM: Clupea harengus
<220> FEATURE:
<223> OTHER INFORMATION: Clupea_harengus

<400> SEQUENCE: 147

Gly Glu Gly Cys His Pro Glu Lys Val Lys Val Tyr Gly Pro Gly Val
1 5 10 15

Glu Lys Thr Gly Leu Lys Ala Asn Glu Pro Thr Tyr Phe Thr Val Asp
20 25 30

Cys Ser Glu Ala Gly Gln Gly Asp Ile Ser Ile Gly Ile Lys Cys Ala
35 40 45

Pro Gly Val Val Gly Pro Ala Glu Ala Asp Ile Asp Phe Asp Ile Ile
50 55 60

Lys Asn Asp Asn Asp Thr Phe Thr Val Lys Tyr Thr Pro Pro Gly Ala
65 70 75 80

Gly Arg Tyr Thr Ile Met Val Leu Phe Ala Glu Gln Glu Ile Pro Thr
85 90 95

Ser Pro Tyr Lys Val Lys Val
100

<210> SEQ ID NO 148
<211> LENGTH: 103
<212> TYPE: PRT
<213> ORGANISM: Pundamilia nyererei
<220> FEATURE:
<223> OTHER INFORMATION: Pundamilia_nyererei

<400> SEQUENCE: 148

Gly Glu Gly Ser His Pro Asp Arg Val Lys Val Tyr Gly Pro Gly Val
1 5 10 15

Glu Lys Thr Gly Leu Lys Ala Asn Glu Pro Thr Tyr Phe Thr Val Asp
20 25 30

Cys Ser Glu Ala Gly Gln Gly Asp Ile Ser Ile Gly Ile Lys Cys Ala
35 40 45

Pro Gly Val Val Gly Pro Ala Glu Thr Asp Ile Asp Phe Asp Ile Ile
50 55 60

Lys Asn Asp Asn Asp Thr Phe Thr Val Lys Tyr Thr Pro Pro Gly Pro
65 70 75 80

Gly Arg Tyr Thr Ile Met Val Leu Phe Ala Asp Gln Glu Ile Pro Val
85 90 95

Ser Pro Phe Lys Val Lys Val
100

<210> SEQ ID NO 149
<211> LENGTH: 103
<212> TYPE: PRT
<213> ORGANISM: Stegastes partitus
<220> FEATURE:
<223> OTHER INFORMATION: Stegastes_partitus

<400> SEQUENCE: 149

Gly Glu Gly Ser His Pro Asp Arg Val Lys Val Tyr Gly Pro Gly Val
1 5 10 15

Glu Lys Thr Gly Leu Lys Ala Asn Glu Pro Thr Tyr Phe Thr Val Asp
20 25 30

Cys Gly Glu Ala Gly Gln Gly Asp Ile Ser Ile Gly Ile Lys Cys Ala
35 40 45

Pro Gly Val Val Gly Pro Ala Glu Ala Asp Ile Asp Phe Asp Ile Ile
50 55 60

Lys Asn Asp Asn Asp Thr Phe Thr Val Lys Tyr Thr Pro Pro Gly Pro
65 70 75 80

Gly Arg Tyr Thr Ile Met Val Leu Phe Ala Asp Gln Glu Ile Pro Val
85 90 95

Ser Pro Phe Lys Val Lys Val
100

<210> SEQ ID NO 150
<211> LENGTH: 103
<212> TYPE: PRT
<213> ORGANISM: Sinocyclocheilus anshuiensis
<220> FEATURE:
<223> OTHER INFORMATION: Sinocyclocheilus_anshuiensis

<400> SEQUENCE: 150

Gly Glu Gly Ser His Pro Glu Asn Val Lys Val His Gly Pro Gly Val
1 5 10 15

Glu Lys Thr Gly Leu Lys Ala Ser Glu Pro Thr Tyr Phe Thr Val Asp

```
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Ile Lys Val
            100


<210> SEQ ID NO 151
<211> LENGTH: 103
<212> TYPE: PRT
<213> ORGANISM: Esox lucius
<220> FEATURE:
<223> OTHER INFORMATION: Esox_lucius

<400> SEQUENCE: 151

Gly Glu Gly Cys His Pro Asp Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ala Glu Ala Gly Gln Gly Asp Ile Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Lys Tyr Thr Ile Met Val Leu Phe Ala Glu Gln Glu Ile Pro Ile
                85                  90                  95

Ser Pro Phe Arg Val Lys Val
            100


<210> SEQ ID NO 152
<211> LENGTH: 103
<212> TYPE: PRT
<213> ORGANISM: Astyanax mexicanus
<220> FEATURE:
<223> OTHER INFORMATION: Astyanax_mexicanus

<400> SEQUENCE: 152

Gly Glu Gly Cys His Pro Asp Lys Val Lys Val Tyr Gly Pro Gly Val
1               5                   10                  15

Glu Lys Thr Gly Leu Lys Ser Ser Glu Pro Thr Tyr Phe Thr Val Asp
            20                  25                  30

Cys Gly Glu Ala Gly Gln Gly Asp Ile Ser Ile Gly Ile Lys Cys Ala
        35                  40                  45

Ala Gly Val Val Gly Thr Ala Glu Ala Asp Ile Asp Phe Asp Ile Ile
    50                  55                  60

Lys Asn Asp Asn Asp Thr Phe Thr Val Lys Tyr Thr Pro Pro Ala Pro
65                  70                  75                  80

Gly Arg Tyr Thr Val Met Val Leu Phe Ala Glu Lys Glu Ile Pro Ser
                85                  90                  95

Ser Pro Tyr Lys Val Lys Val
            100
```

<210> SEQ ID NO 153
<211> LENGTH: 103
<212> TYPE: PRT
<213> ORGANISM: Latimeria chalumnae
<220> FEATURE:
<223> OTHER INFORMATION: Latimeria_chalumnae

<400> SEQUENCE: 153

```
Gly Glu Gly Ser His Pro Glu Asn Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Ile Lys Val
            100
```

<210> SEQ ID NO 154
<211> LENGTH: 103
<212> TYPE: PRT
<213> ORGANISM: Callorhinchus milii
<220> FEATURE:
<223> OTHER INFORMATION: Callorhinchus_milii

<400> SEQUENCE: 154

```
Gly Glu Gly Ser His Pro Asn Lys Val Arg Val Tyr Gly Pro Gly Val
1               5                   10                  15

Glu Lys Ala Gly Leu Lys Ala Asn Glu Pro Thr Tyr Phe Thr Val Asp
            20                  25                  30

Cys Ser Asp Ala Gly Gln Gly Asp Ile Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asp Gln Glu Ile Pro Ile
                85                  90                  95

Ser Pro Phe Arg Ile Lys Val
            100
```

<210> SEQ ID NO 155
<211> LENGTH: 103
<212> TYPE: PRT
<213> ORGANISM: Equus
<220> FEATURE:
<223> OTHER INFORMATION: FLNC-E753K

<400> SEQUENCE: 155

```
Gly Glu Gly Ser His Pro Glu Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Lys Ala Gly Gln Gly Asp Val Ser Ile Gly Ile Lys Cys Ala
```

```
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Ala
                85                  90                  95

Ser Pro Phe His Ile Lys Val
            100


<210> SEQ ID NO 156
<211> LENGTH: 100
<212> TYPE: PRT
<213> ORGANISM: Mammalia
<220> FEATURE:
<223> OTHER INFORMATION: mammal1

<400> SEQUENCE: 156

Gln Pro Ala Val Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Glu Val Ala Val Pro Lys Ser Pro Phe
                85                  90                  95

Arg Val Gly Val
            100


<210> SEQ ID NO 157
<211> LENGTH: 100
<212> TYPE: PRT
<213> ORGANISM: Mammalia
<220> FEATURE:
<223> OTHER INFORMATION: mammal2

<400> SEQUENCE: 157

Gln Pro Ala Ile Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Asp Val Ala Val Pro Lys Ser Pro Phe
                85                  90                  95

Arg Val Gly Val
            100


<210> SEQ ID NO 158
<211> LENGTH: 100
```

<212> TYPE: PRT
<213> ORGANISM: Mammalia
<220> FEATURE:
<223> OTHER INFORMATION: mammal3

<400> SEQUENCE: 158

Gln Pro Ala Val Asp Thr Ser Gly Ile Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Glu Val Ala Val Pro Lys Ser Pro Phe
                85                  90                  95

Arg Val Gly Val
            100

<210> SEQ ID NO 159
<211> LENGTH: 100
<212> TYPE: PRT
<213> ORGANISM: Mammalia
<220> FEATURE:
<223> OTHER INFORMATION: mammal4

<400> SEQUENCE: 159

Gln Pro Ala Val Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Asp Val Ala Val Pro Lys Ser Pro Phe
                85                  90                  95

Arg Val Gly Val
            100

<210> SEQ ID NO 160
<211> LENGTH: 100
<212> TYPE: PRT
<213> ORGANISM: Mammalia
<220> FEATURE:
<223> OTHER INFORMATION: mammal5

<400> SEQUENCE: 160

Gln Pro Ala Val Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly

```
    50                  55                  60

Asp Gly Thr Tyr Arg Val Gln Tyr Thr Ala Tyr Glu Glu Gly Ala His
65                  70                  75                  80

Leu Val Glu Val Leu Tyr Asp Asp Val Ala Val Pro Lys Ser Pro Phe
                85                  90                  95

Arg Val Gly Val
            100


<210> SEQ ID NO 161
<211> LENGTH: 100
<212> TYPE: PRT
<213> ORGANISM: Mammalia
<220> FEATURE:
<223> OTHER INFORMATION: mammal6

<400> SEQUENCE: 161

Gln Pro Ala Val Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Met Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Glu Val Ala Val Pro Lys Ser Pro Phe
                85                  90                  95

Arg Val Gly Val
            100


<210> SEQ ID NO 162
<211> LENGTH: 100
<212> TYPE: PRT
<213> ORGANISM: Mammalia
<220> FEATURE:
<223> OTHER INFORMATION: mammal7

<400> SEQUENCE: 162

Gln Pro Ala Val Asp Thr Ser Gly Ile Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Asp Val Ala Val Pro Lys Ser Pro Phe
                85                  90                  95

Arg Val Gly Val
            100


<210> SEQ ID NO 163
<211> LENGTH: 100
<212> TYPE: PRT
<213> ORGANISM: Mammalia
<220> FEATURE:
```

<223> OTHER INFORMATION: mammal8

<400> SEQUENCE: 163

Gln Pro Ala Val Asp Thr Ser Gly Ile Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Ile Thr Ala Arg Val
35 40 45

Leu Asn Pro Ser Gly Ala Lys Thr Asp Thr Tyr Val Thr Asp Asn Gly
50 55 60

Asp Gly Thr Tyr Arg Val Gln Tyr Thr Ala Tyr Glu Glu Gly Val His
65 70 75 80

Leu Val Glu Val Leu Tyr Asp Asp Val Ala Val Pro Lys Ser Pro Phe
85 90 95

Arg Val Gly Val
100

<210> SEQ ID NO 164
<211> LENGTH: 100
<212> TYPE: PRT
<213> ORGANISM: Mammalia
<220> FEATURE:
<223> OTHER INFORMATION: mammal9

<400> SEQUENCE: 164

Gln Pro Ala Val Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Val Thr Asp Asn Gly
50 55 60

Asp Gly Thr Tyr Arg Val Gln Tyr Thr Ala Tyr Glu Glu Gly Met His
65 70 75 80

Leu Val Glu Val Leu Tyr Asp Glu Val Ala Val Pro Lys Ser Pro Phe
85 90 95

Arg Val Gly Val
100

<210> SEQ ID NO 165
<211> LENGTH: 100
<212> TYPE: PRT
<213> ORGANISM: Balaenoptera acutorostrata scammoni
<220> FEATURE:
<223> OTHER INFORMATION: B._acutorostrata_scammoni

<400> SEQUENCE: 165

Gln Pro Ala Val Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Met Thr Asp Asn Gly
50 55 60

Asp Gly Thr Tyr Arg Val Gln Tyr Thr Ala Tyr Glu Glu Gly Val His 65 70 75 80

Leu Val Glu Val Leu Tyr Asp Asp Val Ala Val Pro Lys Ser Pro Phe
85 90 95

Arg Val Gly Val
100

<210> SEQ ID NO 166
<211> LENGTH: 100
<212> TYPE: PRT
<213> ORGANISM: Cebus capucinus imitator
<220> FEATURE:
<223> OTHER INFORMATION: Cebus_capucinus_imitator

<400> SEQUENCE: 166

Gln Pro Ala Val Asp Thr Ser Gly Val Lys Val Ser Gly Pro Gly Ile
1 5 10 15

Glu Pro His Gly Val Leu Arg Glu Val Thr Thr Glu Phe Thr Val Asp
20 25 30

Ala Arg Ser Leu Thr Thr Thr Gly Gly Asn His Val Thr Ala Arg Val
35 40 45

Leu Asn Pro Ser Gly Ala Lys Thr Asp Thr Tyr Met Thr Asp Asn Gly
50 55 60

Asp Gly Thr Tyr Arg Val Gln Tyr Thr Ala Tyr Glu Glu Gly Val His
65 70 75 80

Leu Val Glu Val Leu Tyr Asp Glu Val Ala Val Pro Lys Ser Pro Phe
85 90 95

Arg Val Gly Val
100

<210> SEQ ID NO 167
<211> LENGTH: 98
<212> TYPE: PRT
<213> ORGANISM: Myotis lucifugus
<220> FEATURE:
<223> OTHER INFORMATION: Myotis_lucifugus

<400> SEQUENCE: 167

Gln Pro Ala Val Asp Thr Ser Gly Ile Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Thr Asn Gly Asp Gly
50 55 60

Thr Tyr Arg Val Gln Tyr Thr Ala Tyr Glu Glu Gly Val His Leu Val
65 70 75 80

Glu Val Leu Tyr Asp Glu Val Ala Val Pro Lys Ser Pro Phe Arg Val
85 90 95

Gly Val

<210> SEQ ID NO 168
<211> LENGTH: 100
<212> TYPE: PRT
<213> ORGANISM: Fukomys damarensis
<220> FEATURE:
<223> OTHER INFORMATION: Fukomys_damarensis

<400> SEQUENCE: 168

```
Gln Pro Ala Val Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Thr Met Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Asp Val Ala Val Pro Lys Ser Pro Phe
                85                  90                  95

Arg Val Gly Val
            100


<210> SEQ ID NO 169
<211> LENGTH: 100
<212> TYPE: PRT
<213> ORGANISM: Orcinus orca
<220> FEATURE:
<223> OTHER INFORMATION: Orcinus_orca

<400> SEQUENCE: 169

Gln Pro Ala Val Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Leu Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Asp Val Ala Val Pro Lys Ser Pro Phe
                85                  90                  95

Arg Val Gly Val
            100


<210> SEQ ID NO 170
<211> LENGTH: 100
<212> TYPE: PRT
<213> ORGANISM: Monodelphis domestica
<220> FEATURE:
<223> OTHER INFORMATION: Monodelphis_domestica

<400> SEQUENCE: 170

Gln Pro Ala Val Asp Thr Ser Gly Ile Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Ile His
65                  70                  75                  80

Leu Val Glu Val Leu Tyr Asp Asp Val Ala Val Pro Lys Ser Pro Phe
                85                  90                  95
```

Arg Val Gly Val
100

<210> SEQ ID NO 171
<211> LENGTH: 99
<212> TYPE: PRT
<213> ORGANISM: Ornithorhynchus anatinus
<220> FEATURE:
<223> OTHER INFORMATION: Ornithorhynchus_anatinus

<400> SEQUENCE: 171

His Pro Ala Val Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Ile Thr Asp Asn Gly
50 55 60

Asp Gly Thr Tyr Arg Val Tyr Thr Ala Tyr Glu Glu Gly Val His Leu
65 70 75 80

Val Glu Val Leu Tyr Asp Asp Val Ala Val Pro Lys Ser Pro Phe Arg
85 90 95

Val Gly Val

<210> SEQ ID NO 172
<211> LENGTH: 99
<212> TYPE: PRT
<213> ORGANISM: Aves
<220> FEATURE:
<223> OTHER INFORMATION: bird1

<400> SEQUENCE: 172

Pro Ala Val Asp Thr Ser Gly Val Lys Val Tyr Gly Lys Gly Val Glu
1 5 10 15

Pro Arg Gly Val Leu Arg Glu Val Gly Thr Asp Phe Thr Val Asp Ala
20 25 30

Arg Ala Leu Thr Lys Thr Gly Gly Pro His Val Lys Ala Trp Val Val
35 40 45

Asn Pro Ser Gly Ala Lys Thr Asp Thr Tyr Ile Thr Asp His Gly Asp
50 55 60

Gly Thr Tyr Arg Val Asp Tyr Thr Pro Tyr Glu Asp Gly Met His Arg
65 70 75 80

Val Glu Val Thr Tyr Asn Asp Val Ala Val Pro Lys Ser Pro Phe Arg
85 90 95

Val Gly Val

<210> SEQ ID NO 173
<211> LENGTH: 99
<212> TYPE: PRT
<213> ORGANISM: Aves
<220> FEATURE:
<223> OTHER INFORMATION: bird2

<400> SEQUENCE: 173

Pro Ala Ile Asp Thr Ser Ser Val Lys Val Tyr Gly Lys Gly Val Glu
1 5 10 15

Pro Arg Gly Val Leu Arg Glu Val Gly Thr Glu Phe Thr Val Asp Ala
20 25 30

```
Arg Ala Leu Ala Pro Thr Gly Gly Pro His Ile Arg Ala Arg Val Leu
        35                  40                  45

Asn Pro Ser Gly Thr Pro Ile Asp Thr Phe Val Thr Asp Leu Gly Asp
    50                  55                  60

Gly Thr Tyr Arg Val Glu Tyr Thr Pro Phe Glu Glu Gly Leu His Leu
65                  70                  75                  80

Val Glu Val Thr Tyr Asp Asp Val Ala Val Pro Lys Ser Pro Phe Arg
                85                  90                  95

Val Gly Val


<210> SEQ ID NO 174
<211> LENGTH: 99
<212> TYPE: PRT
<213> ORGANISM: Aves
<220> FEATURE:
<223> OTHER INFORMATION: bird3

<400> SEQUENCE: 174

Pro Ala Val Asp Thr Ser Ser Val Lys Val Tyr Gly Lys Gly Val Glu
1               5                   10                  15

Pro Arg Gly Val Leu Arg Glu Val Gly Thr Glu Phe Thr Val Asp Ala
            20                  25                  30

Arg Ala Leu Ala Pro Thr Gly Gly Pro His Val Arg Ala Arg Val Leu
        35                  40                  45

Asn Pro Ser Gly Thr Pro Ile Asp Thr Phe Val Thr Asp Leu Gly Asp
    50                  55                  60

Gly Thr Tyr Arg Val Glu Tyr Thr Pro Phe Glu Glu Gly Leu His Leu
65                  70                  75                  80

Val Glu Val Thr Tyr Asp Asp Val Ala Val Pro Lys Ser Pro Phe Arg
                85                  90                  95

Val Gly Val


<210> SEQ ID NO 175
<211> LENGTH: 99
<212> TYPE: PRT
<213> ORGANISM: Picoides pubescens
<220> FEATURE:
<223> OTHER INFORMATION: Picoides_pubescens

<400> SEQUENCE: 175

Pro Ala Val Asp Thr Ser Gly Val Lys Val Tyr Gly Lys Gly Val Glu
1               5                   10                  15

Pro Arg Gly Val Leu Arg Glu Val Gly Thr Asp Phe Thr Val Asp Ala
            20                  25                  30

Arg Ala Leu Thr Lys Val Gly Gly Ala His Val Lys Ala Arg Val Val
        35                  40                  45

Asn Pro Ser Gly Ala Thr Thr Glu Thr Tyr Val Thr Asp His Gly Asp
    50                  55                  60

Gly Thr Tyr Arg Val Asp Tyr Thr Pro Tyr Glu Asp Gly Met His Arg
65                  70                  75                  80

Val Glu Val Thr Tyr Asp Asp Val Ala Val Pro Lys Ser Pro Phe Arg
                85                  90                  95

Val Gly Val


<210> SEQ ID NO 176
<211> LENGTH: 99
<212> TYPE: PRT
```

```
<213> ORGANISM: Columba livia
<220> FEATURE:
<223> OTHER INFORMATION: Columba_livia

<400> SEQUENCE: 176

Pro Ala Val Asp Thr Ser Gly Val Lys Val Tyr Gly Lys Gly Val Glu
1               5                   10                  15

Pro Arg Gly Val Leu Arg Glu Val Ala Thr Asp Phe Thr Val Asp Ala
            20                  25                  30

Arg Ala Leu Thr Lys Thr Gly Gly Pro His Val Ala Ala Arg Val Val
        35                  40                  45

Asn Pro Ser Gly Ala Thr Thr Asp Thr Tyr Ile Thr Asp His Gly Asp
    50                  55                  60

Gly Thr Tyr Arg Val Glu Tyr Thr Pro Tyr Glu Asp Gly Val His Arg
65                  70                  75                  80

Val Glu Val Thr Tyr Ala Glu Val Ala Val Pro Lys Ser Pro Phe Arg
                85                  90                  95

Val Ala Val


<210> SEQ ID NO 177
<211> LENGTH: 99
<212> TYPE: PRT
<213> ORGANISM: Melopsittacus undulatus
<220> FEATURE:
<223> OTHER INFORMATION: Melopsittacus_undulatus

<400> SEQUENCE: 177

Pro Ala Val Asp Thr Ser Gly Val Lys Val Tyr Gly Lys Gly Val Glu
1               5                   10                  15

Pro Arg Gly Val Leu Arg Glu Val Ser Thr Asp Phe Thr Val Asp Ala
            20                  25                  30

Arg Ala Leu Thr Lys Thr Gly Gly Pro His Val Thr Ala Arg Val Leu
        35                  40                  45

Asn Pro Ser Gly Ala Lys Thr Asp Thr Phe Ile Thr Asp Leu Gly Asp
    50                  55                  60

Gly Thr Tyr Arg Val Glu Tyr Thr Pro Tyr Glu Asp Gly Val His Arg
65                  70                  75                  80

Val Glu Val Leu Tyr Asp Asp Val Pro Val Pro Lys Ser Pro Phe Arg
                85                  90                  95

Val Ala Val


<210> SEQ ID NO 178
<211> LENGTH: 98
<212> TYPE: PRT
<213> ORGANISM: Sturnus vulgaris
<220> FEATURE:
<223> OTHER INFORMATION: Sturnus_valgaris

<400> SEQUENCE: 178

Pro Ala Val Asp Thr Ser Ser Val Lys Val Tyr Gly Lys Gly Val Glu
1               5                   10                  15

Pro Arg Gly Val Leu Arg Glu Val Gly Thr Glu Phe Thr Val Asp Ala
            20                  25                  30

Arg Ala Leu Ala Pro Thr Gly Gly Pro His Val Arg Ala Arg Val Leu
        35                  40                  45

Asn Pro Ser Gly Thr Pro Ile Asp Thr Phe Val Thr Asp Leu Val Asp
    50                  55                  60

Gly Thr Tyr Arg Val Glu Tyr Thr Pro Phe Glu Glu Gly Leu His Leu
```

65 70 75 80

Val Glu Val Thr Tyr Asp Asp Val Ala Val Pro Lys Ser Pro Phe Arg
85 90 95

Val Gly

<210> SEQ ID NO 179
<211> LENGTH: 99
<212> TYPE: PRT
<213> ORGANISM: Corvus brachyrhynchos
<220> FEATURE:
<223> OTHER INFORMATION: Corvus_brachyrhynchos
<220> FEATURE:
<221> NAME/KEY: VARIANT
<222> LOCATION: 78
<223> OTHER INFORMATION: L or V or M or I or A

<400> SEQUENCE: 179

Pro Ala Ile Asp Thr Ser Ser Val Lys Val Tyr Gly Lys Gly Val Glu
1 5 10 15

Pro Arg Gly Val Leu Arg Glu Val Gly Thr Glu Phe Met Val Asp Ala
20 25 30

Arg Ala Leu Ala Pro Thr Gly Gly Pro His Ile Arg Ala Arg Val Leu
35 40 45

Asn Pro Ser Gly Thr Pro Ile Asp Thr Phe Val Thr Asp Leu Gly Asp
50 55 60

Gly Thr Tyr Arg Val Glu Tyr Thr Pro Phe Glu Glu Gly Xaa His Leu
65 70 75 80

Gly Glu Val Thr Tyr Asp Asp Val Pro Val Pro Lys Ser Pro Phe Arg
85 90 95

Val Gly Val

<210> SEQ ID NO 180
<211> LENGTH: 99
<212> TYPE: PRT
<213> ORGANISM: Lepidothrix coronata
<220> FEATURE:
<223> OTHER INFORMATION: Lepidothrix_coronata

<400> SEQUENCE: 180

Pro Ala Val Asp Thr Ser Ser Val Lys Val Tyr Gly Lys Gly Val Glu
1 5 10 15

Pro Arg Gly Val Leu Arg Glu Val Gly Thr Glu Phe Thr Val Asp Ala
20 25 30

Arg Ala Leu Ala Pro Ala Gly Gly Pro His Val Arg Ala Arg Val Leu
35 40 45

Asn Pro Ser Gly Thr Pro Ile Asp Thr Phe Val Thr Asp Leu Gly Asp
50 55 60

Gly Thr Tyr Arg Val Glu Tyr Thr Pro Phe Glu Glu Gly Leu His Arg
65 70 75 80

Val Glu Val Thr Tyr Asp Asp Val Ala Val Pro Lys Ser Pro Phe Arg
85 90 95

Val Gly Val

<210> SEQ ID NO 181
<211> LENGTH: 99
<212> TYPE: PRT
<213> ORGANISM: Ficedula albicollis
<220> FEATURE:
<223> OTHER INFORMATION: Ficedula_albicollis

<400> SEQUENCE: 181

Pro Ala Val Asp Thr Ser Ser Val Lys Val Tyr Gly Lys Gly Val Glu
1 5 10 15

Pro Arg Gly Val Leu Arg Glu Val Gly Thr Glu Phe Thr Val Asp Ala
20 25 30

Arg Ala Leu Ala Pro Thr Gly Gly Pro His Val Arg Ala Arg Val Leu
35 40 45

Asn Pro Ala Gly Thr Pro Ile Asp Thr Phe Val Thr Asp Leu Gly Asp
50 55 60

Gly Thr Tyr Arg Val Glu Tyr Thr Pro Phe Glu Glu Gly Leu His Leu
65 70 75 80

Val Glu Val Thr Tyr Asp Glu Val Ala Val Pro Lys Ser Pro Phe Arg
85 90 95

Val Gly Val

<210> SEQ ID NO 182
<211> LENGTH: 99
<212> TYPE: PRT
<213> ORGANISM: Cuculus canorus
<220> FEATURE:
<223> OTHER INFORMATION: Cuculus_canorus

<400> SEQUENCE: 182

Pro Ala Val Asp Thr Ser Gly Val Lys Val Tyr Gly Gln Gly Val Glu
1 5 10 15

Pro Arg Gly Val Leu Arg Glu Val Gly Thr Glu Phe Met Val Asp Thr
20 25 30

Arg Ala Leu Ser Arg Thr Gly Gly Pro His Val Gly Val Arg Val Leu
35 40 45

Asn Pro Ser Gly Gly Thr Thr Asp Thr Arg Ile Thr Asp Arg Gly Asp
50 55 60

Gly Thr Tyr Arg Val Gln Tyr Thr Pro Phe Glu Glu Gly Met His Gln
65 70 75 80

Val Glu Val Thr Tyr Asp Asp Val Pro Val Pro Asn Ser Pro Phe Arg
85 90 95

Val Ala Val

<210> SEQ ID NO 183
<211> LENGTH: 100
<212> TYPE: PRT
<213> ORGANISM: Chrysemys picta bellii
<220> FEATURE:
<223> OTHER INFORMATION: Chrysemys_picta_bellii

<400> SEQUENCE: 183

Gln Pro Ala Val Asp Thr Ser Ala Val Lys Val Phe Gly Pro Gly Val
1 5 10 15

Glu Pro Arg Gly Val Leu Arg Glu Val Thr Thr Glu Phe Thr Val Asp
20 25 30

Ala Arg Ser Leu Thr Lys Thr Gly Gly Ser His Ile Lys Ala Arg Val
35 40 45

Ile Asn Pro Ser Gly Ala Lys Thr Glu Thr Tyr Leu Thr Asp Asn Gly
50 55 60

Asp Gly Thr Tyr Arg Val His Tyr Thr Ala Tyr Glu Glu Gly Leu His
65 70 75 80

Arg Val Glu Val Thr Tyr Asp Glu Val Pro Val Pro Lys Ser Pro Phe
85 90 95

Arg Val Ala Val
100

<210> SEQ ID NO 184
<211> LENGTH: 100
<212> TYPE: PRT
<213> ORGANISM: Xenopus (Silurana) tropicalis
<220> FEATURE:
<223> OTHER INFORMATION: Xenopus_tropicalis

<400> SEQUENCE: 184

Glu Pro Ala Val Asp Thr Ser Gly Val Lys Val Phe Gly Pro Gly Val
1 5 10 15

Glu Pro Arg Gly Val Leu Arg Glu Val Thr Thr Glu Phe Thr Val Asp
20 25 30

Ala Arg Ser Leu Thr Lys Thr Gly Gly Ser His Val Thr Thr Arg Ile
35 40 45

Leu Gly Pro Ser Gly Ala Val Thr Glu Ser Phe Leu Ser Asp Asn Gly
50 55 60

Asp Gly Thr Tyr His Val Gln Tyr Thr Ala Tyr Glu Asp Gly Val His
65 70 75 80

Leu Ile Glu Val Leu Tyr Asp Asp Val Pro Val Pro Lys Ser Pro Phe
85 90 95

Arg Val Pro Val
100

<210> SEQ ID NO 185
<211> LENGTH: 100
<212> TYPE: PRT
<213> ORGANISM: Xenopus laevis
<220> FEATURE:
<223> OTHER INFORMATION: Xenopus_laevis

<400> SEQUENCE: 185

Glu Pro Ala Val Asp Thr Ser Gly Val Lys Val Phe Gly Pro Gly Val
1 5 10 15

Glu Pro Arg Gly Val Leu Arg Glu Val Thr Thr Glu Phe Thr Ile Asp
20 25 30

Ala Arg Ser Leu Thr Lys Thr Gly Gly Ser His Val Thr Thr Arg Val
35 40 45

Leu Gly Pro Ser Gly Val Val Thr Glu Ser Phe Ile Ser Asp Asn Gly
50 55 60

Asp Gly Thr Tyr His Val Gln Tyr Thr Ala Tyr Glu Asp Gly Val His
65 70 75 80

Leu Ile Glu Val Leu Tyr Asp Glu Val Pro Val Pro Lys Ser Pro Phe
85 90 95

Arg Val Pro Val
100

<210> SEQ ID NO 186
<211> LENGTH: 100
<212> TYPE: PRT
<213> ORGANISM: Nanorana parkeri
<220> FEATURE:
<223> OTHER INFORMATION: Nanorana_parkeri

<400> SEQUENCE: 186

Glu Pro Ala Val Asp Thr Ser Gly Val Lys Val Phe Gly Pro Gly Val
1 5 10 15

```
Glu Pro Arg Gly Val Leu Arg Glu Val Ala Thr Glu Phe Thr Val Asp
            20                  25                  30

Ala Arg Ser Leu Thr Lys Thr Gly Gly Ser His Val Thr Thr Arg Ile
        35                  40                  45

Ile Ser Pro Ser Gly Ala Val Thr Glu Ser Phe Ile Ser Asp Asn Gly
    50                  55                  60

Asp Gly Thr Tyr His Val Gln Tyr Thr Ala Tyr Glu Asp Gly Ile Gln
65                  70                  75                  80

Leu Val Glu Val Leu Tyr Asn Asp Val Pro Val Pro Lys Ser Pro Phe
                85                  90                  95

Arg Val Gly Val
            100


<210> SEQ ID NO 187
<211> LENGTH: 99
<212> TYPE: PRT
<213> ORGANISM: Protobothrops mucrosquamatus
<220> FEATURE:
<223> OTHER INFORMATION: Protobothrops_mucrosquamatus

<400> SEQUENCE: 187

Pro Ala Val Asp Thr Ser Asn Val Lys Val Phe Gly Pro Gly Val Glu
1               5                   10                  15

Pro Arg Gly Val Leu Arg Glu Val Thr Thr Glu Phe Thr Val Asp Ala
            20                  25                  30

Arg Ser Leu Thr Lys Thr Gly Gly Asn His Val Lys Val Arg Val Ile
        35                  40                  45

Asn Pro Ser Gly Ala Lys Thr Asp Thr Tyr Ile Thr Asp Asn Gly Asp
    50                  55                  60

Gly Thr Tyr Arg Val Gln Tyr Thr Pro Phe Glu Asp Gly Val His Leu
65                  70                  75                  80

Val Glu Val Thr Tyr Asp Asp Val Pro Val Pro Lys Ser Pro Phe Arg
                85                  90                  95

Val Gly Val


<210> SEQ ID NO 188
<211> LENGTH: 99
<212> TYPE: PRT
<213> ORGANISM: Python bivittatus
<220> FEATURE:
<223> OTHER INFORMATION: Python_bivittatus

<400> SEQUENCE: 188

Pro Ala Val Asp Thr Ser Asn Val Lys Val Phe Gly Pro Gly Val Glu
1               5                   10                  15

Pro Arg Gly Val Leu Arg Glu Val Thr Thr Glu Phe Thr Val Asp Ala
            20                  25                  30

Arg Ser Leu Thr Lys Thr Gly Gly Thr His Ile Lys Val Arg Val Ile
        35                  40                  45

Asn Pro Ser Gly Ala Lys Thr Asp Thr Tyr Ile Thr Asp Asn Gly Asp
    50                  55                  60

Gly Thr Tyr Arg Val Gln Tyr Thr Pro Phe Glu Asp Gly Met His Leu
65                  70                  75                  80

Val Glu Val Thr Tyr Asp Asp Val Pro Val Pro Lys Ser Pro Phe Arg
                85                  90                  95

Val Gly Val
```

<210> SEQ ID NO 189
<211> LENGTH: 99
<212> TYPE: PRT
<213> ORGANISM: Anolis carolinensis
<220> FEATURE:
<223> OTHER INFORMATION: Anolis_carolinensis

<400> SEQUENCE: 189

Pro Ala Val Asp Thr Ser Asn Val Lys Val Phe Gly Pro Gly Val Glu
1 5 10 15

Pro Arg Gly Val Leu Arg Glu Val Thr Thr Glu Phe Thr Val Asp Ala
20 25 30

Arg Ser Leu Thr Lys Thr Gly Gly Asn His Ile Lys Val Arg Val Ile
35 40 45

Asn Pro Ser Gly Ala Lys Thr Asp Ser Tyr Ile Thr Asp Asn Gly Asp
50 55 60

Gly Thr Tyr Arg Val Gln Tyr Thr Pro Phe Glu Asp Gly Val His Leu
65 70 75 80

Val Glu Val Thr Tyr Asp Asp Val Pro Val Pro Lys Ser Pro Phe Arg
85 90 95

Val Gly Val

<210> SEQ ID NO 190
<211> LENGTH: 99
<212> TYPE: PRT
<213> ORGANISM: Alligator mississippiensis
<220> FEATURE:
<223> OTHER INFORMATION: Alligator_mississippiensis

<400> SEQUENCE: 190

Pro Ala Val Asp Thr Ser Pro Ile Lys Val Tyr Gly Pro Gly Val Glu
1 5 10 15

Pro Arg Gly Val Leu Arg Glu Val Thr Thr Glu Phe Thr Val Asp Ala
20 25 30

Arg Ala Leu Thr Lys Thr Gly Gly Ser His Ile Lys Ala Arg Val Val
35 40 45

Asn Pro Ser Gly Ala Lys Thr Asp Thr Tyr Ile Thr Asp Asn Ala Asp
50 55 60

Gly Thr Tyr Arg Val Gln Tyr Thr Ala Tyr Glu Asp Gly Val His Arg
65 70 75 80

Val Glu Val Thr Tyr Asp Asp Val Pro Val Pro Lys Ser Pro Phe Arg
85 90 95

Val Ala Val

<210> SEQ ID NO 191
<211> LENGTH: 100
<212> TYPE: PRT
<213> ORGANISM: Chelonia mydas
<220> FEATURE:
<223> OTHER INFORMATION: Chelonia_mydas

<400> SEQUENCE: 191

Gln Pro Ala Val Asp Thr Ser Ala Val Lys Val Phe Gly Pro Gly Val
1 5 10 15

Glu Pro Arg Gly Val Leu Arg Glu Val Thr Thr Glu Phe Thr Val Asp
20 25 30

Ala Arg Ser Leu Thr Lys Thr Gly Gly Ser His Ile Lys Ala Arg Val
35 40 45

Ile Asn Pro Ser Gly Ala Lys Thr Glu Thr Tyr Leu Thr Asp Asn Gly

```
    50                  55                  60

Asp Gly Thr Tyr Arg Val Gln Tyr Thr Ala Tyr Glu Glu Gly Leu His
65                  70                  75                  80

Arg Val Glu Val Thr Tyr Asp Glu Val Pro Val Pro Lys Ser Pro Phe
                85                  90                  95

Arg Val Ala Val
            100


<210> SEQ ID NO 192
<211> LENGTH: 99
<212> TYPE: PRT
<213> ORGANISM: Chordata
<220> FEATURE:
<223> OTHER INFORMATION: fish1

<400> SEQUENCE: 192

Pro Ala Leu Asp Thr Ser Gly Ile Lys Val Tyr Gly Pro Gly Val Glu
1               5                   10                  15

Pro Arg Gly Val Leu Arg Glu Val Thr Thr His Phe Val Val Asp Thr
            20                  25                  30

Arg Val His Ser Lys Met Gly Gly Asn His Ile Lys Val Arg Ile Val
        35                  40                  45

Asn Pro Ser Gly Ala Asn Thr Asp Ala Tyr Ile Thr Asp Lys Gly Asp
    50                  55                  60

Gly Thr Tyr Arg Val Glu Tyr Thr Ala Tyr Glu Asp Gly Val His Leu
65                  70                  75                  80

Ile Glu Val Leu Tyr Asp Asp Val Pro Val Pro Lys Ser Pro Phe Arg
                85                  90                  95

Val Ala Val


<210> SEQ ID NO 193
<211> LENGTH: 99
<212> TYPE: PRT
<213> ORGANISM: Sinocyclocheilus grahami
<220> FEATURE:
<223> OTHER INFORMATION: Sinocyclocheilus_grahami

<400> SEQUENCE: 193

Pro Ala Leu Asp Thr Ser Gly Ile Lys Val Tyr Gly Pro Gly Val Glu
1               5                   10                  15

Pro Arg Gly Val Leu Arg Glu Val Thr Thr His Phe Val Val Asp Thr
            20                  25                  30

Arg Val His Ser Lys Met Gly Gly Asn His Ile Lys Val Arg Ile Val
        35                  40                  45

Asn Pro Ser Gly Ala Asn Thr Asp Ala Tyr Ile Thr Asp Lys Gly Asp
    50                  55                  60

Cys Thr Tyr Arg Val Glu Tyr Thr Ala Tyr Glu Asp Gly Val His Leu
65                  70                  75                  80

Ile Glu Val Leu Tyr Asp Asp Val Pro Val Pro Lys Ser Pro Phe Arg
                85                  90                  95

Val Ala Val


<210> SEQ ID NO 194
<211> LENGTH: 99
<212> TYPE: PRT
<213> ORGANISM: Larimichthys crocea
<220> FEATURE:
<223> OTHER INFORMATION: Larimichthys_crocea
```

<400> SEQUENCE: 194

Pro Ala Ile Asp Thr Ser Gly Val Glu Val Tyr Gly Pro Gly Val Glu
1 5 10 15

Pro Arg Gly Val Leu Arg Glu Val Thr Thr His Phe Thr Val Asp Ala
20 25 30

Leu Ala His Tyr Lys Ser Gly Ser Ser His Val Lys Ala Cys Ile Ser
35 40 45

Asn Pro Ser Gly Ala Asn Thr Asp Ala Tyr Ile Thr Asp Lys Gly Asp
50 55 60

Gly Thr Tyr Arg Val Glu Tyr Thr Pro Tyr Glu Asp Gly Leu His Leu
65 70 75 80

Ile Glu Val Leu Phe Asp Glu Val Ser Val Pro Lys Ser Pro Phe Arg
85 90 95

Val Ser Val

<210> SEQ ID NO 195
<211> LENGTH: 100
<212> TYPE: PRT
<213> ORGANISM: Pygocentrus nattereri
<220> FEATURE:
<223> OTHER INFORMATION: Pygocentrus_nattereri

<400> SEQUENCE: 195

Glu Pro Ala Val Asp Thr Ser Gly Val Lys Val Tyr Gly Pro Gly Val
1 5 10 15

Glu Pro Lys Gly Val Leu Arg Asp Val Thr Thr His Phe Ile Val Asp
20 25 30

Ala Arg Ala Met Asn Lys Thr Gly Gly Asn His Val Lys Val Arg Ile
35 40 45

Ile Asn Pro Ser Gly Ser Asn Thr Asp Ala His Ile Thr Asp Lys Gly
50 55 60

Asp Gly Thr Cys Arg Val Glu Tyr Thr Ala Phe Glu Asp Gly Val His
65 70 75 80

Val Ile Glu Val Phe Tyr Asp Asp Val Ala Val Pro Lys Ser Pro Phe
85 90 95

Arg Val Ser Val
100

<210> SEQ ID NO 196
<211> LENGTH: 99
<212> TYPE: PRT
<213> ORGANISM: Astyanax mexicanus
<220> FEATURE:
<223> OTHER INFORMATION: Astyanax_mexicanus

<400> SEQUENCE: 196

Pro Ala Val Asp Thr Ser Gly Val Lys Val Phe Gly Pro Gly Val Glu
1 5 10 15

Pro Arg Gly Val Leu Arg Glu Val Thr Thr His Phe Ile Val Asp Thr
20 25 30

Arg Ala His Asn Lys Thr Gly Gly Asn His Ile Lys Thr Arg Ile Val
35 40 45

Asn Pro Ser Gly Ser Asn Thr Asp Ala Tyr Ile Thr Asp Lys Gly Asp
50 55 60

Gly Thr Tyr Arg Val Glu Tyr Thr Ala Tyr Glu Asp Gly Val His Leu
65 70 75 80

Ile Glu Val Leu Tyr Asp Glu Val Ser Val Pro Lys Ser Pro Phe Arg 85 90 95

Val Ser Val

<210> SEQ ID NO 197
<211> LENGTH: 99
<212> TYPE: PRT
<213> ORGANISM: Cyprinus carpio
<220> FEATURE:
<223> OTHER INFORMATION: Cyprinus_carpio

<400> SEQUENCE: 197

Pro Ala Leu Asp Thr Ser Gly Ile Lys Val Tyr Gly Pro Gly Val Glu
1 5 10 15

Pro Arg Gly Val Leu Arg Glu Val Thr Thr His Phe Val Val Asp Thr
20 25 30

Arg Val His Ser Lys Met Gly Gly Asn His Ile Lys Val Arg Ile Val
35 40 45

Asn Pro Thr Gly Ala Asn Thr Asp Ser Tyr Ile Thr Asp Asn Gly Asp
50 55 60

Gly Thr Tyr Arg Val Glu Tyr Thr Ala Tyr Glu Asp Gly Val His Leu
65 70 75 80

Ile Glu Val Leu Tyr Asp Asp Val Pro Val Pro Lys Ser Pro Phe Arg
85 90 95

Val Ala Val

<210> SEQ ID NO 198
<211> LENGTH: 100
<212> TYPE: PRT
<213> ORGANISM: Ictalurus punctatus
<220> FEATURE:
<223> OTHER INFORMATION: Ictalurus_punctatus

<400> SEQUENCE: 198

Glu Pro Ala Val Asn Thr Ser Gly Val Lys Val Tyr Gly Pro Gly Val
1 5 10 15

Glu Pro Thr Gly Val Leu Arg Glu Val Ser Thr His Phe Ile Val Asp
20 25 30

Ala Arg Ser Leu Thr Lys Met Gly Gly Asn His Val Thr Val Arg Ile
35 40 45

Val Ser Pro Ser Gly Ser Ile Thr Asp Ala Tyr Ile Thr Asp Lys Gly
50 55 60

Asp Gly Thr Tyr Arg Val Glu Tyr Thr Ala Phe Gln Asp Gly Met His
65 70 75 80

Leu Ile Glu Val Leu Tyr Asp Asp Val Met Val Pro Asn Ser Pro Phe
85 90 95

Arg Val Ser Val
100

<210> SEQ ID NO 199
<211> LENGTH: 100
<212> TYPE: PRT
<213> ORGANISM: Clupea harengus
<220> FEATURE:
<223> OTHER INFORMATION: Clupea_harengus

<400> SEQUENCE: 199

Glu Pro Ala Val Asp Thr Thr Gly Val Thr Val Tyr Gly Pro Gly Val
1 5 10 15

Glu Ala Arg Gly Val Leu Arg Asp Val Thr Thr His Phe Ile Val Asp

```
            20                  25                  30

Ala Arg Ala Gln Thr Lys Ser Gly Gly Asn His Val Lys Ala Arg Ile
        35                  40                  45

Met Asn Pro Ser Gly Asn Asn Thr Asp Ala Tyr Leu Thr Asp Lys Gly
    50                  55                  60

Asp Gly Thr Tyr Arg Val Glu Tyr Thr Ala Tyr Glu Glu Gly Ile His
65                  70                  75                  80

Leu Ile Glu Val Leu Tyr Asp Asp Val Pro Ile Pro Lys Ser Pro Phe
                85                  90                  95

Arg Val Ser Val
            100
```

<210> SEQ ID NO 200
<211> LENGTH: 100
<212> TYPE: PRT
<213> ORGANISM: Oncorhynchus mykiss
<220> FEATURE:
<223> OTHER INFORMATION: Oncorhynchus_mykiss

<400> SEQUENCE: 200

```
Asp Pro Ala Val Asp Thr Ser Gly Val Lys Val Tyr Gly Pro Gly Val
1               5                   10                  15

Glu Pro Arg Gly Val Leu Arg Glu Val Thr Thr His Phe Ile Val Asp
            20                  25                  30

Ala Arg Ala Lys Ser Lys Thr Gly Gly Ser His Val Lys Ala Arg Ile
        35                  40                  45

Val Asn Pro Thr Gly Ala Asn Thr Asp Ala Tyr Ile Thr Asp Lys Gly
    50                  55                  60

Glu Gly Thr Tyr Arg Val Glu Tyr Thr Ala Tyr Glu Asp Gly Met His
65                  70                  75                  80

Leu Ile Glu Val Leu Tyr Asp Asp Val Ala Val Pro Asn Ser Pro Phe
                85                  90                  95

Arg Val Pro Val
            100
```

<210> SEQ ID NO 201
<211> LENGTH: 100
<212> TYPE: PRT
<213> ORGANISM: Salmo salar
<220> FEATURE:
<223> OTHER INFORMATION: Salmo_salar

<400> SEQUENCE: 201

```
Glu Pro Ala Val Asp Thr Ser Gly Val Gln Val Tyr Gly Pro Gly Val
1               5                   10                  15

Glu Pro Arg Gly Val Leu Lys Glu Val Thr Thr His Phe Ile Val Asp
            20                  25                  30

Ala Arg Lys Thr Thr Lys Ser Gly Gly Asp His Val Lys Ala Arg Ile
        35                  40                  45

Ile Asn Pro Ser Gly Ala Asn Thr Asp Ala Tyr Ile Thr Asp Lys Gly
    50                  55                  60

Asp Gly Thr Tyr Arg Val Glu Tyr Thr Ala Phe Glu Asp Gly Met His
65                  70                  75                  80

Leu Ile Glu Val Leu Tyr Asp Asp Val Ala Val Pro Lys Ser Pro Phe
                85                  90                  95

Arg Val Ser Val
            100
```

<210> SEQ ID NO 202
<211> LENGTH: 100
<212> TYPE: PRT
<213> ORGANISM: Esox lucius
<220> FEATURE:
<223> OTHER INFORMATION: Esox_lucius

<400> SEQUENCE: 202

Glu Pro Ala Val Asp Thr Ser Gly Val Gln Val Tyr Gly Pro Gly Val
1               5                   10                  15

Glu Pro Arg Gly Val Leu Lys Glu Val Thr Thr His Phe Ile Val Asp
            20                  25                  30

Ala Arg Lys Thr Thr Lys Thr Gly Gly Asp His Val Lys Ala Cys Ile
        35                  40                  45

Ile Asn Pro Ser Gly Thr Asn Thr Glu Thr Tyr Ile Thr Asp Lys Gly
    50                  55                  60

Asp Gly Thr Tyr Arg Val Glu Tyr Thr Ala Phe Glu Asp Gly Met His
65                  70                  75                  80

Leu Ile Glu Val Leu Tyr Asp Asp Val Ala Val Pro Lys Ser Pro Phe
                85                  90                  95

Arg Val Ser Val
            100

<210> SEQ ID NO 203
<211> LENGTH: 99
<212> TYPE: PRT
<213> ORGANISM: Lepisosteus oculatus
<220> FEATURE:
<223> OTHER INFORMATION: Lepisosteus_oculatus

<400> SEQUENCE: 203

Pro Ala Val Asp Thr Ser Gly Ile Lys Val Tyr Gly Pro Gly Ile Glu
1               5                   10                  15

Pro Arg Gly Val Leu Arg Glu Val Thr Thr His Phe Ile Val Asp Val
            20                  25                  30

Arg Thr Leu Asn Lys Thr Gly Gly Asn His Val Lys Ala Arg Ile Val
        35                  40                  45

Asn Pro Ser Gly Ala Lys Thr Asp Ala Tyr Ile Thr Asp Lys Gly Asp
    50                  55                  60

Gly Thr Tyr Arg Val Glu Tyr Thr Ala Tyr Glu Asp Gly Ile His Leu
65                  70                  75                  80

Ile Glu Val Leu Tyr Asp Asp Val Ala Val Pro Lys Ser Pro Phe Arg
                85                  90                  95

Val Ala Ile

<210> SEQ ID NO 204
<211> LENGTH: 99
<212> TYPE: PRT
<213> ORGANISM: Latimeria chalumnae
<220> FEATURE:
<223> OTHER INFORMATION: Latimeria_chalumnae

<400> SEQUENCE: 204

Pro Ala Val Asp Thr Ser Thr Val Lys Val Phe Gly Pro Gly Val Glu
1               5                   10                  15

Pro Arg Gly Val Leu Arg Glu Val Thr Thr Glu Phe Thr Val Asp Ala
            20                  25                  30

Cys Thr Leu Thr Lys Thr Gly Gly Asn His Val Lys Val Arg Ile Leu
        35                  40                  45

```
Asn Pro Ser Gly Ala Lys Thr Asp Pro Tyr Val Thr Asp Lys Gly Asp
    50                  55                  60

Gly Thr Tyr Arg Val Glu Tyr Thr Ala Tyr Glu Asp Gly Ile His Leu
65                  70                  75                  80

Ile Glu Val Leu Tyr Asp Asp Val Ala Val Pro Lys Ser Pro Phe Arg
                85                  90                  95

Val Ala Val


<210> SEQ ID NO 205
<211> LENGTH: 99
<212> TYPE: PRT
<213> ORGANISM: Callorhinchus milii
<220> FEATURE:
<223> OTHER INFORMATION: Callorhinchus_milii

<400> SEQUENCE: 205

Pro Ala Ile Asp Leu Ser Gly Val Lys Val Phe Gly Pro Gly Val Glu
1               5                   10                  15

Pro Arg Gly Val Leu Arg Glu Val Thr Thr Glu Phe Thr Val Asp Cys
            20                  25                  30

Arg Ser Val Ser Arg Ser Gly Gly Ala His Val Lys Ala Arg Ile Thr
        35                  40                  45

Asn Pro Ser Gly Ala Ala Thr Asp Ser Tyr Val Arg Asp Asn Gly Asp
    50                  55                  60

Gly Thr Tyr Arg Val Glu Tyr Ser Ala Tyr Glu Asp Gly Leu His Val
65                  70                  75                  80

Ile Glu Val Leu Tyr Asp Asp Ile Pro Leu Pro Lys Ser Pro Phe Arg
                85                  90                  95

Val Gly Val


<210> SEQ ID NO 206
<211> LENGTH: 68
<212> TYPE: PRT
<213> ORGANISM: Mammalia
<220> FEATURE:
<223> OTHER INFORMATION: mammal1

<400> SEQUENCE: 206

Met Ile Pro Lys Glu Gln Lys Gly Pro Val Met Ala Ala Met Gly Asp
1               5                   10                  15

Leu Thr Glu Pro Val Pro Thr Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Leu Ala Ala
65


<210> SEQ ID NO 207
<211> LENGTH: 68
<212> TYPE: PRT
<213> ORGANISM: Mammalia
<220> FEATURE:
<223> OTHER INFORMATION: mammal2

<400> SEQUENCE: 207

Met Ile Pro Lys Glu Gln Lys Gly Pro Val Met Ala Ala Met Gly Asn
1               5                   10                  15
```

```
Phe Thr Glu Pro Val Pro Thr Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Leu Ala Ala
65


<210> SEQ ID NO 208
<211> LENGTH: 68
<212> TYPE: PRT
<213> ORGANISM: Mammalia
<220> FEATURE:
<223> OTHER INFORMATION: mammal3

<400> SEQUENCE: 208

Met Ile Pro Lys Glu Gln Lys Gly Pro Val Met Ala Ala Met Gly Asp
1               5                   10                  15

Leu Thr Glu Pro Val Pro Thr Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Leu Ala Glu
65


<210> SEQ ID NO 209
<211> LENGTH: 68
<212> TYPE: PRT
<213> ORGANISM: Mammalia
<220> FEATURE:
<223> OTHER INFORMATION: mammal4

<400> SEQUENCE: 209

Met Ile Pro Lys Glu Gln Lys Gly Pro Val Met Ala Ala Met Glu Asp
1               5                   10                  15

Leu Ala Gly Pro Val Pro Val Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Phe Ala Ala
65


<210> SEQ ID NO 210
<211> LENGTH: 68
<212> TYPE: PRT
<213> ORGANISM: Mammalia
<220> FEATURE:
<223> OTHER INFORMATION: mammal5

<400> SEQUENCE: 210

Met Ile Pro Lys Glu Gln Lys Gly Pro Val Met Thr Thr Met Gly Asp
1               5                   10                  15

Leu Thr Glu Pro Val Pro Leu Leu Asp Leu Gly Lys Lys Leu Ser Val
            20                  25                  30
```

```
Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Phe Ala Ala
65


<210> SEQ ID NO 211
<211> LENGTH: 68
<212> TYPE: PRT
<213> ORGANISM: Mammalia
<220> FEATURE:
<223> OTHER INFORMATION: mammal6

<400> SEQUENCE: 211

Met Ile Pro Lys Glu Gln Lys Gly Pro Val Met Ala Ala Met Gly Asp
1               5                   10                  15

Leu Thr Gly Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Arg Phe Thr Phe
    50                  55                  60

Glu Phe Ala Ala
65


<210> SEQ ID NO 212
<211> LENGTH: 68
<212> TYPE: PRT
<213> ORGANISM: Mammalia
<220> FEATURE:
<223> OTHER INFORMATION: mammal7

<400> SEQUENCE: 212

Met Ile Pro Lys Glu Gln Lys Gly Pro Val Met Thr Thr Thr Gly Asp
1               5                   10                  15

Leu Thr Glu Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Phe Ala Ala
65


<210> SEQ ID NO 213
<211> LENGTH: 68
<212> TYPE: PRT
<213> ORGANISM: Mammalia
<220> FEATURE:
<223> OTHER INFORMATION: mammal8

<400> SEQUENCE: 213

Met Ile Pro Lys Glu Gln Lys Gly Pro Val Met Ala Ala Met Gly Asp
1               5                   10                  15

Gln Ala Thr Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
```

```
    50                  55                  60

Glu Leu Ala Asp
65


<210> SEQ ID NO 214
<211> LENGTH: 68
<212> TYPE: PRT
<213> ORGANISM: Propithecus coquereli
<220> FEATURE:
<223> OTHER INFORMATION: Propithecus_coquereli

<400> SEQUENCE: 214

Met Ile Pro Lys Glu Gln Lys Gly Pro Val Met Ala Ala Met Gly Asp
1               5                   10                  15

Leu Ala Gly Pro Val Pro Ser Leu Asp Leu Gly Lys Lys Leu Ser Val
            20                  25                  30

Pro Gln Asp Leu Met Ile Glu Glu Leu Ser Leu His Asn Asn Arg Gly
        35                  40                  45

Ser Leu Leu Phe Gln Lys Arg Gln Arg Arg Val Gln Lys Phe Thr Phe
    50                  55                  60

Glu Leu Ala Glu
65


<210> SEQ ID NO 215
<211> LENGTH: 68
<212> TYPE: PRT
<213> ORGANISM: Pongo abelii
<220> FEATURE:
<223> OTHER INFORMATION: Pongo_abelii

<400> SEQUENCE: 215

Met Ile Pro Lys Glu Gln Lys Gly Pro Val Met Ala Ala Met Gly Asp
1               5                   10                  15

Leu Thr Glu Pro Val Pro Met Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Leu Ala Ala
65


<210> SEQ ID NO 216
<211> LENGTH: 68
<212> TYPE: PRT
<213> ORGANISM: Callithrix jacchus
<220> FEATURE:
<223> OTHER INFORMATION: Callithrix_jacchus

<400> SEQUENCE: 216

Met Ile Pro Lys Glu Gln Lys Gly Pro Val Met Ala Ala Met Gly Asn
1               5                   10                  15

Leu Thr Glu Ser Val Pro Thr Leu Asp Leu Gly Lys Lys Leu Ser Val
            20                  25                  30

Pro Gln Asp Leu Met Met Glu Glu Leu Ser Leu Cys Asn Asn Arg Gly
        35                  40                  45

Ser Leu Leu Phe Gln Lys Arg Gln Arg Arg Val Gln Lys Phe Thr Phe
    50                  55                  60

Glu Leu Ala Ala
65
```

<210> SEQ ID NO 217
<211> LENGTH: 68
<212> TYPE: PRT
<213> ORGANISM: Macaca mulatta
<220> FEATURE:
<223> OTHER INFORMATION: Macaca_mulatta

<400> SEQUENCE: 217

Met Ile Pro Lys Glu Gln Lys Gly Pro Val Met Ala Ala Met Gly Asn
1 5 10 15

Phe Thr Glu Pro Val Pro Thr Leu Asp Leu Gly Lys Lys Leu Ser Val
20 25 30

Pro Gln Asp Leu Met Met Glu Glu Leu Ser Leu Cys Asn Asn Arg Gly
35 40 45

Ser Leu Leu Phe Gln Lys Arg Gln Arg Arg Val Gln Lys Phe Thr Phe
50 55 60

Glu Leu Ala Ala
65

<210> SEQ ID NO 218
<211> LENGTH: 68
<212> TYPE: PRT
<213> ORGANISM: Chlorocebus sabaeus
<220> FEATURE:
<223> OTHER INFORMATION: Chlorocebus_sabaeus

<400> SEQUENCE: 218

Met Ile Pro Lys Glu Gln Lys Gly Pro Val Met Ala Ala Met Gly Asn
1 5 10 15

Phe Thr Glu Pro Val Pro Thr Leu Asp Leu Gly Lys Lys Leu Ser Val
20 25 30

Pro Gln Asp Leu Met Met Glu Glu Leu Ser Leu Pro Asn Asn Arg Gly
35 40 45

Ser Leu Leu Phe Gln Lys Arg Gln Arg Arg Val Gln Lys Phe Thr Phe
50 55 60

Glu Leu Ala Ala
65

<210> SEQ ID NO 219
<211> LENGTH: 68
<212> TYPE: PRT
<213> ORGANISM: Camelus bactrianus
<220> FEATURE:
<223> OTHER INFORMATION: Camelus_bactrianus

<400> SEQUENCE: 219

Met Ile Pro Lys Glu Gln Asn Gly Gln Val Met Thr Ala Met Gly Asp
1 5 10 15

Leu Thr Gly Pro Val Pro Val Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Lys Phe Thr Phe
50 55 60

Glu Phe Thr Ala
65

<210> SEQ ID NO 220
<211> LENGTH: 68

<212> TYPE: PRT
<213> ORGANISM: Vicugna pacos
<220> FEATURE:
<223> OTHER INFORMATION: Vicugna_pacos
<220> FEATURE:
<221> NAME/KEY: VARIANT
<222> LOCATION: 47
<223> OTHER INFORMATION: R or K or P

<400> SEQUENCE: 220

Met Ile Pro Lys Glu Gln Asn Gly Gln Val Met Thr Ala Met Gly Asp
1 5 10 15

Leu Thr Gly Pro Val Pro Val Leu Asp Leu Gly Lys Lys Leu Ser Val
20 25 30

Pro Gln Asp Leu Met Met Glu Glu Leu Ser Leu Arg Asn Asn Xaa Gly
35 40 45

Ser Leu Leu Phe Gln Lys Arg Gln Arg Arg Val Gln Lys Phe Thr Phe
50 55 60

Glu Phe Thr Asp
65

<210> SEQ ID NO 221
<211> LENGTH: 68
<212> TYPE: PRT
<213> ORGANISM: Ursus maritimus
<220> FEATURE:
<223> OTHER INFORMATION: Ursus_maritimus

<400> SEQUENCE: 221

Met Ile Pro Lys Glu Gln Lys Gly Pro Ala Met Ala Ala Val Gly Asp
1 5 10 15

Leu Ser Gly Pro Glu Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Arg Phe Thr Phe
50 55 60

Glu Phe Ala Ala
65

<210> SEQ ID NO 222
<211> LENGTH: 68
<212> TYPE: PRT
<213> ORGANISM: Ailuropoda melanoleuca
<220> FEATURE:
<223> OTHER INFORMATION: Ailuropoda melanoleuca

<400> SEQUENCE: 222

Met Ile Pro Lys Glu Gln Lys Gly Pro Ala Met Ala Ala Val Gly Asp
1 5 10 15

Leu Thr Gly Pro Glu Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Ala Gln Lys Phe Thr Phe
50 55 60

Glu Phe Ala Ala
65

<210> SEQ ID NO 223
<211> LENGTH: 68

<212> TYPE: PRT
<213> ORGANISM: Miniopterus natalensis
<220> FEATURE:
<223> OTHER INFORMATION: Miniopterus natalensis

<400> SEQUENCE: 223

Met Ile Pro Lys Glu Gln Lys Glu Pro Val Met Ala Ala Met Gly Asp
1 5 10 15

Gln Ala Gly Pro Val Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Lys Phe Thr Phe
50 55 60

Glu Leu Ala Ala
65

<210> SEQ ID NO 224
<211> LENGTH: 68
<212> TYPE: PRT
<213> ORGANISM: Ceratotherium simum simum
<220> FEATURE:
<223> OTHER INFORMATION: C. simum simum

<400> SEQUENCE: 224

Met Ile Pro Lys Glu Gln Lys Gly Pro Val Met Ala Ala Thr Gly Asp
1 5 10 15

Leu Ala Gly Pro Val Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Lys Phe Thr Phe
50 55 60

Glu Phe Ala Ala
65

<210> SEQ ID NO 225
<211> LENGTH: 68
<212> TYPE: PRT
<213> ORGANISM: Mustela putorius furo
<220> FEATURE:
<223> OTHER INFORMATION: Mustela putorius furo

<400> SEQUENCE: 225

Met Ile Pro Lys Glu Gln Lys Gly Pro Val Met Ala Ala Met Gly Asp
1 5 10 15

Leu Ala Gly Pro Ala Pro Leu Leu Asp Leu Gly Lys Lys Leu Ser Val
20 25 30

Pro Gln Asp Leu Met Met Glu Glu Leu Ser Leu Arg Asn Asn Lys Gly
35 40 45

Ser Leu Leu Phe Gln Lys Arg Gln Arg Arg Val Gln Arg Phe Thr Phe
50 55 60

Glu Phe Ala Ala
65

<210> SEQ ID NO 226
<211> LENGTH: 68
<212> TYPE: PRT
<213> ORGANISM: Felis catus
<220> FEATURE:
<223> OTHER INFORMATION: Felis catus

<400> SEQUENCE: 226

Met Ile Pro Lys Glu Gln Lys Gly Ser Val Met Ala Ala Met Gly Asp
1 5 10 15

Leu Thr Glu Pro Val Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Arg Phe Thr Phe
50 55 60

Glu Phe Pro Ala
65

<210> SEQ ID NO 227
<211> LENGTH: 68
<212> TYPE: PRT
<213> ORGANISM: Acinonyx jubatus
<220> FEATURE:
<223> OTHER INFORMATION: Acinonyx jubatus

<400> SEQUENCE: 227

Met Ile Pro Lys Glu Gln Lys Gly Ser Val Met Ala Ala Met Gly Asp
1 5 10 15

Leu Thr Gly Pro Val Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Arg Phe Thr Phe
50 55 60

Glu Phe Pro Ala
65

<210> SEQ ID NO 228
<211> LENGTH: 68
<212> TYPE: PRT
<213> ORGANISM: Canis lupus familiaris
<220> FEATURE:
<223> OTHER INFORMATION: Canis lupus familiaris

<400> SEQUENCE: 228

Met Ile Pro Lys Glu Gln Lys Gly Ser Val Met Ala Ala Met Gly Asp
1 5 10 15

Leu Thr Gly Pro Val Pro Leu Leu Asp Leu Gly Lys Lys Leu Ser Val
20 25 30

Pro Gln Asp Leu Met Met Glu Glu Leu Ser Leu Arg Asn Asn Arg Gly
35 40 45

Ser Leu Leu Phe Gln Lys Arg Gln Arg Arg Val Gln Arg Phe Thr Phe
50 55 60

Glu Phe Ala Ala
65

<210> SEQ ID NO 229
<211> LENGTH: 68
<212> TYPE: PRT
<213> ORGANISM: Panthera tigris altaica
<220> FEATURE:
<223> OTHER INFORMATION: Panthera tigris altaica

<400> SEQUENCE: 229

Met Ile Pro Lys Glu Gln Lys Arg Pro Val Met Ala Ala Met Gly Asp

```
1               5                   10                  15

Leu Thr Gly Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Arg Phe Thr Phe
    50                  55                  60

Glu Phe Pro Ala
65


<210> SEQ ID NO 230
<211> LENGTH: 68
<212> TYPE: PRT
<213> ORGANISM: Ochotona princeps
<220> FEATURE:
<223> OTHER INFORMATION: Ochotona princeps

<400> SEQUENCE: 230

Met Ile Pro Lys Asp His Lys Gly Pro Ala Val Ser Ala Met Gly Asp
1               5                   10                  15

Phe Ser Glu Pro Val Pro Leu Leu Asp Leu Gly Lys Lys Leu Ser Val
            20                  25                  30

Pro Gln Asp Leu Met Ile Glu Glu Leu Ser Leu Arg Asn Asn Arg Gly
        35                  40                  45

Ser Leu Leu Phe Gln Lys Arg Gln Arg Arg Val Gln Arg Phe Thr Phe
    50                  55                  60

Glu Leu Pro Asp
65


<210> SEQ ID NO 231
<211> LENGTH: 68
<212> TYPE: PRT
<213> ORGANISM: Oryctolagus cuniculus
<220> FEATURE:
<223> OTHER INFORMATION: Oryctolagus cuniculus

<400> SEQUENCE: 231

Met Ile Pro Lys Glu Gln Lys Gly Leu Ala Met Ser Ala Pro Gly Asp
1               5                   10                  15

Leu Ser Glu Pro Val Pro Leu Leu Asp Leu Gly Lys Lys Leu Ser Val
            20                  25                  30

Pro Gln Asp Leu Met Ile Glu Glu Leu Ser Leu Arg Asn Asn Arg Gly
        35                  40                  45

Ser Leu Leu Phe Gln Lys Arg Gln Arg Arg Val Gln Arg Phe Thr Phe
    50                  55                  60

Glu Leu Pro Asp
65


<210> SEQ ID NO 232
<211> LENGTH: 68
<212> TYPE: PRT
<213> ORGANISM: Ictidomys tridecemlineatus
<220> FEATURE:
<223> OTHER INFORMATION: I. tridecemlineatus

<400> SEQUENCE: 232

Met Ile Pro Lys Glu Gln Lys Glu Pro Val Met Ala Val Met Gly Asp
1               5                   10                  15

Leu Ala Gly Pro Val Pro Thr Leu Asp Leu Gly Lys Lys Leu Ser Val
            20                  25                  30
```

```
Pro Gln Asp Leu Met Ile Glu Glu Leu Ser Leu Arg Asn Asn Pro Gly
        35                  40                  45

Ser Leu Leu Phe Gln Lys Arg Gln Arg Arg Val Gln Arg Phe Thr Phe
    50                  55                  60

Glu Leu Glu Glu
65


<210> SEQ ID NO 233
<211> LENGTH: 68
<212> TYPE: PRT
<213> ORGANISM: Marmota marmota marmota
<220> FEATURE:
<223> OTHER INFORMATION: Marmota marmota marmota

<400> SEQUENCE: 233

Met Ile Pro Arg Glu Gln Lys Glu Pro Val Met Ala Val Met Gly Asp
1               5                   10                  15

Leu Ala Gly Pro Val Pro Leu Leu Asp Leu Gly Lys Lys Leu Ser Val
            20                  25                  30

Pro Gln Asp Leu Met Ile Glu Glu Leu Ser Leu Arg Asn Asn Pro Gly
        35                  40                  45

Ser Leu Leu Phe Gln Lys Arg Gln Arg Arg Val Gln Arg Phe Thr Phe
    50                  55                  60

Glu Leu Glu Glu
65


<210> SEQ ID NO 234
<211> LENGTH: 68
<212> TYPE: PRT
<213> ORGANISM: Tupaia chinensis
<220> FEATURE:
<223> OTHER INFORMATION: Tupaia chinensis

<400> SEQUENCE: 234

Met Ile Pro Lys Glu Gln Lys Gly Pro Val Thr Ala Thr Met Gly Asp
1               5                   10                  15

Leu Cys Glu Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Arg Phe Thr Phe
    50                  55                  60

Glu Leu Ser Ala
65


<210> SEQ ID NO 235
<211> LENGTH: 68
<212> TYPE: PRT
<213> ORGANISM: Physeter catodon
<220> FEATURE:
<223> OTHER INFORMATION: Physeter catodon

<400> SEQUENCE: 235

Met Ile Pro Lys Glu Gln Lys Gly Pro Val Met Thr Thr Met Gly Asp
1               5                   10                  15

Leu Thr Glu Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45
```

```
Ser Leu Leu Phe Gln Lys Arg Arg Arg Arg Val Gln Lys Phe Thr Phe
    50                  55                  60

Glu Phe Ala Ser
65


<210> SEQ ID NO 236
<211> LENGTH: 68
<212> TYPE: PRT
<213> ORGANISM: Panthera pardus
<220> FEATURE:
<223> OTHER INFORMATION: Panthera pardus

<400> SEQUENCE: 236

Met Ile Pro Lys Glu Gln Lys Gly Pro Val Met Ala Ala Met Gly Asp
1               5                   10                  15

Leu Thr Gly Pro Val Pro Leu Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Arg Phe Thr Phe
    50                  55                  60

Glu Phe Pro Ala
65


<210> SEQ ID NO 237
<211> LENGTH: 67
<212> TYPE: PRT
<213> ORGANISM: Sarcophilus harrisii
<220> FEATURE:
<223> OTHER INFORMATION: Sarcophilus harrisii

<400> SEQUENCE: 237

Val Leu Lys Lys Gln Lys Ala Leu Thr Met Ala Lys Ala Gln Asp Phe
1               5                   10                  15

Met Glu Thr Ala Pro Ser Leu Asp Leu Gly Lys Lys Val Ser Val Pro
            20                  25                  30

Gln Asp Leu Met Val Glu Glu Leu Ser Leu Arg Ser Asn Arg Gly Ser
        35                  40                  45

Leu Leu Phe Gln Lys Arg Gln Arg Arg Val Gln Arg Phe Thr Phe Glu
    50                  55                  60

Tyr Ala Thr
65


<210> SEQ ID NO 238
<211> LENGTH: 65
<212> TYPE: PRT
<213> ORGANISM: Fukomys damarensis
<220> FEATURE:
<223> OTHER INFORMATION: Fukomys damarensis

<400> SEQUENCE: 238

Met Asp Pro Lys Glu Gln Gln Asp Ala Val Ile Gly Asp Phe Thr Gly
1               5                   10                  15

Pro Glu Pro Ser Leu Asp Leu Gly Lys Lys Val Ser Val Pro Gln Asp
            20                  25                  30

Leu Met Ile Glu Glu Leu Ser Leu Arg Asn Asn Arg Gly Ser Leu Leu
        35                  40                  45

Phe Gln Lys Arg Gln Arg Arg Val Gln Arg Phe Thr Phe Glu Leu Ala
    50                  55                  60

Ala
```

65

<210> SEQ ID NO 239
<211> LENGTH: 66
<212> TYPE: PRT
<213> ORGANISM: Python bivittatus
<220> FEATURE:
<223> OTHER INFORMATION: Python bivittatus

<400> SEQUENCE: 239

```
Arg Glu Gln His Ala Pro Ile Gln Ala Ile Ala Arg Glu Ile Gln Arg
1               5                   10                  15

Gly Lys Ala Pro Glu Leu Asp Leu Gly Lys Lys Val Ser Thr Pro Gln
            20                  25                  30

Asp Leu Met Met Glu Glu Leu Ser Leu Pro Ile Asn Arg Gly Ser Arg
        35                  40                  45

Leu Tyr Gln Gln Arg Gln Lys Arg Val Gln Arg Phe Val Leu Glu Tyr
    50                  55                  60

Pro Thr
65
```

<210> SEQ ID NO 240
<211> LENGTH: 70
<212> TYPE: PRT
<213> ORGANISM: Pelodiscus sinensis
<220> FEATURE:
<223> OTHER INFORMATION: Pelodiscus sinensis

<400> SEQUENCE: 240

```
Arg Glu Arg Lys Arg Gln Val Ala Ala Ile Leu Arg Glu Thr Ala Gly
1               5                   10                  15

Asp Val Leu Gln Leu Asp Leu Gly Lys Lys Val Ser Val Pro Gln Asp
            20                  25                  30

Leu Met Val Glu Glu Leu Ser Leu Gln Ser Asn Arg Gly Ser Gln Leu
        35                  40                  45

Phe Gln Lys Arg Gln Lys Arg Val Gln Lys Phe Ile Leu Glu His Pro
    50                  55                  60

Met Gly Tyr Gly Ala Gly
65                  70
```

<210> SEQ ID NO 241
<211> LENGTH: 69
<212> TYPE: PRT
<213> ORGANISM: Chrysemys picta bellii
<220> FEATURE:
<223> OTHER INFORMATION: Chrysemys picta bellii

<400> SEQUENCE: 241

```
Arg Glu Arg Lys Lys Gln Ala Met Ala Ile Val Thr Glu Met Met Gly
1               5                   10                  15

Asp Val Pro Gln Leu Asp Leu Gly Lys Lys Val Ser Ile Pro Gln Asp
            20                  25                  30

Leu Met Val Glu Glu Leu Ser Leu Gln Thr Asn Arg Gly Ser Gln Leu
        35                  40                  45

Phe Gln Gln Arg Gln Lys Arg Val Gln Lys Phe Ile Leu Glu His Pro
    50                  55                  60

Thr Gly Tyr Arg Ala
65
```

<210> SEQ ID NO 242

<211> LENGTH: 64
<212> TYPE: PRT
<213> ORGANISM: Chelonia mydas
<220> FEATURE:
<223> OTHER INFORMATION: Chelonia mydas

<400> SEQUENCE: 242

Glu Arg Lys Arg Gln Ala Ile Ala Ile Val Arg Glu Met Ala Glu Asp
1               5                   10                  15

Val Pro Gln Leu Asp Leu Gly Lys Lys Val Ser Ile Pro Gln Asp Leu
            20                  25                  30

Met Val Glu Glu Leu Ser Leu Gln Thr Asn Arg Gly Ser Gln Leu Phe
        35                  40                  45

Gln Gln Arg Gln Lys Arg Val Gln Lys Phe Ile Leu Glu His Pro Thr
    50                  55                  60

<210> SEQ ID NO 243
<211> LENGTH: 67
<212> TYPE: PRT
<213> ORGANISM: Anolis carolinensis
<220> FEATURE:
<223> OTHER INFORMATION: Anolis carolinensis

<400> SEQUENCE: 243

Glu Gln His Ala Pro Val Ser Ala Ile Met Lys Glu Ile Arg Glu Lys
1               5                   10                  15

Tyr Gly Pro Lys Leu Asp Leu Gly Lys Lys Val Ser Ile Pro Gln Asp
            20                  25                  30

Leu Met Met Glu Glu Leu Ser Leu Pro Val Asn Arg Gly Ser Gln Leu
        35                  40                  45

Tyr Gln Lys Arg Gln Lys Arg Val Gln Gln Phe Val Leu Glu Arg Pro
    50                  55                  60

Thr Ala Tyr
65

<210> SEQ ID NO 244
<211> LENGTH: 61
<212> TYPE: PRT
<213> ORGANISM: Alligator mississippiensis
<220> FEATURE:
<223> OTHER INFORMATION: A. mississippiensis

<400> SEQUENCE: 244

Lys Arg Gln Ala Met Ile Val Arg Glu Ser Pro Gly Asp Ala Pro His
1               5                   10                  15

Leu Asp Leu Gly Lys Lys Val Ser Ile Pro Gln Asp Leu Met Met Glu
            20                  25                  30

Glu Leu Ser Leu Lys Thr Asn Arg Gly Ser Arg Leu Tyr Gln Glu Arg
        35                  40                  45

Gln Lys Arg Met Gln Arg Phe Val Leu Glu His Pro Ser
    50                  55                  60

<210> SEQ ID NO 245
<211> LENGTH: 59
<212> TYPE: PRT
<213> ORGANISM: Calidris pugnax
<220> FEATURE:
<223> OTHER INFORMATION: Calidris pugnax

<400> SEQUENCE: 245

Val Met Thr Ile Met Arg Pro Gly Pro Glu Asp Ala Pro Gln Leu Asp
1               5                   10                  15

Leu Gly Lys Lys Met Ser Thr Pro Gln Asp Leu Met Ile Glu Glu Leu
            20                  25                  30

Ser Leu Gly Asn Asn Arg Gly Ser Gln Leu Phe His Gln Arg Gln Lys
        35                  40                  45

Arg Met Gln Arg Phe Val Tyr Glu His Pro Ser
    50                  55

<210> SEQ ID NO 246
<211> LENGTH: 58
<212> TYPE: PRT
<213> ORGANISM: Chlamydotis undulata macqueenii
<220> FEATURE:
<223> OTHER INFORMATION: Chlamydotis macqueenii

<400> SEQUENCE: 246

Met Thr Ile Met Lys Pro Gly Pro Glu Asp Val Pro Gln Leu Asp Leu
1               5                   10                  15

Gly Lys Lys Met Ser Thr Pro Gln Asp Leu Met Ile Glu Glu Leu Ser
            20                  25                  30

Leu Arg Asn Asn Arg Gly Ser Gln Leu Phe Gln Glu Arg Gln Lys Arg
        35                  40                  45

Met Gln Arg Phe Val Phe Glu Tyr Pro Arg
    50                  55

<210> SEQ ID NO 247
<211> LENGTH: 58
<212> TYPE: PRT
<213> ORGANISM: Monodelphis domestica
<220> FEATURE:
<223> OTHER INFORMATION: Monodelphis domestica

<400> SEQUENCE: 247

Met Ala Thr Val Gln Asp Phe Met Gly Ala Ala Pro Ser Leu Asp Leu
1               5                   10                  15

Gly Lys Lys Val Ser Ile Pro Gln Asp Leu Met Val Glu Glu Leu Ser
            20                  25                  30

Leu Arg Ser Asn Arg Gly Ser Leu Leu Phe Gln Lys Arg Gln Lys Arg
        35                  40                  45

Val Gln Arg Phe Thr Phe Glu Tyr Ala Ala
    50                  55

<210> SEQ ID NO 248
<211> LENGTH: 58
<212> TYPE: PRT
<213> ORGANISM: Picoides pubescens
<220> FEATURE:
<223> OTHER INFORMATION: Picoides pubescens

<400> SEQUENCE: 248

Met Ala Ile Met Lys Ser Gly Pro Glu Asp Val Pro Arg Leu Asp Leu
1               5                   10                  15

Gly Lys Lys Ile Ser Thr Pro Gln Asp Leu Met Ile Glu Glu Leu Ser
            20                  25                  30

Leu Arg Asp Asn Arg Gly Ser Gln Leu Phe Gln Gln Arg Gln Arg Arg
        35                  40                  45

Met Gln Arg Phe Ile Phe Glu His Pro Ser
    50                  55

<210> SEQ ID NO 249
<211> LENGTH: 58

<212> TYPE: PRT
<213> ORGANISM: Pelecanus crispus
<220> FEATURE:
<223> OTHER INFORMATION: Pelecanus crispus

<400> SEQUENCE: 249

Met Thr Ile Met Lys Pro Gly Pro Glu Asp Val Pro Arg Leu Asp Leu
1               5                   10                  15

Gly Lys Lys Met Ser Thr Pro Gln Asp Leu Met Ile Glu Glu Leu Ser
            20                  25                  30

Leu Arg Asn Asn Arg Gly Ser Gln Leu Phe Gln Gln Arg Gln Arg Arg
        35                  40                  45

Met Gln Arg Phe Ile Phe Glu His Pro Ser
    50                  55

<210> SEQ ID NO 250
<211> LENGTH: 58
<212> TYPE: PRT
<213> ORGANISM: Charadrius vociferus
<220> FEATURE:
<223> OTHER INFORMATION: Charadrius vociferus

<400> SEQUENCE: 250

Met Thr Ile Met Arg Pro Ala Pro Glu Asp Ala Pro Gln Leu Asp Leu
1               5                   10                  15

Gly Lys Lys Met Ser Thr Pro Gln Asp Leu Met Ile Glu Glu Leu Ser
            20                  25                  30

Leu Arg Asn Asn Arg Gly Ser Gln Leu Phe Gln Gln Arg Gln Lys Arg
        35                  40                  45

Met Gln Arg Phe Val Phe Glu His Pro Ser
    50                  55

<210> SEQ ID NO 251
<211> LENGTH: 58
<212> TYPE: PRT
<213> ORGANISM: Pygoscelis adeliae
<220> FEATURE:
<223> OTHER INFORMATION: Pygoscelis adeliae

<400> SEQUENCE: 251

Met Ala Ile Met Arg Pro Gly Pro Glu Asp Ala Pro Arg Leu Asp Leu
1               5                   10                  15

Gly Lys Lys Met Ser Thr Pro Gln Asp Leu Met Ile Glu Glu Leu Ser
            20                  25                  30

Leu Arg Asn Asn Arg Gly Ser Gln Leu Phe Gln Gln Arg Gln Arg Arg
        35                  40                  45

Met Gln Arg Phe Val Phe Glu His Pro Ser
    50                  55

<210> SEQ ID NO 252
<211> LENGTH: 52
<212> TYPE: PRT
<213> ORGANISM: Nipponia nippon
<220> FEATURE:
<223> OTHER INFORMATION: Nipponia nippon

<400> SEQUENCE: 252

Val Arg Asp Pro Val Pro Gln Leu Asp Leu Gly Lys Lys Met Ser Thr
1               5                   10                  15

Pro Gln Asp Leu Met Ile Glu Glu Leu Ser Leu Arg Asn Asn Arg Gly
            20                  25                  30

Ser Gln Leu Phe Gln Gln Arg Gln Lys Arg Met Gln Arg Phe Val Phe
35 40 45

Glu His Pro Ser
50

<210> SEQ ID NO 253
<211> LENGTH: 50
<212> TYPE: PRT
<213> ORGANISM: Egretta garzetta
<220> FEATURE:
<223> OTHER INFORMATION: Egretta garzetta

<400> SEQUENCE: 253

Glu Asp Ala Pro Arg Leu Asp Leu Gly Lys Lys Val Ser Thr Pro Gln
1 5 10 15

Asp Leu Met Ile Glu Glu Leu Ser Leu Arg Asn Asn Arg Gly Ser Gln
20 25 30

Leu Phe Gln Gln Arg Gln Lys Arg Met Gln Arg Phe Val Phe Glu His
35 40 45

Pro Gly
50

<210> SEQ ID NO 254
<211> LENGTH: 49
<212> TYPE: PRT
<213> ORGANISM: Cathartes aura
<220> FEATURE:
<223> OTHER INFORMATION: Cathartes aura

<400> SEQUENCE: 254

Pro Val Pro Arg Leu Asp Leu Gly Lys Lys Val Ser Val Ala Gln Asp
1 5 10 15

Leu Met Ile Glu Glu Leu Ser Leu Pro Asn Asn Arg Gly Ser Gln Leu
20 25 30

Phe Gln Gln Arg Gln Arg Arg Met His Gly Phe Leu Phe Leu Pro Gly
35 40 45

Gln

<210> SEQ ID NO 255
<211> LENGTH: 46
<212> TYPE: PRT
<213> ORGANISM: Taeniopygia guttata
<220> FEATURE:
<223> OTHER INFORMATION: Taeniopygia guttata

<400> SEQUENCE: 255

Pro Glu Pro Gln Leu Asp Leu Gly Lys Lys Met Ser Thr Thr His Asp
1 5 10 15

Leu Met Ile Glu Glu Leu Ser Leu Pro His Asn Arg Gly Ser Arg Leu
20 25 30

Phe Gln Gln Arg Gln Lys Arg Val Gln Arg Phe Val Leu Glu
35 40 45

<210> SEQ ID NO 256
<211> LENGTH: 49
<212> TYPE: PRT
<213> ORGANISM: Corvus brachyrhynchos
<220> FEATURE:
<223> OTHER INFORMATION: Corvus brachyrhynchos

<400> SEQUENCE: 256

Pro Glu Pro Gln Leu Asp Leu Gly Lys Lys Met Ser Thr Thr Gln Asp

```
1               5                   10                  15

Val Met Ile Glu Glu Leu Ser Leu Arg Asn Asn Arg Gly Ser Arg Leu
            20                  25                  30

Phe Gln Gln Arg Gln Lys Arg Met Gln Arg Phe Val Phe Glu His Pro
        35                  40                  45

Ser


<210> SEQ ID NO 257
<211> LENGTH: 52
<212> TYPE: PRT
<213> ORGANISM: Columba livia
<220> FEATURE:
<223> OTHER INFORMATION: Columba livia

<400> SEQUENCE: 257

Pro Ala Pro Gln Leu Asp Leu Gly Lys Lys Val Ser Thr Pro Gln Asp
1               5                   10                  15

Leu Met Met Glu Glu Leu Ser Leu Arg Asn Asn Arg Gly Ser Arg Leu
            20                  25                  30

Phe Gln Gln Arg Gln Lys Arg Met Gln Arg Phe Val Phe Glu His Pro
        35                  40                  45

Arg Val Gly Gly
    50


<210> SEQ ID NO 258
<211> LENGTH: 49
<212> TYPE: PRT
<213> ORGANISM: Chaetura pelagica
<220> FEATURE:
<223> OTHER INFORMATION: Chaetura pelagica

<400> SEQUENCE: 258

Pro Val Pro Gln Leu Ile Leu Gly Lys Lys Met Ser Thr Pro Gln Asp
1               5                   10                  15

Leu Met Ile Glu Glu Leu Ser Leu Arg Asn Asn Arg Gly Ser Gln Leu
            20                  25                  30

Phe Gln Gln Arg Gln Arg Arg Met Gln Arg Phe Val Phe Glu His Pro
        35                  40                  45

Ser


<210> SEQ ID NO 259
<211> LENGTH: 49
<212> TYPE: PRT
<213> ORGANISM: Aptenodytes forsteri
<220> FEATURE:
<223> OTHER INFORMATION: Aptenodytes forsteri

<400> SEQUENCE: 259

Pro Ala Pro Arg Leu Asp Leu Gly Lys Lys Val Ser Thr Pro Gln Asp
1               5                   10                  15

Leu Met Ile Glu Glu Leu Ser Leu Arg Asn Asn Arg Gly Ser Gln Leu
            20                  25                  30

Phe Gln Gln Arg Gln Arg Arg Met Gln Arg Phe Val Phe Glu His Pro
        35                  40                  45

Ser


<210> SEQ ID NO 260
<211> LENGTH: 46
<212> TYPE: PRT
<213> ORGANISM: Tauraco erythrolophus
```

<220> FEATURE:
<223> OTHER INFORMATION: Tauraco erythrolophus

<400> SEQUENCE: 260

```
Pro Ala Pro Arg Leu Asp Leu Gly Lys Lys Val Ser Thr Pro Gln Asp
1               5                   10                  15

Leu Met Ile Glu Glu Leu Ser Leu Arg Asn Asn Arg Gly Ser Gln Leu
            20                  25                  30

Phe Gln Gln Arg Gln Arg Arg Met Gln Arg Phe Val Phe Glu
        35                  40                  45
```

<210> SEQ ID NO 261
<211> LENGTH: 48
<212> TYPE: PRT
<213> ORGANISM: Alligator sinensis
<220> FEATURE:
<223> OTHER INFORMATION: Alligator sinensis

<400> SEQUENCE: 261

```
Ala Pro His Leu Asp Leu Gly Lys Lys Val Ser Ile Pro Gln Asp Leu
1               5                   10                  15

Met Met Glu Glu Leu Ser Leu Lys Thr Asn Arg Gly Ser Arg Leu Tyr
            20                  25                  30

Gln Glu Arg Gln Lys Arg Met Gln Arg Phe Val Leu Glu His Pro Ser
        35                  40                  45
```

<210> SEQ ID NO 262
<211> LENGTH: 48
<212> TYPE: PRT
<213> ORGANISM: Struthio camelus australis
<220> FEATURE:
<223> OTHER INFORMATION: S. camelus australis

<400> SEQUENCE: 262

```
Ala Pro Arg Leu Asp Leu Gly Lys Lys Val Ser Thr Pro Gln Asp Val
1               5                   10                  15

Met Ile Glu Glu Leu Ser Leu Arg Thr Asn Arg Gly Ser Gln Leu Phe
            20                  25                  30

Gln Gln Arg Gln Arg Arg Met Gln Arg Phe Ile Phe Glu Tyr Pro Ser
        35                  40                  45
```

<210> SEQ ID NO 263
<211> LENGTH: 48
<212> TYPE: PRT
<213> ORGANISM: Tinamus guttatus
<220> FEATURE:
<223> OTHER INFORMATION: Tinamus guttatus

<400> SEQUENCE: 263

```
Val Pro Arg Leu Asp Leu Gly Lys Lys Val Ser Thr Pro Gln Asp Val
1               5                   10                  15

Met Ile Glu Glu Leu Ser Leu Arg Thr Asn Arg Gly Ser Gln Leu Phe
            20                  25                  30

Gln Gln Arg Gln Arg Arg Met Gln Arg Phe Ile Phe Glu Tyr Pro Ser
        35                  40                  45
```

<210> SEQ ID NO 264
<211> LENGTH: 47
<212> TYPE: PRT
<213> ORGANISM: Aves
<220> FEATURE:
<223> OTHER INFORMATION: bird1

<400> SEQUENCE: 264

Pro Arg Leu Asp Leu Gly Lys Lys Met Ser Thr Thr Gln Asp Leu Met
1 5 10 15

Ile Glu Glu Leu Ser Leu Arg Asn Asn Arg Gly Ser Gln Leu Phe Gln
20 25 30

Gln Arg Gln Arg Arg Met Gln Arg Phe Ile Phe Glu His Pro Ser
35 40 45

<210> SEQ ID NO 265
<211> LENGTH: 47
<212> TYPE: PRT
<213> ORGANISM: Pseudopodoces humilis
<220> FEATURE:
<223> OTHER INFORMATION: Pseudopodoces humilis

<400> SEQUENCE: 265

Pro Gln Leu Asp Leu Gly Lys Lys Met Ser Thr Ala Gln Asp Leu Met
1 5 10 15

Ile Glu Glu Leu Ser Leu Gln Asn Asn Arg Gly Ser Arg Leu Phe Gln
20 25 30

Gln Arg Gln Lys Arg Val Gln Arg Phe Val Phe Glu His Pro Arg
35 40 45

<210> SEQ ID NO 266
<211> LENGTH: 47
<212> TYPE: PRT
<213> ORGANISM: Serinus canaria
<220> FEATURE:
<223> OTHER INFORMATION: Serinus canaria

<400> SEQUENCE: 266

Pro His Leu Asp Leu Gly Lys Lys Met Ser Thr Thr His Asp Leu Met
1 5 10 15

Ile Glu Glu Leu Ser Leu Pro Asn Asn Arg Gly Ser Arg Leu Phe Gln
20 25 30

Gln Arg Gln Lys Arg Val Gln Arg Phe Val Phe Glu His Pro Ser
35 40 45

<210> SEQ ID NO 267
<211> LENGTH: 47
<212> TYPE: PRT
<213> ORGANISM: Parus major
<220> FEATURE:
<223> OTHER INFORMATION: Parus major

<400> SEQUENCE: 267

Pro Gln Leu Asp Leu Gly Lys Lys Met Ser Thr Thr Gln Asp Leu Met
1 5 10 15

Ile Glu Glu Leu Ser Leu Gln Asn Asn Arg Gly Ser Arg Leu Phe Gln
20 25 30

Gln Arg Gln Lys Arg Val Gln Arg Phe Val Phe Glu His Pro Ser
35 40 45

<210> SEQ ID NO 268
<211> LENGTH: 47
<212> TYPE: PRT
<213> ORGANISM: Zonotrichia albicollis
<220> FEATURE:
<223> OTHER INFORMATION: Zonotrichia albicollis

<400> SEQUENCE: 268

Pro Gln Leu Asp Leu Gly Lys Lys Met Ser Thr Thr Gln Asp Leu Met

```
1               5                   10                  15

Ile Glu Glu Leu Ser Leu Pro Asn Asn Arg Gly Ser Arg Leu Phe Gln
            20                  25                  30

Gln Arg Gln Lys Arg Val Gln Arg Phe Val Phe Glu His Pro Ser
        35                  40                  45


<210> SEQ ID NO 269
<211> LENGTH: 47
<212> TYPE: PRT
<213> ORGANISM: Cuculus canorus
<220> FEATURE:
<223> OTHER INFORMATION: Cuculus canorus

<400> SEQUENCE: 269

Pro Arg Leu Asp Leu Gly Lys Lys Met Ser Thr Pro Gln Asp Leu Met
1               5                   10                  15

Ile Glu Glu Leu Ser Leu Arg Asn Asn Arg Gly Ser Gln Leu Phe Gln
            20                  25                  30

Gln Arg Gln Arg Arg Met Gln Arg Phe Val Phe Glu His Pro Ser
        35                  40                  45


<210> SEQ ID NO 270
<211> LENGTH: 45
<212> TYPE: PRT
<213> ORGANISM: Apteryx australis mantelli
<220> FEATURE:
<223> OTHER INFORMATION: A. australis mantelli

<400> SEQUENCE: 270

Leu Asp Leu Gly Lys Lys Val Ser Thr Pro Gln Asp Val Met Ile Glu
1               5                   10                  15

Glu Leu Ser Leu Arg Thr Asn Arg Gly Ser Gln Leu Phe Gln Gln Arg
            20                  25                  30

Gln Lys Arg Met Gln Arg Phe Ile Phe Glu Tyr Pro Ser
        35                  40                  45


<210> SEQ ID NO 271
<211> LENGTH: 68
<212> TYPE: PRT
<213> ORGANISM: Equus
<220> FEATURE:
<223> OTHER INFORMATION: MYOZ3-S42L

<400> SEQUENCE: 271

Met Ile Pro Lys Glu Gln Lys Gly Pro Val Met Ala Ala Met Glu Asp
1               5                   10                  15

Leu Ala Gly Pro Val Pro Val Leu Asp Leu Gly Lys Lys Leu Ser Val
            20                  25                  30

Pro Gln Asp Leu Met Met Glu Glu Leu Leu Leu Arg Asn Asn Arg Gly
        35                  40                  45

Ser Leu Leu Phe Gln Lys Arg Gln Arg Arg Val Gln Lys Phe Thr Phe
    50                  55                  60

Glu Phe Ala Ala
65


<210> SEQ ID NO 272
<211> LENGTH: 51
<212> TYPE: PRT
<213> ORGANISM: Homo sapiens
<220> FEATURE:
<223> OTHER INFORMATION: Human
```

<400> SEQUENCE: 272

```
Ala Gln Asp Ser Gln Gln His Asn Ser Glu His Ala Arg Leu Gln Val
1               5                   10                  15

Pro Thr Ser Gln Val Arg Ser Arg Ser Thr Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu
    50
```

<210> SEQ ID NO 273
<211> LENGTH: 51
<212> TYPE: PRT
<213> ORGANISM: Artificial Sequence
<220> FEATURE:
<223> OTHER INFORMATION: Consensus_sequence
<220> FEATURE:
<221> NAME/KEY: VARIANT
<222> LOCATION: 26
<223> OTHER INFORMATION: T or S

<400> SEQUENCE: 273

```
Ala Gln Asp Ser Gln Gln His Asn Ser Glu His Ala Arg Leu Gln Val
1               5                   10                  15

Pro Thr Ser Gln Val Arg Ser Arg Ser Xaa Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu
    50
```

<210> SEQ ID NO 274
<211> LENGTH: 51
<212> TYPE: PRT
<213> ORGANISM: Equus
<220> FEATURE:
<223> OTHER INFORMATION: Horse

<400> SEQUENCE: 274

```
Ala Gln Asp Ser Gln Gln His Asn Ser Glu His Ala Arg Leu Gln Val
1               5                   10                  15

Pro Thr Ser Gln Val Arg Ser Arg Ser Ser Ser Arg Gly Asp Val Asn
            20                  25                  30

Asp Gln Asp Ala Ile Gln Glu Lys Phe Tyr Pro Pro Arg Phe Ile Gln
        35                  40                  45

Val Pro Glu
    50
```

<210> SEQ ID NO 275
<211> LENGTH: 103
<212> TYPE: PRT
<213> ORGANISM: Homo sapiens
<220> FEATURE:
<223> OTHER INFORMATION: Human

<400> SEQUENCE: 275

```
Gly Glu Gly Ser His Pro Glu Arg Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
```

```
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Ala
                85                  90                  95

Ser Pro Phe His Ile Lys Val
            100


<210> SEQ ID NO 276
<211> LENGTH: 103
<212> TYPE: PRT
<213> ORGANISM: Artificial Sequence
<220> FEATURE:
<223> OTHER INFORMATION: Horse filamin-C protein
<220> FEATURE:
<221> NAME/KEY: misc_feature
<222> LOCATION: (8)..(8)
<223> OTHER INFORMATION: Xaa can be R or K

<400> SEQUENCE: 276

Gly Glu Gly Ser His Pro Glu Xaa Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Ala
                85                  90                  95

Ser Pro Phe His Ile Lys Val
            100


<210> SEQ ID NO 277
<211> LENGTH: 103
<212> TYPE: PRT
<213> ORGANISM: Equus
<220> FEATURE:
<223> OTHER INFORMATION: ENS

<400> SEQUENCE: 277

Gly Glu Gly Ser His Pro Glu Lys Val Lys Val Tyr Gly Pro Gly Val
1               5                   10                  15

Glu Lys Thr Gly Leu Lys Ala Asn Glu Pro Thr Tyr Phe Thr Val Asp
            20                  25                  30

Cys Ser Glu Ala Gly Gln Gly Asp Val Ser Ile Gly Ile Lys Cys Ala
        35                  40                  45

Pro Gly Val Val Gly Pro Ala Glu Ala Asp Ile Asp Phe Asp Ile Ile
    50                  55                  60

Lys Asn Asp Asn Asp Thr Phe Thr Val Lys Tyr Thr Pro Pro Gly Ala
65                  70                  75                  80

Gly Arg Tyr Thr Ile Met Val Leu Phe Ala Asn Gln Glu Ile Pro Ala
                85                  90                  95

Ser Pro Phe His Ile Lys Val
            100
```

<210> SEQ ID NO 278
<211> LENGTH: 103
<212> TYPE: PRT
<213> ORGANISM: Equus
<220> FEATURE:
<223> OTHER INFORMATION: XP

<400> SEQUENCE: 278

Gly Glu Gly Ser His Pro Glu Lys Val Lys Val Tyr Gly Pro Gly Val
1 5 10 15

Glu Lys Thr Gly Leu Lys Ala Asn Glu Pro Thr Tyr Phe Thr Val Asp
20 25 30

Cys Ser Glu Ala Gly Gln Gly Asp Val Ser Ile Gly Ile Lys Cys Ala
35 40 45

Pro Gly Val Val Gly Pro Ala Glu Ala Asp Ile Asp Phe Asp Ile Ile
50 55 60

Lys Asn Asp Asn Asp Thr Phe Thr Val Lys Tyr Thr Pro Pro Gly Ala
65 70 75 80

Gly Arg Tyr Thr Ile Met Val Leu Phe Ala Asn Gln Glu Ile Pro Ala
85 90 95

Ser Pro Phe His Ile Lys Val
100

<210> SEQ ID NO 279
<211> LENGTH: 100
<212> TYPE: PRT
<213> ORGANISM: Homo sapiens
<220> FEATURE:
<223> OTHER INFORMATION: Human

<400> SEQUENCE: 279

Gln Pro Ala Val Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Val Thr Asp Asn Gly
50 55 60

Asp Gly Thr Tyr Arg Val Gln Tyr Thr Ala Tyr Glu Glu Gly Val His
65 70 75 80

Leu Val Glu Val Leu Tyr Asp Glu Val Ala Val Pro Lys Ser Pro Phe
85 90 95

Arg Val Gly Val
100

<210> SEQ ID NO 280
<211> LENGTH: 100
<212> TYPE: PRT
<213> ORGANISM: Artificial Sequence
<220> FEATURE:
<223> OTHER INFORMATION: horse filamin-C protein
<220> FEATURE:
<221> NAME/KEY: misc_feature
<222> LOCATION: (4)..(4)
<223> OTHER INFORMATION: Xaa can be V or I
<220> FEATURE:
<221> NAME/KEY: misc_feature
<222> LOCATION: (88)..(88)
<223> OTHER INFORMATION: Xaa can be E or D

<400> SEQUENCE: 280

Gln Pro Ala Xaa Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Val Thr Asp Asn Gly
50 55 60

Asp Gly Thr Tyr Arg Val Gln Tyr Thr Ala Tyr Glu Glu Gly Val His
65 70 75 80

Leu Val Glu Val Leu Tyr Asp Xaa Val Ala Val Pro Lys Ser Pro Phe
85 90 95

Arg Val Gly Val
100

<210> SEQ ID NO 281
<211> LENGTH: 100
<212> TYPE: PRT
<213> ORGANISM: Equus
<220> FEATURE:
<223> OTHER INFORMATION: ENS

<400> SEQUENCE: 281

Gln Pro Ala Ile Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Val Thr Asp Asn Gly
50 55 60

Asp Gly Thr Tyr Arg Val Gln Tyr Thr Ala Tyr Glu Glu Gly Val His
65 70 75 80

Leu Val Glu Val Leu Tyr Asp Asp Val Ala Val Pro Lys Ser Pro Phe
85 90 95

Arg Val Gly Val
100

<210> SEQ ID NO 282
<211> LENGTH: 100
<212> TYPE: PRT
<213> ORGANISM: Equus
<220> FEATURE:
<223> OTHER INFORMATION: XP

<400> SEQUENCE: 282

Gln Pro Ala Ile Asp Thr Ser Gly Val Lys Val Ser Gly Pro Gly Val
1 5 10 15

Glu Pro His Gly Val Leu Arg Glu Val Thr Thr Glu Phe Thr Val Asp
20 25 30

Ala Arg Ser Leu Thr Ala Thr Gly Gly Asn His Val Thr Ala Arg Val
35 40 45

Leu Asn Pro Ser Gly Ala Lys Thr Asp Thr Tyr Val Thr Asp Asn Gly
50 55 60

Asp Gly Thr Tyr Arg Val Gln Tyr Thr Ala Tyr Glu Glu Gly Val His
65 70 75 80

```
Leu Val Glu Val Leu Tyr Asp Asp Val Ala Val Pro Lys Ser Pro Phe
                85                  90                  95

Arg Val Gly Val
            100


<210> SEQ ID NO 283
<211> LENGTH: 337
<212> TYPE: DNA
<213> ORGANISM: Equus
<220> FEATURE:
<223> OTHER INFORMATION: Flanking DNA Sequence (5')

<400> SEQUENCE: 283

ctatgacaat ggaaacccaa ttcttattat acaatctttg cacatgataa gaattgtcca     60

tggggtactc tgcattttaa cagatcagct tcttcattaa ttcgttgcac tgtaaaaagg    120

aaacaaagat gtataatttg ggccagatgt ttctaaattg ctaccatttc taccagtcat    180

caaatatacc acagctaaat atagcctctc tccattgtta ttacactatc agatcaaacc    240

cactctaggg ttttaaattt gatgactaaa ctatatctgt gtgaaaggaa gagcaatgat    300

aattttccgc atggtgatga ttaaactatt tttgcag                             337


<210> SEQ ID NO 284
<211> LENGTH: 120
<212> TYPE: DNA
<213> ORGANISM: Equus
<220> FEATURE:
<223> OTHER INFORMATION: Flanking DNA Sequence (3')

<400> SEQUENCE: 284

gtaagagaag agttcaaaag tactggagga aaattaacaa tgtgatacta agttttgaaa     60

aatgtgctct tcctcttcat agcttgctcc acagcttgag aagcagcacg tacagtggag    120


<210> SEQ ID NO 285
<211> LENGTH: 60
<212> TYPE: DNA
<213> ORGANISM: Equus
<220> FEATURE:
<223> OTHER INFORMATION: Flanking DNA Sequence (5')

<400> SEQUENCE: 285

ggggaagagg atgggctttg agggaggggc accatgctga gcattgaccc cttcccacag     60


<210> SEQ ID NO 286
<211> LENGTH: 240
<212> TYPE: DNA
<213> ORGANISM: Equus
<220> FEATURE:
<223> OTHER INFORMATION: Flanking DNA Sequence (3')

<400> SEQUENCE: 286

gtgcaccagc caggcggggg agtaggagac ggggcctggg gcggggtctg ggtgggtagg     60

gctagtactc ctggcagagc tgtttcctgg cagagctcta gtgggactgc tcaggtgggg    120

caggttgttg agcccccatc tcatggcctc ctgtctgcct accctcaggc gatgtgagca    180

ttggcatcaa gtgcgccccc ggcgtggtgg gccccgcaga ggctgacatt gactttgaca    240


<210> SEQ ID NO 287
<211> LENGTH: 60
<212> TYPE: DNA
<213> ORGANISM: Equus
<220> FEATURE:
<223> OTHER INFORMATION: Flanking DNA Sequence (5')
```

<400> SEQUENCE: 287
gaaggccaag cacgggtgag gccaagtgta gggaactcac atacctgctc ttccctctag 60

<210> SEQ ID NO 288
<211> LENGTH: 120
<212> TYPE: DNA
<213> ORGANISM: Equus
<220> FEATURE:
<223> OTHER INFORMATION: Flanking DNA Sequence (3')

<400> SEQUENCE: 288
gtgagtgaga gaggagccag gagcccgtca gggagccagg ggaggcagca gaagggacgg 60
aagcaagcct gagtgcttag cagagcacca tagtctgaag ggaggacttg gggacagccc 120

<210> SEQ ID NO 289
<211> LENGTH: 120
<212> TYPE: DNA
<213> ORGANISM: Equus
<220> FEATURE:
<223> OTHER INFORMATION: Flanking DNA Sequence (5')

<400> SEQUENCE: 289
ggggagaaac caggtttctc acacacaatg gacagtgtgc tgaggaggcc tcctgagagg 60
cggcagccta ggaagcctgc gggtttggta gtaagagctg cctctggcct ctcctggcag 120

<210> SEQ ID NO 290
<211> LENGTH: 420
<212> TYPE: DNA
<213> ORGANISM: Equus
<220> FEATURE:
<223> OTHER INFORMATION: Flanking DNA Sequence (3')

<400> SEQUENCE: 290
gtgagtaagc ccccactgtg ctcacaggga aactgaggcc cagagagagc cagtggttag 60
tctaaagccc aacagtgagc caggggagga cctctggccc ctggggagtc cctcaagctc 120
cagctgggga agactgtgat gttcccatcg gactgagccc cgccctgccg ggtgatccta 180
gaaaagggtt acctctttag gcgtctcccc agatgtgaaa catgaagtgg catgggcagg 240
aggagctgtg gagtgaagga ctctggctcc tataaaaagg gctgaagcat agtcatgtgc 300
tctgggctga atttacagca agccggattt aggttagact tgagcttgat ctaaggtgga 360
aaatgcagaa tgccttttc tcttcttccc actggaagaa ggaaaaggcc acggcacagt 420

<210> SEQ ID NO 291
<211> LENGTH: 11
<212> TYPE: DNA
<213> ORGANISM: Equus
<220> FEATURE:
<223> OTHER INFORMATION: Homozygous mutant

<400> SEQUENCE: 291
tgaaggtgat c 11

<210> SEQ ID NO 292
<211> LENGTH: 11
<212> TYPE: DNA
<213> ORGANISM: Equus
<220> FEATURE:
<223> OTHER INFORMATION: Heterozygous

<400> SEQUENCE: 292
gcagcaaggc g 11

<210> SEQ ID NO 293
<211> LENGTH: 11
<212> TYPE: DNA
<213> ORGANISM: Equus
<220> FEATURE:
<223> OTHER INFORMATION: Homozygous mutant

<400> SEQUENCE: 293
agcccactat c 11

<210> SEQ ID NO 294
<211> LENGTH: 11
<212> TYPE: DNA
<213> ORGANISM: Equus
<220> FEATURE:
<223> OTHER INFORMATION: Heterozygous

<400> SEQUENCE: 294
aagagctgtt g 11

<210> SEQ ID NO 295
<211> LENGTH: 11
<212> TYPE: DNA
<213> ORGANISM: Equus
<220> FEATURE:
<223> OTHER INFORMATION: Homozygous mutant

<400> SEQUENCE: 295
gctgttgctc c 11

<210> SEQ ID NO 296
<211> LENGTH: 337
<212> TYPE: DNA
<213> ORGANISM: Equus
<220> FEATURE:
<223> OTHER INFORMATION: Flanking DNA Sequence (5')

<400> SEQUENCE: 296
ctatgacaat ggaaacccaa ttcttattat acaatctttg cacatgataa gaattgtcca 60
tggggtactc tgcattttaa cagatcagct tcttcattaa ttcgttgcac tgtaaaaagg 120
aaacaaagat gtataatttg ggccagatgt ttctaaattg ctaccatttc taccagtcat 180
caaatatacc acagctaaat atagcctctc tccattgtta ttacactatc agatcaaacc 240
cactctaggg ttttaaattt gatgactaaa ctatatctgt gtgaaaggaa gagcaatgat 300
aattttccgc atggtgatga ttaaactatt tttgcag 337

<210> SEQ ID NO 297
<211> LENGTH: 120
<212> TYPE: DNA
<213> ORGANISM: Equus
<220> FEATURE:
<223> OTHER INFORMATION: Flanking DNA Sequence (3')

<400> SEQUENCE: 297
gtaagagaag agttcaaaag tactggagga aaattaacaa tgtgatacta agttttgaaa 60
aatgtgctct tcctcttcat agcttgctcc acagcttgag aagcagcacg tacagtggag 120

<210> SEQ ID NO 298
<211> LENGTH: 180
<212> TYPE: DNA
<213> ORGANISM: Equus

<220> FEATURE:
<223> OTHER INFORMATION: Flanking DNA Sequence (5')

<400> SEQUENCE: 298
gagggtgaag ccctatgcag gagatgtcgg ctgtcgctgg gccctggtca ctgctcccca 60
cctcaaggcc cccacgaagg agctaagatt gatcccatta aggctgaggc gcctagtgct 120
ggggaagagg atgggctttg agggaggggc accatgctga gcattgaccc cttcccacag 180

<210> SEQ ID NO 299
<211> LENGTH: 120
<212> TYPE: DNA
<213> ORGANISM: Equus
<220> FEATURE:
<223> OTHER INFORMATION: Flanking DNA Sequence (3')

<400> SEQUENCE: 299
gtgcaccagc caggcggggg agtaggagac ggggcctggg gcggggtctg ggtgggtagg 60
gctagtactc ctggcagagc tgtttcctgg cagagctcta gtgggactgc tcaggtgggg 120

<210> SEQ ID NO 300
<211> LENGTH: 60
<212> TYPE: DNA
<213> ORGANISM: Equus
<220> FEATURE:
<223> OTHER INFORMATION: Flanking DNA Sequence (5')

<400> SEQUENCE: 300
gaaggccaag cacgggtgag gccaagtgta gggaactcac atacctgctc ttccctctag 60

<210> SEQ ID NO 301
<211> LENGTH: 140
<212> TYPE: DNA
<213> ORGANISM: Equus
<220> FEATURE:
<223> OTHER INFORMATION: Flanking DNA Sequence (3')

<400> SEQUENCE: 301
gtgagtgaga gaggagccag gagcccgtca gggagccagg ggaggcagca gaagggacgg 60
aagcaagcct gagtgcttag cagagcacca tagtctgaag ggaggacttg gggacagccc 120
tggcgtcctt agggctcaga 140

<210> SEQ ID NO 302
<211> LENGTH: 120
<212> TYPE: DNA
<213> ORGANISM: Equus
<220> FEATURE:
<223> OTHER INFORMATION: Flanking DNA Sequence (5')

<400> SEQUENCE: 302
ggggagaaac caggtttctc acacacaatg gacagtgtgc tgaggaggcc tcctgagagg 60
cggcagccta ggaagcctgc gggtttggta gtaagagctg cctctggcct ctcctggcag 120

<210> SEQ ID NO 303
<211> LENGTH: 180
<212> TYPE: DNA
<213> ORGANISM: Equus
<220> FEATURE:
<223> OTHER INFORMATION: Flanking DNA Sequence (3')

<400> SEQUENCE: 303
gtgagtaagc ccccactgtg ctcacaggga aactgaggcc cagagagagc cagtggttag 60

```
tctaaagccc aacagtgagc caggggagga cctctggccc ctggggagtc cctcaagctc    120

cagctgggga agactgtgat gttcccatcg gactgagccc cgccctgccg ggtgatccta    180


<210> SEQ ID NO 304
<211> LENGTH: 68
<212> TYPE: PRT
<213> ORGANISM: Homo sapiens
<220> FEATURE:
<223> OTHER INFORMATION: UniProt_Q8TDC0_MYOZ3

<400> SEQUENCE: 304

Met Ile Pro Lys Glu Gln Lys Gly Pro Val Met Ala Ala Met Gly Asp
1               5                   10                  15

Leu Thr Glu Pro Val Pro Thr Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Leu Ala Ala
65


<210> SEQ ID NO 305
<211> LENGTH: 68
<212> TYPE: PRT
<213> ORGANISM: Artificial Sequence
<220> FEATURE:
<223> OTHER INFORMATION: Alignment
<220> FEATURE:
<221> NAME/KEY: VARIANT
<222> LOCATION: 15
<223> OTHER INFORMATION: G or E
<220> FEATURE:
<221> NAME/KEY: VARIANT
<222> LOCATION: 18..19
<223> OTHER INFORMATION: TE or AG
<220> FEATURE:
<221> NAME/KEY: VARIANT
<222> LOCATION: 23
<223> OTHER INFORMATION: T or V
<220> FEATURE:
<221> NAME/KEY: VARIANT
<222> LOCATION: 66
<223> OTHER INFORMATION: L or F

<400> SEQUENCE: 305

Met Ile Pro Lys Glu Gln Lys Gly Pro Val Met Ala Ala Met Xaa Asp
1               5                   10                  15

Leu Xaa Xaa Pro Val Pro Xaa Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Xaa Ala Ala
65


<210> SEQ ID NO 306
<211> LENGTH: 68
<212> TYPE: PRT
<213> ORGANISM: Equus
<220> FEATURE:
<223> OTHER INFORMATION: MYOZ3

<400> SEQUENCE: 306
```

```
Met Ile Pro Lys Glu Gln Lys Gly Pro Val Met Ala Ala Met Glu Asp
1               5                   10                  15

Leu Ala Gly Pro Val Pro Val Leu Asp Leu Gly Lys Lys Leu Ser Val
            20                  25                  30

Pro Gln Asp Leu Met Met Glu Glu Leu Ser Leu Arg Asn Asn Arg Gly
        35                  40                  45

Ser Leu Leu Phe Gln Lys Arg Gln Arg Arg Val Gln Lys Phe Thr Phe
    50                  55                  60

Glu Phe Ala Ala
65


<210> SEQ ID NO 307
<211> LENGTH: 100
<212> TYPE: PRT
<213> ORGANISM: Equus
<220> FEATURE:
<223> OTHER INFORMATION: FLNC-A1207T

<400> SEQUENCE: 307

Gln Pro Thr Ile Asp Thr Ser Gly Val Lys Val Ser Gly Pro Gly Val
1               5                   10                  15

Glu Pro His Gly Val Leu Arg Glu Val Thr Thr Glu Phe Thr Val Asp
            20                  25                  30

Ala Arg Ser Leu Thr Ala Thr Gly Gly Asn His Val Thr Ala Arg Val
        35                  40                  45

Leu Asn Pro Ser Gly Ala Lys Thr Asp Thr Tyr Val Thr Asp Asn Gly
    50                  55                  60

Asp Gly Thr Tyr Arg Val Gln Tyr Thr Ala Tyr Glu Glu Gly Val His
65                  70                  75                  80

Leu Val Glu Val Leu Tyr Asp Asp Val Ala Val Pro Lys Ser Pro Phe
                85                  90                  95

Arg Val Gly Val
            100
```

METHOD OF DETECTING INHERITED EQUINE MYOPATHY

CROSS-REFERENCE TO RELATED APPLICATION

This application is the § 371 U.S. National Stage of International Application No. PCT/US2017/023969, filed Mar. 24, 2017, which claims the benefit of U.S. Provisional Application No. 62/313,272, filed Mar. 25, 2016, and U.S. Provisional Patent Application No. 62/421,625, filed Nov. 14, 2016, each of which is incorporated herein by reference in its entirety.

SEQUENCE LISTING

This application contains a Sequence Listing electronically submitted via EFS-Web to the United States Patent and Trademark Office as an ASCII text file entitled "P6738EP.TXT" having a size of 321 kilobytes and created on Jan. 10, 2019. The information contained in the Sequence Listing is incorporated by reference herein.

SUMMARY

This disclosure describes, in one aspect, a method for detecting the presence or absence of a set of biomarkers in a horse. Generally, the method includes obtaining a biological sample from a horse that includes a nucleic acid that includes the coding regions for myotilin (MYOT), filamin-C (FLNC), and myozenin-3 (MYOZ3), and determining whether the nucleic acid has specific substitutions as follows: (1) a guanine (G) substituted for an adenine (A) at chr14:38,519,183 of the current horse genome assembly (EquCab2, GCA_000002305.1) as displayed in the UCSC Genome Browser and as shown in FIG. 1, or the equivalent substitution in the complement thereof; (2) an adenine (A) substituted for a guanine (G) at chr4:83,736,244 and an adenine (A) substituted for a guanine (G) at chr4:83,738,769 of the current horse genome assembly (EquCab2, GCA_000002305.1) as displayed in the UCSC Genome Browser and as shown in FIG. 2 and FIG. 3, respectively, or the equivalent substitution in the complement thereof; and (3) an adenine (A) substituted for a guanine (G) at chr14: 27,399,222 of the current horse genome assembly (EquCab2, GCA_000002305.1) as displayed in the UCSC Genome Browser and as shown in FIG. 4, or the equivalent substitution in the complement thereof. These base substitutions, corresponding to position 38,519,183 in SEQ ID NO:1, position 83,736,244 in SEQ ID NO:2, position 83,738,769 in SEQ ID NO:3, and position 27,399,222 in SEQ ID NO:4, result in nonconservative amino acid substitutions in the myotilin (MYOT), filamin-C (FLNC), and myozenin3 (MYOZ3) proteins, respectively. The amino acid substitutions caused by these base substitutions are shown in FIG. 8, FIG. 9, and FIG. 10. FIG. 8 shows an altered myotilin with proline (P) substituted for serine (S) at position 232, with SEQ ID NO:9 showing the protein sequence encoded by the wild-type or common allele and SEQ ID NO:10 showing the protein sequence encoded by the variant. FIG. 9 shows an altered filamin-C (FLNC) with lysine (K) substituted for glutamic acid (E) in filamin repeat 6 at position 753 in SEQ ID NO:11 and position 836 in SEQ ID NO:12 and threonine (T) substituted for alanine (A) filamin repeat 11 at position 1207 in SEQ ID NO:11 and position 1290 in SEQ ID NO:12, with SEQ ID NO: 11 and SEQ ID NO:12 showing the protein sequence encoded by the wild-type or common allele and SEQ ID NO: 13 and SEQ ID NO:14 showing the protein sequence encoded by the variants; both variants as typically seen as a single haplotype. FIG. 10 shows an altered myozenin-3 (MYOZ3) with leucine (L) substituted for serine (S) at position 42, with SEQ ID NO:15 showing the wild-type or common allele and SEQ ID NO:16 showing the protein sequence encoded by the variant.

In some embodiments, the method further includes amplifying at least a portion of the MYOT, FLNC, or MYOZ3 coding regions. In some of these embodiments, exon 6 of the MYOT coding region, exons 15 and 21 of the FLNC coding region, and exon 3 of the MYOZ3 coding region are amplified. These specified exons correspond to the gene models presented in FIG. 5, FIG. 6, FIG. 7, FIG. 8, FIG. 9, and FIG. 10 in this disclosure; the specific base substitutions detected are presented in FIG. 1, FIG. 2, FIG. 3 and FIG. 4, even if alternative gene models or different isoforms result in these exons being numbered differently. In another aspect, this disclosure describes a method for detecting the presence or absence of a biomarker in a physiological sample. Generally, the method includes obtaining a physiological sample from a horse that includes a nucleic acid that includes at least a portion of SEQ ID NO:1 that includes nucleotide 38,519,183 of SEQ ID NO:1, determining whether the nucleic acid has a guanine (G) at nucleotide 38,519,183 of the forward strand of SEQ ID NO:1, at least a portion of SEQ ID NO:2 that includes nucleotide 83,736,244 of SEQ ID NO:2, determining whether the nucleic acid has an adenine (A) at 83,736,244 of the forward strand of SEQ ID NO:2; at least a portion of SEQ ID NO:3 that includes nucleotide 83,738,769 of SEQ ID NO:3, determining whether the nucleic acid has an adenine (A) at 83,738,769 of the forward strand of SEQ ID NO:3; and at least a portion of SEQ ID NO:4 that includes nucleotide 27,399,222 of SEQ ID NO:4, determining whether the nucleic acid has an adenine (A) at 27,399,222 of the forward strand of SEQ ID NO:4. In all cases, the nucleotide at the specified position of the forward strand may be inferred by the determination of the nucleotide at the specified position on the reverse (complementary) strand. In some embodiments, the method further includes amplifying at least a portion of the nucleic acid.

In another aspect, this disclosure describes a method for detecting the presence or absence of a biomarker in a physiological sample. Generally, the method includes obtaining a physiological sample from a horse that includes a nucleic acid encoding a myotilin, filamin-C, or myozenin-3 polypeptide, then determining whether the nucleic acid encodes a myotilin, filamin-C, or myozenin-3 polypeptide altered as described as follows: (1) a myotilin polypeptide having the amino acid sequence of SEQ ID NO:9 or a myotilin polypeptide having a proline (P) substituted for serine (S) at position 232 as shown in SEQ ID NO:10, (2) a filamin-C polypeptide having the amino acid sequence of SEQ ID NO:11 (equivalent to SEQ ID NO:12) or a filamin-C polypeptide having a lysine (K) substituted for glutamic acid (E) at position 753 in SEQ ID NO:11 (equivalent to position 836 in SEQ ID NO:12) as shown in SEQ ID NO:13 (equivalent to SEQ ID NO:14) or a filamin-C polypeptide having the amino acid sequence of SEQ ID NO:11 (equivalent to SEQ ID NO:12) or a filamin-C polypeptide having a threonine (T) substituted for alanine (A) at position 1207 in SEQ ID NO:11 (equivalent to position 1290 in SEQ ID NO:12), as shown in SEQ ID NO:13 (equivalent to SEQ ID NO:14), or (3) a myozenin-3 polypeptide having the amino acid sequence of SEQ ID NO:15 or a myozenin-3 polypeptide having a leucine (L) substituted for a serine (S) at position 42 in SEQ ID NO:15 as shown in SEQ ID NO:16.

The above summary is not intended to describe each disclosed embodiment or every implementation. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. A portion of the current horse genome assembly (EquCab2, GCA_000002305.1) with coordinates as displayed in the UCSC Genome Browser centered on the chr14:38,519,183 position, the site of a substitution of a guanine (G) for an adenine (A) that results in the substitution of a proline (P) for serine (S) at amino acid position 232 in myotilin as shown in FIG. 8. The reverse complement sequence is shown (SEQ ID NO:1), with the site of a substitution of a cytosine (C) for a thymine (T) indicated.

FIG. 2. A portion of the current horse genome assembly (EquCab2, GCA_000002305.1) with coordinates as displayed in the UCSC Genome Browser centered on the chr4:83,736,244 position, the site of a substitution of an adenine for a guanine (G) that results in the substitution of a lysine (K) for glutamic acid (E) in filamin-C, at amino acid position 753 in filamin-C as shown in FIG. 9. The forward strand sequence is shown (SEQ ID NO:2).

FIG. 3. A portion of the current horse genome assembly (EquCab2, GCA_000002305.1) with coordinates as displayed in the UCSC Genome Browser centered on the chr4:83,738,769 position, the site of a substitution of an adenine (A) for a guanine (G) that results in the substitution of a threonine (T) for alanine (A) in filarnin-C, at amino acid position 1207 as shown in FIG. 9. The forward strand sequence is shown (SEQ ID NO:3).

FIG. 4. A portion of the current horse genome assembly (EquCab2, GCA_000002305.1) with coordinates as displayed in the UCSC Genome Browser centered on the chr14:27,399,222 position, the site of a substitution of an adenine (A) for a guanine (G) that results in the substitution of a leucine (L) for a serine (S) in myozenin-3, at amino acid position 42 as shown in FIG. 10. The reverse complement sequence is shown (SEQ ID NO:4), with the site of a substitution of a thymine (T) for a cytosine (C) indicated.

FIG. 5. Normal equine MYOT Coding DNA Sequence (SEQ ID NO:5), also known as XM_014730661.1. Exon 6 is indicated in bold. The site of a T to C mutation site at nucleotide position 694 in SEQ ID NO:5 (38,519,183 in SEQ ID NO:1, as shown in FIG. 1) is underlined. The region of sequence comprising exon 6 is displayed as codons in the correct reading frame in FIG. 11.

FIG. 6. Alignment of normal equine FLNC Coding DNA Sequence (SEQ ID NO:6), also known as Ensembl CDS 00000012220, and normal equine FLNC Coding DNA Sequence (SEQ ID NO:7), also known as XM_014739030.1. The sequences are identified in FIG. 6 as ENS and XM, respectively. Exons 15 and 21 are shown in bold. The sites of two G to A mutation sites, (83,736,244 in SEQ ID NO:2 as shown in FIG. 2 and 83,738,769 in SEQ ID NO:3 as shown in FIG. 3) in exons 15 and 21, at nucleotides 2257 and 3619 of SEQ ID NO:6 and nucleotides 2506 and 3868 of SEQ ID NO:7, are underlined. The regions of sequence comprising exons 15 and 21 are displayed as codons in the correct reading frame in FIG. 12 and FIG. 13.

FIG. 7. Normal equine MYOZ3 Coding DNA Sequence (SEQ ID NO:8), derived from XM_014730574.1. Exon 3 is indicated in bold. The site of a C to T mutation site at nucleotide position 125 in SEQ ID NO:8 (27,399,222 of SEQ ID NO:4, as shown in FIG. 4) is underlined. The region of sequence comprising exon 3 is displayed as codons in the correct reading frame in FIG. 14.

FIG. 8. The entire MYOT coding nucleotide sequence shown in FIG. 5 was translated to give the wild-type amino acid sequence (SEQ ID NO:9) also known as XP_014586147.1. The amino acids encoded by exon 6 are in bold, with the site of the serine (S) to proline (P) mutation at codon 232 underlined. The MYOT-S232P amino acid sequence is also shown (SEQ ID NO:10), with the amino acids encoded by exon 6 shown in bold and the site of the serine (S) to proline (P) mutation at codon 232 underlined.

FIG. 9. The entire FLNC coding nucleotide sequences shown in FIG. 6 were translated to give these amino acid sequences (SEQ ID NO:11, also known as F6ZWZ3, and SEQ ID NO:12, also known as XP_014594516.1). The amino acids encoded by exons 15 and 21 are shown in bold. Underlining indicates the sites of the substitution of a lysine (K) for a glutamic acid (E) at position 753 in SEQ ID NO:11 and at position 836 in SEQ ID NO:12 and the substitution of a threonine (T) for an alanine (A) at position 1207 in SEQ ID NO:11 and at position 1290 in SEQ ID NO:12. The amino acid sequences of proteins with both of these amino acid substitutions are shown as SEQ ID NO:13 and SEQ ID NO:14, with the amino acids encoded by exons 15 and 21 shown in bold, and the sites of the FLNC-E753K and FLNC-A1207T substitutions (positions 753 and 1207 in SEQ ID NO:13 and positions 836 and 1290 in SEQ ID NO:14) indicated by underlining.

FIG. 10. The entire MYOZ3 coding nucleotide sequence shown in FIG. 7 was translated to give the wild-type amino acid sequence (SEQ ID NO:15), also known as XP_014586060.1 (identical to XP_005599348.1 and XP_014586061.1). The amino acids encoded by exon 3 are in bold, with the site of the serine (S) to leucine (L) mutation at codon 42 underlined. The MYOZ3-S42L amino acid sequence is shown (SEQ ID NO:16), with the amino acids encoded by exon 3 shown in bold and the site of the serine (S) to leucine (L) mutation at codon 42 underlined.

FIG. 11. Horse MYOT exon 6 and flanking genomic DNA sequence from which PCR primers to amplify genomic DNA containing the site of the MYOT-S232P mutation would be most appropriately derived. Genomic coordinates are as in FIG. 1. Exon 6 from chr14:38,519,913 to chr14:38,519,061 is shown broken into codons in the correct reading frame for the wild-type allele (SEQ ID NO:17) and the MYOT-S232P allele (SEQ ID NO:18). Only the reference sequence from the assembly is shown for the flanking sequences. The site of a A to G mutation site at nucleotide position chr14:38,519,183 is shown in bold (T to C in the reverse complement as shown). This changes the underlined three base codon from one coding for a serine (TCT) to one coding for a proline (CCT). Example primers used experimentally to amplify genomic DNA containing the mutation site are shown in lower case (SEQ ID NO:19 and SEQ ID NO:20).

FIG. 12. Horse FLNC exon 15 and flanking genomic DNA sequence from which PCR primers to amplify genomic DNA containing the site of the FLNC-E753K mutation would be most appropriately derived. Genomic coordinates are as in FIG. 2. Exon 15 from chr4:83,736,133 to chr4:83,736,256 is shown broken into codons in the correct reading frame for the wild-type allele (SEQ ID NO:21) and the FLNC-E753K allele (SEQ ID NO:22). Only the reference sequence from the assembly is shown for the flanking sequences. The site of a G to A mutation site at nucleotide position chr4:83,736,244 is shown in bold. This mutation changes the underlined three base codon from one coding for a glutamic acid (GAG) to one coding for a lysine (AAG). Example primers used experimentally to amplify genomic DNA containing the mutation site are shown in lower case (SEQ ID NO:23 and SEQ ID NO:24).

FIG. 13. Horse FLNC exon 21 and flanking genomic DNA sequence from which PCR primers to amplify genomic DNA containing the site of the FLNC-A1207T mutation would be most appropriately derived. Genomic coordinates are as in FIG. 3. Exon 21 from chr4:83,738,223 to chr4:83,738,820 is shown broken into codons in the correct reading frame for the wild-type allele (SEQ ID NO:25) and the FLNC-A1207T allele (SEQ ID NO:26). Only the reference sequences from the assembly are shown for the flanking sequences. The site of a G to A mutation site at nucleotide position chr4:83,738,769 is shown in bold. This mutation changes the underlined three base codon from one coding for an alanine (GCT) to one coding for a threonine (ACT). Example primers used experimentally to amplify genomic DNA containing the mutation site are shown in lower case (SEQ ID NO:27 and SEQ ID NO:28).

FIG. 14. Horse MYOZ3 exon 3 and flanking genomic DNA sequence from which PCR primers to amplify genomic DNA containing the site of the MYOZ3-S42L mutation would be most appropriately derived. Genomic coordinates are as in FIG. 4. Exon 3 from chr14:27,399,285 to chr14:27,399,131 is shown broken into codons in the correct reading frame for the wild-type allele (SEQ ID NO:29) and the MYOZ3-S42L allele (SEQ ID NO:30). Only the reference sequences from the assembly are shown for the flanking sequences. The site of a G to A mutation site at nucleotide position chr14:27,399,222 is shown in bold (C to T in the reverse complement as shown). This mutation changes the underlined three base codon from one coding for a serine (TCG) to one coding for a leucine (TTG). Example primers used experimentally to amplify genomic DNA containing the mutation site are shown in lower case (SEQ ID NO:31 and SEQ ID NO:32).

FIG. 19. Horse MYOT exon 6 and flanking genomic DNA sequence from which allele-specific PCR primers to amplify genomic DNA containing the site of the MYOT-S232P mutation would be most appropriately derived. Genomic coordinates are as in FIG. 1. Exon 6 from chr14:38,519,913 to chr14:38,519,061 is shown broken into codons in the correct reading frame for the wild-type allele (SEQ ID NO:17) and the MYOT-S232P allele (SEQ ID NO:18). Only the reference sequence from the assembly is shown for the flanking sequences. The site of a A to G mutation site at nucleotide position chr14:38,519,183 is shown in bold (T to C in the reverse complement as shown). This changes the underlined three base codon from one coding for a serine (TCT) to one coding for a proline (CCT). Example primers used experimentally to amplify genomic DNA containing the mutation site are shown in lower case. SEQ ID NO:33 is the common primer that is not allele-specific; the allele-specific primers SEQ ID NO:34 and SEQ ID NO:35 preferentially amplify the wild-type and MYOT-S232P alleles, respectively. Reaction conditions are described in the text.

FIG. 20. Horse FLNC exon 15 and flanking genomic DNA sequence from which allele-specific PCR primers to amplify genomic DNA containing the site of the FLNC-E753K mutation would be most appropriately derived. Genomic coordinates are as in FIG. 2. Exon 15 from chr4:83,736,133 to chr4:83,736,256 is shown broken into codons in the correct reading frame for the wild-type allele (SEQ ID NO:21) and the FLNC-E753K allele (SEQ ID NO:22). Only the reference sequence from the assembly is shown for the flanking sequences. The site of a G to A mutation site at nucleotide position chr4:83,736,244 is shown in bold. This mutation changes the underlined three base codon from one coding for a glutamic acid (GAG) to one coding for a lysine (AAG). Example primers used experimentally to amplify genomic DNA containing the mutation site are shown in lower case. SEQ ID NO:36 is the common primer that is not allele-specific; the allele-specific primers SEQ ID NO:37 and SEQ ID NO:38 preferentially amplify the wild-type and FLNC-E753K alleles, respectively. Note that both allele-specific primers span the exon-intron boundary. Note also that additional mismatches have been introduced into both allele-specific primers. Reaction conditions are described in the text.

FIG. 21. Horse FLNC exon 21 and flanking genomic DNA sequence from which allele-specific PCR primers to amplify genomic DNA containing the site of the FLNC-A1207T mutation would be most appropriately derived. Genomic coordinates are as in FIG. 3. Exon 21 from chr4:83,738,223 to chr4:83,738,820 is shown broken into codons in the correct reading frame for the wild-type allele (SEQ ID NO:25) and the FLNC-A1207T allele (SEQ ID NO:26). Only the reference sequences from the assembly are shown for the flanking sequences. The site of a G to A mutation site at nucleotide position chr4:83,738,769 is shown in bold. This mutation changes the underlined three base codon from one coding for an alanine (GCT) to one coding for a threonine (ACT). Example primers used experimentally to amplify genomic DNA containing the mutation site are shown in lower case. SEQ ID NO:39 is the common primer that is not allele-specific; the allele-specific primers SEQ ID NO:40 and SEQ ID NO:41 preferentially amplify the wild-type and FLNC-A1207T alleles, respectively. Note that additional mismatches have been introduced into both allele-specific primers. Reaction conditions are described in the text.

FIG. 22. Horse MYOZ3 exon 3 and flanking genomic DNA sequence from which allele-specific PCR primers to amplify genomic DNA containing the site of the MYOZ3-S42L mutation would be most appropriately derived. Genomic coordinates are as in FIG. 4. Exon 3 from chr14:27,399,285 to chr14:27,399,131 is shown broken into codons in the correct reading frame for the wild-type allele (SEQ ID NO:29) and the MYOZ3-S42L allele (SEQ ID NO:30). Only the reference sequences from the assembly are shown for the flanking sequences. The site of a G to A mutation site at nucleotide position chr14:27,399,222 is shown in bold (C to T in the reverse complement as shown). This mutation changes the underlined three base codon from one coding for a serine (TCG) to one coding for a leucine (TTG). Example primers used experimentally to amplify genomic DNA containing the mutation site are shown in lower case. SEQ ID NO:42 is the common primer that is not allele-specific; the allele-specific primers SEQ ID NO:43 and SEQ ID NO:44 preferentially amplify the wild-type and MYOZ3-S42L alleles, respectively. Note that additional mismatches have been introduced into both allele-specific primers. Reaction conditions are described in the text.

FIG. 23. Alignment of the sequence of a portion of the human MYOT protein with the horse protein sequence SEQ ID NO:9 shown in FIG. 8. The top line (indicated as Human; SEQ ID NO:45) corresponds to a portion of the human myotilin protein (MYOT) from UniProt Q9UBF9. The second line shows the alignment of the human sequence to the horse sequence (SEQ ID NO:46). A single conservative amino acid substitution is seen at amino acid 232. The last line, indicated as MYOT-S232P, shows the position of the S232P non-conservative substitution, at the same position as the conservative substitution between human and horse.

FIG. 24. Alignment of the sequence of filamin repeat 6 of the human FLNC protein with the horse protein sequences SEQ ID NO:11 and SEQ ID NO:12 shown in FIG. 9. The top line (indicated as Human; SEQ ID NO:272) corresponds to filamin repeat 6 of human filamin-C protein (FLNC) from UniProt Q14315. The second line (indicated as ENS; SEQ ID NO:273) corresponds to filamin repeat 6 of horse filamin-C protein (FLNC) with the numbering of amino acid positions as in SEQ ID NO:11. A single conservative amino acid substitution between human and horse is seen at amino acid 766 in the human sequence. The third line (indicated as XP; SEQ ID NO: 274) corresponds to filamin repeat 6 of horse filamin-C protein (FLNC) with the numbering of amino acid positions as in SEQ ID NO:12. The last line (indicated as E753K) shows the position of the E753K substitution.

FIG. 25. Alignment of the sequence of filamin repeat 11 of the human FLNC protein with the horse protein sequences SEQ ID NO:11 and SEQ ID NO:12 shown in FIG. 9. The top line (indicated as Human; SEQ ID NO:275) corresponds to filamin repeat 11 of human filamin-C protein (FLNC) from UniProt Q14315. The second line (indicated as ENS; SEQ ID NO:276) corresponds to filamin repeat 11 of horse filamin-C protein (FLNC) with the numbering of amino acid positions as in SEQ ID NO:11. Two conservative amino acid substitutions between human and horse are seen at amino acids 1248 and 1332 in the human sequence. The third line (indicated as XP; SEQ ID NO:277) corresponds to filamin repeat 11 of horse filamin-C protein (FLNC) with the numbering of amino acid positions as in SEQ ID NO:12. The last line (indicated as A1207T) shows the position of the A1207T substitution.

FIG. 31. Amino acid sequences (SEQ ID NO:51-108) of proteins encoded by MYOT genes, centered on the position of the equine MYOT-S232P substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of myotilin in horse with the MYOT-S232P substitution shown and highlighted in bold. The position of the MYOT-S232P substitution is indicated in bold in all of the sequences.

FIG. 32. Amino acid sequences (SEQ ID NO:109-155) of proteins encoded by FLNC genes, showing filamin repeat 6, which contains the equine FLNC-E753K substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of filamin repeat 6 in horse with the FLNC-E753K substitution shown and highlighted in bold. The position of the FLNC-E753K substitution is indicated in bold in all of the sequences.

FIG. 33. Amino acid sequences (SEQ ID NO:156-205) of proteins encoded by FLNC genes, showing filamin repeat 11, which contains the equine FLNC-A1207T substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of filamin repeat 11 in horse with the FLNC-A1207T substitution shown and highlighted in bold. The position of the FLNC-A1207T substitution is indicated in bold in all of the sequences.

FIG. 34. Amino acid sequences (SEQ ID NO:206-271) of proteins encoded by MYOZ3 genes, centered on the position of the equine MYOZ3-S42L substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of myozenin-3 in horse with the MYOZ3-S42L substitution shown and highlighted in bold. The position of the MYOZ3-S42L substitution is indicated in bold in all of the sequences.

DETAILED DESCRIPTION OF ILLUSTRATIVE EMBODIMENTS

Figure 15:
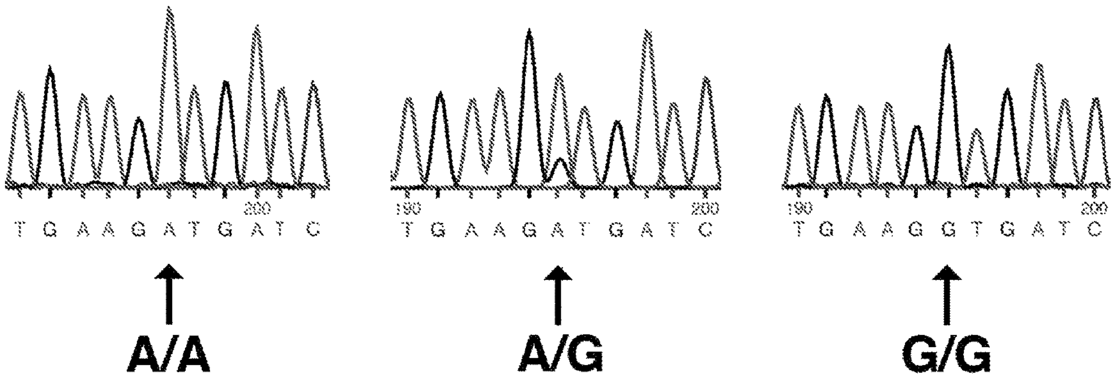
FIG. 15. Traces from Sanger DNA sequencing of amplified MYOT genomic DNA using primers shown in FIG. 11 (SEQ ID NO:19 and SEQ ID NO:20). The sequence of the forward strand is shown (SEQ ID NO:47). The arrows in the figure indicate nucleotide position chr14:38,519,183, the site of a substitution of a guanine (G) for an adenine (A) in this position that creates the MYOT-S232P variant. The traces show, from left to right, results for a horse homozygous for the wild-type or common allele, results for a horse heterozygous for the substitution, and results for a horse homozygous for the substitution.

This disclosure describes methods for detecting the presence or absence of biomarkers associated with inherited equine myopathies. These disease conditions have been variously referred to Polysaccharide Storage Myopathy, type 2 (PSSM2), Myofibrillar Myopathy (MFM), or idiopathic myopathy. The term PSSM2 is commonly used to describe horses that show exercise intolerance, a negative test result for the GYS1-R309H variant of Glycogen Synthase 1 that is associated with Polysaccharide Storage Myopathy, type 1 (PSSM1), and abnormal findings on muscle biopsy, including abnormally shaped muscle fibers, nuclei displaced to the center of muscle fibers rather than the normal position at the edge of fibers, and pools of glycogen granules of normal size in regions of disorganization that give the false appearance of a glycogen storage disease. Myofibrillar Myopathy is a subtype of PSSM2 characterized by protein aggregates displaced from the Z disc that stain positive for desmin, a protein component of the Z disc. In the absence of the immunological stain for desmin, muscle biopsies of this type are simply scored as PSSM2. In one embodiment, the method involves obtaining a physiological sample from a horse and determining whether the biomarker is present in the sample. As used herein, the phrase "physiological sample" refers to a biological sample obtained from a horse that contains nucleic acid. For example, a physiological sample can be a sample collected from an individual horse such as, for example, a cell sample, such as a blood cell, e.g., a lymphocyte, a peripheral blood cell; a sample collected from the spinal cord; a tissue sample such as cardiac tissue or muscle tissue, e.g., cardiac or skeletal muscle; an organ sample, e.g., liver or skin; a hair sample, e.g., a hair sample with roots; and/or a fluid sample, such as blood.

Examples of breeds of affected horse include, but are not limited to, Quarter Horses, Percheron Horses, Paint Horses, Draft Horses, Warmblood Horses, or related or unrelated breeds. The phrase "related breed" is used herein to refer to breeds that are related to a breed, such as Quarter Horse, Draft Horse, or Warmblood Horse. Such breeds include, but are not limited to stock breeds such as the American Paint horse, the Appaloosa, and the Palomino. The term "Draft Horse" includes many breeds including but not limited to Clydesdale, Belgian, Percheron, and Shire horses. The term "Warmblood" is also a generic term that includes a number of different breeds. "Warmblood" simply distinguishes this type of horse from the "cold bloods" (draft horses) and the "hot bloods" (Thoroughbreds and Arabians). The method described herein also may be performed using a sample obtained from a crossed or mixed breed horse.

The term "biomarker" is generally refers herein to a biological indicator, such as a particular molecular feature, that may affect, may be an indicator, and/or be related to diagnosing or predicting an individual's health. For example, in certain embodiments, the biomarker can refer to (1) a mutation in the equine myotilin (MYOT) coding region (SEQ ID NO:1), such as a polymorphic allele of MYOT that has a substitution of a guanine (G) for an adenine (A) at nucleotide position 38,519,183 on the forward strand of SEQ ID NO:1, (2) a mutation of the equine filamin-C (FLNC) coding region (SEQ ID NO:2 and SEQ ID NO: 3), such as a polymorphic allele of FLNC that has a substitution of an adenine (A) for a guanine (G) at nucleotide position 83,736,244 on the forward strand of SEQ ID NO:2 or a substitution of an adenine (A) for a guanine (G) at nucleotide position 83,738,769 on the forward strand of SEQ ID NO:3, or (3) a mutation of the equine myozenin-3 (MYOZ3) coding region, such as a polymorphic allele of MYOZ3 that has a substitution of an adenine (A) for a guanine (G) at nucleotide position 27,399,222 on the forward strand of SEQ ID NO:4. In each of these cases, the specified nucleotide substitution may be inferred by the detection of the complementary base on the reverse strand.

"Oligonucleotide probe" can refer to a nucleic acid segment, such as a primer, that is useful to amplify a sequence in the MYOT, FLNC, or MYOZ3 coding regions that are complementary to, and hybridizes specifically to, a particular nucleotide sequence in MYOT, FLNC, or MYOZ3, or to a nucleic acid region that flanks MYOT, FLNC, or MYOZ3.

As used herein, the term "nucleic acid" and "polynucleotide" refers to deoxyribonucleotides or ribonucleotides and polymers thereof in either single-stranded or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to DNA or RNA that can be single-stranded or double-stranded, optionally containing synthetic, non-natural, or altered nucleotide bases capable of incorporation into DNA or RNA.

In some embodiments, the method can involve contacting the sample with at least one oligonucleotide probe to form a hybridized nucleic acid and then amplifying the hybridized nucleic acid. "Amplifying" utilizes methods such as the polymerase chain reaction (PCR), ligation amplification (or ligase chain reaction, LCR), strand displacement amplification, nucleic acid sequence-based amplification, and amplification methods based on the use of Qβ-replicase. These methods are well known and widely practiced in the art. Reagents and hardware for conducting PCR are commercially available. For example, in certain embodiments, exon 6 of the equine myotilin coding region (also referred to as MYOT), exons 15 and 21 of the equine filamin-C coding region (also referred to as FLNC), or exon 3 of the equine myozenin-3 coding region (also referred to as MYOZ3) or portions thereof, may be amplified by PCR. In another embodiment, at least one oligonucleotide probe is immobilized on a solid surface or a semisolid surface.

The methods described herein can be used to detect the presence or absence of a biomarker associated with equine Polysaccharide Storage Myopathy type 2 (PSSM2), also known as Myofibrillar Myopathy (MFM), in a horse (live or dead) regardless of age (e.g., an embryo, a foal, a neonatal foal, aborted foal, a breeding-age adult, or any horse at any stage of life) or sex (e.g., a mare (dam) or stallion (sire)).

As used herein, the term "presence or absence" refers to affirmatively detecting the presence of a biomarker or detecting the absence of the biomarker within the experimental limits of the detection methods used to detect the biomarker.

This disclosure further provides a method for detecting and/or diagnosing Polysaccharide Storage Myopathy type 2 (PSSM2), also known as Myofibrillar Myopathy (MFM), in a horse, the method involving obtaining a physiological sample from the horse and detecting the presence or absence of biomarkers in the sample, wherein the presence of the biomarkers is indicative of the disease. One embodiment of the method further involves contacting the sample with at least one oligonucleotide probe to form a hybridized nucleic acid and amplifying the hybridized nucleic acid. For example, in one embodiment, exon 6 of equine MYOT, exons 15 and 21 of equine FLNC, or exon 3 of equine MYOZ3 (or portions thereof) are amplified using, for example, polymerase chain reaction, strand displacement amplification, ligase chain reaction, amplification methods based on the use of Qβ-replicase and/or nucleic acid sequence-based amplification. In one embodiment of the method, the biomarkers can include (1) an equine myotilin (MYOT) coding region having an A to G substitution on the forward strand at nucleotide 38,519,183 of SEQ ID NO:1, (2) an equine filamin-C (FLNC) coding region having a G to A substitution on the forward strand at nucleotide 83,736,244 of SEQ ID NO:2 or a G to A substitution on the forward strand at nucleotide 83,738,769 of SEQ ID NO: 3, or (3) an equine myozenin-3 (MYOZ3) coding region having a G to A substitution on the forward strand at nucleotide 27,399,222 of SEQ ID NO:4. Biomarkers can also include (1) a coding region that encodes a myotilin (MYOT) polypeptide (SEQ ID NO:9) having a Serine-to-Proline (S to P) substitution at amino acid residue 232 of SEQ ID NO:9, as shown in SEQ ID NO:10, (2) a coding region that encodes a filamin-C (FLNC) polypeptide (SEQ ID NO:11) having an Glutamic Acid-to-Lysine (E-to-K) substitution at amino acid residue 753 (equivalent to amino acid residue 836 in SEQ ID NO: 12), as shown in SEQ ID NO:13 (equivalent to SEQ ID NO:14), or an Alanine-to-Threonine (A-to-T) substitution at amino acid residue 1207 (equivalent to amino acid residue 1290 in SEQ ID NO:12), as shown in SEQ ID NO:13 (equivalent to SEQ ID NO:14), or (3) a coding region that encodes a myozenin-3 (MYOZ3) polypeptide (SEQ ID NO:15) having a Serine-to-Leucine (S-to-L) substitution at amino acid residue 42 of SEQ ID NO15, as shown in SEQ ID NO:16. The method can be used to detect Polysaccharide Storage Myopathy type 2 (PSSM2), also known as Myofibrillar Myopathy (MFM) in a horse.

This disclosure further provides a kit that includes a test for diagnosing and/or detecting the presence of equine Polysaccharide Storage Myopathy type 2 (PSSM2), also known as Myofibrillar Myopathy (MFM), in a horse. The kit generally includes packing material containing, separately packaged, at least one oligonucleotide probe capable of forming a hybridized nucleic acid with MYOT, FLNC, or MYOZ3 and instructions directing the use of the probe in accord with the methods described herein.

Horses affected with Polysaccharide Storage Myopathy type 2 (PSSM2), also known as Myofibrillar Myopathy (MFM), are typically heterozygous for the affected MYOT, FLNC, or MYOZ3 alleles. An "allele" is a variant form of a particular genomic nucleic acid sequence. In the context of the methods described herein, some alleles of the MYOT, FLNC, or MYOZ3 coding regions cause Polysaccharide Storage Myopathy type 2 (PSSM2), also known as Myofibrillar Myopathy (MFM), in horses. A "MYOT allele," "FLNC allele," or "MYOZ3 allele" refers to a normal allele of the MYOT, FLNC, or MYOZ3 loci as well as an allele carrying one or more variations that predispose a horse to develop Polysaccharide Storage Myopathy type 2 (PSSM2), also known as Myofibrillar Myopathy (MFM). The coexistence of multiple alleles at a locus is known as "genetic polymorphism." Any site at which multiple alleles exist as stable components of the population is by definition "polymorphic." An allele is defined as polymorphic if it is present at a frequency of at least 1% in the population. A "single nucleotide polymorphism (SNP)" is a DNA sequence variation that involves a change in a single nucleotide.

The methods described herein involve the use of isolated or substantially purified nucleic acid molecules. An "isolated" or "purified" nucleic acid molecule is one that, by human intervention, exists apart from its native environment and is therefore not a product of nature. An isolated nucleic acid molecule may exist in a purified form or may exist in a non-native environment. For example, an "isolated" or "purified" nucleic acid molecule, or portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An isolated or purified nucleic acid molecule can be a fragment and/or variant of a reference nucleotide sequence expressly disclosed herein.

A "fragment" or "portion" of a sequence refers to anything less than full-length of the nucleotide sequence encoding—or the amino acid sequence of—a polypeptide. As it relates to a nucleic acid molecule, sequence, or segment when linked to other sequences for expression, a "portion" or a "fragment" refers to a sequence having, for example, at least 80 nucleotides, at least 150 nucleotides, or at least 400 nucleotides. Alternatively, when not employed for expressing—e.g., in the context of a probe or a primer—a "portion" or a "fragment" means, for example, at least 9, at least 12, at least 15, or at least 20 consecutive nucleotides. Alternatively, a fragment or a portion of a nucleotide sequence that is useful as a hybridization probe generally does not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides, or more.

A "variant" of a molecule is a sequence that is substantially similar to the sequence of the reference—e.g., native, naturally-occurring, and/or wild-type—molecule. For nucleotide sequences, a variant includes any nucleotide sequence that, because of the degeneracy of the genetic code, encodes the native amino acid sequence of a protein. Naturally occurring allelic variants such as these can be identified with the use of well-known molecular biology techniques, as, for example, with polymerase chain reaction (PCR) and/or hybridization techniques. A variant nucleotide sequence also can include a synthetically-derived nucleotide sequence such as one generated, for example, by using site-directed mutagenesis that encodes the native protein, as well as variant nucleotide sequences that encode a polypeptide having amino acid substitutions. Generally, a nucleotide sequence variant will have at least 40%, at least 50%, at least 60%, at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) sequence identity to the native (endogenous) nucleotide sequence.

"Synthetic" polynucleotides are those prepared by chemical synthesis.

"Recombinant DNA molecule" is a combination of DNA sequences that are joined together using recombinant DNA technology and procedures that are used to join together DNA sequences as described, for example, in Sambrook and Russell (2001).

"Naturally-occurring," "native," or "wild-type" refers to an amino acid sequence or polynucleotide sequence that can be found in nature, without any known mutation, as distinct from being produced artificially or producing a mutated, non-wild-type phenotype. For example, a nucleotide sequence present in an organism (including a virus) that can be isolated from a source in nature and that has not been intentionally modified in the laboratory is naturally occurring. Furthermore, "wild-type" refers to a coding region or organism as found in nature without any known mutation.

A "mutant" myotilin (MYOT) polypeptide, filamin-C polypeptide (FLNC), or myozenin-3 (MYOZ3) polypeptide refers to a myotilin, filamin-C, or myozenin-3 polypeptide or a fragment thereof that is encoded by a MYOT, FLNC, or MYOZ3 coding region having a mutation, e.g., such as might occur at the MYOT, FLNC, or MYOZ3 locus. A mutation in one MYOT, FLNC, or MYOZ3 allele may lead to an alteration in the ability of the encoded polypeptide to interact with actin, alpha actinin, myotilin, filamin-c, myozenin-3, or other proteins that are structural components of the Z disc in myofibrils, or other proteins that are expressed in skeletal or cardiac muscle that are required for the integrity of myofibrils, leading to alterations in the integrity of myofibrils in a horse heterozygous for the allele. Alterations in the interactions of specific proteins can be determined by methods known to the art. Mutations in MYOT, FLNC, or MYOZ3 may be disease-causing in a horse heterozygous for the mutant MYOT, FLNC, or MYOZ3 allele, e.g., a horse heterozygous for a mutation leading to a mutant MYOT, FLNC, or MYOZ3 polypeptide such as substitution mutations in exon 6 of MYOT, exons 15 and 21 of FLNC, or exon 3 of MYOZ3, such as those designated herein as MYOT-S232P, FLNC-E753K, FLNC-A1207T, or MYOZ3-S42L.

A "somatic mutation" is a mutation that occurs only in certain tissues, e.g., in liver tissue, and are not inherited in the germline. A "germline" mutation can be found in any of a body's tissues and are inherited. The present MYOT, FLNC, and MYOZ3 mutations are germline mutations.

"Homology" refers to the percent identity between two polynucleotide sequences or two amino acid sequences. Two sequences are "homologous" to each other when the sequences exhibit at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) contiguous sequence identity over a defined length of the sequences.

The following terms are used to describe the sequence relationships between two or more nucleic acids or polynucleotides: "reference sequence," "comparison window," "sequence identity," "percentage of sequence identity," and "substantial identity."

As used herein, "reference sequence" refers to a sequence used as a basis for sequence comparison. A reference sequence may be a subset or the entirety of a specified sequence. For example, a reference sequence may be a segment of a full length cDNA or coding region sequence, or the complete cDNA or coding region sequence.

As used herein, "comparison window" refers to a contiguous and specified segment of a polynucleotide sequence, wherein the polynucleotide sequence in the comparison window may reflect one or more additions and/or deletions (i.e., gaps) compared to the reference sequence (which does not exhibit the additions and/or deletions) for optimal alignment of the two sequences. Generally, the comparison window is at least 20 contiguous nucleotides in length, and optionally can be 30, 40, 50, 100, or longer. To avoid a high similarity to a reference sequence due to inclusion of gaps in the polynucleotide sequence, a gap penalty is typically introduced and is subtracted from the number of matches. Methods of alignment of sequences for comparison are well known in the art. Thus, the determination of percent identity between any two sequences can be accomplished using a mathematical algorithm.

Computer implementations of these mathematical algorithms can be used for comparing sequences to determine sequence identity. Such implementations include, but are not limited to: Clustal Omega (online at EMBL-EBI), COBALT (online at ncbi.nlm.hih.gov), the ALIGN program (Version 2.0), and GAP, BESTFIT, BLAST, FASTA, and TFASTA in the Wisconsin Genetics Software Package, Version 8 (available from the Genetics Computer Group (GCG) Madison, WI, USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection. For purposes of the methods described herein, comparison of nucleotide sequences for determination of percent sequence identity to the promoter sequences disclosed herein is preferably made using the BlastN program (version 2.3.0 or later) with its default parameters or any equivalent program. By "equivalent program" is intended any sequence comparison program that, for any two sequences in question, generates an alignment having identical nucleotide of amino acid residue matches and an identical percent sequence identity when compared to the corresponding alignment generated by a BLAST program.

A used herein, "sequence identity" or "identity" in the context of two nucleic acid or polypeptide sequences refers to a specified percentage of residues in the two sequences that are the same when aligned for maximum correspondence over a specified comparison window, as measured by sequence comparison algorithms or by visual inspection. When percentage of sequence identity is used in reference to a protein, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Methods for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, CA).

A used herein, "percentage of sequence identity" refers to the value determined by comparing two optimally aligned sequences over a comparison window, wherein the portion of the polynucleotide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity," in the context of polynucleotide sequences, means that a polynucleotide sequence possesses at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) sequence identity compared to a reference sequence using one of the alignment programs described using standard parameters. These values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, or at least 80%, 90%, or even at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that the two nucleic acid sequences are substantially identical is when the polypeptide encoded by the first nucleic acid is immunologically cross reactive with the polypeptide encoded by the second nucleic acid.

The term "substantial identity," in the context of a polypeptide, indicates that a polypeptide possesses a sequence with at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) amino acid sequence identity to the reference sequence over a specified comparison window. An indication that two polypeptide sequences are substantially identical is that one polypeptide is immunologically reactive with antibodies raised against the second polypeptide.

Thus, a polypeptide is substantially identical to a second polypeptide when, for example, the two polypeptides differ only by a conservative substitution. For sequence comparison, typically one amino acid sequence acts as a reference sequence to which test amino acid sequences are compared. When using a sequence comparison algorithm, test and reference amino acid sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation of Meinkoth and Wahl:

$$T_m=81.5° \text{ C.}+16.6(\log M)+0.41(\%\ GC)-0.61(\%\text{ form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point (Tm); moderately stringent conditions can utilize a hybridization and/or wash at 6° C., 7° C., 8° C., 9° C., or 10° C. lower than the thermal melting point (Tm); low stringency conditions can utilize a hybridization and/or wash at 11° C., 12° C., 13° C., 14° C., 15° C., or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration (20×SSC=3.0 M NaCl, 0.3 M trisodium citrate) so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for about 15 minutes. Often, a high stringency wash is preceded by a low stringency wash to remove background probe signal. An example medium stringency wash for a duplex of, e.g., more than 100 nucleotides is 4-6×SSC at 40° C. for 15 minutes. For short probes (e.g., about 10 to 50 nucleotides), stringent conditions typically involve salt concentrations of less than about 1.5 M, more preferably about 0.01 M to 1.0 M, $Na^+$ ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code. Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C.; and a wash in 0.1×SSC at 60° C. to 65° C. Exemplary low stringency conditions include hybridization with a buffer solution of 30 to 35% formamide, 1 M NaCl, 1% SDS (sodium dodecyl sulfate) at 37° C., and a wash in 1× to 2×SSC at 50° C. to 55° C. Exemplary moderate stringency conditions include hybridization in 40% to 45% formamide, 1.0 M NaCl, 1% SDS at 37° C., and a wash in 0.5× to 1×SSC at 55° C. to 60° C.

The term "variant" polypeptide refers to a polypeptide derived from the native protein by deletion (so-called truncation) and/or addition of one or more amino acids to the N-terminal and/or C-terminal end of the native protein, deletion and/or addition of one or more amino acids at one or more sites in the native protein, and/or substitution of one or more amino acids at one or more sites in the native protein. Such variants may result from, for example, genetic polymorphism or human manipulation. Methods for such manipulations are generally known in the art. A variant MYOT, FLNC, or MYOZ3 polypeptide may be altered in various ways including, for example, being altered to exhibit one or more amino acid substitutions, one or more deletions, one or more truncations, and/or one or more insertions. For example, an amino acid sequence can be prepared by one or more mutations in the DNA encoding the MYOT, FLNC, or MYOZ3 polypeptide. Guidance regarding appropriate amino acid substitutions that do not affect biological activity of the protein of interest is well known in the art. Conservative substitutions, such as exchanging one amino acid with another having similar properties, are preferred.

Thus, the nucleotide sequences used to practice the methods described herein can include both naturally-occurring sequences or mutant forms. Likewise, the polypeptides referred to herein can include naturally-occurring polypeptides as well as variations and modified forms thereof. Such variants may continue to possess the desired activity. The deletions, insertions, or substitutions of the polypeptide sequence encompassed herein are not expected to produce radical changes in the characteristics of the polypeptide. However, when it is difficult to predict the exact effect of the substitution, deletion, or insertion in advance of doing so, the effect can be evaluated by routine screening assays.

An individual substitution, deletion, or addition that alters, adds, or deletes a single amino acid or a small percentage of amino acids (typically less than 5%, more typically less than 1%) in an encoded sequence are "conservatively modified variations."

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance, the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill will recognize that each codon in a nucleic acid (except ATG, which is ordinarily the only codon for methionine, and TGG, which is ordinarily the only codon for tryptophan) can be modified to yield a functionally identical molecule by standard techniques. Accordingly, each "silent variation" of a nucleic acid that encodes a polypeptide is implicit in each described sequence.

Known methods of PCR include, but are not limited to, methods using paired primers, nested primers, single specific primers, degenerate primers, gene-specific primers, vector-specific primers, partially mismatched primers, and the like.

The terms "heterologous DNA sequence," "exogenous DNA segment," or "heterologous nucleic acid" refer to a sequence that originates from a source foreign to the particular host cell or, if from the same source, is modified from its original form. Thus, a heterologous coding region in a host cell includes a coding region that is endogenous to the particular host cell but has been modified through, for example, the use of single-stranded mutagenesis. The terms also include non-naturally-occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments, when expressed, yield exogenous polypeptides.

A "homologous" DNA sequence is a DNA sequence that is naturally associated with a host cell into which it is introduced.

"Genome" refers to the complete genetic material of an organism.

"Coding sequence" refers to a DNA or RNA sequence that codes for a specific amino acid sequence and excludes non-coding (e.g., regulatory) nucleotide sequences. For example, a DNA "coding sequence" or a "sequence encoding" a particular polypeptide is a DNA sequence that is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and/or synthetic DNA sequences. A transcription termination sequence will usually be located 3' to the coding sequence. It may constitute an "uninterrupted coding sequence,"—i.e., lacking an intron, such as in cDNA or it may include one or more introns bounded by appropriate splice junctions. An "intron" is a sequence of RNA that is contained in the primary transcript but that is removed through cleavage and re-ligation of the RNA within the cell to create the mature mRNA that can be translated into a protein.

The terms "open reading frame" and "ORF" refer to the nucleotide sequence between translation initiation and termination codons of a coding sequence. The terms "initiation codon" and "termination codon" refer to a unit of three adjacent nucleotides ("codon") in a coding sequence that specifies initiation and chain termination, respectively, of protein synthesis (mRNA translation).

The term "RNA transcript" refers to the product resulting from RNA polymerase catalyzed transcription of a DNA sequence. When the RNA transcript is a perfect complementary copy of the DNA sequence, it is referred to as a primary transcript or it may be an RNA sequence derived from post transcriptional processing of the primary transcript and is referred to as the mature RNA. "Messenger RNA" (mRNA) refers to the RNA that is without introns and can be translated into protein by the cell. "cDNA" refers to a single- or double-stranded DNA that is complementary to and derived from mRNA.

The term "regulatory sequence" refers to a nucleotide sequence that includes, for example, a promoter, an enhancer, and/or other expression control elements (e.g., polyadenylation signals). Such regulatory sequences are known to those skilled in the art. The design of an expression vector may depend on such factors as the choice of the host cell to be transfected and/or the amount of fusion protein to be expressed.

The term "DNA control elements" refers collectively to promoters, ribosome binding sites, polyadenylation signals, transcription termination sequences, upstream regulatory domains, enhancers, and the like, that collectively provide for the transcription and translation of a coding sequence in a host cell. Not all of these control sequences need always be present in a recombinant vector so long as the desired coding region is capable of being transcribed and translated.

A control element, such as a promoter, "directs the transcription" of a coding sequence in a cell when RNA polymerase binds to the promoter and transcribes the coding sequence into mRNA, which is then translated into the polypeptide encoded by the coding sequence.

A cell has been "transformed" by exogenous DNA when the exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to other eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

"Operably linked" refers to the association of nucleic acid sequences on single nucleic acid fragments so that the function of one is affected by the other, e.g., an arrangement of elements wherein the components so described are configured so as to perform their usual function. For example, a regulatory DNA sequence is said to be "operably linked to" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Transcription stop fragment" refers to nucleotide sequences that contain one or more regulatory signals, such as polyadenylation signal sequences, capable of terminating transcription. Examples include the 3' non-regulatory regions of the genes encoding myotilin, filamin-C, and myozenin-3 (MYOT, FLNC, and MYOZ3).

"Translation stop fragment" or "translation stop code" or "stop codon" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. The change of at least one nucleotide in a nucleic acid sequence can result in an interruption of the coding sequence of the gene, e.g., a premature stop codon. Such sequence changes can cause a mutation in the polypeptide encoded by the MYOT, FLNC, or MYOZ3 genes. For example, if the mutation is a nonsense mutation, the mutation results in the generation of a premature stop codon, causing the generation of a truncated MYOT, FLNC, or MYOZ3 polypeptide.

Nucleic Acids

Nucleotide sequences that are subjected to the methods described herein can be obtained from any prokaryotic or eukaryotic source. For example, they can be obtained from a mammalian, such as equine, cellular source. Alternatively, nucleic acid molecules can be obtained from a library, such as the CHORI-241 Equine BAC library or a similar resource available elsewhere.

As discussed above, the terms "isolated and/or purified" refer to a nucleic acid—e.g. a DNA or RNA molecule—that has been isolated from its natural cellular environment and from association with other components of the cell, such as nucleic acid or polypeptide, so that it can be sequenced, replicated, and/or expressed. For example, an "isolated nucleic acid" may be a DNA molecule that is complementary or hybridizes to a sequence in a coding region of interest—e.g., a nucleic acid sequence encoding an equine filamin-C protein, and remains stably bound under stringent conditions (as defined by methods well known in the art). Thus, an RNA or a DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA that has been derived or isolated from any appropriate cellular source, that may be substantially chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from the source by chemical means, e.g., by the use of restriction endonucleases, so that it can be further manipulated, e.g. amplified, for use in the methods described herein. Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or non-variant version of the nucleic acid molecule.

Nucleic Acid Amplification Methods

DNA present in a physiological sample may be amplified by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ-replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be performed according to known techniques. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be performed according to known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction: the oligonucleotide probe portion is about 13 to 15 nucleotides in length in one embodiment of the invention.

Ligase chain reaction (LCR) also may be performed according to known techniques. In general, the reaction is carried out with two pairs of oligonucleotide probes: one pair binds to one strand of the sequence to be detected; the other pair binds to the other strand of the sequence to be detected; each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In some embodiments, each exon of the MYOT, FLNC, or MYOZ3 coding region is amplified by PCR using primers based on the known sequence. The amplified exons are then sequenced using, for example, an automated sequencer. In this manner, the exons of the MYOT, FLNC, or MYOZ3 coding region from horses suspected of having Polysaccharide Storage Myopathy type 2 (PSSM2), also known as Myofibrillar Myopathy (MFM), in their pedigree are then sequenced until a mutation is found. Examples of such mutations include those in exon 6 of the MYOT DNA, exons 15 and 21 of the FLNC DNA, or exon 3 of the MYOZ3 DNA. For example, mutations in the MYOT gene include an adenine (A) to guanine (G) substitution on the forward strand at nucleotide base chr14:38,519,183 in exon 6 (FIG. 1); two mutations in the FLNC gene include a guanine (G) to adenine (A) substitution on the forward strand at nucleotide base chr4:83736244 in exon 15 and a guanine (G) to adenine (A) substitution on the forward strand at nucleotide base chr4:83738769 in exon 21 (FIG. 2 and FIG. 3); mutations in the MYOZ3 gene include a guanine (G) to adenine (A) substitution on the forward strand at nucleotide base chr14:27,399,222 (FIG. 4). Using this technique, additional mutations causing equine Polysaccharide Storage Myopathy type 2 (PSSM2), also known as Myofibrillar Myopathy (MFM), can be identified. Thus, the methods described herein may be used to detect and/or identify an alteration within the wild-type MYOT, FLNC, or MYOZ3 locus. "Alteration of" a specified locus encompasses all forms of mutations including, for example, a deletion, an insertion, and/or a point mutation in the coding and non-coding regions. A deletion can involve the deletion of all or any portion of the coding region. A point mutation may result in an aberrant stop codon, a frameshift mutation, an amino acid substitution, and/or an alteration in pre-mRNA processing (splicing) that produces a protein with an altered amino acid sequence. Point mutational events may occur in regulatory regions, such as in the promoter of the gene, leading to decreased expression of the mRNA. A point mutation also may interfere with proper RNA processing, leading to decreased expression of the MYOT, FLNC, or MYOZ3 translation products, decreased mRNA stability, and/or decreased translation efficiency. Polysaccharide Storage Myopathy type 2 (PSSM2), also known as Myofibrillar Myopathy (MFM), is a disease caused by point mutations at nucleic acid chr14:38,519,183 (MYOT), chr4:83736244 and chr4:83738769 (FLNC), and chr14:27,399,222 (MYOZ3). Horses predisposed to or having Polysaccharide Storage Myopathy type 2 (PSSM2), also known as Myofibrillar Myopathy (MFM), need only have one mutated MYOT, FLNC, or MYOZ3 allele.

Techniques that are useful in performing the methods described herein include, but are not limited to direct DNA sequencing, PFGE analysis, allele-specific oligonucleotide (ASO), dot blot analysis, and/or denaturing gradient gel electrophoresis.

There are several methods that can be used to detect DNA sequence variation. Direct DNA sequencing, either manual or automated (e.g., fluorescent or semiconductor-based sequencing), can detect sequence variation. Another approach is the single-stranded conformation polymorphism assay (SSCA). This method does not detect all sequence changes, especially if the DNA fragment size is greater than 200 bp, but can be used to detect most DNA sequence variation. SSCA allows for increased throughput compared to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA), and chemical mismatch cleavage (CMC). Once a mutation is known, an allele specific detection approach such as allele specific oligonucleotide (ASO) hybridization can be utilized to rapidly screen large numbers of other samples for that same mutation. Such a technique can utilize probes that are labeled with gold nanoparticles to yield a visual color result.

Detecting point mutations may be accomplished by molecular cloning and then sequencing one or more MYOT, FLNC, or MYOZ3 alleles. Alternatively, the coding region sequences can be amplified directly from a genomic DNA preparation from equine tissue, using known techniques. The DNA sequence of the amplified sequences can then be determined.

Exemplary methods for a more complete, yet still indirect, test for confirming the presence of a mutant allele include, for example, single stranded conformation analysis (SSCA), denaturing gradient gel electrophoresis (DDGE), an RNase protection assay, allele-specific oligonucleotides (ASOs), the use of a protein that recognizes nucleotide mismatches (e.g., the *E. coli* mutS protein), and allele-specific PCR. For allele-specific PCR, primers are used that hybridize at their 3' ends to a particular MYOT, FLNC, or MYOZ3 mutation. If the particular mutation is not present, an amplification product is not observed. Allele-specific PCR may also be carried out using quantitative PCR or real-time PCR using a specialized instrument that is capable of detecting and quantifying the appearance of amplification products during each amplification cycle. An Amplification Refractory Mutation System (ARMS) can also be used. Insertions and deletions of genes can also be detected by cloning, sequencing, and amplification. In addition, restriction fragment length polymorphism (RFLP) probes for the target locus or a surrounding marker locus can be used to score alteration of an allele or an insertion in a polymorphic fragment. Other techniques for detecting insertions or deletions as known in the art can also be used.

In the first three methods (i.e., SSCA, DGGE, and RNase protection assay), a new electrophoretic band appears. SSCA detects a band that migrates differently because the sequence change causes a difference in single-strand, intramolecular base pairing. RNase protection involves cleaving the mutant polynucleotide into two or more smaller fragments. DGGE detects differences in migration rates of mutant sequences compared to wild-type sequences using a denaturing gradient gel. In an allele-specific oligonucleotide assay, an oligonucleotide is designed that detects a specific sequence, and the assay is performed by detecting the presence or absence of a hybridization signal. In the mutS assay, the protein binds only to sequences that contain a nucleotide mismatch in a heteroduplex between mutant and wild-type sequence.

As used herein, a "nucleotide mismatch" refers to a hybridized nucleic acid duplex in which the two strands are not 100% complementary. Lack of total homology may be due to a deletion, an insertion, an inversion, and/or a substitution. Mismatch detection can be used to detect point mutation in the coding region or its mRNA product. While these techniques are less sensitive than sequencing, they are simpler to perform on a large number of samples. An example of a mismatch cleavage technique is the RNase protection method. In the context of detecting a MYOT-, FLNC-, or MYOZ3-associated mismatch, the method involves the use of a labeled riboprobe that is complementary to the horse wild-type MYOT, FLNC, or MYOZ3 coding region coding sequence. The riboprobe and either mRNA or DNA isolated from tissue are annealed (i.e., hybridized) and subsequently digested with the enzyme RNase A, which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen that is smaller than the full length duplex RNA for the riboprobe and the mRNA or DNA. The riboprobe need not be the full length of the MYOT, FLNC, or MYOZ3 mRNA or coding region but can be a segment of either. If the riboprobe includes only a segment of the MYOT, FLNC, or MYOZ3 mRNA or DNA, it may be desirable to use a number of probes to screen the whole mRNA sequence for mismatches.

In a similar fashion, DNA probes can be used to detect a mismatch through enzymatic and/or chemical cleavage. Alternatively, a mismatch can be detected by shifts in the electrophoretic mobility of mismatched duplexes relative to matched duplexes. With either riboprobes or DNA probes, the cellular mRNA or DNA that might contain a mutation can be amplified using PCR before hybridization.

Nucleic Acid Analysis via Microchip Technology

A DNA sequence of the MYOT, FLNC, or MYOZ3 coding regions that has been amplified by PCR may be screened using an allele-specific probe. Allele-specific probes are nucleic acid oligomers, each of which contains a region of the MYOT, FLNC, or MYOZ3 coding region harboring a known mutation. For example, one oligomer may be about 30 nucleotides in length, corresponding to a portion of the MYOT, FLNC, or MYOZ3 coding region sequence. Using a battery of such allele-specific probes, a PCR amplification product can be screened to identify the presence of a previously identified mutation in the MYOT, FLNC, or MYOZ3 coding region. Hybridizing an allele-specific probe with an amplified MYOT, FLNC, or MYOZ3 sequence can be performed, for example, on a nylon filter. Hybridizing to a particular probe under stringent hybridization conditions indicates the presence of the same mutation in the tissue as in the allele-specific probe.

An alteration of MYOT, FLNC, or MYOZ3 mRNA expression can be detected by any technique known in the art. Exemplary techniques include, for example, Northern blot analysis, PCR amplification, and/or RNase protection. Decreased mRNA expression indicates an alteration of the wild-type MYOT, FLNC, or MYOZ3 locus.

Alteration of wild-type MYOT, FLNC, or MYOZ3 coding region also can be detected by screening for alteration of a wild-type MYOT, FLNC, or MYOZ3 polypeptide such as, for example, the wild-type MYOT, FLNC, or MYOZ3 protein or a portion the wild-type MYOT, FLNC, or MYOZ3 protein. For example, a monoclonal antibody immunoreactive with wild-type MYOT, FLNC, or MYOZ3 (or to a specific portion of the MYOT, FLNC, or MYOZ3 protein) can be used to screen a tissue. Lack of cognate antigen would indicate a mutation. An antibody specific for a product of a mutant allele also can be used to detect a mutation in the MYOT, FLNC, or MYOZ3 coding region. Such an immunological assay can be performed using conventional methods. Exemplary methods include, for example, Western blot analysis, an immunohistochemical assay, an ELISA assay, and/or any method for detecting an altered MYOT, FLNC, or MYOZ3 polypeptide. In some embodiments, a functional assay can be used such as, for example, protein binding determination. In addition, an assay can be used that detects MYOT, FLNC, or MYOZ3 biochemical function. Finding a mutant MYOT, FLNC, or MYOZ3 polypeptide indicates a mutation at the MYOT, FLNC, or MYOZ3 locus.

A mutant MYOT, FLNC, or MYOZ3 coding region or translation product can be detected in a variety of physiological samples collected from a horse. Examples of appropriate samples include a cell sample, such as a blood cell (e.g., a lymphocyte, a peripheral blood cell), a sample collected from the spinal cord, a tissue sample such as cardiac tissue or muscle tissue (e.g. cardiac or skeletal muscle) an organ sample (e.g., liver or skin), a hair sample, especially a hair sample with the hair bulb (roots) attached, and/or a fluid sample (e.g., blood).

The methods described herein are applicable to any equine disease in which MYOT, FLNC, or MYOZ3 has a role. The method may be particularly useful for, for example, a veterinarian, a Breed Association, and/or individual breeders, so they can decide upon an appropriate course of treatment, and/or to determine if an animal is a suitable candidate as a brood mare or sire.

Oligonucleotide Probes

As described above, the method may be used to detect the presence and/or absence of a polymorphism in equine DNA. In particular, mutations in the MYOT gene include an adenine (A) to guanine (G) substitution on the forward strand at nucleotide base chr14:38,519,183 in exon 6 (FIG. 1); two mutations in the FLNC gene include a guanine (G) to adenine (A) substitution on the forward strand at nucleotide base chr4:83736244 in exon 15 and a guanine (G) to adenine (A) substitution on the forward strand at nucleotide base chr4:83738769 in exon 21 (FIG. 2 and FIG. 3); mutations in the MYOZ3 gene include a guanine (G) to adenine (A) substitution on the forward strand at nucleotide base chr14:27,399,222 (FIG. 4). These substitutions result in: (1) a serine (S) at codon 232 in the myotilin (MYOT) protein (SEQ ID NO:9) being replaced by a proline (P), as shown in SEQ ID NO: 10, (2) a glutamic acid (E) at codon 753 in the filamin-C (FLNC) protein (SEQ ID NO:11, equivalent to SEQ ID NO:12) being replaced by a lysine (K), as shown in SEQ ID NO:13 (equivalent to SEQ ID NO:14), and an alanine (A) at codon 1207 in the filamin-C (FLNC) protein (SEQ ID NO:11, equivalent to SEQ ID NO:12) being replaced by a threonine (T), as shown in SEQ ID NO:13 (equivalent to SEQ ID NO:14), and (3) a serine (S) at codon 42 in the myozenin-3 (MYOZ3) protein (SEQ ID NO:15) being replaced by a leucine (L), as shown in SEQ ID NO:16.

A primer pair may be used to determine the nucleotide sequence of a particular MYOT, FLNC, or MYOZ3 allele using PCR. A pair of single-stranded DNA primers can be annealed to sequences within or surrounding the FLNC coding region in order to prime amplifying DNA synthesis of the MYOT, FLNC, or MYOZ3 coding region itself. A complete set of primers allows one to synthesize all of the nucleotides of the MYOT, FLNC, or MYOZ3 coding sequence. In some embodiments, a set of primers can allow synthesis of both intron and exon sequences. In some embodiments, allele-specific primers can be used. Such primers anneal only to particular MYOT, FLNC, or MYOZ3 mutant alleles, and thus will only amplify product efficiently in the presence of the mutant allele as a template.

The first step of the process involves contacting a physiological sample obtained from a horse, which sample contains nucleic acid, with an oligonucleotide probe to form a hybridized DNA. The oligonucleotide probe can be any probe having from about 4 or 6 bases up to about 80 or 100 bases or more. In one embodiment, the oligonucleotide probe can have between about 10 and about 20 bases.

The primers themselves can be synthesized using conventional techniques and, in some cases, can be made using an automated oligonucleotide synthesizing machine. Given the MYOT genomic sequence as partially set forth in SEQ ID NO:1, the FLNC genomic sequence as partially set forth in SEQ ID NO:2 and SEQ ID NO:3, and the MYOZ3 genomic sequence as partially set forth in SEQ ID NO:4, one can design a set of oligonucleotide primers to probe any portion of the MYOT, FLNC, or MYOZ3 coding sequences. The primers may be designed to hybridize entirely to coding sequence (exons), to noncoding sequence (introns or other noncoding sequences), or to regions spanning the junction of coding and noncoding sequences in genomic DNA.

An oligonucleotide probe may be prepared according to conventional techniques to have any suitable base sequence.

Suitable bases for preparing the oligonucleotide probe may be selected from naturally-occurring bases such as adenine, cytosine, guanine, uracil, and thymine. An oligonucleotide probe also can incorporate one or more non-naturally-occurring or "synthetic" nucleotide bases. Exemplary synthetic bases include, for example, 7-deaza-guanine, 8-oxo-guanine, 6-mercaptoguanine, N4-acetylcytidine, 5-(carboxyhydroxyethyl)uridine, 2'-O-methylcytidine, 5-(carboxymethylaminomethyl)-2-thiouridine, 5-carboxymethylaminomethyluridine, dihydrouridine, 2'-O-methylpseudouridine, β,D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, N2-methylguanosine, 3-methylcytidine, 5-methylcytidine, N6-methyladenosine, 7-methylguanosine, 5-methylaminomethyluridine, 5-methoxyaminomethyl-2-thiouridine, β,D-mannosylqueuosine, 5-methloxycarbonylmethyluridine, 5-methoxyuridine, 2-methylthio-N6-isopentenyladenosine, N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queuosine, 2-thiocytidine, 5-methyl-2-thiouridine, 2-thiouridine, 5-methyluridine, N-((9-beta-D-ribofuranosylpurine-6-yl)carbamoyl) threonine, 2'-O-methyl-5-methyluridine, 2-O-methyluridine, wybutosine, and/or 3-(3-amino-3-carboxypropyl)uridine. Any oligonucleotide backbone may be employed, including DNA, RNA (although RNA may be less preferred than DNA in certain circumstances), modified sugars such as carbocycles, and sugars containing 2' substitutions (e.g., fluoro or methoxy). The oligonucleotides may be oligonucleotides wherein at least one, or all, of the internucleotide bridging phosphate residues is a modified phosphate such as, for example, a methyl phosphate, a methyl phosphonotlioate, a phosphoroinorpholidate, a phosphoropiperazidate, and/or a phospholioramidate—for example, every other one of the internucleotide bridging phosphate residues may be modified. The oligonucleotide may be a "peptide nucleic acid" such as described in Nielsen et al., Science, 254, 1497-1500 (1991).

The oligonucleotide probe should possess a sequence at least a portion of which is capable of binding to a known portion of the sequence of the nucleic acid in the physiological sample.

In some embodiments, the nucleic acid in the sample may be contacted with a plurality of oligonucleotide probes having different base sequences (e.g., where there are two or more target nucleic acids in the sample, or where a single target nucleic acid is hybridized to two or more probes in a "sandwich" assay).

The oligonucleotide probes provided herein may be useful for a number of purposes. For example, the oligonucleotide probes can be used to detect PCR amplification products and/or to detect mismatches with the FLNC coding region or mRNA.

Hybridization Methodology

The nucleic acid from the physiological sample may be contacted with the oligonucleotide probe in any conventional manner. For example, the sample nucleic acid may be solubilized in solution and contacted with the oligonucleotide probe by solubilizing the oligonucleotide probe in solution with the sample nucleic acid under condition that permit hybridization. Suitable hybridization conditions are well known to those skilled in the art. Alternatively, the sample nucleic acid may be solubilized in solution with the oligonucleotide probe immobilized on a solid or semisolid support, whereby the sample nucleic acid may be contacted with the oligonucleotide probe by immersing the solid or semisolid support having the oligonucleotide probe immobilized thereon in the solution containing the sample nucleic acid.

Certain embodiments of the methods described herein relate to mutations in the MYOT, FLNC, or MYOZ3 coding regions or the diagnosis of Polysaccharide Storage Myopathy type 2 (PSSM2), also known as Myofibrillar Myopathy (MFM), the detection of a predisposition for Polysaccharide Storage Myopathy type 2 (PSSM2), also known as Myofibrillar Myopathy (MFM), or to the detection of a mutant MYOT, FLNC, or MYOZ3 allele in a horse.

Mutations in the equine MYOT, FLNC, or MYOZ3 coding regions (encoding the skeletal muscle proteins myotilin, filamin-C, or myozenin-3) are present in many populations of horses affected by Polysaccharide Storage Myopathy type 2 (PSSM2), also known as Myofibrillar Myopathy (MFM). The differences in the genomic DNA between horses affected by Polysaccharide Storage Myopathy type 2 (PSSM2), also known as Myofibrillar Myopathy (MFM), include point mutations at nucleic acid chr14:38,519,183 (MYOT), chr4:83736244 and chr4:83738769 (FLNC), and chr14:27,399,222 (MYOZ3).

Scientific Narrative

FIG. 1 shows the equine genomic sequence from the reference assembly (EquCab2) around the position of the adenine (A) to guanine (G) substitution at chr14:38,519,183 in MYOT. The reverse complement sequence is shown, so the substitution appears as a thymine (T) to cytosine (C) substitution in SEQ ID NO:1.

FIG. 2 shows the equine genomic sequence from the reference assembly (EquCab2) around the position of the guanine (G) to adenine (A) substitution at chr4:83736244 in FLNC (SEQ ID NO:2). The forward strand sequence is shown.

FIG. 3 shows the equine genomic sequence from the reference assembly (EquCab2) around the position of the guanine (G) to adenine (A) substitution at chr4:83738769 in FLNC (SEQ II) NO:3), The forward strand sequence is shown.

FIG. 4 shows the equine genomic sequence from the reference assembly (EquCab2) around the position of the guanine (G) to adenine (A) substitution at chr14:27,399,222 in MYOZ3. The reverse complement sequence is shown, so the substitution appears as a cytosine (C) to thymine (T) substitution in SEQ ID NO:4.

FIG. 5 shows the equine MYOT coding sequence (SEQ ID NO:5, also known as XM_014730661.1), with exon 6 indicated in bold. The position of the thymine (T) to cytosine (C) substitution at position 664 in SEQ ID NO:5 (chr14:38,519,183 in SEQ ID NO:1) is underlined.

FIG. 6 shows the alignment of two models of the equine FLNC coding sequence. SEQ ID NO:6, also known as Ensembl CDS 00000012220, is shown aligned to SEQ ID NO:7, also known as XM_014739030.1. Exons 15 and 21 are shown in bold. The position of the guanine (G) to adenine (A) substitution at chr4:83736244 in exon 15 is underlined, as is the position of the guanine (G) to adenine (A) substitution at chr4:83738769 in exon 21. The guanine (G) to adenine (A) base substitution in exon 15 at nucleotide position chr4:83736244 corresponds to base 2257 in SEQ ID NO:6 and 2506 in SEQ ID NO:7. The guanine (G) to adenine (A) base substitution in exon 21 at nucleotide position chr4:83738769 corresponds to base 3619 in SEQ ID NO:6 and 3868 in SEQ ID NO:7. The two models for the CDS of equine FLNC differ slightly. First, the two models differ at the 5' end. The horse genome assembly EquCab 2.0 contains a gap in the assembly near the 5' end of the FLNC gene. This results in a model in which the initiation codon of SEQ ID NO:6 is an ACG rather than the more typical ATG as in SEQ ID NO:7. Second, SEQ ID NO:7 contains a 63 base insertion from positions 1478 to 1540. It is likely that this is an annotation error in one of the models. Third, SEQ ID NO:6 and SEQ ID NO:7 differ with respect to the sequence starting at position 5652 in SEQ ID NO:6 and position 5415 in SEQ ID NO:7. The three-base sequence at this position is GAG in SEQ ID NO:6 and TGA in SEQ ID NO:7. Finally, SEQ ID NO:6 contains a 29 base insertion from positions 7856 to 7884. It is likely that this is an annotation error in one of the models. Note that the two base substitutions found in horses with Polysaccharide Storage Myopathy type 2 (PSSM2) or Myofibrillar Myopathy (MFM) do not occur in any of the areas of disagreement between the two models.

FIG. 7 shows the equine MYOZ3 coding sequence (SEQ ID NO:8, derived from XM_014730574.1), with exon 6 indicated in bold. The position of the thymine (T) to cytosine (C) substitution at position 125 in SEQ ID NO:8 (chr4:27,399,222 in SEQ ID NO:4) is underlined.

FIG. 8 shows two protein sequences derived from the translation of the equine MYOT coding sequence shown in FIG. 5. The wild-type or common protein sequence is shown as SEQ ID NO:9, while the MYOT-S232P variant sequence derived from the sequence bearing the thymine (T) to cytosine (C) substitution shown at chr14:38,519,183 in SEQ ID NO:1 (FIG. 1) and position 664 in SEQ ID NO:5 (FIG. 5) is shown as SEQ ID NO:10.

FIG. 9 shows an alignment of protein sequences derived from the translation of the equine FLNC sequences shown in FIG. 6 (SEQ ID NO:6 and SEQ ID NO:7). The entire FLNC coding nucleotide sequences shown in FIG. 6 were translated to give the wild-type or common amino acid sequences (SEQ ID NO:11, also known as F6ZWZ3, and SEQ ID NO:12, also known as XP_014594516.1). FIG. 9 shows translations of sequences bearing the guanine (G) to adenine (A) substitution at chr4:83736244 in FLNC (SEQ ID NO:2) shown in FIG. 2 and the guanine (G) to adenine (A) substitution at chr4:83738769 in FLNC (SEQ ID NO:3) shown in FIG. 3. These substitution positions are also shown in FIG. 6 as position 2257 in SEQ ID NO:6 (corresponding to position 2506 in SEQ ID NO:7) and position 3619 in SEQ ID NO:6 (corresponding to position 3868 in SEQ ID NO:7). The protein sequences derived from translation of the sequences with the substitutions are presented as SEQ ID NO:13 and SEQ ID NO:14.

The guanine (G) to adenine (A) substitution at chr4:83736244 in FLNC (SEQ ID NO:2) changes the glutamic acid (E) at position 753 in SEQ ID NO:11 and at position 836 in SEQ ID NO:12 to a lysine (K) at the corresponding positions in SEQ ID NO:13 and SEQ ID NO:14. This variant is referred to as FLNC-E753K.

The guanine (G) to adenine (A) substitution at chr4:83738769 in FLNC (SEQ ID NO:3) changes the alanine (A) at position 1207 in SEQ ID NO:11 and at position 1290 in SEQ ID NO:12 to a threonine (T) at the corresponding positions in SEQ ID NO:13 and SEQ ID NO:14. This variant is referred to as FLNC-A1207T.

The differences between the two models for the coding sequence of equine FLNC described in the discussion of FIG. 6 above produce differences in the amino acid sequences of the predicted proteins, as shown in SEQ ID NO:13 and SEQ II) NO:14 in FIG. 9. As noted above, the two predicted protein sequences do not differ in the regions encoded by exon 15 or exon 21, which contain the sites of the FLNC-E753K and FLNC-A1207T substitutions.

FIG. 10 shows two protein sequences derived from the translation of the equine MYOZ3 coding sequence shown in FIG. 7. The wild-type or common protein sequence is shown as SEQ ID NO:15, while the MYOZ3-S42L variant sequence derived from the sequence bearing the cytosine (C) to thymine (T) substitution shown at chr14:38,519,183 in SEQ ID NO:4 (FIG. 4) and position 125 in SEQ ID NO:8 (FIG. 7) is shown as SEQ ID NO:16.

FIG. 11 shows MYOT exon 6 and flanking genomic DNA sequence from which PCR primers to amplify genomic DNA containing the site of the MYOT-S232P mutation would be most appropriately derived. Genomic coordinates are as in FIG. 1. Exon 6 from chr14:38,519,913 to chr14:38,519,061 is shown broken into codons in the correct reading frame for the wild-type allele (SEQ ID NO:17) and the MYOT-S232P allele (SEQ ID NO:18). Only the reference sequence from the assembly is shown for the flanking sequences. The site of a A to G mutation site at nucleotide position chr14:38,519,183 is shown in bold (T to C in the reverse complement as shown). This changes the underlined three base codon from one coding for a serine (TCT) to one coding for a proline (CCT). Example primers used experimentally to amplify genomic DNA containing the mutation site are shown in lower case (SEQ ID NO:19 and SEQ ID NO:20).

FIG. 12 shows FLNC exon 15 and flanking genomic DNA sequence from which PCR primers to amplify genomic DNA containing the site of the FLNC-E753K mutation would be most appropriately derived. Genomic coordinates are as in FIG. 2. Exon 15 from chr4:83,736,133 to chr4:83,736,256 is shown broken into codons in the correct reading frame for the wild-type allele (SEQ ID NO:21) and the FLNC-E753K allele (SEQ ID NO:22). Only the reference sequence from the assembly is shown for the flanking sequences. The site of a G to A mutation site at nucleotide position chr4:83,736,244 is shown in bold. This mutation changes the underlined three base codon from one coding for a glutamic acid (GAG) to one coding for a lysine (AAG). Example primers used experimentally to amplify genomic DNA containing the mutation site are shown in lower case (SEQ ID NO:23 and SEQ ID NO:24).

FIG. 13 shows FLNC exon 21 and flanking genomic DNA sequence from which PCR primers to amplify genomic DNA containing the site of the FLNC-A1207T mutation would be most appropriately derived. Genomic coordinates are as in FIG. 3. Exon 21 from chr4:83,738,223 to chr4:83,738,820 is shown broken into codons in the correct reading frame for the wild-type allele (SEQ ID NO:25) and the FLNC-A1207T allele (SEQ ID NO:26). Only the reference sequences from the assembly are shown for the flanking sequences. The exon sequences are broken into codons in the correct reading frame. The site of a G to A mutation site at nucleotide position chr4:83,738,769 is shown in bold. This mutation changes the underlined three base codon from one coding for an alanine (GCT) to one coding for a threonine (ACT). Example primers used experimentally to amplify genomic DNA containing the mutation site are shown in lower case (SEQ ID NO:27 and SEQ ID NO:28).

FIG. 14 shows MYOZ3 exon 3 and flanking genomic DNA sequence from which PCR primers to amplify genomic DNA containing the site of the MYOZ3-S42L mutation would be most appropriately derived. Genomic coordinates are as in FIG. 4. Exon 3 from chr14:27,399,285 to chr14:27,399,131 is shown broken into codons in the correct reading frame for the wild-type allele (SEQ ID NO:29) and the MYOZ3-S42L allele (SEQ ID NO:30). Only the reference sequences from the assembly are shown for the flanking sequences. The exon sequences are broken into codons in the correct reading frame. The site of a G to A mutation site at nucleotide position chr14:27,399,222 is shown in bold (C to T in the reverse complement as shown). This mutation changes the underlined three base codon from one coding for a serine (TCG) to one coding for a leucine (TTG). Example primers used experimentally to amplify genomic DNA containing the mutation site are shown in lower case (SEQ ID NO:31 and SEQ ID NO:32).

Genomic DNA obtained from horses can be genotyped by amplifying a region containing a variant in the MYOT, FLNC, or MYOZ3 using Polymerase Chain Reaction (PCR), then sequencing the amplified DNA using Sanger sequencing. The results can be scored as homozygous for the common or wild-type allele, heterozygous for a nucleotide substitution, or homozygous for the nucleotide substitution.

FIG. 15 shows traces from Sanger DNA sequencing of amplified MYOT genomic DNA using primers shown in FIG. 11 (SEQ ID NO:19 and SEQ ID NO:20). The sequence of the forward strand is shown. The arrows in the figure indicate nucleotide position chr14:38,519,183, the site of a substitution of a guanine (G) for an adenine (A) in this position that creates the MYOT-S232P variant. The traces show, from left to right, results for a horse homozygous for the wild-type or common allele, results for a horse heterozygous for the substitution, and results for a horse homozygous for the substitution.

Figure 16:
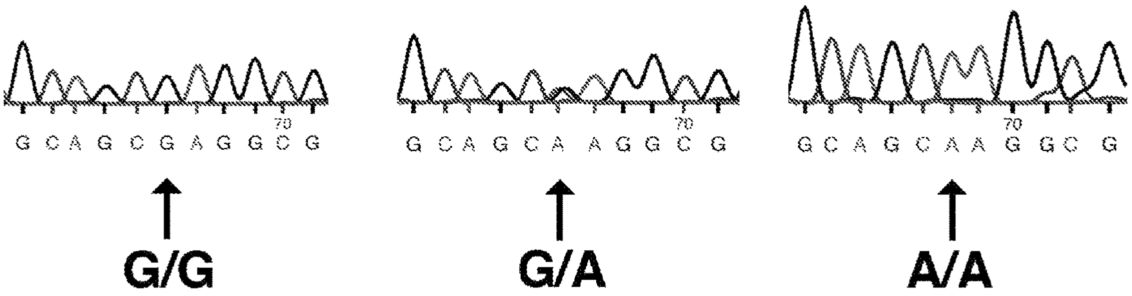
FIG. 16. Traces from Sanger DNA sequencing of amplified FLNC genomic DNA using primers shown in FIG. 12 (SEQ ID NO:23 and SEQ ID NO:24). The sequence of the forward strand is shown (SEQ ID NO:48). The arrows in the figure indicate nucleotide position chr4:83,736,244, the site of a substitution of an adenine (A) for a guanine (G) in this position that creates the FLNC-E753K variant. The traces show, from left to right, results for a horse homozygous for the wild-type or common allele, results for a horse heterozygous for the substitution, and results for a horse homozygous for the substitution.

FIG. 16 shows traces from Sanger DNA sequencing of amplified FLNC genomic DNA using primers shown in FIG. 12 (SEQ ID NO:23 and SEQ ID NO:24). The sequence of the forward strand is shown. The arrows in the figure indicate nucleotide position chr4:83,736 44, the site of a substitution of an adenine (A) for a guanine (G) in this position that creates the FLNC-E753K variant. The traces show, from left to right, results for a horse homozygous for the wild-type or common allele, results for a horse heterozygous for the substitution, and results for a horse homozygous for the substitution.

Figure 17:
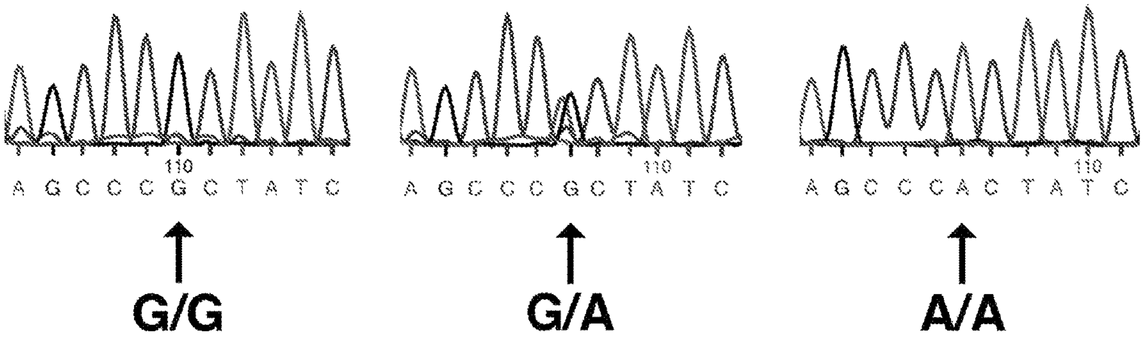
FIG. 17. Traces from Sanger DNA sequencing of amplified FLNC genomic DNA using primers shown in FIG. 13 (SEQ ID NO:27 and SEQ ID NO:28). The sequence of the forward strand is shown (SEQ ID NO:49). The arrows in the figure indicate nucleotide position chr4:83,738,769, the site of a substitution of an adenine (A) for a guanine (G) in this position that creates the FLNC-A1207T variant. The traces show, from left to right, results for a horse homozygous for the wild-type or common allele, results for a horse heterozygous for the substitution, and results for a horse homozygous for the substitution.

FIG. 17 shows traces from Sanger DNA sequencing of amplified FLNC genomic DNA using primers shown in FIG. 13 (SEQ ID NO:27 and SEQ ID NO:28). The sequence of the forward strand is shown. The arrows in the figure indicate nucleotide position chr4:83,738,769, the site of a substitution of an adenine (A) for a guanine (G) in this position that creates the FLNC-A1207T variant. The traces show, from left to right, results for a horse homozygous for the wild-type or common allele, results for a horse heterozygous for the substitution, and results for a horse homozygous for the substitution.

Figure 18:
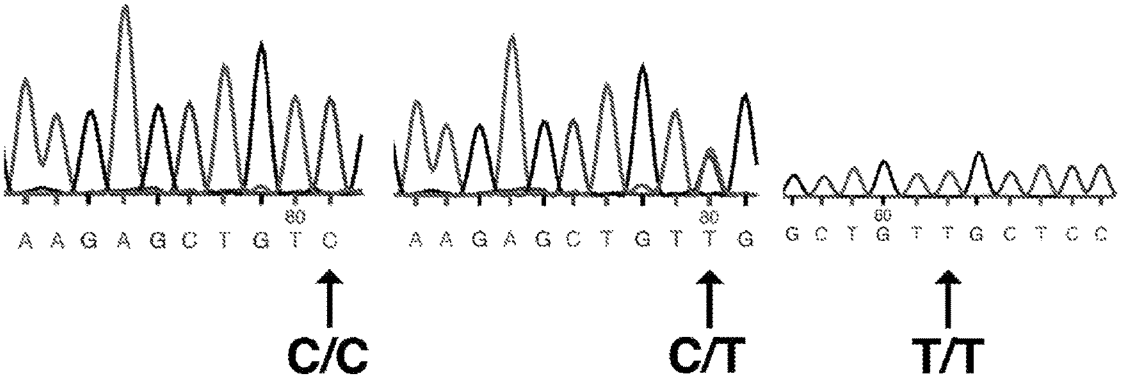
FIG. 18. Traces from Sanger DNA sequencing of amplified MYOZ3 genomic DNA using primers shown in FIG. 14 (SEQ ID NO:31 and SEQ ID NO:32). The sequence of the reverse strand is shown (SEQ ID NO:50). The arrows in the figure indicate nucleotide position chr14:27,399,222, the site of a substitution of a thymine (T) for a cytosine (C) in this position that creates the MYOZ3-S42L variant. The traces show, from left to right, results for a horse homozygous for the wild-type or common allele, results for a horse heterozygous for the substitution, and results for a horse homozygous for the substitution.

FIG. 18 shows traces from Sanger DNA sequencing of amplified MYOZ3 genomic DNA using primers shown in FIG. 14 (SEQ ID NO:31 and SEQ ID NO:32). The sequence of the reverse strand is shown. The arrows in the figure indicate nucleotide position chr14:27,399,222, the site of a substitution of an thymine (T) for a cytosine (C) in this position that creates the MYOZ3-S42L variant. The traces show, from left to right, results for a horse homozygous for the wild-type or common allele, results for a horse heterozygous for the substitution, and results for a horse homozygous for the substitution.

FIG. 19 shows horse MYOT exon 6 and flanking genomic DNA sequence from which allele-specific PCR primers to amplify genomic DNA containing the site of the MYOT-S232P mutation would be most appropriately derived. Genomic coordinates are as in FIG. 1. Exon 6 from chr14:38,519,913 to chr14:38,519,061 is shown broken into codons in the correct reading frame for the wild-type allele (SEQ ID NO:17) and the MYOT-S232P allele (SEQ ID NO:18). Only the reference sequence from the assembly is shown for the flanking sequences. The site of a A to G mutation site at nucleotide position chr14:38,519,183 is shown in bold (T to C in the reverse complement as shown). This changes the underlined three base codon from one coding for a serine (TCT) to one coding for a proline (CCT). Example primers used experimentally to amplify genomic DNA containing the mutation site are shown in lower case. SEQ ID NO:33 is the common primer that is not allele-specific; the allele-specific primers SEQ ID NO:34 and SEQ ID NO:35 preferentially amplify the wild-type and MYOT-S232P alleles, respectively.

Two separate allele-specific real time reactions were prepared and were run together on the same PCR plate using the Strategene MX3000P real time PCR machine. The forward allele-specific primers, SEQ ID NO:34 (5'-TTG-CATCCTGATCATTCACATCTCCCCTTGACGA-3'), which was used to detect the A-allele, and SEQ ID NO:35 (5'-TTGCATCCTGATCATTCACATCTCCCCTTGACGG-3'), which was used to detect the G-allele, were separately combined with the reverse common primer SEQ ID NO:33 (5'-GCACATGATAAGAATTGTC-CATGGGGTACTCTGCA-3') in PCR reaction mix that contained 0.25 uM forward primer; 0.25 uM reverse primer; 1.5 mM $Mg_2Cl$; 50 mM KCl; 10 mM Tris-HCl (pH 8.3); 5% DMSO (v/v), 0.2 mM each of dATP, dCTP, dGTP and dTTP; 6.25 uM SYTO 21; and 0.5 unit of Amplitaq Gold (ThermoFisher). Reactions were carried out for 95° C. for 10 min, 40 amplification cycles at 95° C. for 15 s, 60° C. for 30 s and 72° C. for 30 s. The CCD camera was set to capture the fluorescent signal during polymerization at 720C. At the end of the PCR amplification, a melting curve analysis was performed by heating the PCR extension product to 95° C. for 1 min and then cooling to 55° C. for 1 min before heating up to 95° C. again at a rate of 0.3° C. per second. The fluorescent signal was captured during the heating up of the PCR extension product from 55° C. to 95° C.

The threshold cycles (Ct) of two separate allele-specific real time reactions were determined by the real time PCR machine. When an individual is homozygous for the A allele, i.e. A/A, there is a wide separation between the A-allele amplification curve and the G-allele amplification curve. The separation can be represented by ΔCt, i.e. subtracting the Ct value of the A-allele amplification curve from that of the G-allele amplification curve. When an individual is homozygous for the G allele, i.e. C/C, the ΔCt value will decrease to a negative value. The ΔCt values were determined and matched with their genotypes. A genotype of A/A, A/G and G/G were concluded if ΔCt was >5, −2<ΔCt>2, and <−5 respectively.

| Genotype | ΔCt |
|---|---|
| Normal | >5 |
| Heterozygous for mutation | −2 to 2 |
| Homozygous for mutation (affected) | <−5 |

FIG. 20 shows horse FLNC exon 15 and flanking genomic DNA sequence from which allele-specific PCR primers to amplify genomic DNA containing the site of the FLNC-E753K mutation would be most appropriately derived. Genomic coordinates are as in FIG. 2. Exon 15 from chr4:83,736,133 to chr4:83,736,256 is shown broken into codons in the correct reading frame for the wild-type allele (SEQ ID NO:21) and the FLNC-E753K allele (SEQ ID NO:22). Only the reference sequence from the assembly is shown for the flanking sequences. The site of a G to A mutation site at nucleotide position chr4:83,736,244 is shown in bold. This mutation changes the underlined three base codon from one coding for a glutamic acid (GAG) to one coding for a lysine (AAG). Example primers used experimentally to amplify genomic DNA containing the mutation site are shown in lower case. SEQ ID NO:36 is the common primer that is not allele-specific; the allele-specific primers SEQ ID NO:37 and SEQ ID NO:38 preferentially amplify the wild-type and FLNC-E753K alleles, respectively. Note that both allele-specific primers span the exon-intron boundary Note also that additional mismatches have been introduced into both allele-specific primers.

Two separate allele-specific real time reactions were prepared and were run together on the same PCR plate using the Strategene MX3000P real time PCR machine. The forward allele-specific primers, SEQ ID NO:37 (5'-GGCTGGTGCACCTTGCCCCGCGTC-3'), which was used to detect the G-allele, and SEQ ID NO:38 (5'-GGCTGGTGCACCTTGCCCCGCGTT-3), which was used to detect the A-allele, were separately combined with the reverse common primer SEQ ID NO:36 (5'-TGTCGCTGGGCCCTGGTCACTGCTC-3') in PCR reaction mix that contained 0.25 uM forward primer; 0.25 uM reverse primer; 1.5 mM $Mg_2Cl$; 50 mM KCl; 10 mM Tris-HCl (pH 8.3); 5% DMSO (v/v), 0.2 mM each of dATP, dCTP, dGTP and dTTP; 6.25 uM SYTO 21; and 0.5 unit of Amplitaq Gold (ThermoFisher). Reactions were carried out for 95° C. for 10 min, 40 amplification cycles at 95° C. for 15 s, 60° C. for 30 s and 72° C. for 30 s. The CCD camera was set to capture the fluorescent signal during polymerization at 72° C. At the end of the PCR amplification, a melting curve analysis was performed by heating the PCR extension product to 95° C. for 1 min and then cooling to 55° C. for 1 min before heating up to 95° C. again at a rate of 0.3° C. per second. The fluorescent signal was captured during the heating up of the PCR extension product from 55° C. to 95° C.

The threshold cycles (Ct) of two separate allele-specific real time reactions were determined by the real time PCR machine. When an individual is homozygous for the G allele, i.e. G/G, there is a wide separation between the G-allele amplification curve and the A-allele amplification curve. The separation can be represented by ΔCt, i.e. subtracting the Ct value of the G-allele amplification curve from that of the A-allele amplification curve. When an individual is homozygous for the A allele, i.e. A/A, the ΔCt value will decrease to a negative value. The ΔCt values were determined and matched with their genotypes. A genotype of G/G, G/A and A/A were concluded if ΔCt was >5, −2<ΔCt>2, and <−5 respectively.

| Genotype | ΔCt |
|---|---|
| Normal | >5 |
| Heterozygous for mutation | −2 to 2 |
| Homozygous for mutation (affected) | <−5 |

FIG. 21 shows horse FLNC exon 21 and flanking genomic DNA sequence from which allele-specific PCR primers to amplify genomic DNA containing the site of the FLNC-A1207T mutation would be most appropriately derived. Genomic coordinates are as in FIG. 3. Exon 21 from chr4:83,738,223 to chr4:83,738,820 is shown broken into codons in the correct reading frame for the wild-type allele (SEQ ID NO:25) and the FLNC-A1207T allele (SEQ ID NO:26). Only the reference sequences from the assembly are shown for the flanking sequences. The site of a G to A mutation site at nucleotide position chr4:83,738,769 is shown in bold. This mutation changes the underlined three base codon from one coding for an alanine (GCT) to one coding for a threonine (ACT). Example primers used experimentally to amplify genomic DNA containing the mutation site are shown in lower case. SEQ ID NO:39 is the common primer that is not allele-specific; the allele-specific primers SEQ ID NO:40 and SEQ ID NO:41 preferentially amplify the wild-type and FLNC-A1207T alleles, respectively. Note that additional mismatches have been introduced into both allele-specific primers.

Two separate allele-specific real time reactions were prepared and were run together on the same PCR plate using the Strategene MX3000P real time PCR machine. The forward allele-specific primers, SEQ ID NO:40 (5'-ACCCGCGTCCATGTGCAGCGCG-3'), which was used to detect the G-allele, and SEQ ID NO:41 (5'-ACCCGCGTCCATGTGCAGCGCA-3'), which was used to detect the A-allele, were separately combined with the reverse common primer SEQ ID NO:39 (5'-CCAGGGCTGTCCCCAAGTCCTCCC-3') in PCR reaction mix that contained 0.25 uM forward primer; 0.25 uM reverse primer; 1.5 mM $Mg_2Cl$; 50 mM KCl; 10 mM Tris-HCl (pH 8.3); 5% DMSO (v/v), 0.2 mM each of dATP, dCTP, dGTP and dTTP; 6.25 uM SYTO 21; and 0.5 unit of Amplitaq Gold (ThermoFisher). Reactions were carried out for 95° C. for 10 min, 40 amplification cycles at 95° C. for 15 s, 60° C. for 30 s and 72° C. for 30 s. The CCD camera was set to capture the fluorescent signal during polymerization at 720C. At the end of the PCR amplification, a melting curve analysis was performed by heating the PCR extension product to 95° C. for 1 min and then cooling to 55° C. for 1 min before heating up to 95° C. again at a rate of 0.3° C. per second. The fluorescent signal was captured during the heating up of the PCR extension product from 55° C. to 95° C.

The threshold cycles (Ct) of two separate allele-specific real time reactions were determined by the real time PCR machine. When an individual is homozygous for the G allele, i.e. G/G, there is a wide separation between the G-allele amplification curve and the A-allele amplification curve. The separation can be represented by ΔCt, i.e. subtracting the Ct value of the G-allele amplification curve from that of the A-allele amplification curve. When an individual is homozygous for the A allele, i.e. A/A, the ΔCt value will decrease to a negative value. The ΔCt values were determined and matched with their genotypes. A genotype of G/G, G/A and A/A were concluded if ΔCt was >5, −2<ΔCt>2, and <−5 respectively.

| Genotype | ΔCt |
|---|---|
| Normal | >5 |
| Heterozygous for mutation | −2 to 2 |
| Homozygous for mutation (affected) | <−5 |

FIG. 22 shows horse MYOZ3 exon 3 and flanking genomic DNA sequence from which allele-specific PCR primers to amplify genomic DNA containing the site of the MYOZ3-S42L mutation would be most appropriately derived. Genomic coordinates are as in FIG. 4. Exon 3 from chr14:27,399,285 to chr14:27,399,131 is shown broken into codons in the correct reading frame for the wild-type allele (SEQ ID NO:29) and the MYOZ3-S42L allele (SEQ ID NO:30). Only the reference sequences from the assembly are shown for the flanking sequences. The site of a G to A mutation site at nucleotide position chr14:27,399,222 is shown in bold (C to T in the reverse complement as shown). This mutation changes the underlined three base codon from one coding for a serine (TCG) to one coding for a leucine (TTG). Example primers used experimentally to amplify genomic DNA containing the mutation site are shown in lower case. SEQ ID NO:42 is the common primer that is not allele-specific; the allele-specific primers SEQ ID NO:43 and SEQ ID NO:44 preferentially amplify the wild-type and MYOZ3-S42L alleles, respectively. Note that additional mismatches have been introduced into both allele-specific primers.

Two separate allele-specific real time reactions were prepared and were run together on the same PCR plate using the Strategene MX3000P real time PCR machine. The forward allele-specific primers, SEQ ID NO:43 (5'-GCCCCAGGACCTGATGATGGAAGAGCTCTC-3'), which was used to detect the C-allele, and SEQ ID NO:44 (5'-GCCCCAGGACCTGATGATGGAAGAGCTCTT-3'), which was used to detect the T-allele, were separately combined with the reverse common primer SEQ ID NO:42 (5'-GGCCAGAGGTCCTCCCCTGGCT-3') in PCR reaction mix that contained 0.25 uM forward primer; 0.25 uM reverse primer; 2.5 mM $Mg_2Cl$; 50 mM KCl; 10 mM Tris-HCl (pH 8.3); 5% DMSO (v/v), 0.2 mM each of dATP, dCTP, dGTP and dTTP; 6.25 uM SYTO 21; and 0.5 unit of Amplitaq Gold (ThermoFisher). Reactions were carried out for 95° C. for 10 min, 40 amplification cycles at 95° C. for 15 s, 60° C. for 30 s and 72° C. for 30 s. The CCD camera was set to capture the fluorescent signal during polymerization at 72° C. At the end of the PCR amplification, a melting curve analysis was performed by heating the PCR extension product to 950C for 1 min and then cooling to 55° C. for 1 min before heating up to 95° C. again at a rate of 0.3° C. per second. The fluorescent signal was captured during the heating up of the PCR extension product from 55° C. to 95° C.

The threshold cycles (Ct) of two separate allele-specific real time reactions were determined by the real time PCR machine. When an individual is homozygous for the C allele, i.e. C/C, there is a wide separation between the C-allele amplification curve and the T-allele amplification curve. The separation can be represented by Act, i.e. subtracting the Ct value of the C-allele amplification curve from that of the T-allele amplification curve. When an individual is homozygous for the T allele, i.e. T/T, the ΔCt value will decrease to a negative value. The ΔCt values were determined and matched with their genotypes. A genotype of C/c, C/T and T/T were concluded if ΔCt was >5, −2<ΔCt>2, and <−5 respectively.

| Genotype | ΔCt |
|---|---|
| Normal | >5 |
| Heterozygous for mutation | −2 to 2 |
| Homozygous for mutation (affected) | <−5 |

The human orthologs of the equine MYOT, FLNC, and MYOZ3 genes and the human proteins that these genes encode are richly annotated with experimental data derived from genetic and biochemical studies. It is informative to compare the amino acid substitutions in MYOT, FLNC, and MYOZ3 found in horses to the information on protein domains and clinically significant variation in the human myotilin (MYOT), filamin-C (FLNC), and myozenin-3 (MYOZ3) proteins. In order to do this, the equine protein models used in this disclosure must be compared to the canonical or reference sequence of the human proteins in a public database that captures data from the published literature, such as UniProt.

FIG. 23 shows the alignment of the sequence of a portion of the human MYOT protein with the horse protein sequence SEQ ID NO:9 shown in FIG. 8. The top line (indicated as Human) corresponds to a portion of the human myotilin protein (MYOT) from UniProt Q9UBF9. The second line shows the alignment of the human sequence to the horse sequence SEQ ID NO:9. A single conservative amino acid substitution is seen at amino acid 232. The last line, indicated as MYOT-S232P, shows the position of the S232P nonconservative substitution, at the same position as the conservative substitution between human and horse. The numbering of the amino acid positions in the horse myotilin protein model presented as SEQ ID NO:9 in FIG. 8 corresponds precisely to the numbering of the human amino acid positions in the human myotilin model UniProt Q9UBF9.

FIG. 24 shows the alignment of the sequence of filamin repeat 6 of the human FLNC protein with the horse protein sequences SEQ ID NO:11 and SEQ ID NO:12 shown in FIG. 9. The top line (indicated as Human) corresponds to filamin repeat 6 of human filamin-C protein (FLNC) from UniProt Q14315. The second line shows the alignment of the human sequence to the horse sequences SEQ ID NO:11 and SEQ ID NO:12, which are identical over this region. A single conservative amino acid substitution between human and horse is seen at amino acid 766 in the human sequence. The third line (indicated as ENS) corresponds to filamin repeat 6 of horse filamin-C protein (FLNC) with the numbering of amino acid positions as in SEQ ID NO:11. The fourth line (indicated as XP) corresponds to filamin repeat 6 of horse filamin-C protein (FLNC) with the numbering of amino acid positions as in SEQ ID NO:12. The last line (indicated as E753K) shows the position of the E753K substitution. The equine FLNC-E753K missense allele corresponds to amino acid position 793 in the human FLNC protein, located in filamin repeat 6.

FIG. 25 shows the alignment of the sequence of filamin repeat 11 of the human FLNC protein with the horse protein sequences SEQ ID NO:11 and SEQ ID NO:12 shown in FIG. 9. The top line (indicated as Human) corresponds to filamin repeat 11 of human filamin-C protein (FLNC) from UniProt Q14315. The second line shows the alignment of the human sequence to the horse sequences SEQ ID NO:11 and SEQ ID NO:12, which are identical over this region. Two conservative amino acid substitutions between human and horse are seen at amino acids 1248 and 1332 in the human sequence. The third line (indicated as ENS) corresponds to filamin repeat 11 of horse filamin-C protein (FLNC) with the numbering of amino acid positions as in SEQ ID NO:11. The fourth line (indicated as XP) corresponds to filamin repeat 11 of horse filamin-C protein (FLNC) with the numbering of amino acid positions as in SEQ ID NO:12. The last line (indicated as A1207T) shows the position of the A1207T substitution. The equine FLNC-A1207T missense allele corresponds to amino acid position 1247 in the human FLNC protein, located in filamin repeat 11.

Figures 26, 27:
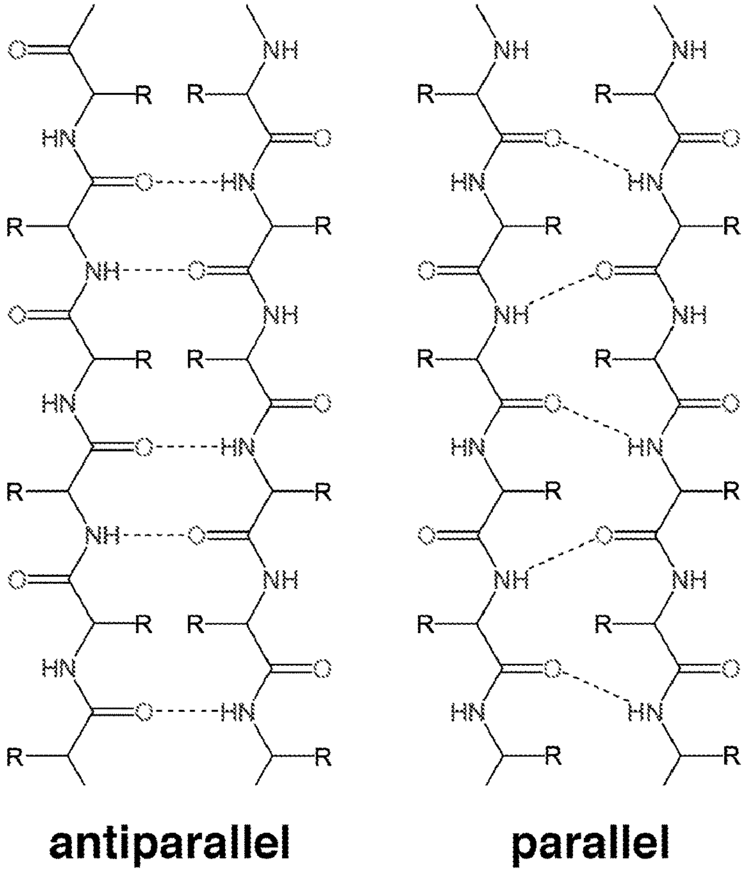
FIG. 26. Comparison of antiparallel and parallel beta sheet protein structures. Beta sheets are held together by hydrogen bonding between N-H groups in the backbone of one strand and the C═O groups in the backbone of the adjacent strand. In an antiparallel beta sheet, the adjacent strands have opposite polarity with respect to the N- and C-termini. In a parallel beta sheet, the adjacent strands have the same polarity with respect to the N- and C-termini. Comparison of the two structures shows that R groups are in close opposition in an antiparallel beta sheet, while R groups in a parallel beta sheet occupy the space between the N—H group and the C═O group of the adjacent strand.
FIG. 27. Alignment of the sequence of a portion of the human MYOZ3 protein with the horse protein sequence SEQ ID NO:15 shown in FIG. 10. The top line (indicated as Human; SEQ ID NO:278) corresponds to a portion of the human myozenin-3 protein (MYOZ3) from UniProt Q8TDC0. The second line shows the alignment of the human sequence to the horse sequence (SEQ ID NO:279). Five nonconservative substitutions are seen at positions 14, 17, 18, 22, and 66. The last line, indicated as MYOZ3-S42L, shows the position of the S42L nonconservative substitution.

The immunoglobulin-like filamin repeats found in filamin C (as well as in the paralogs filamin A and filamin B) are antiparallel beta sheets. FIG. 26 shows the general structure of antiparallel and parallel beta sheets. Beta sheets are held together by hydrogen bonding between N—H groups in the backbone of one strand and the C═O groups in the backbone of the adjacent strand. In an antiparallel beta sheet, the adjacent strands have opposite polarity with respect to the N- and C-termini. In a parallel beta sheet, the adjacent strands have the same polarity with respect to the N- and C-termini. Comparison of the two structures shows that R groups are in close opposition in an antiparallel beta sheet, while R groups in a parallel beta sheet occupy the space between the N—H group and the C═O group of the adjacent strand.

The structure of the antiparallel beta sheet in immunoglobulin-like filamin repeats makes it possible to understand why the equine FLNC-E753K and FLNC-A1207T alleles potentially disrupt the protein structure of filamin C. In the protein encoded by FLNC-E753K, a negatively-charged amino acid, glutamic acid, is replaced by a positively-charged amino acid, lysine. The R groups are relatively large and of comparable size. The R group of the negatively charged glutamic acid in the wild-type filamin C is in close proximity to an unknown R group on the adjacent stand. If the opposite R group is positively charged, the interaction of the R groups in the wild-type protein would stabilize the antiparallel beta sheet of filamin repeat 6. Substitution of the R group of the positively charged amino acid lysine in this position would be expected to be destabilizing.

In the protein encoded by FLNC-A1207T, a hydrophobic amino acid, alanine, is replaced by a polar uncharged amino acid, threonine. The R group of alanine is among the smallest R groups found in amino acids, and would show hydrophobic interactions with seven other amino acids (valine, isoleucine, leucine, methionine, phenylalanine, tyrosine, and tryptophan) with larger R groups. Substitution of the R group of the larger polar uncharged amino acid threonine in this position would be expected to be destabilizing. In addition, the human FLNC-A1539T allele, associated with a dominant pathogenic phenotype, has the same amino acid substitution in a comparable position in filamin repeat 14.

FIG. 27 shows the alignment of the sequence of a portion of the human MYOZ3 protein with the horse protein sequence SEQ ID NO:15 shown in FIG. 10. The top line (indicated as Human) corresponds to a portion of the human myozenin-3 protein (MYOZ3) from UniProt Q8TDCO. The second line shows the alignment of the human sequence to the horse sequence SEQ ID NO:15. Five nonconservative substitutions are seen at positions 14, 17, 18, 22, and 66. The last line, indicated as MYOZ3-S42L, shows the position of the S42L non-conservative substitution. The numbering of the amino acid positions in the horse myozenin-3 protein model presented as SEQ ID NO:15 in FIG. 10 corresponds precisely to the numbering of the human amino acid positions in the human myozenin-3 model UniProt Q8TDCO.

Figure 28:
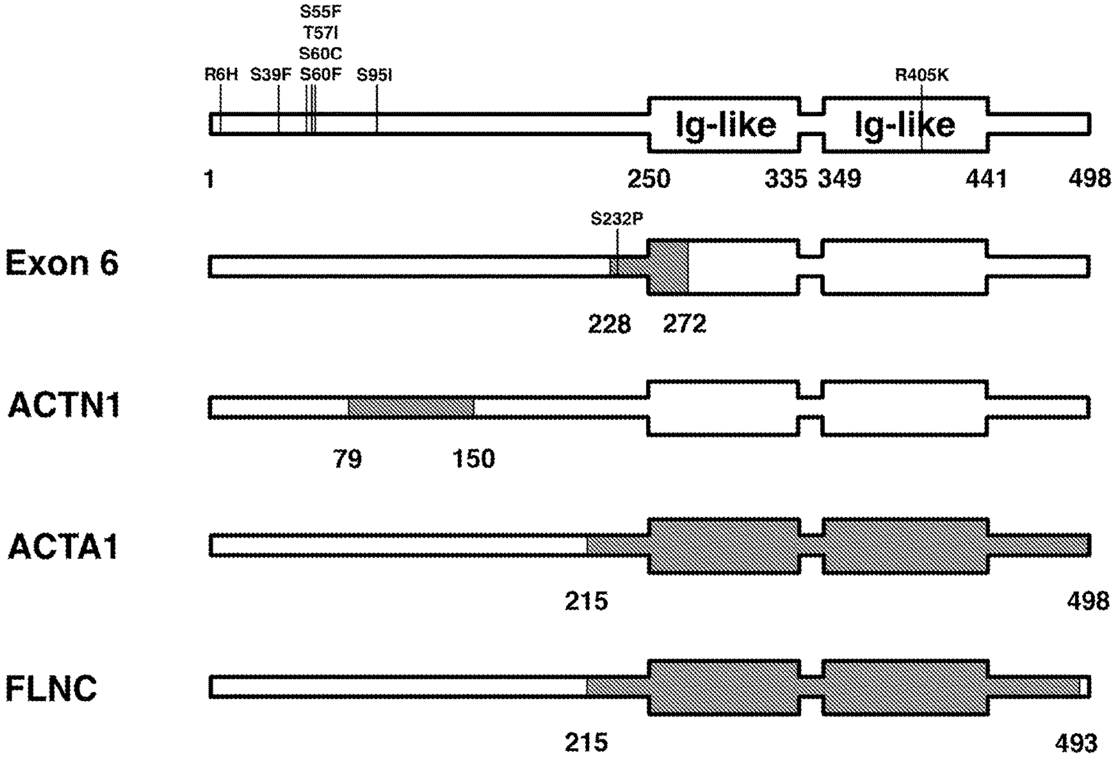
FIG. 28. Features of the human MYOT protein. The top line shows a linear representation of the 498 amino acid human myotilin protein (UniProt Q9UBF9). The locations of pathogenic amino acid substitutions summarized in TABLE 1 are indicated. The second line shows the amino acids encoded by exon 6 (228 to 272), with the position of the equine MYOT-S 323P mutation indicated. The third line shows the region (79 to 150) that has been shown to interact with alpha-actinin (ACTN1). The fourth line shows the region (215 to 498) that has been shown to interact with actin (ACTA1). The last line shows the region (215 to 493) that has been shown to interact with filamin-C (FLNC).

FIG. 28 shows features of the human MYOT protein. The top line shows a linear representation of the 498 amino acid human myotilin protein. The locations of pathogenic amino acid substitutions summarized in TABLE 1 below are indicated. The second line shows the amino acids encoded by exon 6 (228 to 272), with the position of the equine MYOT-S323P mutation indicated. The third line shows the region (79 to 150) that has been shown to interact with alpha-actinin (ACTN1). The fourth line shows the region (215 to 498) that has been shown to interact with actin (ACTA1). The last line shows the region (215 to 493) that has been shown to interact with filamin-C (FLNC).

TABLE 1

Pathogenic variants of human MYOT and the associated diseases.

| MYOT substitution | Disease |
|---|---|
| R6H | Limb-Girdle Muscular Dystrophy, type 1A |
| S39F | Spheroid Body Myopathy |
| S55F | Limb-Girdle Muscular Dystrophy, type 1A; Myofibrillar Myopathy, type 3 |
| T57I | Limb-Girdle Muscular Dystrophy, type 1A |
| S60C | Myofibrillar Myopathy, type 3; Distal Myopathy |
| S60F | Myofibrillar Myopathy, type 3; Distal Myopathy |
| S95I | Myofibrillar Myopathy, type 3 |
| R405K | Limb-Girdle Muscular Dystrophy, type 1A |

All of the pathogenic MYOT alleles listed in TABLE 1 are amino acid substitutions inherited as dominant variants—i.e., individuals heterozygous for the variant and a normal allele are affected. In contrast, mice homozygous for a knock-out allele of MYOT (i.e., a mutation that has been created in vitro that completely eliminates the expression of MYOT) appear normal, with normal viability, fertility, and lifespan. Their muscle capacity does not appear to differ from wild-type mice. They show normal muscle sarcomeric and sarcolemmal integrity. There are no alterations in the heart or other organs of newborn or adult mice homozygous for the MYOT knockout allele. These results suggest that, in mouse, MYOT either plays no role in muscle development or function, or that the MYOT protein is redundant, and proteins encoded by other regions of the genome are capable of fulfilling the role of myotilin when it is absent.

Because human alleles of MYOT with single amino acid substitutions are pathogenic, myotilin may normally be involved in muscle development and function, but that other proteins may substitute for myotilin when it is absent.

Myotilin is one of a group of structural proteins in muscle that are important for the integrity of sarcomeres. The amino terminus of myotilin is unique—i.e., it does not share significant sequence similarity with other proteins—and is rich in serine residues. The carboxy terminus of myotilin is highly conserved within the family, consisting of immunoglobulin (Ig)-like domains similar in amino acid sequence to immunoglobulin (Ig)-like domains in the muscle proteins myosin-binding protein C, titin, palladin, and myopallidin. The immunoglobulin (Ig)-like domains of these proteins are known to bind to actin, myosin, or both, and in myotilin, are involved in homodimer formation. Myotilin is expressed in skeletal and cardiac muscle, where it co-localizes with the actin binding protein alpha-actinin in sarcomeric I bands. It binds F-actin and filamin and interacts directly with alpha-actinin. The regions of the myotilin protein that interact with other proteins have been defined in yeast two-hybrid experiments.

Figure 29:
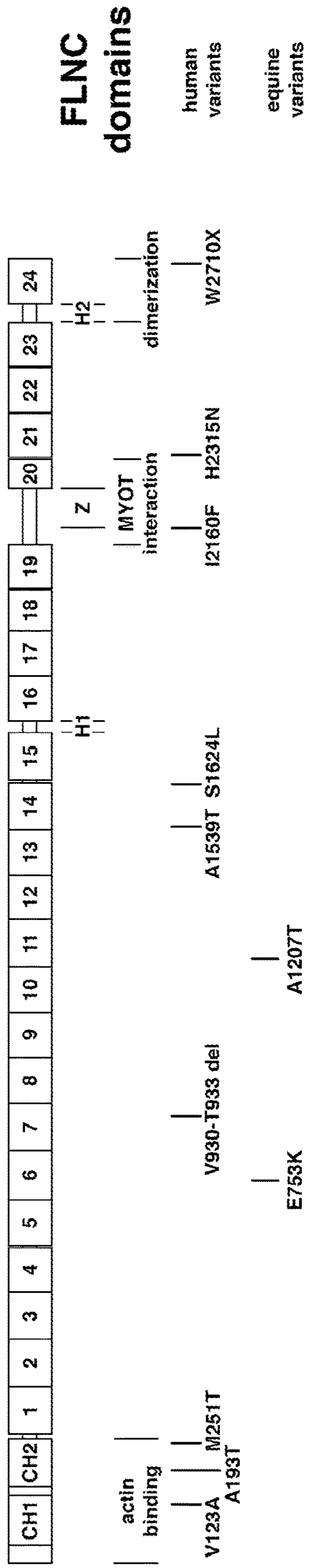
FIG. 29. Features of the human FLNC protein. The top line shows a linear representation of the 2725 amino acid human filamin-C protein (UniProt Q14315) with key features indicated. The actin binding domain with domains CH1 and CH2 is located at the amino terminus. Most of the molecule consists of filamin repeats, numbered 1-24. There are two hinge domains, H1 and H2. Between filamin repeat 19 and the partial filamin repeat 20 is an 82 amino acid region not found in filamin A or filamin B that is required for localization to the Z disc and for interaction with myotilin. The carboxy-terminal region including H2 and filamin repeat 24 is required for dimerization. The locations of pathogenic amino acid substitutions found in human patients and summarized in TABLE 2 are indicated (human variants). The locations of amino acid substitutions found in horses with Polysaccharide Storage Myopathy type 2 (PSSM2), also known as Myofibrillar Myopathy (MFM), are shown in the second line (equine variants). The substitution shown in FIG. 24 is indicated as E753K while the substitution shown in FIG. 25 is indicated as A1207T. The amino acid positions affected by the E753K and A1207T variants in horse correspond to positions 793 and 1247 in the human FLNC sequence represented by Q14315.

FIG. 29 shows features of the human FLNC protein. The top line shows a linear representation of the 2725 amino acid human filamin-C protein (UniProt Q14315) with key features indicated. The actin binding domain with domains CH1 and CH2 is located at the amino terminus. Most of the molecule consists of filamin repeats, numbered 1-24. There are two hinge domains, H1 and H2. Between filamin repeat 19 and the partial filamin repeat 20 is an 82 amino acid region not found in filamin-A or filamin-B that is required for localization to the Z disc and for interaction with myotilin. The carboxy-terminal region including H2 and filamin repeat 24 is required for dimerization. The locations of pathogenic amino acid substitutions found in human patients and summarized in TABLE 2 below are indicated (human variants). The locations of amino acid substitutions found in horses with Polysaccharide Storage Myopathy type 2 (PSSM2), also known as Myofibrillar Myopathy (MFM), are shown in the second line (equine variants). The substitution shown in FIG. 24 is indicated as E753K while the substitution shown in FIG. 25 is indicated as A1207T. The amino acid positions affected by the E753K and A1207T variants in horse correspond to positions 793 and 1247 in the human FLNC sequence represented by UniProt Q14315.

Filamin-C is one of a group of structural proteins in muscle that are important for the development and integrity of sarcomeres. Filamin-C consists of an amino-terminal actin-binding domain, 24 filamin repeats that are structurally similar to immunoglobulin repeats, and a carboxy-terminal dimerization domain. The paralogs filamin-A and filamin-B are actin-binding proteins expressed in a wide variety of tissues whose structure is very similar to filamin C. One unique feature of filamin-C is the insertion of a segment of 82 amino acids between filamin repeat 19 and the partial filamin repeat 20. This segment is required for the targeting of filamin-C to the Z disc and its interaction with myotilin.

Mice homozygous for an allele of FLNC that is missing the last eight exons, encoding a protein that is missing the segment beginning in filamin repeat 20, die shortly after birth due to respiratory failure. They exhibit defects in primary myogenesis including variations in muscle fiber size with centrally located nuclei. Mice heterozygous for the truncated FLNC allele are viable and fertile, and do not exhibit a gross defect in muscle development or function. The protein product of the truncated FLNC allele is expressed at very low levels in both homozygotes and heterozygotes. These results demonstrate that filamin-C is required for the normal development of muscle fibers, and that a hypomorphic (partial loss-of-function) allele is recessive.

Mutations in the FLNC coding region have been shown to cause various myopathies in humans. Most of these diseases are produced by missense alleles (amino acid substitutions), with one example of an in-frame deletion that removes four amino acids. They are inherited as dominant mutations and are fully penetrant—i.e., there are no unaffected individuals heterozygous for the mutant allele. In humans, various mutations in FLNC cause Myofibrillar Myopathy 5, Familial Hypertrophic Cardiomyopathy 26, Distal Myopathy 4, and Familial Restrictive Cardiomyopathy 5. Some of the specific mutations and the disease states produced are summarized in TABLE 2.

TABLE 2

Pathogenic variants of human FLNC and the associated diseases.

| FLNC substitution | Disease |
|---|---|
| V123A | Familial Hypertrophic Cardiomyopathy 26 |
| A193T | Distal Myopathy 4 |
| M251T | Distal Myopathy 4 |
| V930-T933del | Myofibrillar Myopathy 5 |
| A1539T | Familial Hypertrophic Cardiomyopathy 26 |
| S1624L | Familial Restrictive Cardiomyopathy 5 |
| I2160F | Familial Hypertrophic Cardiomyopathy 26 |
| H2315N | Familial Hypertrophic Cardiomyopathy 26 |
| W2710X | Myofibrillar Myopathy 5 |

The in-frame deletion V930-T933del and all of the amino acid substitutions listed in TABLE 2 are pathogenic FLNC alleles inherited as dominant variants—i.e., individuals heterozygous for the variant and a normal allele are affected. Filamin-C is known to function as a dimer. If normal and mutant alleles of filamin-C are expressed at comparable levels, an individual heterozygous for a missense allele is expected to have only 25% fully normal dimers, with 50% of the dimers having one normal and one mutant protein, and 25% having two mutant proteins. This explains why missense alleles are identified as dominant pathogenic variants in humans, while a loss-of-function allele is a recessive lethal mutation in mice.

FIG. 29 also shows the position of the equine FLNC-E753K and FLNC-A1207T alleles found in horses mapped against the amino acid sequence of the human FLNC protein. The evidence used to assign the horse missense alleles to appropriate positions in the human FLNC protein is shown in FIG. 24 and FIG. 25. The equine FLNC-E753K missense allele corresponds to amino acid position 793 in the human FLNC protein, located in filamin repeat 6. The equine FLNC-A1207T missense allele corresponds to amino acid position 1247 in the human FLNC protein, located in filamin repeat 11.

Figure 30:
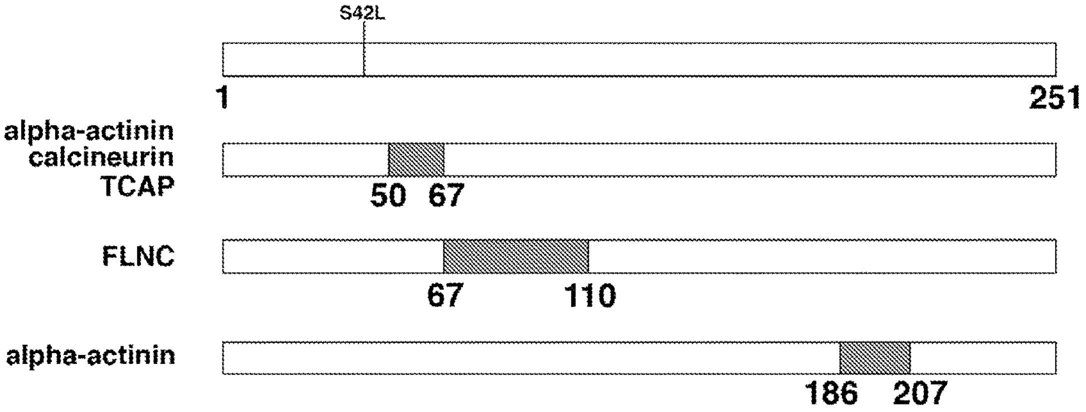
FIG. 30. Features of the human MYOZ3 protein. The top line shows a linear representation of the 251 amino acid human myozenin-3 protein (UniProt Q8TDC0). No pathogenic human alleles are known. The location of the equine MYOZ3-S42L is shown. The second line shows a region of the human MYOZ3 protein shown to bind the alpha-actinin (ACTN1), calcineurin, and telethonin (TCAP) proteins. Calcineurin is a calcium- and calmodulin-dependent serine/threonine protein phosphatase made up of one calmodulin-binding catalytic subunit encoded by three different genes (PPP3CA, PPP3CB, and PPP3CC) and a one regulatory subunit encoded by two different genes (PPP3R1 and PPP3R2). The third line shows a region of the human MYOZ3 protein shown to bind filamin-C (FLNC) protein. The fourth line shows a second region of the human MYOZ3 protein shown to bind alpha-actinin (ACTN1) protein.

FIG. 30 shows features of the human MYOZ3 protein. The top line shows a linear representation of the 251 amino acid human myozenin-3 protein (UniProt Q8TDC0). No pathogenic human alleles are known. The location of the equine MYOZ3-S42L is shown. The second line shows a region of the human MYOZ3 protein shown to bind the alpha-actinin (ACTN1), calcineurin, and telethonin (TCAP) proteins. Calcineurin is a calcium- and calmodulin-dependent serine/threonine protein phosphatase made up of one calmodulin-binding catalytic subunit encoded by three different genes (PPP3CA, PPP3CB, and PPP3CC) and a one regulatory subunit encoded by two different genes (PPP3R1 and PPP3R2). The third line shows a region of the human MYOZ3 protein shown to bind filamin-C (FLNC) protein. The fourth line shows a second region of the human MYOZ3 protein shown to bind alpha-actinin (ACTN1) protein.

Myozenin-3, originally called calsarcin-3, is expressed solely in skeletal muscle. It was identified biochemically as a protein that coimmunoprecipitated with cacineurin, telethonin (TCAP), alpha-actinin-2 (ACTN2), and filamin-C (FLNC). Myozenin-3 interacts with LIM Domain-binding 3 (LDB3) as determined by a yeast two-hybrid assay. Myozenin-3 is localized to the Z disc and may serve to link its various binding proteins at the Z disc.

There is no information on clinically significant alleles of human MYOZ3, and there are currently no mouse knock-out alleles of Myoz3 or other mouse models.

In order to assess the effects of amino acid substitutions resulting from mutations detected in horses with Polysaccharide Storage Myopathy type 2 (PSSM2), also known as Myofibrillar Myopathy, described in this disclosure as MYOT-S232P, FLNC-E753K, FLNC-A1207T, and MYOZ3-S42L, are pathogenic, the predicted sequences of myotilin (MYOT), filamin-C (FLNC), and myozenin-3 (MYOZ3) from diverse organisms were retrieved from GenBank using BLASTP searches with query sequences derived from canonical human sequences. The retrieved sequences were grouped into clusters of identical sequences if any amino acid sequences retrieved from different species were identical. The clustered sequences were aligned using CLUSTAL OMEGA with the default parameters. Amino acids observed in particular positions in the aligned sequences may be fully conserved (no change in the amino acid found at this position is observed in any species), highly conserved (with only highly conservative substitutions, such as serine (S) for threonine (T)), moderately conserved (such as serine (S) for arginine (R)), or not conserved (with nonconservative substitutions such as serine (S) for proline (P)). If substitutions like MYOT-S232P, FLNC-E753K, FLNC-A1207T, and MYOZ3-S42L occur in positions that are poorly conserved across different species, they are not likely to be pathogenic. If, on the other hand, substitutions like MYOT-S232P, FLNC-E753K, FLNC-A1207T, and MYOZ3-S42L occur in positions that are highly conserved across species, and these specific substitutions are not seen in natural populations, it is likely that these substitutions negatively affect muscle function and therefore reproductive fitness, and when they have occurred in natural populations, they have been eliminated by natural selection.

FIG. 31 shows the amino acid sequences of proteins encoded by MYOT genes, centered on the position of the equine MYOT-S232P substitution. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of myotilin in horse with the MYOT-S232P substitution shown and highlighted in bold. The position of the MYOT-S232P substitution is indicated in bold in all of the sequences.

The 99 species in the alignment shown in FIG. 31 are: primate1 [Human (*Homo sapiens*), Chimpanzee (*Pan troglodytes*), Bonobo (*Pan paniscus*), Western lowland gorilla (*Gorilla gorilla gorilla*), Sumatran orangutan (*Pongo abelii*)], primate2 [Crab-eating macaque (*Macaca fascicularis*), Rhesus macaque (*Macaca mulatta*), Drill (*Mandrillus leucophaeus*), Olive baboon (*Papio anubis*), Sooty mangabey (*Cercocebus atys*), Golden snub-nosed monkey (*Rhinopithecus roxellana*)], mammal1 [Horse (*Equus caballus*), Siberian tiger (*Panthera tigris altaica*), Cheetah (*Acinonyx jubatus*), Cat (*Felis catus*), Cape golden mole (*Chrysochloris asiatica*), Ferret (*Mustela putorius furo*)], mammal2 [Cattle (*Bos taurus*), Domestic yak (*Bos mutus*)], mammal3 [Alpaca (*Vicugnapacos*), Bactrian camel (*Camelus ferus*)], mammal4 [Brandt's bat (*Myotis brandtii*), Little brown bat (*Myotis lucifugus*), Big brown bat (*Eptesicus fuscus*)], mammal5 [Bottle-nosed dolphin (*Tursiops truncates*), Orca (*Orcinus orca*)], mammal6 [Polar bear (*Ursus maritimus*), Giant panda (*Ailuropoda melanoleuca*)], mammal7 [Black flying fox (*Pteropus alecto*), Large flying fox (*Pteropus vampyrus*)], mammal8 [Alpine marmot (*Marmota marmota marmota*), Thirteen-lined ground squirrel (*Ictidomys tridecemlineatus*)], White-headed capuchin (*Cebus capucinus imitator*), Green monkey (*Chlorocebus sabaeus*), Gray mouse lemur (*Microcebus murinus*), Northern greater galago (*Otolemur garnettii*), Water buffalo (*Bubalus bubalis*), Norway rat (*Rattus norvegicus*), Naked mole-rat (*Heterocephalus glaber*), Mouflon (*Ovis aries musimon*), North American beaver (*Castor canadensis*), Dog (*Canis lupus familiaris*), Natal long-fingered bat (*Miniopterus natalensis*), Black flying fox (*Pteropus alecto*), Sperm whale (*Physeter catodon*), Florida manatee (*Trichechus manatus latirostris*), Lesser hedgehog tenrec (*Echinops telfairi*), European hedgehog (*Erinaceus europaeus*), Nine-banded armadillo (*Dasypus novemcinctus*), Sunda pangolin (*Manis javanica*), Aardvark (*Orycteropus afer afer*), Gray short-tailed opossum (*Monodelphis domestica*), Tasmanian devil (*Sarcophilus harrisii*), Platypus (*Ornithorhynchus anatinus*), bird1 [Swan goose (*Anser cygnoides domesticus*), Mallard (*Anas platyrhynchos*)], bird2 [Blue-crowned manakin (*Lepidothrix coronata*), Golden-collared manakin (*Manacus vitellinus*)], bird3 [Adelie penguin (*Pygoscelis adeliae*), Japanese quail (*Coturnix japonica*), Common cuckoo (*Cuculus canorus*), Great cormorant (*Phalacrocorax carbo*), American flamingo (*Phoenicopterus ruber ruber*), Red-legged seriema (*Cariama cristata*), Turkey vulture (*Cathartes aura*), Grey crowned crane (*Balearica regulorum gibbericeps*), White-tailed tropicbird (*Phaethon lepturus*), Chuck-will's-widow (*Caprimulgus carolinensis*), Red-throated loon (*Gavia stellata*), Red-crested turaco (*Tauraco erythrolophus*)], bird4 [White-throated sparrow (*Zonotrichia albicollis*), Medium ground finch (*Geospiza fortis*)], bird5 [Atlantic canary (*Serinus canaria*), European starling (*Sturnus vulgaris*), Ground tit (*Pseudopodoces humilis*), Rock dove (*Columba livia*), Ruff (*Calidris pugnax*), Zebra finch (*Taeniopygia guttata*), Rifleman (*Acanthisitta chloris*)], Red junglefowl (*Gallus gallus*), White-tailed eagle (*Haliaeetus albicilla*), White-throated tinamou (*Tinamus guttatus*), Emperor penguin (*Aptenodytes forsteri*), Turkey (*Meleagris gallopavo*), Golden eagle (*Aquila chrysaetos canadensis*), Sunbittern (*Eurypyga helias*), Speckled mousebird (*Colius striatus*), Budgerigar (*Melopsittacus undulatus*), Collared flycatcher (*Ficedula albicollis*), Southern ostrich (*Struthio camelus australis*), North island brown kiwi (*Apteryx australis mantelli*), Northern carmine bee-eater (*Merops nubicus*), Dalmatian pelican (*Pelecanus crispus*), Little egret (*Egretta garzetta*), Barn owl (*Tyto alba*), Peregrine falcon (*Falco peregrinus*), Kea (*Nestor notabilis*), Downy woodpecker (*Picoides pubescens*), Hoatzin (*Opisthocomus hoazin*).

In most of the species shown in FIG. 31, the amino acid affected by the equine MYOT-S 232P variant is a serine (S). The sole exception is the primate1 cluster [Human (*Homo sapiens*), Chimpanzee (*Pan troglodytes*), Bonobo (*Pan paniscus*), Western lowland gorilla (*Gorilla gorilla gorilla*), Sumatran orangutan (*Pongo abelii*)]. The closely related species in the primate1 cluster have a conservative substitution of a threonine (T) for a serine (S) in this position. The equine variant MYOT-S232P is a nonconservative substitution in a highly conserved position, with sequence conservation extending to birds, which diverged from mammals approximately 300 million years ago. Many other positions in the aligned sequences show no conservation over this evolutionary distance. This is evidence that the MYOT-S232P variant is pathogenic, and has been eliminated from populations by natural selection when it has occurred.

FIG. 32 shows the amino acid sequences of filamin repeat 6 of FLNC genes, showing filamin repeat 6, which contains the equine FLNC-E753K substitution. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of filamin repeat 6 in horse with the FLNC-E753K substitution shown and highlighted in bold. The position of the FLNC-E753K substitution is indicated in bold in all of the sequences.

The 124 species in the alignment shown in FIG. 32 are: mammal1 [Human (*Homo sapiens*), Common chimpanzee (*Pan troglodytes*), Bonobo (*Pan paniscus*), Western lowland gorilla (*Gorilla gorilla gorilla*), Sumatran orangutan (*Pongo abelii*), Southern pig-tailed macaque (*Macaca nemestrina*), Olive baboon (*Papio anubis*), White-headed capuchin (*Cebus capucinus imitator*), Coquerel's sifaka (*Propithecus coquereli*), Bolivian Squirrel Monkey (*Saimiri boliviensis boliviensis*), Sooty mangabey (*Cercocebus atys*), Angola colobus (*Colobus angolensis palliates*), Green monkey (*Chlorocebus sabaeus*), Common marmoset (*Callithrix jac-

*chus*), Black snub-nosed monkey (*Rhinopithecus bieti*), Crab-eating macaque (*Macaca fascicularis*), Drill (*Mandrillus leucophaeus*), Rhesus macaque (*Macaca mulatta*), Nancy Ma's night monkey (*Aotus nancymaae*), Golden snub-nosed monkey (*Rhinopithecus roxellana*), Northern greater galago (*Otolemur garnettii*), Damara mole rat (*Fukomys damarensis*), Cape elephant shrew (*Elephantulus edwardii*), Malayan flying fox (*Pteropus vampyrus*), Black flying fox (*Pteropus alecto*), Big brown bat (*Eptesicus fuscus*), Natal long-fingered bat (*Miniopterus natalensis*), Egyptian fruit bat (*Rousettus aegyptiacus*), David's myotis (*Myotis davidii*), Alpaca (*Vicugna pacos*), Goat (*Capra hircus*), Tibetan antelope (*Pantholops hodgsonii*), Mouflon (*Ovis aries musimon*), Dromedary (*Camelus dromedarius*), Bactrian camel (*Camelus bactrianus*), Cattle (*Bos taurus*), Yak (*Bos mutus*), Water buffalo (*Bubalus bubalis*), Giant panda (*Ailuropoda melanoleuca*), Polar bear (*Ursus maritimus*), Dog (*Canis lupus familiaris*), Cat (*Felis catus*), Siberian Tiger (*Panthera tigris altaica*), Wild boar (*Sus scrofa*), White rhinoceros (*Ceratotherium simum simum*), Weddell seal (*Leptonychotes weddellii*), West Indian manatee (*Trichechus manatus latirostris*), Minke whale (*Balaenoptera acutorostrata scammoni*), Baiji (*Lipotes vexillifer*), Killer whale (*Orcinus orca*), Sperm whale (*Physeter catodon*), Aardvark (*Orycteropus afer afer*), Sunda pangolin (*Manis javanica*)], mammal2 [Horse (*Equus caballus*), Donkey (*Equus asinus*), Przewalski's horse (*Equus przewalskii*)], mammal3 [Gray mouse lemur (*Microcebus murinus*), Brown rat (*Rattus norvegicus*), Upper Galilee Mountains blind mole-rat (*Nannospalax galili*), Ord's kangaroo rat (*Dipodomys ordii*), Lesser hedgehog tenrec (*Echinops telfairi*), Platypus (*Ornithorhynchus anatinus*)], mammal4 [Mouse (*Mus musculus*), Prairie vole (*Microtus ochrogaster*)], mammal5 [Little brown bat (*Myotis lucifugus*), Brandt's bat (*Myotis brandtii*)], Philippine tarsier (*Carlito syrichta*), Chinese hamster (*Cricetulus griseus*), Star-nosed mole (*Condylura cristata*), marsupial1 [Gray short-tailed opossum (*Monodelphis domestica*), Tasmanian devil (*Sarcophilus harrisii*)], bird1 [Atlantic canary (*Serinus canaria*), Ground tit (*Pseudopodoces humilis*), Common starling (*Sturnus vulgaris*), Great tit (*Panus major*), Medium ground finch (*Geospiza fortis*), American crow (*Corvus brachyrhynchos*)], bird2 [Peregrine falcon (*Falco peregrinus*), Saker falcon (*Falco cherrug*), Downy woodpecker (*Picoides pubescens*)], bird3 [Blue-fronted amazon (*Amazona aestiva*), Budgerigar (*Melopsittacus undulatus*)], Bald eagle (*Haliaeetus leucocephalus*), Chinese goose (*Anser cygnoides domesticus*), Common cuckoo (*Cuculus canorus*), Rock dove (*Columba livia*), Collared flycatcher (*Ficedula albicollis*), Blue-crowned manakin (*Lepidothrix coronata*), Burmese python (*Python bivittatus*), Taiwan habu (*Protobothrops mucrosquamatus*), Green sea turtle (*Chelonia mydas*), Painted turtle (*Chrysemys picta bellii*), Schlegel's Japanese gecko (*Gekko japonicas*), Carolina anole (*Anolis carolinensis*), American alligator (*Alligator mississippiensis*), Western clawed frog (*Xenopus tropicalis*), African clawed frog (*Xenopus laevis*), High Himalaya frog (*Nanorana parkeri*), fish1 [Zebrafish (*Danio rerio*), Horned golden-line barbel (*Sinocyclocheilus rhinocerous*), Golden-line barbel (*Sinocyclocheilus grahami*), Common carp (*Cyprinus carpio*)], fish 2 [Zebra mbuna (*Maylandia zebra*), Lake Tanganyika cichlid (*Neolamprologus brichardi*), Burton's mouthbrooder (*Haplochromis burtoni*), Nile tilapia (*Oreochromis niloticus*)], fish 3 [Channel catfish (*Ictalurus punctatus*), Red-bellied piranha (*Pygocentrus nattereri*)], fish4 [Rainbow trout (*Oncorhynchus mykiss*), Atlantic salmon (*Salmo salar*)], Spotted gar (*Lepisosteus oculatus*), Tongue sole (*Cynoglossus semilaevis*), Turquoise killifish (*Nothobranchius furzeri*), Large yellow croaker (*Larimichthys crocea*), Asian arowana (*Scleropages formosus*), Barramundi (*Lates calcarifer*), Atlantic herring (*Clupea harengus*), Lake Victoria cichlid (*Pundamilia nyererei*), Bicolor damselfish (*Stegastes partitus*), Eyeless goldenline fish (*Sinocyclocheilus anshuiensis*), Northern pike (*Esox lucius*), Mexican tetra (*Astyanax mexicanus*), West Indian Ocean coelacanth (*Latimeria chalumnae*), Australian ghostshark (*Callorhinchus milii*).

In most of the species shown in FIG. 32, the amino acid affected by the equine FLNC-E753K variant is a glutamic acid (E). Only two species, Carolina anole (*Anolis carolinensis*), and Australian ghostshark (*Callorhinchus milii*), have an amino acid substitution at this position. In both cases, it is a conservative substitution of an aspartic acid (D) for a glutamic acid (E), the conservative substitution of one negatively charged amino acid for another. This is distinctly different from the substitution of lysine (K) for glutamic acid (E) found in the FLNC-E753K variant, a nonconservative substitution of a positively charged amino acid for a negatively charged one. The equine variant FLNC-E753K is a nonconservative substitution in a highly conserved position, with sequence conservation extending to cartilaginous fishes, which diverged from mammals over 500 million years ago. This is evidence that the FLNC-E753K variant is pathogenic, and has been eliminated from populations by natural selection when it has occurred.

FIG. 33 shows the amino acid sequences encoded by FLNC genes, showing filamin repeat 11, which contains the equine FLNC-A1207T substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of filamin repeat 11 in horse with the FLNC-A1207T substitution shown and highlighted in bold. The position of the FLNC-A1207T substitution is indicated in bold in all of the sequences.

The 106 species in the alignment shown in FIG. 33 are: mammal1 [Human (*Homo sapiens*), Common chimpanzee (*Pan troglodytes*), Bonobo (*Pan paniscus*), Western lowland gorilla (*Gorilla gorilla gorilla*), Sumatran orangutan (*Pongo abelii*), Olive baboon (*Papio anubis*), Angola colobus (*Colobus angolensis palliatus*), Black snub-nosed monkey (*Rhinopithecus bieti*), Sooty mangabey (*Cercocebus atys*), Green monkey (*Chlorocebus sabaeus*), Drill (*Mandrillus leucophaeus*), Crab-eating macaque (*Macaca fascicularis*), Rhesus macaque (*Macaca mulatta*), Nancy Ma's night monkey (*Aotus nancymaae*), Southern pig-tailed macaque (*Macaca nemestrina*), Philippine tarsier (*Carlito syrichta*), Ord's kangaroo rat (*Dipodomys ordii*)], mammal2 [Horse (*Equus caballus*), Przewalski's horse (*Equus przewalskii*), Donkey (*Equus asinus*), Gray mouse lemur (*Microcebus murinus*), Coquerel's sifaka (*Propithecus coquereli*)], mammal3, [Malayan flying fox (*Pteropus vampyrus*), Big brown bat (*Eptesicus fuscus*), David's myotis (*Myotis davidii*), Black flying fox (*Pteropus alecto*), Mouse (*Mus musculus*), Prairie vole (*Microtus ochrogaster*), Aardvark (*Orycteropus afer afer*), Brandt's bat (*Myotis brandtii*), Bolivian Squirrel Monkey (*Saimiri boliviensis boliviensis*), Polar bear (*Ursus maritimus*), Chinese hamster (*Cricetulus griseus*), Brown rat (*Rattus norvegicus*), Giant panda (*Ailuropoda melanoleuca*), Sunda pangolin (*Manis javanica*), Egyptian fruit bat (*Rousettus aegyptiacus*)], mammal4 [Baiji (*Lipotes vexillifer*), Siberian Tiger (*Panthera tigris altaica*), Cat (*Fells catus*), Wild boar (*Sus scrofa*), Sperm whale (*Physeter catodon*), Star-nosed mole (*Condylura cristata*), Tasmanian devil (*Sarcophilus harrisii*), Alpaca (*Vicugna pacos*), Bactrian camel (*Camelus bactrianus*), Dromedary (*Camelus dromedarius*)], mammal5 [Cattle (*Bos taurus*), Yak (*Bos mutus*), Water buffalo (*Bubalus bubalis*), Mouflon (*Ovis aries musimon*), Goat (*Capra hircus*)], mammal6 [Common marmoset (*Callithrix jacchus*), Natal long-fingered bat (*Miniopterus natalensis*), Lesser hedgehog tenrec (*Echinops telfairi*)], mammal7 [Dog (*Canis lupus familiaris*), Weddell seal (*Leptonychotes weddellii*)], mammal8 [West Indian manatee (*Trichechus manatus latirostris*), White rhinoceros (*Ceratotherium simum simum*)], mammal9 [Northern greater galago (*Otolemur garnettii*), Upper Galilee Mountains blind mole-rat (*Nannospalax galili*)], Coquerel's sifaka (*Balaenoptera acutorostrata scammoni*), White-headed capuchin (*Cebus capucinus imitator*), Little brown bat (*Myotis lucifugus*), Damara mole-rat (*Fukomys damarensis*), Killer whale (*Orcinus orca*), Gray short-tailed opossum (*Monodelphis domestica*), Platypus (*Ornithorhynchus anatinus*), bird1 [Peregrine falcon (*Falco peregrinus*), Saker falcon (*Falco cherrug*)], bird2 [Ground tit (*Pseudopodoces humilis*), Great tit (*Panus major*)], bird3 [Medium ground finch (*Geospiza fortis*), Atlantic canary (*Serinus canaria*)], Downy woodpecker (*Picoides pubescens*), Rock dove (*Columba livia*), Budgerigar (*Melopsittacus undulatus*), Common starling (*Sturnus vulgaris*), American crow (*Corvus brachyrhynchos*), Blue-crowned manakin (*Lepidothrix coronata*), Collared flycatcher (*Ficedula albicollis*), Common cuckoo (*Cuculus canorus*), Painted turtle (*Chrysemys picta bellii*), Western clawed frog (*Xenopus tropicalis*), African clawed frog (*Xenopus laevis*), High Himalaya frog (*Nanorana parkeri*), Taiwan habu (*Protobothrops mucrosquamatus*), Burmese python (*Python bivittatus*), Carolina anole (*Anolis carolinensis*), American alligator (*Alligator mississippiensis*), Green sea turtle (*Chelonia mydas*), fish1 [Eyeless goldenline fish (*Sinocyclocheilus anshuiensis*), Golden-line barbel (*Sinocyclocheilus rhinocerous*)], Golden-line barbel (*Sinocyclocheilus grahami*), Large yellow croaker (*Larimichthys crocea*), Red-bellied piranha (*Pygocentrus nattereri*), Mexican tetra (*Astyanax mexicanus*), Common carp (*Cyprinus carpio*), Channel catfish (*ktalurus punctatus*), Atlantic herring (*Clupea harengus*), Rainbow trout (*Oncorhynchus mykiss*), Atlantic salmon (*Salmo salar*), Northern pike (*Esox lucius*), Spotted gar (*Lepisosteus oculatus*), West Indian Ocean coelacanth (*Latimeria chalumnae*), Australian ghostshark (*Callorhinchus milii*).

In all of the species presented in FIG. 33, the amino acid affected by the equine FLNC-A1207T variant is an alanine (A). Only the equine FLNC-A1207T variant has a substitution of a threonine (T) at this position; this is a nonconservative substitution of a polar uncharged amino acid for a hydrophobic one. The sequence conservation at this position extends to cartilaginous fishes, which diverged from mammals over 500 million years ago. This is evidence that the FLNC-A1207T variant is pathogenic, and has been eliminated from populations by natural selection when it has occurred.

FIG. 34 shows the amino acid sequences of proteins encoded by MYOZ3 genes, centered on the position of the equine MYOZ3-S42L substitution. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the sequence of myozenin-3 in horse with the MYOZ3-S42L substitution shown and highlighted in bold. The position of the MYOZ3-S42L substitution is indicated in bold in all of the sequences.

The 88 species in the alignment shown in FIG. 34 are: mammal1 [Human (*Homo sapiens*), Bonobo (*Pan paniscus*), Western lowland gorilla (*Gorilla gorilla gorilla*), Northern white-cheeked gibbon (*Nomascus leucogenys*), Nancy Ma's night monkey (*Aotus nancymaae*)], mammal2 [Olive baboon (*Papio anubis*), Rhesus macaque (*Macaca mulatta*), Crab-eating macaque (*Macaca fascicularis*), Black snub-nosed monkey (*Rhinopithecus bieti*), Sooty mangabey (*Cercocebus atys*), Angola colobus (*Colobus angolensis palliates*), Golden snub-nosed monkey (*Rhinopithecus roxellana*)], mammal3 [White-headed capuchin (*Cebus capucinus imitator*), Black-capped squirrel monkey (*Saimiri boliviensis boliviensis*)], mammal4 [Horse (*Equus caballus*), Donkey (*Equus asinus*)], mammal5 [Bottle-nosed dolphin (*Tursiops truncates*), Domestic yak (*Bos mutus*), Baiji (*Lipotes vexillifer*)], mammal6 [Weddell seal (*Leptonychotes weddellii*), Walrus (*Odobenus rosmarus divergens*)], mammal7 [Cattle (*Bos taurus*), Water buffalo (*Bubalus bubalis*), Killer whale (*Orcinus orca*), American bison (*Bison bison bison*), Tibetan antelope (*Pantholops hodgsonii*), Goat (*Capra hircus*)], mammal8 [Large flying fox (*Pteropus vampyrus*), Black flying fox (*Pteropus alecto*)], bird1 [Common starling (*Sturnus vulgaris*), Medium ground finch (*Geospiza fortis*), Collared flycatcher (*Ficedula albicollis*)], Coquerel's sifaka (*Propithecus coquereli*), Sumatran orangutan (*Pongo abelii*), Common marmost (*Callithrix jacchus*), Rhesus macaque (*Macaca mulatta*), Green monkey (*Chlorocebus sabaeus*), Bactrian camel (*Camelus bactrianus*), Alpaca (*Vicugnapacos*), Polar bear (*Ursus maritimus*), Giant panda (*Ailuropoda melanoleuca*), Natal long-fingered bat (*Miniopterus natalensis*), White rhinoceros (*Ceratotherium simum simum*), Ferret (*Mustela putorius furo*), Cat (*Felis catus*), Cheetah (*Acinonyx jubatus*), Dog (*Canis lupus familiaris*), Siberian tiger (*Panthera tigris altaica*), American pika (*Ochotona princeps*), European rabbit (*Oryctolagus cuniculus*), Thirteen-lined ground squirrel (*Ictidomys tridecemlineatus*), Alpine marmot (*Marmota marmota marmota*), Chinese tree shrew (*Tupaia chinensis*), Sperm whale (*Physeter catodon*), Leopard (*Panthera pardus*), Tasmanian devil (*Sarcophilus harrisii*), Damaraland mole-rat (*Fukomys damarensis*), Burmese python (*Python bivittatus*), Chinese softshell turtle (*Pelodiscus sinensis*), Painted turtle (*Chrysemys picta bellii*), Green turtle (*Chelonia mydas*), Carolina anole (*Anolis carolinensis*), American alligator (*Alligator mississippiensis*), Ruff (*Calidris pugnax*), MacQueen's bustard (*Chlamydotis macqueenii*), Gray short-tailed opossum (*Monodelphis domestica*), Downy woodpecker (*Picoides pubescens*), Dalmatian penguin (*Pelecanus crispus*), Killdeer (*Charadrius vociferus*), Adelie penguin (*Pygoscelis adeliae*), Crested ibis (*Nipponia nippon*), Little egret (*Egretta garzetta*), Turkey vulture (*Cathartes aura*), Zebra finch (*Taeniopygia guttata*), American crow (*Corvus brachyrhynchos*), Rock dove (*Columba livia*), Chimney swift (*Chaetura pelagica*), Emperor penguin (*Aptenodytes forsteri*), Red-crested turaco (*Tauraco erythrolophus*), Chinese alligator (*Alligator sinensis*), Ostrich (*Struthio camelus australis*), White-throated tinamou (*Tinamus guttatus*), Ground tit (*Pseudopodoces humilis*), Atlantic canary (*Serinus canaria*), Great tit (*Panus major*), White-throated sparrow (*Zonotrichia albicollis*), Common cuckoo (*Cuculus canorus*), North Island brown kiwi (*Apteryx australis mantelli*).

In all of the species presented in FIG. 34, the amino acid affected by the equine MYOZ3-S42L variant is a serine (S). Only the equine MYOZ3-S42L variant has a substitution of a leucine (L) at this position; this is a nonconservative substitution of a hydrophobic amino acid for a polar uncharged one. The sequence conservation at this position extends to birds, which diverged from mammals 300 million years ago. This is evidence that the MYOZ3-S42L variant is pathogenic, and has been eliminated from populations by natural selection when it has occurred.

Phenotypic effects of the MYOT-S232P, FLNC-E753K, FLNC-A1207T, and MYOZ3-S42L variants The MYOT-S232P variant (hereafter abbreviated as P2) was discovered by analysis of whole genome sequencing data from six Quarter Horses diagnosed via muscle biopsy with Polysaccharide Storage Myopathy type 2 (PSSM2). All six individuals were heterozygous, that is, n/P2. The FLNC-E753K and FLNC-A1207T variants (hereafter abbreviated as P3a and P3b, respectively) were discovered by analysis of whole genome sequencing data from two Thoroughbreds diagnosed via muscle biopsy with either Polysaccharide Storage Myopathy type 2 (PSSM2) or Myofibrillar Myopathy (MFM). Both individuals were heterozygous, that is n/P3a n/P3b. Subsequent genotyping of additional cases shows that the two FLNC variants are inherited together as a single haplotype (hereafter abbreviated P3). The MYOZ3-S42L variant (hereafter abbreviated as P4) was discovered by analysis of whole genome sequencing data from two horses, a Paso Fino and a Quarter Horse. In both cases, one parent had contributed the P2 variant and the other parent had contributed the P4 variant. Both n/P2 n/P4 horses were symptomatic, while both owners reported that both parents in both cases were apparently asymptomatic.

All three variants (treating FLNC-E753K+FLNC-A1207T as a single haplotype designated P3) behave as semidominant variants with incomplete penetrance. Homozygotes have been observed for each variant (P2/P2, P3/P3, and P4/P4); in each case, the phenotype of homozygous individuals is more severe than that of heterozygotes, with an earlier age of onset and more severe symptoms.

All possible compound heterozygotes with two variants (n/P2 n/P3, n/P2 n/P4, and n/P3 n/P4) have been identified. In addition, some horses homozygous for one variant and heterozygous for a second variant (P2/P2 n/P3, n/P2 P3/P3, P3/P3 n/P4, and n/P3 P4/P4) and have been identified. Some of these horses have been severely affected, with one P2/P2 n/P3 being euthanized following recumbency as a yearling.

The following account of symptoms is a generalization; the symptoms produced by the P2, P3, and P4 variants are similar.

One of the earliest symptoms is a change in behavior apparently associated with pain. Owners note a difference in temperament, with horses reacting badly to being ridden or even saddled. Common behaviors include biting at the flanks or even at the rider or trainer, and bucking, rearing, and other displays of resistance that trainers often blame on lack of discipline from the owner.

Another early symptom is stifle problems. The stifle is the largest joint in the horse's body, equivalent to the human knee, but in contrast to the human knee, the equine stifle is held at an angle when the horse is standing still. Stifle problems commonly result from injury or arthritis, degenerative joint disease, or injury. In stifle problems resulting from Polysaccharide Storage Myopathy type 2 (PSSM2), there will be no radiographic findings. Stifle problems are one example of shifting lameness. A horse with Polysaccharide Storage Myopathy type 2 (PSSM2) will exhibit lameness that appears first in one limb, then another. There will be no radiographic findings.

Changes in gait are often apparent. These include stiffness in the hindquarters and limited range of motion of the hind legs ("short-gaited"). At canter, disunited canter ("cross-firing") and "bunny hopping" (bringing both hind legs forward at the same time) are seen. "Rope walking" (placing one foot directly in front of the other along the centerline as if walking a tightrope) is sometimes seen in all for legs or in the rear legs only.

Other gait changes resulting from weakness in the hind limbs are described by horse owners as "heavy on the forehand, not able to come from behind." This means that the horse's gait is altered in such a way that it appears to be pulling itself forward with its front hooves instead of pushing from the rear. Farriers note this as a pattern of wear in the front hooves for unshod horses.

Muscle wasting in the hindquarters (pelvic girdle and proximal limb) and in the topline (shoulder girdle) becomes evident as symptoms progress. Owners report that they are able to partially reverse this symptom by dietary supplementation with complete protein (whey or soy) or with essential amino acids typically limiting in plant protein (lysine, methionine, and threonine). Events that cause negative nitrogen balance, such as viral infections or an injury requiring stitches, can trigger a rapid loss of muscle mass, quickly reversing gains made through dietary supplementation.

Some horses exhibit "divots," focal muscle atrophy that can sometimes be reversed through dietary supplementation with complete protein or essential amino acids typically limiting in plant protein. The locations of focal muscle atrophy are typically asymmetric, appearing on one side only. Some horses exhibit a washboard-like pattern of focal muscle atrophy.

There are reports of respiratory difficulty in the end stages of Polysaccharide Storage Myopathy type 2 (PSSM2), and in one case, a necropsy revealed that the diaphragm was affected. The end stage of symptoms typically involves recumbency, with either all four limbs affected or the hind limbs only. In the latter case, the horse may attempt to retain an upright stance by supporting its hindquarters on a fence or wall.

Many owners report that as symptoms progress, veterinarians are perplexed by the appearance of these symptoms of muscle wasting while blood work shows levels of serum creatine kinase (CK) and aspartate aminotransferase (AST) that are frequently in the normal range.

There is no evidence of cardiomyopathy.

Muscle wasting in the hindquarters (pelvic girdle and proximal limb) and topline (shoulder girdle) in Polysaccharide Storage Myopathy type 2 (PSSM2) or Myofibrillar Myopathy (MFM) appears similar to human cases of Limb-Girdle Muscular Dystrophy, a genetically diverse group of disorders with similar clinical features. Human patients with Limb-Girdle Muscular Dystrophy also develop gait abnormalities as symptoms progress.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

This is illustrated by the following examples. It is to be understood that the particular examples, materials, amounts, and procedures are to be interpreted broadly in accordance with the scope and spirit of the invention as set forth herein.

EXAMPLES

Example 1—Method of Detecting DNA Mutations Associated with Equine Polysaccharide Storage Myopathy type 2 (PSSM2), also known as Myofibrillar Myopathy (MFM)

The complete DNA sequence of the horse MYOT, FLNC, and MYOZ3 coding regions were obtained from the current version of the public horse genome assembly (EquCab2).

Using the MYOT, FLNC, and MYOZ3 sequences, PCR primers are developed that can amplify the sites of genomic DNA containing MYOT-S232P, FLNC-E753K, FLNC-A1207T, and MYOZ3-S42L mutations. For example, a PCR primer pair that has been successfully and reliably used to amplify the region including MYOT-S232P from isolated horse DNA samples lies in the region around exon 6 (FIG. 11). These sequences are 5'-TATGACAATGGAAAGGGAATTC-3' (SEQ ID NO:19) and 5'-TTCTCAAGCTGTGGAGCAAG-3' (SEQ ID NO:20). A PCR primer pair that has been successfully and reliably used to amplify the region including FLNC-E753K from isolated horse DNA samples lies in the region around exon 15 (FIG. 12). These sequences are 5'-GGCAGTCACCCTGAGAAAGT-3' (SEQ ID NO:23) and 5'-ACTTGATGCCAATGCTCAC-3' (SEQ ID NO:24). A PCR primer pair that has been successfully and reliably used to amplify the region including FLNC-A1207T from isolated horse DNA samples lies in the region around exon 21 (FIG. 13). These sequences are 5'-GGTGCTGATCCACAACAATG-3' (SEQ ID NO:27) and 5'-CCCAAGTCCTCCCTTCAGAC-3' (SEQ ID NO:28). A PCR primer pair that has been successfully and reliably used to amplify the region including MYOZ3-S42L from isolated horse DNA samples lies in the region around exon 3 (FIG. 14). These sequences are 5'-CAGGTTTCTCACACACAATGG-3' (SEQ ID NO:31) and 5'-AGGCATTCTGCATTTTCCAC-3' (SEQ ID NO:32). Many other primer pairs are also possible.

Using the above PCR primers to amplify the two regions, the genotype of any horse (A/A, A/G, or G/G for the DNA sequence of the forward strand at chr14:38,519,183, and S/S, S/P, or P/P for the amino acid sequence of the MYOT-S232P variant, G/G, G/A, or A/A for the DNA sequence of the forward strand at chr4:83,736,244, and E/E, E/K, and K/K for the amino acid sequence of the FLNC-E753K variant, G/G, G/A, or A/A for the DNA sequence of the forward strand at chr4:83,738,769, and A/A, A/T, or T/T for the amino acid sequence of the FLNC-A1207T variant, or G/G, G/A, or A/A for the DNA sequence of the forward strand at chr14:27,399,222, and S/S, S/L, or L/L for the amino acid sequence of the MYOZ3-S42L variant) can be obtained. In this method, the amplified DNA may be cloned and then sequenced or sequenced directly without cloning. Alternatively, the appearance of amplified product in the presence of primers specific to the wild type or mutant allele may be monitored in real time using a qPCR instrument designed for this purpose. Many other methods of detecting the nucleotides at the positions of the horse MYOT, FLNC, and MYOZ3 sequence are possible.

DNA testing based on now provides veterinarians and veterinary pathologists with a means to more accurately determine if a horse with the clinical signs of Polysaccharide Storage Myopathy type 2 (PSSM2), also known as Myofibrillar Myopathy (MFM), has the heritable and common form of the disease that can be specifically attributed to the MYOT-S232P, FLNC-E753K, FLNC-A1207T, or MYOZ3-S42L coding region mutations. All that is needed are a tissue sample containing the individual's DNA (typically hair root or blood) and appropriate PCR and sequence analysis technology to detect the four distinct nucleotide changes. Such PCR primers are based in MYOT exon 6 and the flanking intron sequences, as shown in FIG. 11, FLNC exons 15 and 21 and their flanking intron sequences as shown in FIG. 12 and FIG. 13, and MYOZ3 exon 3 and the flanking intron sequences, as shown in FIG. 14, or in other DNA sequences of these genes.

Also, DNA testing provides owners and breeders with a means to determine if any horse can be expected to produce offspring with this form of Polysaccharide Storage Myopathy type 2 (PSSM2), also known as Myofibrillar Myopathy (MFM). Abbreviating the MYOT-S232P allele as P2, the FLNC-E753K+FLNC-A1207T allele as P3, and the MYOZ3-S42L allele as P4, and the wild-type alleles (MYOT-S232, FLNC-E753+FLNC-A1207, and MYOZ3-S42) as n; a P2/P2, P3/P3, or P4/P4 horse would produce an affected foal 100% of the time, while an n/P2, n/P3, or n/P4 horse would produce an affected foal 50% of the time when mated to an n/n horse. Mating of an n/P2 horse to an n/P2 horse, an n/P3 horse to an n/P3 horse, or an n/P4 horse to an n/P4 horse would produce an affected foal 75% of the time. Breeding programs could incorporate this information in the selection of parents that could eventually reduce and even eliminate this form of Polysaccharide Storage Myopathy type 2 (PSSM2), also known as Myofibrillar Myopathy (MFM), in their herds.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of mating a horse comprising:

(a) detecting in a biological sample obtained from said horse, the biological sample comprising nucleic acids that include the coding regions for myotilin (MYOT), filamin-C(FLNC) and myozenin-3 (MYOZ3):

1) a guanine (G) or an adenine (A) at nucleotide 1001 of the forward strand of SEQ ID NO:1, wherein detection of the guanine indicates the presence of variant P2;

2) an adenine (A) or a guanine (G) at nucleotide 1001 of SEQ ID NO:2, wherein detection of the adenine indicates the presence of variant P3a,;

3) an adenine (A) or a guanine (G) at nucleotide 1001 of SEQ ID NO:3, wherein detection of the adenine indicates the presence of variant P3b; and 4) an adenine (A) or a guanine (G) at nucleotide 1001 of the forward strand of SEQ ID NO:4, wherein detection of the adenine indicates the presence of variant P4;

wherein in each case the presence of the specified nucleotide can be inferred from detecting the nucleotide present at the complement thereof;

wherein said horse is not homozygous for the presence of P2, P3a, P3b or P4;

wherein and said horse is heterozygous for at least one of P2, P3a, P3b or P4; and (b) mating said horse with a mare or sire.

2. The method according to claim 1 wherein said mare or sire is free from variants P2, P3a, P3b and P4.

3. The method according to claim 1 wherein said mare or sire is heterozygous for variant P2, P3a, P3b or P4.

4. The method of claim 1, further comprising:

contacting the nucleic acids of the sample with at least one oligonucleotide probe to form a hybridized nucleic acid; and amplifying the hybridized nucleic acid.

5. The method of claim 4, wherein:

Exon 6 of the equine myotilin coding region (MYOT) or a portion thereof is amplified; Exon 15 of the equine filamin-C coding region (FLNC) or a portion thereof is amplified; exon 21 of the equine filamin-C coding region (FLNC) or a portion thereof is amplified and exon 3 of the equine myozenin-3 coding region (MYOZ3), or a portion thereof is amplified.

6. The method according to claim 5, wherein the nucleic acid is genomic DNA.

7. The method according to claim 5, wherein the nucleic acid is RNA.

8. The method according to claim 7, wherein the method comprises converting the RNA into DNA by reverse transcriptase.

9. The method of claim 4, wherein the hybridized nucleic acid is amplified using polymerase chain reaction, strand displacement amplification, ligase chain reaction, or nucleic acid sequence-based amplification.

10. The method according to claim 9, wherein the nucleic acid is genomic DNA.

11. The method according to claim 9, wherein the nucleic acid is RNA.

12. The method according to claim 11, wherein the method comprises converting the RNA into DNA by reverse transcriptase.

13. The method of claim 4, wherein said at least one oligonucleotide probe is immobilized on a solid surface or a semisolid surface.

14. The method according to claim 13, wherein the nucleic acid is genomic DNA.

15. The method according to claim 13, wherein the nucleic acid is RNA.

16. The method according to claim 15 wherein the method comprises converting the RNA into DNA by reverse transcriptase.

17. A method according to claim 4, wherein the nucleic acid is genomic DNA.

18. The method according to claim 4, wherein the nucleic acid is RNA.

19. The method according to claim 18, wherein the method comprises converting the RNA into DNA by reverse transcriptase.

20. The method according to claim 1, wherein the nucleic acid is genomic DNA.

21. The method according to claim 1, wherein the nucleic acid is RNA.

22. The method according to claim 21, wherein the method comprises converting the RNA into DNA by reverse transcriptase.

23. The method according to claim 21, wherein the method comprises detecting in said nucleic acid:

(1) a cytosine (C) or a thymine (T) at nucleotide position 694 of SEQ ID NO: 5, wherein detection of the cytosine indicates the presence of variant P2;

(2) an adenine (A) for a guanine (G) at nucleotide position 2257 of SEQ ID NO: 6, wherein detection of the adenine indicates the presence of variant P3a;

(3) an adenine (A) for a guanine (G) at nucleotide position 3619 of SEQ ID NO: 6, wherein detection of the adenine indicates the presence of variant P3b, and (4) a thymine (T) for cytosine (C) at nucleotide position 125 of SEQ ID NO: 8, wherein detection of the thymine indicates the presence of variant P4;

wherein in each case the presence of the nucleotide can be inferred from detecting the nucleotide present at the complement thereof;

wherein said horse is not homozygous for the presence of P2, P3a, P3b or P4;

wherein said horse is heterozygous for at least one of P2, P3a, P3b or P4; and (b) mating said horse with a mare or sire.

24. The method according to claim 23 wherein said mare or sire is free from variants P2, P3a, P3b and P4.

25. The method according to claim 23 wherein said mare or sire is heterozygous for variant P2, P3a, P3b or P4.

26. A method of mating a horse (a) detecting in a biological sample obtained from said horse, the biological sample comprising nucleic acids that includes the coding regions for myotilin (MYOT), filamin-C(FLNC) and myozenin-3 (MYOZ3):

(1) a proline (P) or a serine(S) at position 232 of SEQ ID NO:10, wherein detection of proline indicates the presence of variant P2;

(2) a lysine (K) or a glutamate (E) residue at position 753 of SEQ ID NO: 13, wherein detection of proline indicates the presence of variant P3a, (3) a threonine (T) or an alanine (A) at position 1207 of SEQ ID NO:13, wherein detection of threonine indicates the presence of of variant P3b and (4) a leucine (L) or a serine(S) at position 42 of SEQ ID NO:16, wherein detection of leucine indicates the presence of variant P4, wherein said horse is not homozygous for the presence of P2, P3a, P3b or P4;

wherein said horse is heterozygous for at least one of P2, P3a, P3b or P4; and (b) mating said horse with a mare or sire.

27. The method according to claim 26 wherein said mare or sire is free from variants P2, P3a, P3b and P4.

28. The method according to claim 26 wherein said mare or sire is heterozygous for variant P2, P3a, P3b or P4.

* * * * *